United States Patent [19]
Bold et al.

[11] Patent Number: 5,643,878
[45] Date of Patent: Jul. 1, 1997

[54] 5-AMINO-4-HYDROXYHEXANOIC ACID DERIVATIVES

[75] Inventors: Guido Bold, Gipf-Oberfrick, Switzerland; Marc Lang, Mulhouse, France; Alexander Fässler, Oberwils; Hans-Georg Capraro, Rheinfelden, both of Switzerland; Shripad Bhagwat, Scotch Plains, N.J.; Peter Schneider, Bottmingen; Peter van Hoogevest, Riehen, both of Switzerland

[73] Assignee: Ciba-Geigy Corporation, Tarrytown, N.Y.

[21] Appl. No.: 207,646

[22] Filed: Mar. 8, 1994

Related U.S. Application Data

[63] Continuation-in-part of Ser. No. 941,595, Sep. 8, 1992, abandoned.

[30] Foreign Application Priority Data

| Sep. 12, 1991 | [CH] | Switzerland | 2689/91 |
| Mar. 27, 1992 | [CH] | Switzerland | 890/92 |
| Jun. 25, 1992 | [CH] | Switzerland | 2007/92 |
| Mar. 11, 1993 | [CH] | Switzerland | 772/92 |

[51] Int. Cl.$^6$ .................... A61K 31/535; C07P 265/06
[52] U.S. Cl. .................... 514/19; 514/18; 544/168; 530/331
[58] Field of Search .................... 544/106, 124, 544/168; 530/331; 514/18, 19

[56] References Cited

U.S. PATENT DOCUMENTS

| 4,713,445 | 12/1987 | Szelice et al. | 530/330 |
| 4,880,781 | 11/1989 | Hester, Jr. et al. | 514/18 |
| 4,894,437 | 1/1990 | TenBrink | 530/328 |

FOREIGN PATENT DOCUMENTS

| 0045161 | 2/1982 | European Pat. Off. . |
| 0053017 | 6/1982 | European Pat. Off. . |
| 0118223 | 9/1984 | European Pat. Off. . |
| 0156322 | 10/1985 | European Pat. Off. . |
| 0173481 | 3/1986 | European Pat. Off. . |
| 0337714 | 10/1989 | European Pat. Off. . |
| 0356223 | 2/1990 | European Pat. Off. . |
| 0357322 | 3/1990 | European Pat. Off. . |
| 0401675 | 12/1990 | European Pat. Off. . |
| 0434365 | 6/1991 | European Pat. Off. . |
| 0487270 | 5/1992 | European Pat. Off. . |
| 0532466 | 3/1993 | European Pat. Off. . |
| 4308095 | 9/1994 | Germany . |
| 8909558 | 8/1990 | South Africa . |
| 9104136 | 2/1992 | South Africa . |
| 8403044 | 8/1984 | WIPO . |
| 8702986 | 5/1987 | WIPO . |
| 8802374 | 4/1988 | WIPO . |
| 9106561 | 5/1991 | WIPO . |
| 9217490 | 10/1992 | WIPO . |
| 9421604 | 9/1994 | WIPO . |

OTHER PUBLICATIONS

Richards et al. Sensitive Soluble Chromogenic Substances For HIV–1 Proteinase. J. Biol. Chem. 265(14) p. 7733–36, 1990.

Billich et al. Synthetic Peptides as Substrates and Inhibitors of Human Immune Deficiency Virus–1 Protease. J. Biol. Chem. 263(34) 17905–908 (1988).

Schneider et al. Enzymatic Activity of A Synthetic 99 Residue Protein Corresponding to The Putative HIV–1 Protease. Cell, 54, pp. 363–368 (Jul. 29, 1988).

Short Abstract Showing Formula of Ro 31–8959 (1988).

Muirhead et al. Pharmacokinetics of the HIV–Proteinase Inhibitor Ro 318959 After Single and Multiple Doses in Healthy Volunteers. Brit. J. Clim Pharmacol. 34(2) 170P–171P (1992).

Roche Statement on HIV Proteinase Inhibitor Ro 318959 European Trial Results. Distributed Berlin Jun. 7–11, 1993.

Roberts et al. HIV Proteinase Inhibitors. Biochemical Soc. Transactions, 20, p. 513–516 (1992).

(List continued on next page.)

*Primary Examiner*—David B. Springer
*Attorney, Agent, or Firm*—Marla J. Mathias; Ronald J. Campbell; Irving M. Fishman

[57] ABSTRACT

Compounds of formula I

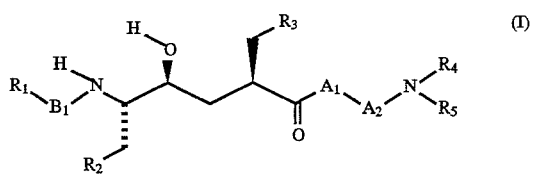

or their hydroxy-protected derivatives, and compounds of formula I'

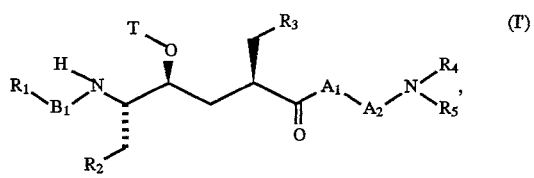

wherein T is an acyl radical of formula Z

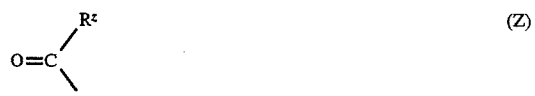

wherein $R^z$ is unsubstituted or substituted hydrocarbyl wherein at least one carbon atom has been replaced by a hetero atom with the proviso that a hetero atom is not bonded directly to the carbonyl to which the radical $R^z$ is bonded, alkyl having two or more carbon atoms, lower alkenyl, lower alkynyl, aryl or unsubstituted or substituted amino, and wherein the radicals $R_1$, $B_1$, $R_2$, $R_3$, $A_1$, $A_2$ and $NR_4R_5$ are as defined in the description, and precursors thereof, are described. The compounds have pharmaceutical activity, for example in the treatment of retroviral diseases, such as AIDS.

25 Claims, No Drawings

OTHER PUBLICATIONS

Vacca et al. L–687,908, a potent hydroxyethylene—containing HIV Protease Inhibitor. J. Med. Chem. 1991 (34) pp. 1225–1228.

Sammes et al. Comprehensive Medicinal Chem. vol. 2, 1990 Pergamon Press, Oxford, England pp. 419–422.

Payne et. al. Structure–activity Studies and anti–viral properties of hydroxyethylene transition state inhibitors of HIV Protease Proceedings of the 12th American Peptide Symposium. Jun. 1991, pp. 740–742.

Harada et al. Infection of HTLV–III/LAV in HTLV–1–Carrying Cells MT–2 and MT–4 and Application in a Plaque Assay, Science 229, pp. 563–566 (1985).

Denkewalter et al. Progress in Drug Research vol. 10 pp. 510–512 (1966).

Plattner et al. J. Med. Chem 31, 2277–2288 (1988).

Haber et al. J. Cardiovascular Pharm. vol 10 (Suppl. 7) 554–558 (1987).

Bolis et al. J. Med. Chem. 30, 1729–1737 (1987).

Burger, Medicinal Chemistry 2nd Ed. Interscience Publishers Inc. Ltd. London (1960).

De Camp et al. Tetrahedron Lett. 32, 1867–70 (1991).

De Solms et al. J. Med Chem. 1991, 34, 2852–2857. Design and Synthesis of Protease Inhibitors.

Evans et al. J. Org. Chem. 50, 4615–4625 (1985). A Stereocontrolled synthesis of Hydroxethylene Dipeptide Isosteres . . .

Evans et al. Pept. : Structs, Funct, Proc. Am. Pept. Symp. 9th Eds. Deber et al. 743–6 (1985).

Kempf J. Org. Chem. 51,3921–6 (1986).

Lyle et al., J. Med Chem 34, 1228–1230 (1991).

5-AMINO-4-HYDROXYHEXANOIC ACID DERIVATIVES

This is a continuation-in-part of application Ser. No. 07/941,595 filed Sep. 8, 1992, now abandoned.

The invention relates to non-hydrolysable analogues for peptides that can be cleaved by aspartate proteases, namely 5-amino-4-hydroxyhexanoic acid derivatives, processes for the preparation thereof, pharmaceutical compositions comprising those peptide analogues, and the use thereof as medicaments or for the preparation of pharmaceutical compositions for combating diseases caused by retroviruses.

According to present-day knowledge, AIDS is a disease of the immune system that is caused by the retrovirus HIV (Human Immunodeficiency Virus). According to WHO estimates, this disease affects approximately 10 million people and is still spreading. The disease almost always results in the death of the patient.

It has hitherto been possible to identify the retroviruses HIV-1 and HIV-2 (HIV stands for Human Immunodeficiency Virus) as the cause of the disease, and to characterise them by molecular biology. As far as treatment of the disease is concerned, beyond the hitherto limited possibilities of alleviating the symptoms of AIDS, and certain preventive possibilities, there is a particular interest in searching for compositions that impair the multiplication of the virus itself without damaging the intact cells and tissue of the patients.

An interesting possibility are compounds that block the multiplication of the virus by preventing the assembly of infectious virus particles.

HIV-1 and HIV-2 each have in their genome a region that codes for a "gag-protease". This "gag-protease" is responsible for the correct proteolytic cleavage of the precursor proteins that originate from the regions of the genome that code for the "group specific antigens" (gag). In the course of that cleavage, the structural proteins of the virus core are freed. "Gag-protease" itself is a constituent of a precursor protein that is coded for by the pol-genome region of HIV-1 and HIV-2 and that also comprises the regions for the "reverse transcriptase" and the "integrase" and is presumably cleaved autoproteolytically. "Gag-protease" cleaves the major core protein p24 of HIV-1 and HIV-2 preferentially N-terminally from proline radicals, for example in the bivalent radicals Phe-Pro, Leu-Pro or Tyr-Pro. The protease is one having a catalytically active asparate radical in the active site, a so-called aspartate protease.

Owing to the central role of "gag-protease" in the processing of the mentioned core proteins, it is assumed that an effective inhibition of that enzyme in vivo would prevent the assembly of mature virions, so that appropriate inhibitors could be used therapeutically.

A prerequisite for therapeutic activity in vivo is the achievement of good inhibition of virus replication in cell experiments and the attainment of good bioavailability, for example a high level in the blood, in order thus to achieve sufficiently high concentrations at the infected cells.

An additional aim of the present invention is to provide novel compounds that exhibit advantageous pharmacological properties.

Surprisingly it has now been found that the compounds described below according to the invention are capable of achieving that aim.

A number of "gag-protease"-inhibitors have already been synthesised that comprise central groups that are not proteolytically cleavable peptide isosteres. Despite intensive research, however, in the case of the majority of infected patients it has hitherto not been possible to use in the combating of AIDS asparate protease inhibitors that are suitable for administration to humans. Pharmacodynamic problems, especially, are a determining factor in this connection. The aim of the present invention is to make available novel inhibitors of HIV-1 aspartate protease.

The compounds according to the invention are in the fist place compounds of the formula

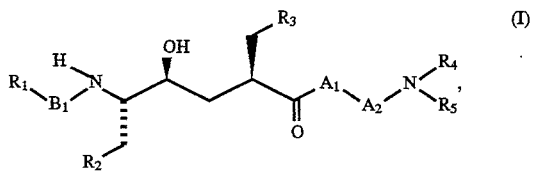 (I)

wherein $R_1$ is hydrogen; lower alkoxycarbonyl; heterocyclylcarbonyl; benzyloxycarbonyl that is unsubstituted or substituted by up to three radicals which may be the same or different and are selected from fluorine, halo-lower alkyl, lower alkanoyl, sulfo, lower alkylsulfonyl and cyano; heterocyclyloxycarbonyl wherein heterocyclyl is bonded by way of a carbon atom; one of the mentioned carbonyl radicals wherein the bonding carbonyl group has been replaced by a thiocarbonyl group; heterocyclylsulfonyl; lower alkylsulfonyl; or N-(heterocyclyl-lower alkyl)-N-lower alkylaminocarbonyl, $B_1$ is a bond or a bivalent radical of an α-amino acid, which radical is bonded N-terminally to $R_1$ and C-terminally to the amino group at the $R_2$-$CH_2$-carrying carbon atom, each of $R_2$ and $R_3$, independently of the other, is phenyl or cyclohexyl, those radicals being unsubstituted or substituted by from one to three radicals which may be the same or different and are selected from hydroxy, lower alkoxy, halogen, halo-lower alkyl, sulfo, lower alkylsulfonyl, cyano and nitro, $A_1$ is a bond between —C=O and $A_2$ or is a bivalent radical of an α-amino acid, which radical is bonded N-terminally to the group —C=O and C-terminally to $A_2$, $A_2$ is a bivalent radical of an α-amino acid, which radical is bonded N-terminally to $A_1$ and C-terminally to the group $NR_4R_5$, or $A_1$ and $A_2$ together form a bivalent radical of a dipeptide, of which the central amide bond is reduced and which is bonded N-terminally to the group —C=O and C-terminally to the group $NR_4R_5$, and $R_4$ and $R_5$, together with the bonding nitrogen atom, are unsubstituted or substituted thiomorpholino or morpholino, or salts of those compounds if salt-forming groups are present, or hydroxy-protected derivatives of those compounds or the salts thereof.

In the description of the present invention, the term "lower" used in the definition of groups or radicals, for example lower alkyl, lower alkoxycarbonyl, etc., denotes that the groups or radicals so defined, unless expressly defined otherwise, contain up to and including 7, and preferably up to and including 4, carbon atoms.

Asymmetric carbon atoms which may be present in the substituents $R_1$, $B_1$ $R_2$, $R_3$, $A_1$ and/or $A_2$, and in substituted thiomorpholino or morpholino formed by $R_4$ and $R_5$ together with the bonding nitrogen atom, may be in the (R)-, (S)- or (R,S)-configuration. Accordingly, the present compounds may be in the form of isomeric mixtures or in the form of pure isomers, especially in the form of diastereoisomeric mixtures, enantiomeric pairs or pure enantiomers.

The general terms and names used in the description of the present invention preferably have the following meanings, it being possible to use, at the various levels of definition, any combination of the radicals indicated hereinbefore and hereinafter or any individual radicals, instead of the general definitions:

Lower alkoxycarbonyl $R_1$ preferably contains a branched lower alkyl radical, especially a sec- or tert-lower alkyl radical, and is, for example, butoxycarbonyl, such as tert-butoxycarbonyl or isobutoxycarbonyl. Tert-butoxycarbonyl is especially preferred.

Heterocyclylcarbonyl $R_1$ contains, especially, a 5- or 6-membered heterocycle that contains from 1 to 3 hetero atoms which may be the same or different and are selected from S, O and N, is unsaturated or completely or partially saturated and is mono- to tribenzo-fused or cyclopenta-, cyclohexa- or cyclohepta-fused, it being possible for the mentioned fused rings to contain a further nitrogen atom as hetero atom, for example a heterocyclyl radical that is selected from pyrrolyl, furanyl, thienyl, imidazolyl, pyrazolyl, oxazolyl, thiazolyl, pyridyl, pyrazinyl, pytimidinyl, indolyl, quinolyl, isoquinolyl, quinoxalinyl, β-carbolinyl and a benzo-fused or cyclopenta-, cyclohexa- or cyclohepta-fused derivative of those radicals, which may also be completely or partially saturated, preferably partially saturated, or is selected from pyridylcarbonyl, for example pyridyl-3-carbonyl, morpholinylcarbonyl, for example morpholinocarbonyl, and benzofuranoyl, for example 3-benzofuranoyl, or, alternatively or additionally thereto, tetrahydroisoquinolyl, carbonyl, for example tetrahydroisoquinolyl-3-carbonyl, preferably tetrahydroisoquinolyl-3(S)-carbonyl.

Benzyloxycarbonyl $R_1$ is unsubstituted or substituted by up to three radicals which may 1 the same or different and are selected from fluorine, halo-lower alkyl, for example fluoromethyl or pentafluoroethyl, lower alkanoyl, such as acetyl, propanoyl, butyryl or pivaloyl, sulfo, lower alkylsulfonyl, for example methylsulfonyl, ethylsulfonyl, n-propyl sulfonyl or isopropylsulfonyl, and cyano. Preferred is benzyloxycarbonyl that is unsubstituted or o-, m- or p-substituted, especially p-substituted, in the phenyl ring by a radical selected from fluorine, tdfluoromethyl, sulfo, methylsulfonyl, ethylsulfonyl and cyano, for example benzyloxycarbonyl, fluorophenylmethoxycarbonyl, such as p-fluorophenylmethoxycarbonyl, trifluoromethylphenylmethoxycarbonyl, such as p-trifluoromethylphenylmethoxycarbonyl, methylsulfonylphenylmethoxycarbonyl, such as p-methylsulfonylphenylmethoxycarbonyl, or cyanophenylmethoxycarbonyl, such as p-cyanophenylmethoxycarbonyl.

Heterocyclyloxycarbonyl $R_1$ contains as heterocyclyl especially a 5- or 6-membered heterocycle that contains from I to 3 hetero atoms which may be the same or different and are selected from S, O and N, is unsaturated or completely or partially saturated and is mono- to tri-benzo-fused or cyclopenta-, cyclohexa- or cyclohepta-fused, it being possible for the mentioned fused rings to contain a further nitrogen atom as hetero atom, for example a radical selected from pyrrolyl, thienyl, imidazolyl, pyrazolyl, oxazolyl, thiazolyl, pyrazinyl, pydmidinyl, indolyl, quinolyl, isoquinolyl, quinoxalinyl, β-carbolinyl and a benzo-fused or cyclopenta-, cyclohexa- or cyclohepta-fused derivative of those radicals, which may also be completely or partially saturated, the heterocyclyl radicals being bonded by way of a ring carbon atom to the oxygen of the associated oxycarbonyl radical, and preferably being selected from pyrrolyl, thienyl, imidazolyl, pyrazolyl, oxazolyl, thiazolyl, pyrazinyl, pyrimidinyl, indolyl, quinolyl, isoquinolyl, quinoxalinyl, β-carbolinyl and a completely or partially saturated derivative of those radicals, for example a partially saturated derivative of those radicals or indol-3-yloxycarbonyl, benzothiazol-6-yloxycarbonyl or quinol-8-yloxycarbonyl. In a very especially preferred variant of the definition of $R_1$, the radicals defined as substituents of heterocyclyloxycarbonyl are not included at any level of definition.

In the mentioned radicals, the bonding carbonyl group may also have been replaced by a thiocarbonyl group. A carbonyl group is preferred.

Lower alkylsulfonyl (=lower alkyl—$SO_2$—) $R_1$ is preferably methylsulfonyl, ethylsulfony n-propylsulfonyl or isopropylsulfonyl. The compounds of formula I wherein $R_1$ is lower alkylsulfonyl and the other radicals are as defined may be omitted from the definition of the compounds of formula I, or they are especially preferred.

Heterocyclylsulfonyl contains as heterocyclyl preferably one of the heterocycles, mentioned under heterocyclylcarbonyl $R_1$, that is unsubstituted or substituted by lower alkyl, such as methyl or ethyl, heterocycles having at least one nitrogen atom that is bonded to the sulfur of the sulfonyl group being preferred, and is especially piperidinosulfonyl, piperazin-1-ylsulfonyl that is unsubstituted or substituted by lower alkyl, such as methyl, at the nitrogen that is not bonded to the sulfonyl-sulfur, pyrrolidin-1-ylsulfonyl, imidazolidin-1-ylsulfonyl, pyrimidin-1-ylsulfonyl, quinolin-1-ylsulfonyl, morpholinosulfonyl or thiomorpholinosulfonyl, especially thiomorpholinosulfonyl or morpholinosulfonyl. The compounds of formula I wherein $R_1$ is heterocyclylsulfonyl and the other radicals are as defined may be omitted from the definition of the compounds of formula I, or they are especially preferred.

N-(heterocyclyl-lower alkyl)-N-lower alkylaminocarbonyl $R_1$ contains as heterocyclyl preferably one of the heterocycles mentioned under heterocyclylcarbonyl $R_1$, especially pyridyl, such as 2-, 3- or 4-pyridyl, pyrazinyl, pyrimidinyl, morpholinyl, such as morpholino, thiomorpholinyl, such as thiomorpholino, or quinolyl, such as 2- or 3-quinolyl, and is, especially, N-(heterocyclylmethyl)-N-methylaminocarbonyl, for example N-(pyridylmethyl)-N-methylaminocarbonyl, such as N-(2-pyridylmethyl)-N-methylaminocarbonyl. The compounds of formula I wherein $R_1$ is N-(heterocyclyl-lower alkyl)-N-lower alkylaminocarbonyl and the other radicals are as defined may be omitted from the definition of the compounds of formula I, or they are especially preferred.

A bivalent radical $B_1$ of an α-amino acid, which radical is bonded N-terminally to $R_1$ and C-terminally to the amino group at the $R_2$-$CH_2$-carrying carbon atom, is preferably selected from glycine (H-Gly-OH), alanine (H-Ala-OH), valine (H-Val-OH), norvaline (α-aminovaleric acid), leucine, (H-Leu-OH), isoleucine (H-He-OH), norleucine (α-amine, hexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), proline (H-Pro-OH), trans-3- and trans-4-hydroxyproline, phenylalanine (H-Phe-OH), p-fluorophenylalanine (H-(p-F-Phe)-OH), tyrosine (H-Tyr-OH), p-methoxyphenylalanine (H-(p-$CH_3$O-Phe)-OH), 4-aminophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), indoline-2-carboxylic acid, 1,2,3,4-tetrahydroisoquinoline-3-carboxylic acid, aminomalonic acid, aminomalonic acid monoamide, aspartic acid (H-Asp-OH), asparagine (H-Asn-OH), glutamic acid (H-Glu-OH), glutamine (H-Gln-OH), histidine (H-His-OH), arginine (H-Arg-OH), lysine (H-Lys-OH), δ-hydroxylysine, ornithine (α,δ-diaminovaleric acid), α,γ-diaminobutylic acid and α,β-diaminopropionic acid, or, alternatively or additionally thereto, 4-cyanophenylalanine (H-(p-CN-Phe)-OH), and is especially preferably the radical of a hydrophobic amino acid, for example proline, phenylalanine, p-fluorophenylalanine, p-methoxyphenylalanine, tyrosine, phenylglycine, α-naphthylalanine, cyclohexylalanine, cyclohexylglycine or an aliphatic α-amino acid selected from glycine, valine, norvaline, alanine, leucine, norleucine and isoleucine, especially valine, each of the mentioned α-amino acids being in the D-, L- or (D,L)-form, preferably in the L-form, and being linked especially with radicals $R_1$ selected from lower alkoxycarbonyl, for example tert-butoxycarbonyl, or heterocyclylcarbonyl, for example morpholinocarbonyl.

When $B_1$ is a bond, $R_1$ is bonded directly to the amino-nitrogen that is bonded by the carbon atom carrying the radical $R_2$-$CH_2$— in formula I.

Phenyl or cyclohexyl $R_2$ or $R_3$ is unsubstituted or substituted by up to three radicals which may be the same or different and are selected from hydroxy, lower alkoxy, such as methoxy or ethoxy, halogen, for example fluorine, halo-lower alkyl, for example trifluoromethyl, sulfo, lower alkylsulfonyl, for example methyl- or ethyl-sulfonyl, cyano and nitro, preferably by one or two of those radicals, especially preferably selected from hydroxy, methoxy, fluorine, trifluoromethyl, sulfo, lower alkylsulfonyl, for example methyl- or ethylsulfonyl, and cyano; in the case of phenyl, very especially preferably from fluorine and cyano, in the case of cyclohexyl, very especially preferably from fluorine, trifluoromethyl, sulfo and lower alkylsulfonyl, especially fluorine; the mentioned substituents being bonded in the 2-, 3- or 4-position of the phenyl or cyclohexyl ring, especially in the 4-position, as in phenyl, cyclohexyl, 4-fluoro- or 4-cyanophenyl or 4-fluorocyclohexyl, especially in phenyl, cyclohexyl, 4-cyanophenyl or 4-fluorophenyl.

Especially preferred are combinations of $R_2$ and $R_3$ in which at least one of the radicals $R_2$ and $R_3$ is substituted by from one to three radicals selected from halogen, especially fluorine, halo-lower alkyl, especially trifluoromethyl, sulfo, lower alkylsulfonyl, especially methyl- or ethyl-sulfonyl, cyano and nitro, a substituent selected from fluorine and cyano being very strongly preferred.

Even more strongly preferred is $R_2$ selected from phenyl, 4-hydroxyphenyl, 4-methoxyphenyl, 4-fluorophenyl, cyclohexyl and 4-trifluoromethylphenyl, while $R_3$ is selected from phenyl, 4-hydroxyphenyl, 4-methoxyphenyl, cyclohexyl, 4-fluorophenyl, 4-trifluoromethylphenyl and 4-cyanophenyl.

$R_2$ is selected especially from phenyl, 4-fluorophenyl and cyclohexyl, while $R_3$ is selected from phenyl, cyclohexyl, 4-fluorophenyl and 4-cyanophenyl.

Most especially preferred are the combinations: $R_2$ phenyl and $R_3$ phenyl; $R_2$ cyclohexyl and $R_3$ 4-cyanophenyl; $R_2$ cyclohexyl and $R_3$ 4-fluorophenyl; and $R_2$ and $R_3$ each cyclohexyl. Alternatively or additionally thereto, the combinations $R_2$ phenyl and $R_3$ 4-fluorophenyl; $R_2$ phenyl and $R_3$ 4-cyanophenyl; $R_2$ 4-fluorophenyl and $R_3$ 4-fluorophenyl; $R_2$ 4-fluorophenyl and $R_3$ 4-trifluoromethylphenyl; $R_2$ 4-trifluoromethylphenyl and $R_3$ phenyl; $R_2$ 4-trifluoromethylphenyl and $R_3$ 4-fluorophenyl; $R_2$ 4-trifluoromethylphenyl and $R_3$ 4-trifluoromethylphenyl; $R_2$ hydroxyphenyl and $R_3$ phenyl; $R_2$ phenyl and $R_3$ hydroxyphenyl; or $R_2$ hydroxyphenyl and $R_3$ hydroxyphenyl are also most especially preferred.

Hydroxy groups, especially the hydroxy group in compounds of formula I at the carbon atom that is vicinal to the carbon atom carrying the radical $R_2$-$CH_2$-, may be free or in protected form, suitable hydroxy-protecting groups being the radicals mentioned hereinafter in the description of the preparation processes for compounds of formula I, especially free or protected in the form of physiologically cleavable esters, for example in the form of lower alkanoyloxy, such as acetoxy.

A bivalent radical of an α-amino acid $A_1$, which radical is bonded N-terminally to the group —C═O and C-terminally to $A_2$, is, for example, one of the α-amino acids mentioned above for $B_1$, it being possible for those amino acids to be in the (D)-, (L)- or (D,L)-form, preferably the (D) or (L)-form, especially the (L)-form. Preferred are the hydrophobic α-amino acids mentioned under $B_1$, especially the aliphatic hydrophobic α-amino acids mentioned there, for example glycine, valine or isoleucine. In the mentioned α-amino acids, the carboxy group bonding to $A_2$ is not reduced or is further reduced, especially to a methylene group, for example in the mentioned hydrophobic α-amino acids, such as in the reduced amino acid radicals Gly(red), Val(red) or Ile(red), especially in Val(red), the suffix (red) indicating the reduction of the carbonyl group of the corresponding amino acid radical to the methylene group.

If $A_1$ is a bond, then $A_2$ is bonded directly to the carbonyl group at the carbon atom carrying the radical $R_3$-$CH_2$—.

A bivalent radical of an α-amino acid $A_2$, which radical is bonded N-terminally to $A_1$ and C-terminally to the group $NR_4R_5$, is, for example, one of the α-amino acids mentioned above for $B_1$, it being possible for those amino acids to be in the (D)-, (L)- or (D,L)-form, preferably the (D) or (L)-form, especially the (L)-form. Preferred are the hydrophobic α-amino acids mentioned under $B_1$, for example glycine, valine, phenylalanine, p-fluorophenylalanine, tyrosine, p-methoxyphenylalanine, phenylglycine, α-naphthylalanine, cyclohexylalanine or cyclohexylglycine, preferably glycine, valine, phenylalanine, p-fluorophenylalanine, p-methoxyphenylalanine or cyclohexylalanine, the mentioned radicals being in the (D)- or (L)-form but preferably, with the exception of phenylalanine which is in the (L)- or (D)-form, in the (L)-form.

A bivalent radical, formed from $A_1$ and $A_2$, of a dipeptide, of which the central peptide bond is reduced and which is bonded N-terminally to the group —C═O and C-terminally to the group $NR_4R_5$, preferably comprises 2 of the above-mentioned hydrophobic α-amino acids, especially one N-terminal amino acid radical selected from Gly(red), Val (red) and Ile(red) and one C-terminal amino acid selected from glycine, phenylalanine, tyrosine, p-methoxyphenylalanine, cyclohexylalanine and p-fluorophenylalanine.

Especially preferably, $A_1$ and $A_2$ together form a bivalent radical of a dipeptide of the formula Val-Phe, Ile-Phe, Val-Cha, Ile-Cha, Val-Gly, Val-(p-F-Phe), Val-(p-$CH_3$O-Phe) or Gly-(p-F-Phe); and, alternatively or additionally, of a dipeptide of the formula Val-Tyr, Ile-Tyr, Gly-Tyr, Ile-Gly or Val-Val; wherein the amino acids are in the (D)- or (L)-form, especially the (L)-form, with the exception of (L)-Val-Phe in which Phe is in the (L)- or (D)-form; or of a derivative thereof having a reduced central amide bond, for example having the formula Val(red)-Phe, which is bonded N-terminally to the group —C═O and C-terminally to the group $NR_4R_5$.

A preferred embodiment of the invention relates either to the compounds of formula I wherein $B_1$ is one of the mentioned bivalent radicals of an α-amino acid and one of the radicals $A_1$ and $A_2$ is a bond and the other is one of the mentioned α-amino acids, or to those compounds of formula I wherein $B_1$ is a bond and each of $A_1$ and $A_2$ is one of the mentioned bivalent radicals of an α-amino acid or they are together one of the mentioned bivalent radicals of a dipeptide having a reduced central amide bond.

Thiomorpholino or morpholino formed from $R_4$ and $R_5$ together with the bonding nitrogen atom is unsubstituted or substituted at one or more of the carbon atoms, preferably at one carbon atom, by lower alkyl, such as ethyl, propyl, butyl, isobutyl or tert-butyl, by phenyl- or naphthyl-lower alkyl, such as benzyl, 1 - or 2-naphthylmethyl or phenyl-1- or phenyl-2-ethyl, especially phenyl-1- or phenyl-2-ethyl, by hydroxy, by lower alkoxy, such as methoxy, ethoxy or tert-butoxy, by amino, by lower alkylamino, such as methyl- or ethylamino, or by di-lower alkylamino, such as dimethylamino or diethylamino, by lower alkanoyl, such as acetyl or propionyl, by phenyl- or naphthyl-lower alkanoyl, such as phenylacetyl or 1- or 2-naphthylacetyl, by carboxy, by lower alkoxycarbonyl, such as isopropoxycarbonyl or tert-butoxycarbonyl, by phenyl-, naphthyl- or fluorenyl-lower alkoxycarbonyl, such as benzyloxycarbonyl, 1- or 2-naphthylmethoxycarbonyl or 9-fluorenylmethoxycarbonyl, by carbamoyl, by mono- or di-lower alkylcarbamoyl, such as dimethylcarbamoyl, by mono- or di-hydroxy-lower alkylcarbamoyl, such as dihydroxymethylcarbamoyl, by sulfo, by lower alkylsulfonyl, such as methylsulfonyl or ethylsulfonyl, by phenyl- or naphthyl-sulfonyl, wherein phenyl may be substituted by lower alkyl, for example methyl or ethyl, for example phenylsulfonyl or toluenesulfonyl, by sulfamoyl, by halogen, for example fluorine or chlorine, by cyano, by nitro and/or by oxo.

Very preferably, $R_4$ and $R_5$ form, together with the bonding nitrogen atom, unsubstituted thiomorpholino or morpholino, especially unsubstituted morpholino.

The compounds according to the invention are in addition compounds of formula I'

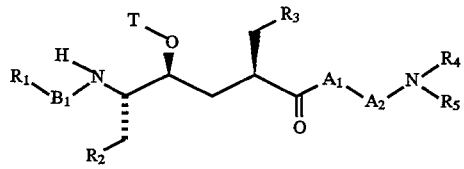 (I')

wherein T is an acyl radical of formula Z

 (Z)

wherein $R^z$ is unsubstituted or substituted hydrocarbyl wherein at least one carbon atom has been replaced by a hetero atom with the proviso that a hetero atom is not bonded directly to the carbonyl to which the radical $R^z$ is bonded, alkyl having two or more carbon atoms, lower alkenyl, lower alkynyl, aryl or unsubstituted or substituted amino, and wherein $R_1$ is hydrogen, lower alkoxycarbonyl, heterocyclylcarbonyl, benzyloxycarbonyl that is unsubstituted or substituted by up to three radicals selected independently of one another from fluorine, halo-lower alkyl, lower alkanoyl, sulfo, lower alkylsulfonyl and cyano, heterocyclyloxycarbonyl wherein heterocyclyl is bonded via a carbon atom, one of the mentioned carbonyl radicals wherein the bonding carbonyl group has been replaced by a thiocarbonyl group, heterocyclylsulfonyl, lower alkylsulfonyl or N-(heterocyclyl-lower alkyl)-N-lower alkylaminocarbonyl, $B_1$ is a bond or a bivalent residue of an α-amino acid bonded N-terminally to $R_1$ and C-terminally to the amino group at the carbon atom carrying $R_2$-$CH_2$—, $R_2$ and $R_3$ are each independently of the other phenyl or cyclohexyl, those radicals being unsubstituted or substituted by from one to three radicals selected independently of one another from hydroxy, lower alkoxy, halogen, halo-lower alkyl, sulfo, lower alkylsulfonyl, cyano and nitro, $A_1$ is a bond between —C═O and $A_2$ or is a bivalent residue of an α-amino acid bonded N-terminally to the group —C═O and C-terminally to $A_2$, $A_2$ is a bivalent residue of an α-amino acid bonded N-terminally to $A_1$ and C-terminal to the group $NR_4R_5$, or $A_1$ and $A_2$ together form a bivalent residue of a dipeptide the central amide bond of which has been reduced and which is bonded N-terminally to the group —C═O and C-terminally to the group $NR_4R_5$, and $R_4$ and $R_s$ together with the bonding nitrogen atom form unsubstituted or substituted thiomorpholino or morpholino, or salts of those compounds where salt-forming groups are present.

Asymmetric carbon atoms which may be present in the substituents T, $R_1$, $B_1$, $R_2$, $R_3$, $A_1$ and/or $A_2$ and also in substituted thiomorpholino or morpholino formed by $R_4$ and $R_5$ together with the bonding nitrogen atom, can be in the (R)-, (S)- or (R,S)-configuration preferably in the (R)- or (S)-configuration. Accordingly the present compounds can be in the form of mixtures of isomers or in the form of pure isomers, especially in the form of diastereoisomeric mixtures, pairs of enantiomers or, preferably, pure enantiomers.

The general terms and names used in the description of compounds of formula I' of this invention preferably have the following definitions; in the various categories of definition it is possible to use instead of the general definitions any combinations of or individual radicals from the radicals mentioned hereinabove and hereinbelow:

Unsubstituted or substituted hydrocarbyl $R^z$ wherein at least one carbon atom has been replaced by a hetero atom with the proviso that a hetero atom is not bonded directly to the carbonyl to which the radical $R^z$ is bonded, is a saturated, partially saturated or unsaturated hydrocarbon radical having a maximum of 30 carbon atoms, preferably having up to 22 carbon atoms, and contains in place of at least one carbon atom, preferably in place of each of from one to four carbon atoms, a hetero atom selected from nitrogen, oxygen and sulfur and is unsubstituted or substituted by one or more radicals, preferably by up to three substituents, especially by hydroxy, by lower alkoxy, such as methoxy, by lower alkoxy-lower alkoxy, such as 2-methoxyethoxy, by lower alkoxy-lower alkoxy-lower alkoxy, such as 2-(2-methoxyethoxy)ethoxy, by phenyl- or naphthyl-lower alkoxy-lower alkoxy (wherein phenyl or naphthyl is unsubstituted or substituted by one or more, preferably one of the radicals halogen, such as fluorine, chlorine or bromine, lower alkyl, such as methy halo-lower alkyl, such as trifluoromethyl, hydroxy, lower alkoxy, such as methoxy, lower alkanoyloxy, carboxy, lower alkoxycarbonyl, phenyl-lower alkoxycarbonyl, cyano, carbamoyl, mono- or di-lower alkylcarbamoyl, mono- or di-hydroxy-lower alkylcarbamoyl, heterocyclyl-lower alkyl wherein heterocyclyl is a saturated, partially saturated or unsaturated single ring containing from 3 to 7, preferably from 5 to 7, ring atoms and up to two hetero atoms selected from nitrogen, sulfur, oxygen and lower alkyl-, benzyl-, di-phenylmethyl-, triphenylmethyl- or lower alkanoyl-substituted nitrogen, for example piperidinomethyl, piperazin-1-ylmethyl, 4-lower alkyl-piperazin-1-ylmethyl, such as 4-methyl- or 4-ethyl-piperazin-1-ylmethyl, morpholinomethyl or thiomorpholinomethyl and nitro, which may be present independently of one another), by phenyl-lower alkanoyloxy, such as benzyloxy, by halogen, such as fluorine, chlorine or bromine, by halo-lower alkyl, such as trifluoromethyl or chloromethyl, by carboxy, by lower alkoxycarbonyl, by phenyl-lower alkoxycarbonyl, such as benzyloxycarbonyl, by carbamoyl, by lower alkylcarbamoyl, by hydroxy-lower alkylcarbamoyl, by di-lower alkylcarbamoyl, by bis-(hydroxy-lower alkyl)carbamoyl, by cyano, by oxo, by $C_3-C_8$-cycloalkyl, such as cyclobutyl, cyclopentyl or cyclohexyl, or by aryl, preferably $C_6-C_{14}$aryl, such as phenyl, naphthyl, such as 1- or 2-naphthyl, or fluorenyl, such as fluoren-9-yl, those substituents being independent of one another when several are present; a hetero atom preferably being directly adjacent to the carbon atom in the radical hydrocarbyl $R^z$ that is bonded to the carbonyl group that bonds $R^z$ in formula I' (that is to say being in the 3-position starting from the $R^z$-bonding carbonyl group included in the count); and is especially heterocyclyl, bonded via a ring carbon atom, which is preferably a saturated, partially saturated or unsaturated ring containing from 3 to 7, especially from 5 to 7, ring atoms and containing one or more, especially up to a maximum of four, more especially up to two, hetero atoms selected independently of one another from nitrogen, sulfur and oxygen; the ring being present either as such or being once or twice, especially once, benzo-fused, cyclopenta-, cyclohexa- or cyclohepta-fused; the ring system being substituted by up to three radicals selected independently of one another from lower alkyl, phenyl-lower alkyl diphenyl-lower alkyl, triphenyl-lower alkyl, such as triphenylmethyl, lower alkanoyl, hydroxy, lower alkoxy, phenyl-lower alkoxy, such as benzyloxy, diphenylmethoxy or triphenylmethoxy, hydroxy-lower alkyl, such as hydroxymethyl, halogen, such as fluorine, chlorine or bromine, cyano, lower alkoxycarbonyl, such as methoxy- or tert-butoxycarbonyl, phenyl-lower alkoxycarbonyl, such as benzyloxycarbonyl, and halo-lower alkyl, such as chloromethyl or trifluoromethyl, or preferably being unsubstituted; selected especially from pyrrolyl, 2,5-dihydropyrrolyl, indolyl, indolizinyl, isoindolyl, pyrrolidinyl, such as pyrrolidin-3-yl or especially pyrrolidin-2-yl (in the (R,S)- or preferably the (R)- or (S)-configuration), hydroxypyrrolidinyl, such as 3- or especially 4-hydroxypyrrolidinyl, furyl, such as furan-3-yl or especially furan-2-yl, tetrahydrofuryl, thienyl, cyclohepta[b]-pyrrolyl, imidazolyl, such as imidazol-2-yl, imidazol-3-yl or especially imidazol-5-yl, N-triphenyl-lower alkyl-imidazolyl, such as N-tfiphenylmethyl-imidazolyl, pyrazolyl, especially pyrazol-3-yl, oxazolyl, isoxazolyl, such as isoxazol-3-yl or -5-yl, thiazolyl, isothiazolyl, such as isothiazol-3-yl or -5-yl, triazolyl, such as 1,2,3-triazol-4- or -5-yl or 1,2,4-triazol-5-yl, tetrazolyl, pyridyl, such as pyridin-4-yl or -3-yl or especially pyridin-2-yl, quinolyl, such as quinolin-2-yl, isoquinolyl, especially isoquinolin-1-yl or-3-yl, piperidyl, especially piperidin-2-yl, γ-pyranyl, 4,5-dihydropyranyl, 4H-chromenyl, chromanyl, 1-thiopyranyl, pyridazinyl, cinnolyl, phthalazinyl, quinazolinyl, quinoxalinyl, pyrimidinyl, pyrazinyl, phenazinyl, phenoxazinyl, phenothiazinyl, morpholinyl and thiazinyl, each of which is bonded via a ring carbon atom; very special preference is given to those of the mentioned radicals which contain a ring hetero atom directly adjacent to the bonding ring carbon atom. Strong preference is given to the radicals furan-2-yl, (S)- or (R)-pyrrolidin-2-yl and imidazol-4-yl, pyridin-2-yl, -3-yl or -4-yl, or isoquinolin-3-yl; also tetrahyctropyranyl, such as 4-tetrahydropyranyl;

lower alkyl (especially methyl, ethyl, n-propyl or n-butyl) which is substituted by at least one radical selected from etherified or esterified hydroxy or (unoxidised or oxidised by 1 or 2 oxo groups) mercapto, unsubstituted or substituted amino and heterocyclyl, especially by one of the mentioned radicals, and which may carry as a further substituent aryl, which is as defined below at the end of this section, wherein etherified hydroxy is especially lower alkoxy, such as methoxy, ethoxy or n-butoxy, or lower alkoxy, such as methoxy, ethoxy or n-butoxy, substituted by one or two substituents, especially by aryl, more especially phenyl or naphthyl, by lower alkoxy, such as ethoxy or methoxy, by lower alkylthio, such as methylthio or ethylthio, by lower alkoxy-lower alkoxy, such as 2-methoxyethoxy, by lower alkylthio-lower alkoxy, such as 2-methylthioethoxy, by aryloxy or arylthio wherein aryl is as defined below, especially phenyl or o-, m- or p-chlorophenyl, for example p-chlorophenyloxy, by amino, N-lower alkylamino or N,N-di-lower alkylamino, such as 2-amino, 2-(N-lower alkyl)amino or 2-(N,N-di-lower alkyl)amino, for example 2-dimethylamino, by heterocyclyl as defined above for heterocyclyl $R^z$ bonded via a ring carbon atom, especially 2-, 3- or 4-pyridyl, or (additionally or preferably) by lower alkoxycarbonyl, such as methoxycarbonyl, by lower alkanoyloxy-lower alkoxycarbonyl, such as pivaloyloxymethoxycarbonyl or acetyloxymethoxycarbonyl, by carboxy, by phenyl-lower alkoxycarbonylamino-lower alkoxy, such as 2-(benzyloxycarbonylamino)-ethoxy, by amino-lower alkoxy, such as 2-aminoethoxy, by di-lower alkylamino-lower alkoxy, such as 2-(dimethylamino)-ethoxy, or by N,N-di-lower alkylamino-lower alkoxy, such as 2-(dimethylamino)-ethoxy, or is aryloxy, especially phenyloxy, or (additionally or especially) tetrahydropyranyloxy, such as 4-tetrahydropyranyloxy;

esterified hydroxy is especially lower alkanoyloxy, such as acetyloxy, benzoyloxy or phenyl-lower alkanoyloxy, such as phenylacetyloxy;

etherified mercapto is especially lower alkylthio, such as methylthio, ethylthio or n-butylthio, or lower alkylthio, such as methylthio, ethylthio or n-butylthio, substitute by one or two substituents, especially by aryl, more especially phenyl or naphthyl, by lower alkoxy, such as ethoxy or methoxy, by lower alkylthio, such as methylthio or ethylthio, by lower alkoxy-lower alkoxy, such as 2-methoxyethoxy, by lower alkylthio-lower alkoxy, such as 2-methylthioethoxy, by aryloxy or arylthio wherein aryl is as defined below, especially phenyl or o-, m- or p-chlorophenyl, for example p-chlorophenyloxy, by amino, N-lower alkylamino or N,N-di-lower alkylamino, such as 2-amino, 2-(N-lower alkyl)amino or 2-(N,N-di-lower alkyl)amino, for example 2-dimethylamino, by heterocyclyl as defined above for heterocyclyl $R^z$ bonded via a ring carbon atom, especially 2-, 3- or 4-pyridyl, or (additionally or especially) by lower alkoxycarbonyl, such as methoxycarbonyl, or is arylthio, such as phenylthio; it being possible for the mercapto sulfur atom additionally or especially to be oxidised by one or preferably two oxo groups, especially in lower alkoxycarbonyl-lower alkylsulfo, such as methoxycarbonylmethylsulfo;

esterified mercapto is especially lower alkanoylthio, benzoylthio or phenyl-lower alkanoylthio, such as phenacetylthio;

unsubstituted or substituted amino is especially amino or amino substituted by one or two radicals selected from lower alkyl, such as methyl, heterocyclyl-lower alkyl wherein heterocyclyl is as defined for heterocyclyl $R^z$ bonded via a ring carbon atom, especially heterocyclylmethyl, such as imidazolylmethyl, for example 4-imidazolylmethyl, or pyridylmethyl, for example 2-, 3- or 4-pyridylmethyl, each bonded via a ring carbon atom, aryl-lower alkyl, such as phenyl- or naphthyl-lower alkyl, for example phenyl- or naphthylmethyl, lower alkanoyl, such as acetyl, lower alkoxycarbonyl, such as tert-butoxycarbonyl, and aryl-lower alkoxycarbonyl, such as phenyl-lower alkoxycarbonyl, for example benzyloxycarbonyl; very especially one of the substituents of amino is lower alkyl, especially methyl, and the other is hydrogen or one of the radicals mentioned above as substituents of amino; and heterocyclyl is especially as defined above for heterocyclyl $R^z$ bonded via a ring carbon atom and is preferably a saturated, partially saturated or unsaturated ring and may also fused or substituted as above, especially as pyridin-2-yl, -3-yl or -4-yl;

or heterocyclyl-lower alkyl wherein lower alkyl is preferably methyl, 1- or 2-ethyl or 3-propyl and wherein heterocyclyl is as defined above for heterocyclyl $R^z$ bonded via a ring carbon atom, which is preferably a saturated, partially saturated or unsaturated ring and may also be fused or substituted as above but may also be bonded via a ring nitrogen atom, especially imidazol-1-yl, imidazol-2-yl, imidazol-5-yl or more especially imidazol-4-yl, N-triphenyl-lower alkylimidazolyl, such as N-triphenylmethyl-imidazol-5-yl or especially-4-yl, or pyrazolyl, such as pyrazol-1-yl, -3-yl, -4-yl or -5-yl.

Alkyl $R^z$ having two or more carbon atoms is especially ethyl, n-propyl, isopropyl, n-butyl or 1,1-dimethylethyl, or more especially $C_7$–$C_{20}$alkyl, so that T is, for example, propionyl, butyryl, methylpropionyl, valeroyl or pivaloyl, or especially octanoyl, decanoyl or palmitoyl.

Lower alkenyl $R^z$ is especially $C_2$–$C_7$alkenyl, more especially $C_2$–$C_3$alkenyl, wherein the double bond is preferably in the 1-position, so that T is, for example, acryloyl, crotonoyl, isocrotonoyl or methacryloyl.

Lower alkynyl $R^z$ is especially $C_2$–$C_7$alkynyl, more especially $C_2$–$C_3$alkynyl, wherein the triple bond is preferably in the 1-position, so that T is, for example, propynoyl.

Aryl $R^z$ by itself or aryl as a substituent in the above-mentioned radicals $R^z$ with the exception of aryl itself is especially $C_6$–$C_{14}$aryl, more especially phenyl, naphthyl, such as 1- or 2-naphthyl, or fluorenyl, such as 9-fluorenyl, and is unsubstituted or substituted by up to three radicals selected independently of one another from lower alkyl, lower alkanoyl, hydroxy, lower alkoxy, phenyl-lower alkoxy, such as benzyloxy, diphenylmethoxy or triphenylmethoxy, hydroxy-lower alkyl, such as hydroxymethyl, halogen, such as fluorine, chlorine or bromine, cyano, lower alkoxycarbonyl, such as methoxy- or tert-butoxy-carbonyl, phenyl-lower alkoxycarbonyl, such as benzyloxycarbonyl, halo-lower alkyl, such as chloromethyl or trifluoromethyl, heterocyclyl-lower alkyl wherein heterocyclyl is a saturated, partially saturated or unsaturated single ring containing from 3 to 7, preferably from 5 to 7, ring atoms and up to two hetero atoms selected from nitrogen, sulfur, oxygen and lower alkyl-, benzyl-, diphenylmethyl-, triphenylmethyl- or lower alkanoyl-substituted nitrogen, for example piperidinomethyl, piperazin-1-ylmethyl, 4-lower alkyl-piperazin-1-yl-methyl, such as 4-methyl- or 4-ethyl-piperazin-1-ylmethyl, morpholinomethyl or thiomorpholinomethyl, and nitro, which may be present independently of one another, especially correspondingly substituted phenyl. Special preference is given to o-, m- or p-chlorophenyl, chloro-lower alkylphenyl, such as p-chloromethylphenyl, p-(morpholino-lower alkyl)phenyl, such as p-morpholinomethyl-phenyl, or p-(thiomorpholino-lower alkyl)phenyl, such as p-thiomorpholinomethyl-phenyl, or also phenyl.

Unsubstituted or substituted amino $R^z$ carries at the nitrogen atom 1 or 2 substituents selected independently of one another from unsubstituted or substituted lower alkyl wherein the substituents of lower alkyl are preferably selected from hydroxy, lower alkoxy, lower alkanoyloxy, phenyl-lower alkanoyloxy, such as benzoyloxy or phenylacetyloxy, halogen, such as fluorine, chlorine, bromine or iodine, especially fluorine or chlorine, carboxy, lower alkoxycarbonyl, phenyl-lower alkoxycarbonyl, such as benzyloxycarbonyl, cyano, oxo and phenyl or naphthyl each of which is unsubstituted or mono- or poly-substituted, preferably mono-substituted, for example by lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkyloxycarbonyl, phenyl-lower alkoxycarbonyl, halo-lower alkyl, such as trifluoromethyl, cyano and/or by nitro, especially phenyl substituted in the p-position by one of the mentioned radicals; especially selected from unsubstituted lower alkyl, such as methyl or ethyl; and aryl that preferably has from 6 to 14 carbon atoms and is unsubstituted or mono- or poly-substituted, preferably mono-substituted, for example by lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkyloxycarbonyl, phenyl-lower alkoxycarbonyl, halo-lower alkyl, such a trifluoromethyl, cyano and/or by nitro, the nitrogen atom of the resulting N-substituted carbamoyl group T carrying not more than one aryl radical; amino $R^z$ being especially amino, mono- or di-lower alkylamino, such as N-methyl-, N-ethyl-, N,N-dimethyl- or N,N-diethyl-amino, or phenyl-lower alkylamino wherein phenyl is unsubstituted or substituted by lower alkyl, for example methyl, halo-lower alkyl, such as chloro- or bromomethyl or trifluoromethyl, halogen, for example fluorine or chlorine, hydroxy, lower alkoxy, such as methoxy, carboxy and/or by cyano, preferably by up to three of those substituents selected independently of one another, especially by one of those substituents, for example in the p-position, such as in N-benzyl-, N-(4-fluorobenzyl)-, N-(4-chlorobenzyl)-, N-(4-trifluoromethylbenzyl)- or N-(4-cyanobenzyl)-amino; special preference is given to amino substituted at the nitrogen atom by only one radical, for example N-lower alkylamino, such as N-methyl- or N-ethyl-amino, or phenyl-lower alkylamino wherein phenyl is unsubstituted or substituted by lower alkyl, such as methyl, halo-lower alkyl, such as chloro- or bromo-methyl or trifluoromethyl, halogen, such as fluorine or chlorine, hydroxy, lower alkoxy, such as methoxy, carboxy and/or by cyano, preferably by up to three of those substituents selected independently of one another, especially by one of those substituents, for example in the p-position, such as in N-benzyl-, N-(4-fluorobenzyl)-, N-(4-chlorobenzyl)-, N-(4-trifluoromethylbenzyl)- or N-(4-cyanobenzyl)-amino. The definitions falling under the definition of unsubstituted or substituted amino $R^z$ and the radical aminocarbonyloxy $R_5$ may preferably be omitted from any of the definitions of compounds of formula I' mentioned hereinabove and hereinbelow.

Especially preferred for $R^z$ are the mentioned definitions with the exception of alkyl having more than 2 carbon atoms, lower alkenyl and lower alkynyl; and also with the exception of aryl.

In all definitions preference is given especially to those radicals $R^z$ that contain in the 2-position or also in a higher position, such as the 3- or 4-position, a hetero atom selected from nitrogen, oxygen and sulfur, especially nitrogen (especially valuable properties, for example especially easy removal of T, are obtained in that case).

T is especially pyrrolidin-2-ylcarbonyl or -3-ylcarbonyl, such as (R)- or (S)-pyrrolidin-2-ylcarbonyl ((D)- or (L)-prolyl), furan-3- or especially furan-2-ylcarbonyl, pyridyl-4-, pyridyl-3- or especially pyridyl-2-ylcarbonyl, isoquinolin-1- or especially isoquinolin-3-ylcarbonyl, pyrazin-2-ylcarbonyl, lower alkoxy-lower alkylcarbonyl, such as methoxyacetyl, n-butoxyacetyl or 3-methoxypropionyl, phenyl- or naphthyl-lower alkoxy-lower alkylcarbonyl, such as benzyloxyacetyl, α-lower alkoxy-α-phenyl-lower alkylcarbonyl, such as (R)- or (S)-α-methoxy-α-phenylacetyl, lower alkoxy-lower alkoxy-lower alkylcarbonyl, such as 2-(methoxyethoxy)acetyl, lower alkoxy-lower alkoxy-lower alkoxy-lower alkylcarbonyl, such as 2-(2-(methoxyethoxy)ethoxy)acetyl, o-, m- or p-chlorophenyloxy-lower alkoxy-lower alkylcarbonyl, N,N-di-lower alkylamino-lower alkoxy-lower alkylcarbonyl, such as 2-(N,N-dimethylamino) ethyloxy-acetyl or -3-propionyl, 2-, 3- or 4-pyridyl-lower alkyloxy-lower alkylcarbonyl, such as pyridin-2-ylmethoxyacetyl, phenyloxy-lower alkylcarbonyl, such as phenoxyacetyl, lower alkylthio-lower alkyl-carbonyl, such as methylthioacetyl, phenyl-lower alkylthio-lower alkylcarbonyl, such as benzylthioacetyl, N,N-di-lower alkylamino-lower alkylcarbonyl, such as N,N-dimethylamino-acetyl, -3-propionyl or -4-butyryl, N-lower alkylamino-lower alkylcarbonyl, such as N-methylamino-acetyl or -3-propionyl, N-imidazol(-2-, -4- or -5-)ylmethyl-N-lower alkylamino-lower alkylcarbonyl, such as N-(imidazol-4-ylmethyl)-N-methylaminoacetyl, N-pyridin(-2-, -3- or -4-)ylmethyl-N-lower alkylamino-lower alkylcarbonyl, such as N-pyridin-2-ylmethyl-N-methylaminoacetyl, N-phenyl-lower alkoxycarbonyl-N-lower alkylamino-lower alkylcarbonyl, such as N-benzyloxycarbonyl-N-methylaminoacetyl, imidazol(-1-, -2-, -4- or -5-)yl-lower alkylcarbonyl, such as 3-(imidazol-4-yl)propionyl, N-triphenyl-lower alkylimidazol(-4- or -5-)yl-lower alkylcarbonyl, such as 3-(N-triphenylmethylimidazol-4-yl) propionyl, or pyrazol(-1-, -3-, -4- or -5-)yl-lower alkylcarbonyl, such as pyrazol-1-ylacetyl, or also halo-lower alkylbenzoyl, such as p-chloromethylbenzoyl, p-(morpholino- or thiomorpholinomethyl)benzoyl or benzoyl, and (additionally or especially) lower alkanoyloxy-lower alkylcarbonyl, such as acetyloxyacetyl, lower alkoxy-carbonyl-lower alkoxy-lower alkylcarbonyl, such as methoxycarbonylmethoxy-acetyl, lower alkoxycarbonyl-lower alkylthio-lower alkylcarbonyl, such as methoxycarbonyl-methylthio-acetyl, lower alkoxycarbonyl-lower alkylsulfo-lower alkylcarbonyl, such as methoxycarbonylmethylsulfo-acetyl, lower alkanoyloxy-lower alkoxycarbonyl-lower alkoxy-lower alkylcarbonyl, such as pivaloyloxymethoxycarbonyl-methoxyacetyl or acetyloxymethoxycarbonylmethoxy-acetyl, carboxy-lower alkoxy-lower alkylcarbonyl, such as carboxymethoxyacetyl, N-phenyl-lower alkoxycarbonylamino-lower alkylcarbonyl, such as 3-benzyloxycarbonylamino-propionyl, amino-lower alkylcarbonyl, such as 3-aminopropionyl, di-lower alkylamino-lower alkoxy-lower alkoxy-lower alkylcarbonyl, such as [2-(2-dimethylaminoethoxy)-ethoxy] -acetyl, N-phenyl-lower alkoxycarbonylamino-lower alkoxy-lower alkoxy-lower alkylcarbonyl, such as 2-(2-N-benzyloxycarbonylaminoethoxy)ethoxy-acetyl, amino-lower alkoxy-lower alkoxy-lower alkylcarbonyl, such as 2-(2-aminoethoxy)ethoxy-acetyl, or tetrahydrofuranyloxy-lower alkylcarbonyl, such as 2-(4-tetrahydrofuranyloxy)-acetyl or 2(R)-, 2(S)- or also 2(R,S)-(4-tetrahydrofuranyloxy)-propionyl.

The definitions of the residues $R_1$, $B_1$, $R_2$, $R_3$, $A_1$, $A_2$ and $NR_4R_5$ corresponds to that given above for the compounds of formula I. In addition to the definitions of these residues as given above or preferably as an alternative, the following definitions apply to these substituents:

Lower alkoxycarbonyl $R_1$ can especially be ethoxycarbonyl.

In Heterocyclyloxycarbonyl $R_1$ heterocylyl can especially be T-pyranyl or furanyl or a benzo-fused, cyclopenta-, cyclohexa- or cyclohepta-fused derivative of those radicals, which may also be fully or partially saturated, the heterocyclyl radicals being bonded via a ring carbon atom to the oxygen of the associated oxycarbonyl radical; heterocyclyloxycarbonyl is then preferably tetrahydropyranyloxycarbonyl, such as 4-tetrahydropyranyloxycarbonyl, or tetrahydrofuranyloxycarbonyl, such as 3(R)-, 3(S)- or also 3(R,S)-tetrahydrofuranyloxycarbonyl.

A bivalent residue $B_1$ of an α-amino acid bonded N-terminally to $R_1$ and C-terminally to the amino group at the carbon atom carrying $R_2$-$CH_2$— is especially p-lower alkoxyphenylalanine wherein lower alkoxy may be unbranched or branched, such as p-methoxy-phenylalanine (H-(p-$CH_3$O-Phe)-OH), or also 4-isobutyloxyphenylalanine (H-(4-isobutyloxy-Phe)-OH) or (especially) 4-(n-butyloxy) -phenylalanine (H-(4-n-butyloxy-Phe)-OH), or also p-phenyl-lower alkoxy-phenylalanine, such as p-benzyloxyphenylalanine (H-(p-BzlOPhe)-OH). From the hydrophobic amino acids defined under formula I, p-benzyloxyphenylalanine is preferred, or in addition 4-isobutyloxyphenylalanine or 4-(n-butyloxy)-phenylalanine.

Lower alkoxy as substituent in phenyl or cyclohexyl $R_2$ or $R_3$ may be branched or linear; additional or alternative residues to those given under formula I are isobutyloxy or n-butyloxy. An additional or alternative substituent of phenyl or cyclohexyl $R_2$ or $R_3$ is also phenyl-lower alkoxy, especially benzyloxy, or 2- or 3-fluoro or 2-or 3-cyano as substituent of phenyl.

In addition or as alternative to the residues $R_2$ that are defined as even even more strongly preferred under formula I, $R_2$ is 4-benzyloxyphenyl.

In addition or as alternative to the most especially preferred combinations of $R_2$ and $R_3$ under formula I, the following combinations are important: $R_2$ phenyl and $R_3$ p-trifluoromethylphenyl; $R_2$ cyclohexyl and $R_3$ p-methoxyphenyl; $R_2$ cyclohexyl and $R_3$ p-trifluoromethylphenyl; $R_2$ phenyl and $R_3$ p-benzyloxyphenyl; R: p-methoxyphenyl and $R_3$ p-benzyloxyphenyl; $R_2$ p-benzyloxyphenyl and $R_3$ phenyl; $R_2$ p-benzyloxyphenyl and $R_3$ p-benzyloxyphenyl; $R_2$ phenyl and $R_3$ o-fluorophenyl; $R_2$ phenyl and $R_3$ m-fluorophenyl; $R_2$ phenyl and $R_3$ p-methoxyphenyl; $R_2$ p-methoxyphenyl and $R_3$ p-hydroxyphenyl; $R_2$ p-methoxyphenyl and $R_3$ phenyl; $R_2$ phenyl and $R_3$ o-methoxyphenyl; $R_2$ phenyl and $R_3$ m-methoxyphenyl; $R_2$ p-methoxyphenyl and $R_3$ p-methoxyphenyl; $R_2$ p-methoxyphenyl and $R_3$ m-methoxyphenyl; $R_2$ p-methoxyphenyl and $R_3$ o-methoxyphenyl; $R_2$ phenyl and $R_3$ m-cyanophenyl; $R_2$ phenyl and $R_3$ o-cyanophenyl; and (additionally or especially) $R_2$=phenyl and $R_3$=2,4-difluorophenyl; $R_2$=phenyl and $R_3$=4-isobutyloxyphenyl; $R_2$=cyclohexyl and $R_3$=4-benzyloxyphenyl; $R_2$=cyclohexyl and $R_3$=4-hydroxyphenyl; $R_2$=phenyl and $R_3$=3,4-dimethoxyphenyl; $R_2$=phenyl and $R_3$=3,4,5-trimethoxyphenyl; or $R_2$=phenyl and $R_3$=2,3,4-trimethoxyphenyl.

Strong preference is given to the compounds of formula I' wherein one of the radicals $R_2$ and $R_3$ is p-methoxyphenyl and the other has one of the meanings mentioned, especially p-methoxyphenyl, p-fluorophenyl, phenyl or p-trifluoromethylphenyl.

In the definition of the bivalent radical of an α-amino acid $A_1$, in addition or as alternative to the aliphatic hydrophobic α-amino acids, mentioned under $B_1$ in formula I, leucine or phenylglycine are especially preferred.

In the definition of the bivalent radical of an α-amino acid $A_2$, in addition or as alternative to the hydrophobic α-amino acids defined under $B_1$ in formula I, alanine, leucine, isoleucine or p-benzyloxyphenylalanine are preferred, especially alanine, leucine or p-benzyloxyphenylalanine; and furthermore 4-isobutyloxyphenylalanine or (especially) 4-n-butyloxyphenylalanine.

In addition or as alternative to a bivalent residue of a dipeptide under formula I, formed by $A_1$ and $A_2$, the central peptide bond of which has been reduced and which is bonded N-terminally to the group —C=O and C-terminally to the group $NR_4R_5$, the C-terminal amino acid is selected from p-benzyloxyphenylalanine; and furthermore 4-isobutyloxyphenylalanine or (especially) 4-n-butyloxyphenylalanine.

In addition or alternatively to the bivalent residue of a dipeptide formed especially preferably under formula I, Val-(p-BzlOPhe); Val-Ile; Val-Ala; Val-Leu; and (in addition or especially) phenylglycyl-(p-$CH_3$O-Phe), Val-(4-isobutyloxy-Phe) or Val-(4-n-butyloxy-Phe).

Thiomorpholino or morpholino formed by $R_4$ and $R_5$ together with the bonding nitrogen, atom is preferably substituted at one or two nitrogen atoms, most especially by methyl.

For compounds of formula I as well as formula II, the following additional general definitions apply:

Salts of compounds of formula I or I' are especially acid addition salts, salts with bases or, when several salt-forming groups are present, optionally also mixed salts or internal salts.

Salts are especially the pharmaceutically acceptable, non-toxic salts of compounds of formula I or I' (salts that are non-toxic when applied in the correct dose).

Such salts are formed, for example, from compounds of formula I or I' having an acidic group, for example a carboxy or sulfo group, and are, for example, their salts with suitable bases, such as non-toxic metal salts derived from metals of groups Ia, Ib, IIa and IIb of the Periodic Table of Elements, especially suitable alkali metal salts, for example lithium, sodium or potassium salts, or alkaline earth metals salts, for example magnesium or calcium salts, furthermore zinc salts or ammonium salts, also those salts that are formed with organic amines, such as unsubstituted or hydroxy-substituted mono-, di- or tri-alkylamines, especially mono-, di- or tri-lower alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris (hydroxymethyl)methylamine, N,N-di-lower alkyl-N-(hydroxy-lower alkyl)-amines, such as N,N-dimethyl-N-(2-hydroxyethyl)-amine or tris-(2-hydroxyethyl)-amine, or N-methyl-D-glucamine, or quaternary ammonium salts, such as tetrabutylammonium salts. The compounds of formula I having a basic group, for example an amino group, can form acid addition salts, for example with inorganic acids, for example a hydrohalic acid, such as hydrochloric acid, sulfuric acid or phosphoric acid, or with organic carboxylic, sulfonic, sulfo or phospho acids or N-substituted sulfamic acids, such as, for example, acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, also with amino acids, such as, for example, the above-mentioned α-amino acids, and also with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (with formation of the cyclamates) or with other acidic organic compounds, such as ascorbic acid. Compounds of formula I having acidic and basic groups can also form internal salts.

For the purpose of isolation or purification, it is also possible to use pharmaceutically unacceptable salts.

The terms "compounds" and "salts" also expressly include individual compounds or individual salts.

The compounds of formula I of the present invention exhibit inhibitory effects on retroviral asparate proteases, especially gag-protease-inhibiting effects. In the tests described hereinafter, in concentrations of from $10^{-6}$ to $10^{-9}$ M, they especially inhibit the action of the gag-protease of HIV-1 and are accordingly suitable agents against diseases caused by that protease or by related retroviruses, such as against AIDS.

The ability of the compounds of formula I to inhibit the proteolytic activity of, for example, HIV-1 protease can be demonstrated, for example, according to the method described by J. Hansen et al., The EMBO Journal 7, 1785–1791 (1988). In that method, the inhibition of the action of HIV-1 protease on a substrate that is a fusion protein, expressed in E. coli, of the gag-precursor protein and MS-2 is measured. The substrate and its cleavage products are separated by polyacrylamide gel electrophoresis and rendered visible by immunoblotting with monoclonal antibodies against MS-2.

In a test that is even more simple to use and enables accurate quantitative predictions to be made, a synthetic peptide corresponding to one of the cleavage sites of the gag-precursor protein is used as the substrate for the gag-protease. That substrate and its cleavage products can be measured by high pressure liquid chromatography (HPLC).

For example (according to the method described by A. D. Richards et al., J. Biol. Chem. 265(14), 7733–7736 (1990)), a synthetic chromophoric peptide (for example HKARVL [NO₂]FEANleS (Bachere, Switzerland; see also M. W. Pennington et at., Peptides 1990, ed.: E. Girault and D. Andrew (1991), ESCOM Sci. Publ. B. V., p. 787–789)) or an eicosapeptide such as RRSNQVSQNYPIVQNIQGRR (prepared by peptide synthesis according to known processes: J. Schneider et al., Cell 54, 363–368 (1988)) corresponding to one of the cleavage sites of the gag-precursor protein is used as the substrate for a recombinant HIV-1 protease (preparation according to Billich, S., et al., J. Biol. Chem. 263(34), 17905–17908 (1990)). That substrate and its cleavage products can be measured by high pressure liquid chromatography (HPLC).

For that purpose, an inhibiting compound of formula I to be tested is dissolved in dimethyl sulfoxide; the enzyme test is carried out by adding suitable dilutions of the inhibiting compound in 20 mM β-morpholinoethanesulfonic acid (MES)-buffer pH 6.0 to the assay mix which comprises 67.2 M of the above-mentioned chromophoric peptide in 0.3 M sodium acetate, 0.1 M NaCl pH 7.4; or 122 µM of the above-mentioned eicosapeptide in 20 mM MES-buffer pH 6.0. The size of the batches is 100 gl. The reaction is started by the addition of, in the first case, 2 gl and, in the second case, 10 µl of HIV-1 protease and is stopped in the first case after 15 minutes by the addition of 100 µl of 0.3 M HClO₄, and, in the second case, after one hour's incubation at 37° C. by the addition of 10 µl of 0.3 M HClO₄. The reaction products, after separating the sample by centrifugation for 5 minutes at 10 000×g in 100 µl (batch with chromophoric peptide) and 20 µl (eicosapeptide batch) of the resulting supernatant and after application to a 125×4.6 mm Nucleosil® C₁₈-5µ-HPLC column (Macherey & Nagel, Düren) and elution, are quantified on the basis of the peak height of the cleavage product at 280 nm (batch with chromophoric peptide) or at 215 nm (batch with eicosapeptide), gradient: 100% el.1–>50% el.1/50% el.2 (el:1: 10% acetonitrile, 90% H₂O, 0.1% trifluoroacetic acid (TFA); el.2:75% acetonitrile, 25% H₂O, 0.08% TFA) over a period of 15 minutes; rate of flow 1 ml/min (el.=eluant).

Preferably, $IC_{50}$ values ($IC_{50}$=the concentration that reduces the activity of the HIV-1 protease by 50% compared with a control without an inhibiting compound) of approximately from $50 \times 10^{-6}$ to $10^{-9}$ M, especially from $10^{-7}$ to $10^{-8}$ M, are determined for compounds of formula I in that test. Preferred are ranges from $10^{-7}$ to $10^{-9}$ M.

In another test, it can be shown that the compounds of the present invention protect cells that are normally infected by HIV from such infection or at least retard such infection. In that test, the human T-cell leukaemia cell-line MT-2 (Science 229, 563 (1985)), which is sensitive to the cytopathogenic effect of HIV, is incubated with HIV-1 alone or with HIV-1 in the presence of a compound of formula I according to the invention and, after a few days, the viability of the cells so treated is assessed.

For that purpose, the MT-2 cells in RPMI 1640-medium (Gibco, Switzerland; RPMI 1640 contains an amino acid mixture without L-Gln) that has been supplemented with 10% heat-inactivated foetal calf's serum, L-glutarnine, Hepes (2-[4-(2-hydroxyethyl)-1-piperazino]-ethanesulfonic acid) and standard antibiotics, are maintained at 37° C. in humidified air containing 5% CO₂. 50 gl of the test compound in culture medium and 100 µl of HIV-1 in culture medium (800 TCID50/ml) (TCID50=Tissue Culture Infectious Dose 50=dose that infects 50% of the MT-2 cells) are added to 4×10³ exponentially growing MT-2 cells in 50 µl of culture medium per well on 96-well microtitre plates. Parallel batches on another microtitre plate with cells and test compound receive 100 µl of culture medium without virus. After 4 days' incubation, reverse transcriptase (RT) activity is determined in 10 µl of cell supernatant. The RT activity is determined in 50 mM tris (α,α,α-tris (hydroxymethyl)methylamine, Ultra pur, Merck, Federal Republic of Germany) pH 7.8; 75 mM KCl, 2 mM dithiothreitol, 5 mM MgCl₂; 0.05% Nonidet P-40 (detergent; Sigma, Switzerland); 50 µg/ml of polyadenylic acid (Pharmacia, Sweden); 1.6 µg/ml of dT(12–18) (Sigma, Switzerland). The mixture is filtered off through a 0.45 g Acrodisc® filter (Cellman Science Inc, Ann Arbor) and stored at –20° C. There are added to aliquots of that solution 0.1% (v/v) [alpha-³²P]dTrP to obtain a final radioactive activity of 10 µCi/ml. 10 µl of the culture supernatant are transferred onto a fresh 96-well microtitre plate and 30 µl of the mentioned RT cocktail are added thereto. After mixing, the plate is incubated for from 1.5 to 3 hours at 37° C. 5 µl of the reaction mixture are transferred onto Whatman DE81 -paper (Whatman). The dried filters are washed 3 times for 5 minutes each time with 300 mM NAG1/25 mM tri-sodium citrate and once with 95% ethanol and air-dried again. Evaluation is carded out in a Matrix Packard 96-well counter (Packard). The ED90 values are calculated and defined as the lowest concentration of the test compound that reduces the RT activity by 90% in comparison with cell batches that have not been treated with the test compound. The RT activity is a measure of HIV-1 multiplication.

In that test, the compounds according to the invention exhibit an ED90 of approximately from $10^{-5}$ to $10^{-8}$ M, preferably from $10^{-6}$ to $10^{-8}$ M, more preferably from approximately $10^{-7}$ to $10^{-8}$ M.

The compounds of formula I of the present invention exhibit advantageous pharmacokinetic properties which would lead to the assumption that they would exhibit the mentioned inhibiting effects in vivo. For example, in the case of the preferred representatives of the mentioned compounds of formula I, the blood level is 4 µg/ml blood and higher 10 minutes after the intravenous or intraperitoneal administration to mice of 20 mg/kg of a compound of formula I; for example, the blood level of a preferred compound 1 h after the intravenous or intraperitoneal administration to mice of 20 mg/kg of a compound of formula I is approximately the same or higher than the ED90 in the cellular assay.

Furthermore, upon the peroral (p.o.) administration of 120 mg/kg of a compound of formula I, the concentration after 90 minutes can be approximately the same as or higher than the above-mentioned ED90 in the cell test. Preferably, about the tenfold concentration with respect to the ED90 in the cellular assay can be found. For example, with Boc-Phe[C] (p-CH₃O)Phe-(L)-Val-(L)-Phe-morpholin-4-ylamide (see Examples) after 30 minutes a concentration of 10.75 µM can be obtained, the compound having an ED90 of 0.1 µM.

The determination of the blood level after administration of a compound of formula I is carried out, for example, as follows: The compounds to be investigated are dissolved in an organic solvent, such as dimethyl sulfoxide (DMSO). A solution of hydroxypropyl-β-cyclodextrin (20% w/v) in water is added until the desired concentration of the active ingredient is reached (for example 2 mg/ml in the case of parenteral administration, 12 mg/ml in the case of oral administration) while at the same time the concentration of DMSO is adjusted to 5% (v/v). Compounds that are insoluble under those conditions are, in the case of parenteral use, administered only intraperitoneally, while soluble compounds can also be administered intravenously. After administering the compounds (for example 20 mg/kg intravenously or intraperitoneally, or 120 mg/kg perorally)

blood is taken at various times, for example after 10 minutes in the case of parenteral administration, or after 90 minutes in the case of peroral administration. Each time, the blood of three mice is used and, either in the case of each mouse individually or from the combined blood of the three mice, the supernatant is obtained after the addition of a solvent, for example acetonitrile, and subsequent centrifugation. The concentration of the active ingredient is determined by HPLC, for example on a Nucleosil® 5C$_{18}$ column 120 mm in length and 4.6 mm in diameter, with either 60% acetonitrile/40% water/0.05% trifluoroacetic acid (v/v) or 50% acetonitrile/50% water/0.05% trifluoroacetic acid (v/v) as eluant at a flow rate of 1 ml/min and detection and quantification at 200 nm.

Also the compounds of formula I' have valuable pharmacological properties. In particular, they are active against retroviral diseases, especially against AIDS which is caused by HIV, especially HIV-I or HIV-2. For example, they act as metabolic precursors of compounds of formula I described above which contain a hydrogen atom in place of the radical T in compounds of formula I', while the remaining definitions are as defined for compounds of formula I'; and which have anti-retroviral activity and are especially suitable in the treatment of AIDS as inhibitors of the asparate proteases of HIV-1 and/or HIV-2 (and possibly other retroviruses that produce AIDS-analogous symptoms). The compounds of formula I' can therefore be used therapeutically against retroviral diseases, especially AIDS.

The compounds of formula I are released from the compounds of formula I' in the body of the animal to be treated, especially a warm-blooded animal, including a human being.

Using the compounds of formula I' it is possible, for example, especially in the case of enteral, preferably oral, administration of the compounds, to obtain advantageous pharmacokinetics different to those obtained on administration of the compounds of formula I themselves.

The pharmacodynamic properties of the compounds of formula I' can be demonstrated, for example, as follows:

The compounds of formula I' to be investigated or (for example as control) the corresponding compounds of formula I are dissolved in an organic solvent, such as dimethyl sulfoxide (DMSO), in a concentration of 240 mg/ml. The resulting solutions are diluted with 20% (w/v) hydroxypropyl-β-cyclodextrin (HPβCD) in order to obtain a concentration of test compound of 12 mg/ml. That solution is administered to mice orally by artificial special feeding in a dose of 120 mg/kg. 30, 60, 90 and 120 minutes after administration the animals are sacrificed and blood is removed. Three or four animals are investigated per time point. The blood is heparinised and prepared for analysis using one of the following two methods: in accordance with the first method whole blood is deproteinised by mixing one part by volume of blood with one part by volume of acetonitrile; after centrifugation (10 000 g, 5 minutes) the supernatant is analysed by reversed-phase HPLC. In accordance with the second method 2 µl of a 1 mM solution of an internal standard (such as a different compound of formula I) are added to 0.5 ml of heparinised blood. The blood is centrifuged (10 000 g, 5 minutes) and the plasma is mixed with the same volume of acetonitrile. The precipitated protein is removed by centrifugation (10 000 g, 5 minutes) and the supernatant is concentrated by evaporation in vacuo. The residue is taken up in 0.1 ml of phthalate buffer (0.05 M, pH 3) and 20 µl of 3 M NaCl. The mixture is extracted with 1 ml and then again with 0.2 ml of diisopropyl ether (=DIPE; Merck, Darmstadt). The DIPE fractions are combined and concentrated by evaporation in vacuo. The residue is dissolved in 50% water (Baker) and 50% acetonitrile (v/v) prior to analysis by reversed-phase HPLC.

The analysis by reversed-phase HPLC is carded out using a 125×4.6 mm Nucleosil® C$_{18}$-column (reversed-phase material supplied by Macherey-Nagel, Düren, Federal Republic of Germany, based on silica gel derivatised with hydrocarbon radicals having 18 carbon atoms) equilibrated with a mobile phase of acetonitrile in water/0.1% trifluoroacetic acid. Depending upon the compound, the proportion of acetonitrile is advantageously, for example, from 35 to 60% by volume. The flow rate is 1 ml/minute. Detection is effected at 215 nm. Standards for the compounds in blood are worked up analogously to the blood samples and used to establish standard curves on the basis of which the in vivo concentrations are determined.

For the compounds of formula I' or of formula I, the concentration of the component of formula I in the blood of mice 60 minutes after oral administration is preferably up to $10^{-4}$ M, preferably from $5 \times 10^{-8}$ M to $5 \times 10^{-5}$ M.

In addition to the pharmacological utility given above, the compounds of formula I mentioned above can be used for the treatment of retroviral infections in cell cultures; this can be especially important when cell cultures with human or animal cell lines or cell lines derived therefrom are used for the large scale production of vaccines, antibodies and other bioactive compounds, such as peptides or proteins. For example, infection by HIV-1 and HIV-2 can be controlled, as exemplified above for MT-2 cells.

Compounds of formula I as well as of formula I' can be used as commercially available standards, for example to compare different animal models that can, for example, be used for the screening of aspartate protease inhibitors on bioavailability in different animal species and/or to compare different compounds, such as aspartate protease inhibitors, with respect to their bioavailability.

In the case of the groups of compounds of formula I mentioned hereinafter, it is possible, where appropriate, for example in order to replace more general definitions by more specific definitions, to use definitions of radicals from the above-mentioned general definitions or to add or omit definitions from the other groups.

A preferred variant of the invention relates to the compounds of formula I wherein $R_1$ is hydrogen, lower alkoxycarbonyl, heterocyclylcarbonyl, benzyloxycarbonyl that is unsubstituted or substituted by up to three radicals which may be the same or different and are selected from fluorine, halo-lower alkyl, lower alkanoyl, sulfo, lower alkylsulfonyl and cyano, or is heterocyclyloxycarbonyl wherein heterocyclyl is bonded by way of a carbon atom, or is one of the mentioned carbonyl radicals wherein the bonding carbonyl group has been replaced by a thiocarbonyl group, $B_1$ is a bond or a bivalent radical of an α-amino acid, which radical is bonded N-terminally to $R_1$ and C-terminally to the amino group at the $R_2$-CH$_2$-carrying carbon atom, each of $R_2$ and $R_3$, independently of the other, is phenyl or cyclohexyl, those radicals being unsubstituted or substituted by from one to three radicals which may be the same or different and are selected from hydroxy, methoxy, halogen, halo-lower alkyl, sulfo, lower alkylsulfonyl, cyano and nitro, $A_1$ is a bond between —C═O and $A_2$ or is a bivalent radical of an α-amino acid, which radical is bonded N-terminally to the group —C═O and C-terminally to $A_2$, $A_2$ is a bivalent radical of an α-amino acid, which radical is bonded N-terminally to $A_1$ and C-terminally to the group NR$_4$R$_5$, or $A_1$ and $A_2$ together form a bivalent radical of a dipeptide, of which the central amide bond is reduced and which is bonded N-terminally to the group —C═O and C-terminally to the group NR$_4$R$_5$, and R$_4$ and R$_5$, together with the bonding nitrogen atom, are unsubstituted or substituted thiomorpholino or morpholino; and, alternatively or additionally thereto, the compounds of formula I wherein R$_1$ is heterocyclylsulfonyl, lower alkylsulfonyl or N-(heterocyclyl-lower alkyl)-N-lower alkylaminocarbonyl, and the other radicals are as defined; and salts of those compounds, if salt-forming groups are present; the hydroxy group in compounds of formula I, at the carbon atom that is vicinal to the carbon atom carrying the radical R$_2$-CH$_2$—, being free or in protected form, especially protected in the form of a physiologically cleavable ester, for example in the form of lower alkanoyloxy, such as acetoxy, both the free compounds of formula I and the protected form in which all the other radicals are as defined, or the salts thereof, being especially preferred. Special mention should be made here of the compounds wherein each of A$_1$ and A$_2$ is a bivalent radical of an α-amino acid and the remaining radicals are as defined, or the salts thereof.

Also preferred are compounds of formula I wherein R$_1$ is hydrogen, lower alkoxycarbonyl, heterocyclylcarbonyl, benzyloxycarbonyl that is unsubstituted or substituted by up to three radicals which may be the same or different and are selected from fluorine, halo-lower alkyl, lower alkanoyl, sulfo, lower alkylsulfonyl and cyano, or is heterocyclyloxycarbonyl wherein heterocyclyl is bonded by way of a carbon atom, or is one of the mentioned carbonyl radicals wherein the bonding carbonyl group has been replaced by a thiocarbonyl group, B$_1$ is a bond or a bivalent radical of an α-amino acid, which radical is bonded N-terminally to R$_1$ and C-terminally to the amino group at the R$_2$-CH$_2$-carrying carbon atom, each of R$_2$ and R$_3$, independently of the other, is phenyl or cyclohexyl, those radicals being unsubstituted or substituted by from one to three radicals which may be the same or different and are selected from halogen, halo-lower alkyl, sulfo, lower alkylsulfonyl, cyano and nitro, A$_1$ forms a bond between —C═O and A$_2$ or is a bivalent radical of an α-amino acid, which radical is bonded N-terminally to the group —C═O and C-terminally to A$_2$, A$_2$ is a bivalent radical of an α-amino acid, which radical is bonded N-terminally to A$_1$ and C-terminally to the group NR$_4$R$_5$, or A$_1$ and A$_2$ together form a bivalent radical of a dipeptide, of which the central amide bond is reduced and which is bonded N-terminally to the group —C═O and C-terminally to the group NR$_4$R$_5$, and R$_4$ and R$_5$, together with the bonding nitrogen atom, are unsubstituted or substituted morpholino; and, alternatively or additionally thereto, the compounds of formula I wherein R$_1$ is heterocyclylsulfonyl, lower alkylsulfonyl or N-(heterocyclyl-lower alkyl)-N-lower alkylaminocarbonyl, and the other radicals are as defined; and salts of those compounds, if salt-forming groups are present; the hydroxy group in compounds of formula I, at the carbon atom that is vicinal to the carbon atom carrying the radical R$_2$-CH$_2$—, being free or in protected form, especially protected in the form of a physiologically cleavable ester, for example in the form of lower alkanoyloxy, such as acetoxy, both the free compounds of formula I and the protected form in which all the other radicals are as defined, or the salts thereof, being especially preferred.

Also preferred are compounds of formula I wherein at least one of the radicals R$_2$ and R$_3$ is substituted by from one to three radicals selected from hydroxy, methoxy, halogen, halo-lower alkyl, sulfo, lower alkylsulfonyl, cyano and nitro, and the radicals R$_1$, B$_1$, A$_1$, A$_2$ and NR$_4$R$_5$ are as defined in the last two paragraphs, and salts thereof, if salt-forming groups are present.

More strongly preferred are the compounds of formula I wherein R$_1$ is hydrogen, tert-but-oxycarbonyl, isobutoxycarbonyl, pyridine-3-carbonyl, morpholinocarbonyl, 3-benzofuranoyl, 1,2,3,4-tetrahydroisoquinoline-3-carbonyl, benzyloxycarbonyl substituted by up to three radicals which may be the same or different and are selected from fluorine, halo-lower alkyl, lower alkanoyl, sulfo, lower alkylsulfonyl and cyano, or is heterocyclyloxycarbonyl wherein heterocyclyl is bonded by way of a carbon atom and is selected from pyrrolyl, thienyl, imidazolyl, pyrazolyl, oxazolyl, thiazolyl, pyrazinyl, pyrimidinyl, indolyl, quinolyl, isoquinolyl, quinoxalinyl, β-carbolinyl and a completely or partially saturated derivative of those radicals, or wherein the meaning heterocyclyloxycarbonyl R$_1$ is omitted, B$_1$ is a bond or a bivalent radical of an α-amino acid, which radical is bonded N-terminally to R$_1$ and C-terminally to the amino group at the R$_2$-CH$_2$-carrying carbon atom, preferably the radical of a hydrophobic amino acid, for example proline, phenylalanine, p-fluorophenylalanine, phenylglycine, α-naphthylalanine, cyclohexylalanine or cyclohexylglycine, or of an aliphatic α-amino acid selected from glycine, valine, norvaline, alanine, leucine, norleucine and isoleucine, especially valine, preferably each of the mentioned α-amino acids being in the D-, L- or (D,L)-form, preferably the L-form, preferably each of the mentioned amino acids being substituted by one of the radicals mentioned under R$_1$ selected from hydrogen, N-tert-butoxycarbonyl or morpholinocarbonyl, each of R$_2$ and R$_3$, independently of the other, is phenyl or cyclohexyl, those radicals being unsubstituted or substituted by one or two radicals which may be the same or different and are selected from hydroxy, methoxy, fluorine, sulfo, lower alkylsulfonyl, trifluoromethyl and cyano, as indicated above in the general definitions, A$_1$ is a bivalent radical of a hydrophobic α-amino acid, as indicated above under the general definitions, which radical is bonded N-terminally to the group —C═O and C-terminally to A$_2$, A$_2$ is a bivalent radical of a hydrophobic α-amino acid, preferably as defined above under the general definitions, which radical is bonded N-terminally to A$_1$ and C-terminally to the radical NR$_4$R$_5$, the mentioned amino acid radicals being in the (D)- or (L)-form but preferably, with the exception of phenylalanine which is in the (L)- or the (D)-form, in the (L)-form, A$_1$ and A$_2$ especially form a bivalent radical of a dipeptide of the formula Val-Phe, Ile-Phe, Val-Cha, Ile-Cha, Ile-Gly, Val-Val, Val-Gly, Val-(p-F-Phe), Val-Tyr, Val-(p-CH$_3$O-Phe) or Gly-(p-F-Phe), wherein the amino acids are in the (D)- or (L)-form, especially the (L)-form, with the exception of (L)-Val-Phe, in which Phe is in the (L)- or (D)-form; or A$_1$ and A$_2$ together form a bivalent radical of a dipeptide comprising two hydrophobic α-amino acids, preferably the hydrophobic α-amino acids mentioned herein-before under the general definitions, of which the central amide bond is reduced and which is bonded N-terminally to the group —C═O and C-terminally to the group NR$_4$R$_5$, as indicated in the general definitions, for example having the formula Val(red)-Phe, and R$_4$ and R$_5$, together with the bonding nitrogen atom, are thiomorpholino or morpholino, especially morpholino; and, alternatively or additionally thereto, the compounds of formula I wherein R$_1$ is morpholinosulfonyl or N-(2-pyridylmethyl)-N-methylaminocarbonyl and the other radicals are as defined; and the pharmaceutically acceptable salts of those compounds, if salt-forming groups are present; the hydroxy group in compounds of formula I, at the carbon atom that is vicinal to the carbon atom carrying the radical R$_2$-CH$_2$—, being free or being in a form protected by lower alkanoyl, especially in free form; and it also being possible for heterocyclyloxycarbonyl to be omitted from the definition of $R_1$.

More strongly preferred are also the compounds of formula I wherein $R_1$ is hydrogen, tert-butoxycarbonyl, isobutoxycarbonyl, pyridine-3-carbonyl, morpholinocarbonyl, 3-benzofuranoyl, 1,2,3,4-tetrahydroisoquinoline-3-carbonyl, benzyloxycarbonyl that is substituted by up to three radicals which may be the same or different and are selected from fluorine, halo-lower alkyl, lower alkanoyl, sulfo, lower alkylsulfonyl and cyano, or is heterocyclyloxycarbonyl wherein heterocyclyl is bonded by way of a carbon atom and is selected from pyrrolyl, thienyl, imidazolyl, pyrazolyl, oxazolyl, thiazolyl, pyrazinyl, pyrimidinyl, indolyl, quinolyl, isoquinolyl, quinoxalinyl, β-carbolinyl and a completely or partially saturated derivative of those radicals, or wherein the meaning heterocyclyloxycarbonyl for $R_1$ is omitted, $B_1$ is a bond or a bivalent radical of an α-amino acid, which radical is bonded N-terminally to $R_1$ and C-terminally to the amino group at the $R_2$-$CH_2$-carrying carbon atom, preferably the radical of a hydrophobic amino acid, for example proline, phenylalanine, p-fluorophenylalanine, phenylglycine, α-naphthylalanine, cyclohexylalanine, cyclohexylglycine or an aliphatic α-amino acid selected from glycine, valine, norvaline, alanine, leucine, norleucine and isoleucine, especially valine, preferably each of the mentioned α-amino acids being in the D-, L- or (D,L)-form, preferably in the L-form, and preferably each of the mentioned amino acids being substituted by one of the radicals mentioned under $R_1$ selected from hydrogen, N-tert-butoxycarbonyl and morpholinocarbonyl, each of $R_2$ and $R_3$, independently of the other, is phenyl or cyclohexyl, those radicals being unsubstituted or substituted by one or two radicals which may be the same or different and are selected from fluorine, sulfo, lower alkylsulfonyl and cyano, as indicated above in the general definitions, Al is a bivalent radical of a hydrophobic α-amino acid, as indicated above under the general definitions, which radical is bonded N-terminally to the group —C=O and C-terminally to $A_2$, $A_2$ is a bivalent radical of a hydrophobic α-amino acid, preferably as defined above under the general definitions, which radical is bonded N-terminally to $A_1$ and C-terminally to the radical $NR_4R_5$, the mentioned amino acid radicals being in the (D)- or (L)-form, but preferably, with the exception of phenylalanine which is in the (L)- or the (D)-form, in the (L)-form, $A_1$ and $A_2$ especially form a bivalent radical of a dipeptide of the formula Val-Phe, Ile-Phe, Val-Cha, Ile-Cha, Ile-Gly, Val-Val, Val-Gly, Val-(p-F-Phe), Val-(p-$CH_3$O-Phe) or Gly-(p-F-Phe), wherein the amino acids are in the (D)- or (L)-form, especially the (L)-form, with the exception of (L)-Val-Phe, in which Phe is in the (L)- or (D)-form; or $A_1$ and $A_2$ together form a bivalent radical of a dipeptide, preferably comprising two of the hydrophobic α-amino acids mentioned above under the general definitions, of which the central amide bond is reduced and which is bonded N-terminally to the group —C=O and C-terminally to the group $NR_4R_5$, as indicated in the general definitions, for example having the formula Val(red)-Phe, and $R_4$ and $R_5$, together with the bonding nitrogen atom, are thiomorpholino or morpholino, especially morpholino; and, alternatively or additionally thereto, the compounds of formula I wherein $R_1$ is morpholinosulfonyl or N-(2-pyridylmethyl)-N-methylaminocarbonyl; and the pharmaceutically acceptable salts of those compounds, if salt-forming groups are present; the hydroxy group in compounds of formula I, at the carbon atom that is vicinal to the carbon atom carrying the radical $R_2$-$CH_2$—, being free or being in a form protected by lower alkanoyl, especially in free form; and it also being possible for heterocyclyloxycarbonyl to be omitted from the definition of $R_1$.

Very preferred are the compounds of formula I wherein $R_1$ is hydrogen, tert-butoxycarbonyl, isobutoxycarbonyl, pyridine-3-carbonyl, morpholinocarbonyl, 3-benzofuranoyl or 1,2,3,4-tetrahydroisoquinoline-3-carbonyl; or, alternatively or additionally thereto, morpholinosulfonyl or N-(2-pyridylmethyl)-N-methylaminocarbonyl, $B_1$ is a bond or a bivalent radical of the α-amino acid valine, which radical is bonded N-terminally to $R_1$ and C-terminally to the amino group at the $R_2$-$CH_2$-carrying carbon atom, in the latter case $R_1$ preferably being hydrogen, tert-butoxycarbonyl or morpholinocarbonyl, or, alternatively or additionally thereto, morpholinosulfonyl or N-(2-pyridylmethyl)-N-methylaminocarbonyl, each of $R_2$ and $R_3$, independently of the other, is phenyl or cyclohexyl, those radicals being unsubstituted or substituted by one or two radicals which may be the same or different and are selected from hydroxy, methoxy, fluorine, sulfo, lower alkylsulfonyl, cyano and trifluoromethyl, $A_1$ is a bivalent radical of one of the α-amino acids glycine, valine and isoleucine, which radical is bonded N-terminally to the group —C=O and C-terminally to $A_2$, $A_2$ is a bivalent radical of one of the α-amino acids glycine, valine, phenylalanine, tyrosine, cyclohexylalanine, p-methoxyphenylalanine and p-fluorophenylalanine, which radical is bonded N-terminally to $A_1$ and C-terminally to the group $NR_4R_5$, or also $A_1$ and $A_2$ together form a bivalent radical of a dipeptide having a reduced central peptide bond, which comprises an N-terminal amino acid radical selected from Gly(red), Val (red) and Tle(red) and a C-terminal amino acid radical selected from glycine, phenylalanine, cyclohexylalanine, tyrosine, p-methoxyphenylalanine and p-fluorophenylalanine, and is bonded N-terminally to the group —C=O and C-terminally to the group $NR_4R_5$, as defined above for $A_1$ and $A_2$, and $R_4$ and $R_5$, together with the bonding nitrogen atom, are thiomorpholino or morpholino, especially morpholino, and the pharmaceutically acceptable salts of those compounds, if salt-forming groups are present.

Very preferred are also the compounds of formula I wherein $R_1$ is hydrogen, tert-butoxycarbonyl, isobutoxycarbonyl, pyridine-3-carbonyl, morpholinocarbonyl, 3-benzofuranoyl or 1,2,3,4-tetrahydroisoquinoline-3-carbonyl; or, alternatively or additionally thereto, is morpholinosulfonyl or N-(2-pyridylmethyl)-N-methylaminocarbonyl, $B_1$ is a bond or a bivalent radical of the α-amino acid valine, which radical is bonded N-terminally to $R_1$ and C-terminally to the amino group at the $R_2$-$CH_2$-carrying carbon atom, in the latter case $R_1$ preferably being hydrogen, tert-butoxycarbonyl or morpholinocarbonyl, or, alternatively or additionally thereto, morpholinosulfonyl or N-(2-pyridylmethyl)-N-methyl-aminocarbonyl, each of $R_2$ and $R_3$, independently of the other, is phenyl or cyclohexyl, those radicals being unsubstituted or substituted by one or two radicals which may be the same or different and are selected from fluorine, sulfo, lower alkylsulfonyl and cyano, and alternatively or additionally thereto, from hydroxy, methoxy and trifluoromethyl, $A_1$ is a bivalent radical of one of the α-amino acids glycine, valine and isoleucine, which radical is bonded N-terminally to the group —C=O and C-terminally to $A_2$, $A_2$ is a bivalent radical of one of the α-amino acids glycine, valine, phenylalanine, tyrosine, cyclohexylalanine, p-methoxyphenylalanine and p-fluorophenylalanine, which radical is bonded N-terminally to $A_1$ and C-terminally to the group $NR_4R_5$, or also $A_1$ and $A_2$ together form a bivalent radical of a dipeptide having a reduced central peptide bond, which comprises an N-terminal amino acid radical selected from Gly(red), Val (red) and Ile(red), and a C-terminal amino acid radical selected from glycine, phenylalanine, tyrosine, cyclohexylalanine, p-methoxyphenylalanine and p-fluorophenylalanine, and is bonded N-terminally to the group C=O and C-terminally to the group $NR_4R_5$, as defined above for $A_1$ and $A_2$, and $R_4$ and $R_5$, together with the bonding nitrogen atom, are thiomorpholino or morpholino, especially morpholino, and the pharmaceutically acceptable salts of those compounds, if salt-forming groups are present.

Even more preferred are the compounds of formula I according to the definitions given hereinbefore wherein $B_1$ is one of the mentioned bivalent radicals of an α-amino acid and one of the radicals $A_1$ and $A_2$ is a bond and the other is one of the mentioned α-amino acids, or compounds of formula I wherein $B_1$ is a bond and each of $A_1$ and $A_2$ is one of the mentioned bivalent radicals of an α-amino acid or they are together one of the mentioned bivalent radicals of a dipeptide having a reduced central amide bond, the other radicals being as defined.

Also even more preferred are the compounds of formula I according to the definitions given hereinbefore wherein $B_1$ is a bond or one of the mentioned bivalent radicals of an α-amino acid and each of $A_1$ and $A_2$ is the bivalent radical of one of the mentioned amino acids, the other radicals being as defined, or the pharmaceutically acceptable salts of those compounds, if at least one salt-forming group is present.

Of especial interest are the compounds of formula I wherein $R_1$ is hydrogen, tert-butoxycarbonyl, isobutoxycarbonyl, pyridine-3-carbonyl, morpholinocarbonyl, 3-benzofuranoyl or 1,2,3,4-tetrahydroisoquinoline-3-carbonyl, or, alternatively or additionally thereto, morpholinosulfonyl or N-(2-pyridylmethyl)-N-methylaminocarbonyl, $B_1$ is a bond or a bivalent radical of the α-amino acid valine, which radical is bonded N-terminally to $R_1$ and C-terminally to the amino group at the $R_2$-$CH_2$-carrying carbon atom, $R_1$ in the latter case preferably being hydrogen, tert-butoxycarbonyl or morpholinocarbonyl or, alternatively or additionally thereto, morpholinosulfonyl or N-(2-pyridylmethyl)-N-methylaminocarbonyl, each of $R_2$ and $R_3$, independently of the other, is phenyl or cyclohexyl, those radicals being unsubstituted or substituted by one or two radicals which may be the same or different and are selected from hydroxy, methoxy, fluorine and cyano, especially by one of the mentioned radicals, preferably in the 4-position, for example in 4-hydroxyphenyl, 4-methoxyphenyl, 4-fluorophenyl, 4-cyanophenyl or 4-fluorocyclohexyl, as in the combinations of $R_2$ and $R_3$ that are mentioned under the general definitions above as being especially preferred, or, alternatively or additionally thereto, each of $R_2$ and $R_3$, independently of the other, is phenyl or cyclohexyl that is unsubstituted or substituted by one or two radicals which may be the same or different and are selected from trifluoromethyl, cyano and fluorine, especially by one of those radicals, preferably in the 4-position, for example in 4-trifluoromethylphenyl, 4-cyanophenyl or 4-fluorophenyl, $A_1$ and $A_2$ together form a bivalent radical of a dipeptide of the formula Val-Phe, Ile-Phe, Val-Cha, Ile-Cha, Ile-Gly, Val-Val, Val-Gly, Val-(p-F-Phe), Val-Tyr, Val-(p-$CH_3$O-Phe) or Gly-(p-F-Phe) or of a derivative thereof having a reduced central amide bond of the formula Val(red)-Phe, which is bonded N-terminally to the group —C=O and C-terminally to the group $NR_4R_5$, and $R_4$ and $R_5$, together with the bonding nitrogen atom, are thiomorpholino or morpholino, especially morpholino, and the pharmaceutically acceptable salts of those compounds, if salt-forming groups are present, the hydroxy group in compounds of formula I, at the carbon atom that is vicinal to the carbon atom carrying the radical $R_2$-$CH_2$—, being free or being in a form protected by acetyl, both the free compounds of formula I and the protected form, in which all the other radicals are as defined, or the salts thereof, being especially preferred.

Also of especial interest are the compounds of formula I wherein $R_1$ is hydrogen, tert-butoxycarbonyl, isobutoxycarbonyl, pyridine-3-carbonyl, morpholinocarbonyl, 3-benzofuranoyl or 1,2,3,4-tetrahydroisoquinoline-3-carbonyl, or, alternatively or additionally thereto, morpholinosulfonyl or N-(2-pyridylmethyl)-N-methylaminocarbonyl, $B_1$ is a bond or a bivalent radical of the α-amino acid valine, which radical is bonded N-terminally to $R_1$ and C-terminally to the amino group at the $R_2$-$CH_2$-carrying carbon atom, $R_1$ in the latter case preferably being hydrogen, tert-butoxycarbonyl or morpholinocarbonyl or, alternatively or additionally thereto, morpholinosulfonyl or N-(2-pyridylmethyl)-N-methylaminocarbonyl, each of $R_2$ and $R_3$, independently of the other, is phenyl or cyclo-hexyl, those radicals being unsubstituted or substituted by one or two radicals which may be the same or different and are selected from fluorine and cyano, especially by one of the mentioned radicals, preferably in the 4-position, for example in 4-fluorophenyl, 4-cyanophenyl or 4-fluorocyclohexyl, as in the combinations of $R_2$ and $R_3$ that are mentioned under the general definitions above as being especially preferred, or alternatively or additionally thereto, each of $R_2$ and $R_3$, independently of the other, is phenyl or cyclohexyl that is unsubstituted or substituted by one or two radicals which may be the same or different and are selected from trifluoromethyl, cyano and fluorine, especially by one of those radicals, preferably in the 4-position, for example in 4-trifluoromethylphenyl, 4-cyanophenyl or 4-fluorophenyl, $A_1$ and $A_2$ together form a bivalent radical of a dipeptide of the formula Val-Phe, Ile-Phe, Val-Cha, Ile-Cha, Ile-Gly, Val-Val, Val-Gly, Val-(p-F-Phe), Val-(p-$CH_3$O-Phe) or Gly-(p-F-Phe) or of a derivative thereof having a reduced central amide bond of the formula Val(red)-Phe, which is bonded N-terminally to the group —C=O and C-terminally to the group $NR_4R_5$, and $R_4$ and $R_5$, together with the bonding nitrogen atom, are thiomorpholino or morpholino, especially morpholino, and the pharmaceutically acceptable salts of those compounds, if salt-forming groups are present, the hydroxy group in compounds of formula I, at the carbon atom that is vicinal to the carbon atom carrying the radical $R_2$-$CH_2$—, being free or being in a form protected by acetyl, both the free compounds of formula I and the protected form wherein all the other radicals are as defined, or the salts thereof, being especially preferred.

Of most especial interest are the compounds mentioned in the Examples and the salts of those compounds, especially the pharmaceutically acceptable salts, if salt-forming groups are present.

These include the compounds of formula I having the names

Boc-Cha[C](p-F)Phe-(L)-Ile-(L)-Phe-morpholin-4-ylamide,

Boc-(p-F) Phe[C](p-F)Phe-(L)-Val-(L)-Phe-morpholin-4-ylamide,

Boc-(p-F)Phe[C](p-F)Phe-(L)-Val-(L)-(p-F-Phe)-morpholin-4-ylamide,

Boc-(p-F)Phe[C](p-F)Phe-(L)-Val-(L)-(p-CH₃O-Phe)-morpholin-4-ylamide,
Boc-(p-F)Phe[C](p-F)Phe-(L)-Val-(L)-Cha-morpholin-4-ylamide,
Boc-(p-F)Phe[C](p-F)Phe-(L)-Ile-(L)-Phe-morpholin-4-ylamide,
Boc-(p-F)Phe[C](p-CN)Phe-(L)-Val-(L)-Phe-morpholin-4-ylamide,
Boc-(p-F)Phe[C](p-CN)Phe-(L)-Val-(L)-(p-F-Phe)-morpholin-4-ylamide,
Boc-(p-F)Phe[C](p-CN)Phe-(L)-Val-(L)-(p-CH₃O-Phe)-morpholin-4-ylamide,
Boc-(p-F)Phe[C](p-CN)Phe-(L)-Val-(L)-Cha-morpholin-4-ylamide,
Boc-(p-F)Phe[C](p-CN)Phe-(L)-Ile-(L)-Phe-morpholin-4-ylamide,
Boc-Phe[C](p-F)Phe-(L)-Val-(L)-Phe-morpholin-4-ylamide,
Boc-Phe[C](p-F)Phe-(L)-Val-(L)-(p-F-Phe)-morpholin-4-ylamide,
Boc-Phe[C](p-F)Phe-(L)-Val-(L)-(p-CH₃O-Phe)-morpholin-4-ylamide,
Boc-Phe[C](p-F)Phe-(L)-Val-(L)-Cha-morpholin-4-ylamide,
Boc-Phe[C](p-F) Phe-(L)-Ile-(L)-Phe-morpholin-4-ylamide,
Boc-Phe[C](p-CN)Phe-(L)-Val-(L)-Phe-morpholin-4-ylamide,
Boc-Phe[C](p-CN)Phe-(L)-Val-(L)-(p-F-Phe)-morpholin-4-ylamide,
Boc-Phe[C](p-CN)Phe-(L)-Val-(L)-(p-CH₃O-Phe)-morpholin-4-ylamide,
Boc-Phe[C](p-CN)Phe-(L)-Val-(L)-Cha-morpholin-4-ylamide,
Boc-Phe[C](p-CN)Phe-(L)-Ile-(L)-Phe-morpholin-4-ylamide,
Boc-Phe[C](p-CH₃O)Phe-(L)-Val-(L)-Phe-morpholin-4-ylamide,
Boc-Phe[C](p-CH₃O)Phe-(L)-Val-(L)-(p-F-Phe)-morpholin-4-ylamide,
Boc-Phe[C](p-CH₃O)Phe-(L)-Val-(L)-(p-CH₃O-Phe)-morpholin-4-ylamide,
Boc-Phe[C](p-CH₃O)Phe-(L)-Val-(L)-Cha-morpholin-4-ylamide,
Boc-Phe[C](p-CH₃O)Phe-(L)-Ile-(L)-Phe-morpholin-4-ylamide,
Boc-Phe[C](p-CF₃)P-(L)-Val-(L)-Phe-morpholin-4-ylamide,
Boc-Phe[C](p-CF₃)P-(L)-Val-(L)-(p-F-Phe)-morpholin-4-ylamide,
Boc-Phe[C](p-CF₃)P-(L)-Val-(L)-(p-CH₃O-Phe)-morpholin-4-ylamide,
Boc-Phe[C](p-CF₃)P-(L)-Val-(L)-Cha-morpholin-4-ylamide,
Boc-Phe[C](p-CF₃)P-(L)-Ile-(L)-Phe-morpholin-4-ylamide,
Boc-Cha[C](p-CN)Phe-(L)-Val-(L)-Phe-morpholin-4-ylamide,
Boc-Cha[C](p-CN)Phe-(L)-Val-(L)-(p-F-Phe)-morpholin-4-ylamide,
Boc-Cha[C](p-CN)Phe-(L)-Val-(L)-(p-CH₃O-Phe)-morpholin-4-ylamide,
Boc-Cha[C](p-CN)Phe-(L)-Val-(L)-Cha-morpholin-4-ylamide,
Boc-Cha[C](p-CN)Phe-(L)-Ile-(L)-Phe-morpholin-4-ylamide,
Boc-Cha[C](p-CH₃O)Phe-(L)-Val-(L)-Phe-morpholin-4-ylamide,
Boc-Cha[C](p-CH₃O)Phe-(L)-Val-(L)-(p-F-Phe)-morpholin-4-ylamide,
Boc-Cha[C](p-CH₃O)Phe-(L)-Val-(L)-(p-CH₃O-Phe)-morpholin-4-ylamide,
Boc-Cha[C](p-CH₃O)Phe-(L)-Val-(L)-Cha-morpholin-4-ylamide,
Boc-Cha[C](p-CH₃O)Phe-(L)-Ile-(L)-Phe-morpholin-4-ylamide,
Boc-Cha[C](p-CF₃)P-(L)-Val-(L)-Phe-morpholin-4-ylamide,
Boc-Cha[C](p-CF₃)P-(L)-Val-(L)-(p-F-Phe)-morpholin-4-ylamide,
Boc-Cha[C](p-CF₃)P-(L)-Val-(L)-(p-CH₃O-Phe)-morpholin-4-ylamide,
Boc-Cha[C](p-CF₃)P-(L)-Val-(L)-Cha-morpholin-4-ylamide, or
Boc-Cha[C](p-CF₃)P-(L)-Ile-(L)-Phe-morpholin-4-ylamide, or the corresponding compounds wherein -morpholin-4-ylamide is replaced by the radical -thiomorpholin-4-yl-amide.

These also include the compounds of formula I according to claim 1 having the names
Boc-(L)-Val-Phe[C]Phe-(L)-Val-(L)-Phe-morpholin-4-ylamide;
H-(L)-Val-Phe[C]Phe-(L)-Val-(L)-Phe-morpholin-4-ylamide;
Boc-Phe[C]Phe-(L)-Val-(D)-Phe-morpholin-4-ylamide;
Boc-Phe[C]Phe-(L)-Val(red)-(L)-Phe-morpholin-4-ylamide;
or isobutoxycarbonyl-Phe[C]Phe-(L)-Val-(L)-Phe-morpholin-4-ylamide; or the corresponding compounds wherein -morpholin-4-ylamide is replaced by the radical-thiomorpholin-4-ylamide; or salts thereof, if salt-forming groups are present; or the compounds of formula I according to claim 1 having the names
Boc-Cha[C](p-CN)Phe-(L)-Val-(L)-Phe-thiomorpholin-4-ylamide; or Boc-Cha[C](p-F)Phe-(L)-Val-(L)-Phe-thiomorpholin-4-ylamide; or the compounds of formula I having the names
Boc-Cha[C](p-F)Phe-(L)-Ile-(L)-Phe-morpholin-4-ylamide,
Boc-Cha[C](p-F)Phe-(L)-Val-(L)-Cha-morpholin-4-ylamide,
Boc-(p-CF₃)[C]Phe-(L)-Val-(L)-Phe-morpholin-4-ylamide,
Boc-(p-CF₃)[C]Phe-(L)-Val-(L)-(p-F)Phe-morpholin-4-ylamide,
Boc-(p-CF₃)[C]Phe-(L)-Val-(L)-(p-CH₃O)Phe-morpholin-4-ylamide,
Boc-(p-CF₃)[C]Phe-(L)-Val-(L)-Cha-morpholin-4-ylamide,
Boc-(p-CF₃)[C]Phe-(L)-Ile-(L)-Phe-morpholin-4-ylamide,
Boc-(p-CF₃)[C](p-F)Phe-(L)-Val-(L)-Phe-morpholin-4-ylamide,
Boc-(p-CF₃)[C](p-F)Phe-(L)-Val-(L)-(p-F)Phe-morpholin-4-ylamide,
Boc-(p-CF₃)[C](p-F)Phe-(L)-Val-(L)-Cha-morpholin-4-ylamide,
Boc-(p-CF₃)[C](p-F)Phe-(L)-Val-(L)-(p-CH₃O)Phe-morpholin-4-ylamide,
Boc-(p-CF₃)[C](p-F)Phe-(L)-Ile-(L)-Phe-morpholin-4-ylamide,
Boc-(p-CF₃)[C](p-CF₃)P-(L)-Val-(L)-Phe-morpholin-4-ylamide,
Boc-(p-CF₃)[C](p-CF₃)P-(L)-Val-(L)-(p-F)Phe-morpholin-4-ylamide, Boc-(p-CF$_3$)[C](p-CF$_3$)P-(L)-Ile-(L)-Phe-morpholin-4-ylamide, Boc-(p-CF$_3$)[C](p-CF$_3$)P-(L)-Val-(L)-(p-CH$_3$O)Phe-morpholin-4-ylamide, or Boc-(p-CF$_3$)[C](p-CF$_3$)P-(L)-Val-(L)-Cha-morpholin-4-ylamide; or the corresponding compounds wherein -morpholin-4-ylamide is replaced by the radical -thiomorpholin-4-ylamide, or the compounds of formula I having the names Boc-Phe[C]Phe-(L)-Val-(L)-Tyr-morpholin-4-ylamide;
Boc-Tyr[C]Phe-(L)-Val-(L)-Phe-morpholin-4-ylamide;
Boc-Tyr[C]Phe-(L)-Val-(L)-Tyr-morpholin-4-ylamide;
Boc-Phe[C]Tyr-(L)-Val-(L)-Phe-morpholin-4-ylamide;
Boc-Phe[C]Tyr-(L)-Val-(L)-Tyr-morpholin-4-ylamide;
Boc-Tyr[C]Tyr-(L)-Val-(L)-Phe-morpholin-4-ylamide;
Boc-Tyr[C]Tyr-(L)-Val-(L)-Tyr-morpholin-4-ylamide, or the corresponding compounds wherein -morpholin-4-ylamide is replaced by the radical -thiomorpholin-4-ylamide.

Of very special importance is the compound of formula I wherein $R_1$ is tert-butoxycarbonyl, $B_1$ is a bond, $R_2$ is cyclohexyl, $R_3$ is p-fluorophenyl, $A_1$ is valine, $A_2$ is phenylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ and $R_3$ are phenyl, $A_1$ is valine, $A_2$ is phenylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ is cyclohexyl, $R_3$ is p-fluorophenyl, $A_1$ is valine, $A_2$ is p-fluorophenylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ is cyclohexyl, $R_3$ is p-fluorophenyl, $A_1$ is valine, $A_2$ is p-methoxyphenylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ is cyclohexyl, $R_3$ is p-fluorophenyl, $A_1$ is valine, $A_2$ is cyclohexylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ is cyclohexyl, $R_3$ is p-fluorophenyl, $A_1$ is valine, $A_2$ is phenylalanine, and $R_4$ and $R_5$, together with the bonding nitrogen atom, are thiomorpholino.

Also of very special importance is the compound of formula I wherein $R_1$ is tert-butoxycarbonyl, $B_1$ is a bond, $R_2$ is cyclohexyl, $R_3$ is p-fluorophenyl, $A_1$ is isoleucine, $A_2$ is phenylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ is phenyl, $R_3$ is p-fluorophenyl, $A_1$ is valine, $A_2$ is phenylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ is p-fluorophenyl, $R_3$ is p-fluorophenyl, $A_1$ is valine, $A_2$ is phenylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ is p-fluorophenyl, $R_3$ is p-fluorophenyl, $A_1$ is valine, $A_2$ is p-fluorophenylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ is cyclohexyl, $R_3$ is p-cyanophenyl, $A_1$ is valine, $A_2$ is phenylalanine, and $R_4$ and $R_5$, together with the bonding nitrogen atom, are morpholino.

Also of very special importance is the compound of formula I wherein $R_1$ is tert-butoxycarbonyl, $B_1$ is a bond, $R_2$ and $R_3$ are phenyl, $A_1$ is valine, $A_2$ is phenylalanine, and $R_4$ and $R_5$, together with the bonding nitrogen atom, are thiomorpholino.

Preferred are in addition compounds of formula I wherein $R_1$ is hydrogen, lower alkoxycarbonyl, heterocyclylcarbonyl, benzyloxycarbonyl that is unsubstituted or substituted by up to three radicals selected independently of one another from fluorine, halo-lower alkyl, lower alkanoyl, sulfo, lower alkylsulfonyl and cyano, heterocyclyloxycarbonyl wherein heterocyclyl is bonded via a carbon atom, one of the mentioned carbonyl radicals wherein the bonding carbonyl group has been replaced by a thiocarbonyl group, heterocyclylsulfonyl, lower alkylsulfonyl or N-(heterocyclyl-lower alkyl)-N-lower alkylaminocarbonyl, as defined for compounds of formula I', especially tert-butoxycarbonyl;

$R_2$ is phenyl, cyclohexyl, lower alkoxyphenyl, especially o-, m- or p-methoxyphenyl, benzyloxyphenyl, especially p-benzyloxyphenyl, p-fluorophenyl, p-trifluoromethylphenyl or p-hydroxyphenyl, $R_3$ is phenyl, lower alkoxyphenyl, especially o-, m- or p-methoxyphenyl, p-trifluoromethylphenyl, o-, m- or p-cyanophenyl, benzyloxyphenyl, especially p-benzyloxyphenyl, o-, m- or p-fluorophenyl or hydroxyphenyl, $A_1$ is the bivalent residue of the amino acid (L)-valine, (L)-isoleucine or glycine bonded N-terminally to the group —C=O and C-terminally to $A_2$, $A_2$ is the bivalent residue of the amino acid glycine, alanine, valine, leucine, isoleucine, phenylalanine, tyrosine, cyclohexylalanine, p-lower alkoxyphenylalanine, such as p-methoxyphenylalanine, p-benzyloxyphenylalanine or p-fluorophenylalanine bonded N-terminally to $A_1$ and C-terminally to the group $NR_4R_5$, and $R_4$ and $R_5$ together with the bonding nitrogen atom form unsubstituted or substituted thiomorpholino or morpholino, especially morpholino, with the proviso that at least either one of the radicals $R_2$ and $R_3$ is benzyloxyphenyl or $A_2$ is the bivalent residue of p-benzyloxyphenylalanine, while the remaining radicals are as defined, when either $R_3$ is other than o- or m-fluorophenyl, o- or m-cyanophenyl or o- or m-methoxyphenyl, or when $A_2$ is other than alanine or leucine;

or salts of those compounds where salt-forming groups are present.

Of those compounds preference is given to the compounds of formula I wherein $R_1$ is tert-butoxycarbonyl, $R_2$ is phenyl, p-benzyloxyphenyl or o-, m- or p-methoxyphenyl, $R_3$ is phenyl, p-benzyloxyphenyl, o-, m- or p-methoxyphenyl, o-, m- or p-fluorophenyl or hydroxyphenyl, $A_1$ is the bivalent residue of the amino acid (L)-valine, (L)-isoleucine or glycine, especially of (L)-valine, bonded N-terminally to the group —C=O and C-terminally to $A_2$, $A_2$ is the bivalent residue of the amino acid glycine, alanine, valine, leucine, isoleucine, phenylalanine, tyrosine, cyclohexylalanine, p-lower alkoxyphenylalanine, such as p-methoxy-phenylalanine, p-benzyloxyphenylalanine or p-fluorophenylalanine, especially of phenylalanine, tyrosine, p-methoxy-phenylalanine, p-benzyloxyphenylalanine or p-fluorophenylalanine, bonded N-terminally to $A_1$ and C-terminally to the group $NR_4R_5$, and $R_4$ and $R_5$ together with the bonding nitrogen atom form morpholino, with the proviso that at least either one of the radicals $R_2$ and $R_3$ is benzyloxyphenyl or $A_2$ is the bivalent residue of p-benzyloxyphenylalanine, while the remaining radicals are as defined.

Special preference is given also to the compounds of formula I wherein $R_1$ is tert-butoxycarbonyl, $R_2$ is phenyl, $R_3$ is o- or m-fluorophenyl, o- or m-cyanophenyl or o- or m-lower alkoxyphenyl, such as o- or m-methoxyphenyl, $A_1$ is the bivalent residue of the amino acid (L)-valine, (L)-isoleucine or glycine, especially of (L)-valine, bonded N-terminally to the group —C=O and C-terminally to $A_2$, $A_2$ is the bivalent residue of the amino acid glycine, alanine, valine, leucine, isoleucine, phenylalanine, tyrosine, cyclohexylalanine, p-lower alkoxyphenylalanine, such as p-methoxy-phenylalanine, p-benzyloxyphenylalanine or p-fluorophenylalanine, especially of phenylalanine, tyrosine, p-lower alkoxyphenylalanine, such as p-methoxy-phenylalanine, p-benzyloxyphenylalanine or p-fluorophenylalanine, bonded N-terminally to $A_1$ and C-terminally to the group $NR_4R_5$, and $R_4$ and $R_5$ together with the bonding nitrogen atom form morpholino.

Special preference is given to a compound of formula I having the name:

Boc-Phe[C](o-CH)Phe-(L)-Val-(L)-Phe-morpholin-4-ylamide,

Boc-Phe[C](m-CN)Phe-(L)-Val-(L)-Phe-morpholin-4-ylamide,

Boc-Phe[C](p-BzlO)Phe-(L)-Val-(L)-Phe-morpholin-4-ylamide,

Boc-Phe [C](p-BzlO)Phe-(L)-Val-(L)-(p-BzlOPhe)-morpholin-4-yl amide,

Boc-(p-BzlO)Phe[C]Phe-(L)-Val-(L)-Phe-morpholin-4-ylamide,

Boc-(p-BzlO)Phe[C]Phe-(L)-Val-(L)-(p-BzlOPhe)-morpholin-4-ylamide,

Boc-(p-BzlO)Phe[C](p-BzlO)Phe-(L)-Val-(L)-Phe-morpholin-4-ylamide,

Boc-(p-BzlO)Phe[C](p-BzlO)Phe-(L)-Val-(L)-(p-BzlOPhe)-morpholin-4-ylamide,

Boc-Phe[C](o-F)Phe-(L)-Val-(L)-Phe-morpholin-4-ylamide,

Boc-Phe[C](o-F)Phe-(L)-Val-(L)-(p-CH$_3$O-Phe)-morpholin-4-ylamide,

Boc-Phe[C](m-F)Phe-(L)-Val-(L)-Phe-morpholin-4-ylamide,

Boc-Phe[C](m-F)Phe-(L)-Val-(L)-(p-CH$_3$O-Phe)-morpholin-4-ylamide,

Boc-Phe[C]Phe-(L)-Val-(L)-Leu-morpholin-4-ylamide,

Boc-Phe[C]Phe-(L)-Val-(L)-Ala-morpholin-4-ylamide,

Boc-(p-CH$_3$O)Phe[C](p-BzlO)Phe-(L)-Val-(L)-Phe-morpholin-4-ylamide,

Boc-(p-CH$_3$O)Phe[C](p-BzlO)Phe-(L)-Val-(L)-(p-CH$_3$O-Phe)-morpholin-4-ylamide, Boc-(p-CH$_3$O)Phe[C](p-BzlO)Phe-(L)-Val-(L)-Tyr-morpholin-4-ylamide, Boc-(p-CH$_3$O)Phe[C](3-CH$_3$O)Phe-(L)-Val-CL)-Phe-morpholin-4-ylamide, Boc-(p-CH$_3$O) Phe[C](2-CH$_3$O)Phe-(L)-Val-(L)-Phe-morpholin-4-ylamide, Boc-Phe[C](3-CH$_3$O)Phe-(L)-V al-(L) -Phe-morpholin-4-ylamide, Boc-Phe[C](2-CH$_3$O)Phe-(L)-Val-(L)-Phe-morpholin-4-ylamide, Boc-Phe[C](3-CH$_3$O)Phe-(L)-Val-(L)-(p-CH$_3$O-Phe)-morpholin-4-ylamide, Boc-Phe[C](2-CH$_3$O)phe-(L)-Val-(L)-(p-CH$_3$O-Phe)-morpholin-4-ylamide or Boc-Phe [C](p-BzlO)Phe-(L)-Val-(L)-(p-CH$_3$O-Phe)-morpholin-4-ylamide or alternatively a compound having the name:

Boc-(p-CH$_3$O)phe[C]phe-(L)-Val-(L)-Phe-morpholin-4-ylamide (very especially preferred), Boc-(p-CH$_3$O)Phe[C](p-CH$_3$O)Phe-(L)-Val-(L)-Phe-morpholin-4-ylamide (very especially preferred), Boc-(p-CH$_3$O)Phe[C]Tyr-(L)-Val-(L)-Phe-morpholin-4-ylamide, Boc-(p-CH$_3$O)Phe [C]Phe-(L)-Val-(L)-(p-CH$_3$O-Phe)-morpholin-4-ylamide, Boc-(p-CH$_3$O)Phe[C]Phe-(L)-Val-(L)-Tyr-morpholin-4-ylamide, Boc-(p-CH$_3$O)Phe[C](p-CH$_3$O)Phe-(L)-Val-(L)-(p-CH$_3$O-Phe)-morpholin-4-ylamide, Boc-(p-CH$_3$O)Phe[C](p-CH$_3$O)Phe-(L)-Val-(L)-Tyr-morpholin-4-ylamide, Boc-(p-CH$_3$O)Phe[C]Tyr-(L)-Val-(L)-(p-CH$_3$O-Phe)-morpholin-4-ylamide or Boc-(p-CH$_3$O)Phe[C]Tyr-(L)-Val-(L)-Tyr-morpholin-4-ylamide.

Finally, the compound of formula I having the name:

Boc-Phe [C](p-CH$_3$O) Phe- (L) -Val-(L) -Phe-morpholin-4-ylamide (=5(S)-(tert-butoxycarbonylamino)-4(S)-hydroxy-2(R)-(p-methoxy-phenylmethyl)-6-phenyl-hexanoyl-(L)-valyl-(L)-phenyl-alanyl-morpholin-4-ylamide) is very especially preferred.

In the definitions of compounds of formula I' mentioned hereinbelow, it is advantageously possible, for example in order to replace more general definitions by more specific definitions, to use definitions of radicals from the above-mentioned general definitions or also to omit individual definitions.

Preference is given to compounds of formula I' wherein T is an acyl radical of the above-mentioned formula Z wherein $R^z$ is heterocyclyl bonded via a ring carbon atom and selected from pyrrolyl, 2,5-dihydropyrrolyl, indolyl, indolizinyl, isoindolyl, pyrrolidinyl, such as pyrrolidin-3-yl or especially pyrrolidin-2-yl (in the (R,S)- or preferably (R)- or (S)-configuration), hydroxypyrrolidinyl, such as 3- or especially 4-hydroxypyrrolidinyl, furyl, such as furan-3-yl or especially furan-2-yl, tetrahydrofuryl, thienyl, cyclohepta[b]pyrrolyl, imidazolyl, such as imidazol-2-yl, imidazol-3-yl or especially imidazol-5-yl, N-triphenyl-lower alkyl-imidazolyl, such as N-triphenylmethyl-imidazolyl, pyrazolyl, especially pyrazol-3-yl, oxazolyl, isoxazolyl, such as isoxazol-3-yl or -5-yl, thiazolyl, isothiazolyl, such as isothiazol-3-yl or -5-yl, triazolyl, such as 1,2,3-triazol-4- or -5-yl or 1,2,4-triazol-5-yl, tetrazolyl, pyridyl, such as pyridin-4-yl or -3-yl or especially pyridin-2-yl, quinolyl, such as quinolin-2-yl, isoquinolyl, especially isoquinolin-1-yl or-3-yl, piperidyl, especially piperidin-2-yl, γ-pyranyl, 4,5-dihydropyranyl, 4H-chromenyl, chromanyl, γ-thiopyranyl, pyridazinyl, cinnolyl, phthalazinyl, quinazolinyl, quinoxalinyl, pyrimidinyl, pyrazinyl, phenazinyl, phenoxazinyl, phenothiazinyl, morpholinyl and thiazinyl, each of which is substituted by up to three radicals selected independently of one another from lower alkyl, phenyl-lower alkyl, diphenyl-lower alkyl, triphenyl-lower alkyl, such as triphenylmethyl, lower alkanoyl, hydroxy, lower alkoxy, phenyl-lower alkoxy, such as benzyloxy, diphenylmethoxy or tri-phenylmethoxy, hydroxy-lower alkyl, such as hydroxymethyl, halogen, such as fluorine, chlorine or bromine, cyano, lower alkoxycarbonyl, such as methoxy- or tert-butoxycarbonyl, phenyl-lower alkoxycarbonyl, such as benzyloxycarbonyl and halo-lower alkyl, such as chloromethyl or trifluoromethyl, or preferably is unsubstituted, and each of which is bonded via a ring carbon atom; very special preference being given to those of the mentioned radicals which contain a ring hetero atom directly adjacent to the bonding ring carbon atom, more especially the radicals furan-2-yl, (S)- or (R)-pyrrolidin-2-yl and imidazol-4-yl, pyridin-2-yl, -3-yl or -4-yl, or isoquinolin-3-yl; or additionally or especially tetrahydropyranyl; or $R^z$ is lower alkyl (especially methyl, ethyl, n-propyl or n-butyl) which is substituted by at least one radical selected from:

lower alkoxy, such as methoxy, ethoxy or n-butoxy; lower alkoxy, such as methoxy, ethoxy or n-butoxy, substituted by one or two substituents, especially aryl, more especially phenyl, naphthyl, lower alkoxy, such as ethoxy or methoxy, lower alkylthio, such as methylthio or ethylthio, lower alkoxy-lower alkoxy, such as 2-methoxyethoxy, lower alkylthio-lower alkoxy, such as 2-methylthioethoxy, aryloxy or arylthio, especially phenyloxy or o-, m- or p-chlorophenyloxy, for example p-chlorophenyloxy, amino, N-lower alkylamino or N,N-di-lower alkylamino, such as 2-amino, 2-(N-lower alkyl)amino or 2-(N,N-di-lower alkyl)amino, for example 2-dimethylamino, and/or heterocyclyl as last defined for heterocyclyl $R^z$ bonded via a ring carbon atom, especially 2-, 3- or 4-pyridyl; aryloxy, especially phenyloxy; lower alkylthio, such as methylthio, ethylthio or n-butylthio; lower alkylthio, such as methylthio, ethylthio or n-butylthio, substituted by one or two substituents, especially aryl, more especially phenyl or naphthyl; arylthio, such as phenylthio; amino or amino substituted by one or two radicals selected from lower alkyl, such as methyl, heterocycly-lower alkyl wherein heterocyclyl is as defined for heterocyclyl $R^z$ bonded via a ring carbon atom, especially heterocyclylmethyl, such as imidazolylmethyl, for example 4-imidazolylmethyl, or pyridylmethyl, for example 2-, 3- or 4-pyridylmethyl, each bonded via a ring carbon atom, aryl-lower alkyl, such as phenyl- or naphthyl-lower alkyl, for example phenyl- or naphthylmethyl, lower alkanoyl, such as acetyl, lower alkoxycarbonyl, such as tert-butoxycarbonyl, and aryl-lower alkoxycarbonyl, such as phenyl-lower alkoxycarbonyl, for example benzyloxycarbonyl, with especially one of the substituents of amino being lower alkyl, especially methyl, and the other being hydrogen or one of the radicals mentioned above as substituents of amino; heterocyclyl as defined above for heterocyclyl $R^z$ bonded via a ring carbon atom, especially as pyridin-2-yl, -3-yl or -4-yl; and heterocyclyl-lower alkyl wherein lower alkyl is preferably methyl, 1- or 2-ethyl or 3-propyl and wherein heterocyclyl is as defined above for heterocyclyl $R^z$ bonded via a ring carbon atom but may also be bonded via a ring nitrogen atom, especially imidazol-1-yl, imidazol-2-yl, imidazol-5-yl or more especially imidazol-4-yl, N-triphenyl-lower alkylimidazolyl, such as N-triphenylmethyl-imidazol-5-yl or especially -4-yl, or pyrazolyl, such as pyrazol-1-yl, -3-yl, -4-yl or -5-yl; and (additionally or preferably) lower alkoxycarbonyl, such as methoxycarbonyl; lower alkanoyloxy-lower alkoxycarbonyl, such as pivaloyloxymethoxycarbonyl or acetyloxymethoxycarbonyl; carboxy; phenyl-lower alkoxycarbonylamino-lower alkoxy, such as 2-(benzyloxycarbonylamino)-ethoxy; amino-lower alkoxy, such as 2-aminoethoxy; di-lower alkylamino-lower alkoxy, such as 2-(dimethylamino)-ethoxy; N,N-di-lower alkylamino-lower alkoxy, such as 2-(dimethylamino)-ethoxy; lower alkoxycarbonyl-lower alkylsulfo, such as methoxycarbonyl-methylsulfo; lower alkanoyloxy, such as acetyloxy; and tetrahydropyranyloxy, such as 4-tetrahydropyranyloxy;

and which may carry as a further substituent aryl, which is as defined below; or $R^z$ is aryl, especially chlorophenyl, chloro-lower alkylphenyl, such as o-, m- or p-chloromethylphenyl, p-morpholinomethyl-phenyl, p-thiomorpholinomethyl-phenyl, or also phenyl;

aryl in the said definitions being especially phenyl, naphthyl, such as 1- or 2-naphthyl, or fluorenyl, such as 9-fluorenyl, that is unsubstituted or substituted by up to three radicals selected independently of one another from lower alkyl, lower alkanoyl, hydroxy, lower alkoxy, phenyl-lower alkoxy, such as benzyloxy, diphenylmethoxy or triphenylmethoxy, hydroxy-lower alkyl, such as hydroxymethyl, halogen, such as fluorine, chlorine or bromine, cyano, lower alkoxycarbonyl, such as methoxy- or tert-butoxy-carbonyl, phenyl-lower alkoxycarbonyl, such as benzyloxycarbonyl, halo-lower alkyl, such as chloromethyl or trifluoromethyl, piperidinomethyl, piperazin-1-ylmethyl, 4-lower alkylpiperazin-1-yl-methyl, such as 4-methyl- or 4-ethyl-piperazin-1-ylmethyl, morpholinomethyl or thiomorpholinomethyl, and nitro, which may be present independently of one another, and being especially correspondingly substituted phenyl;

$R_1$ is hydrogen, tert-butoxycarbonyl, isobutyloxycarbonyl, pyridine-3-carbonyl, morpholinocarbonyl, 3-benzofuranoyl, 1,2,3,4-tetrahydro-isoquinoline-3-carbonyl, benzyloxycarbonyl substituted by up to three radicals selected independently of one another from fluorine, halo-lower alkyl, lower alkanoyl, sulfo, lower alkylsulfonyl and cyano, or heterocyclyloxycarbonyl wherein heterocyclyl is bonded via a carbon atom and is selected from pyrrolyl, thienyl, imidazolyl, pyrazolyl, oxazolyl, thiazolyl, pyrazinyl, pyrimidinyl, indolyl, quinolyl, isoquinolyl, quinoxalinyl, β-carbolinyl, and additionally or especially γ-pyranyl and furanyl; and a fully or partially saturated derivative of those radicals, or wherein the definition heterocyclyloxycarbonyl for $R_1$ is absent, or is additionally or especially ethoxycarbonyl;

$B_1$ is a bond (preferred) or a bivalent residue of an α-amino acid bonded N-terminally to $R_1$ and C-terminally to the amino group at the carbon atom carrying $R_2$-$CH_2$—, preferably the residue of a hydrophobic amino acid, for example proline, phenylalanine, p-fluorophenylalanine, phenylglycine, α-naphthylalanine, cyclohexylalanine, cyclohexylglycine or an aliphatic α-amino acid selected from glycine, alaninc, valine, norvaline, leucine, norleucine and isoleucine, especially valine, each of the mentioned α-amino acids preferably being in the D-, L- or (D,L)-form, especially in the L-form, and each of the mentioned amino acids preferably being substituted by one of the radicals mentioned under $R_1$ selected from hydrogen, N-tert-butoxycarbonyl and morpholinocarbonyl, $R_2$ and $R_3$ are each independently of the other phenyl or cyclohexyl, those radicals being unsubstituted or substituted by from one to three, preferably one or two, radicals selected independently of one another from hydroxy, methoxy, benzyloxy, fluorine, sulfo, lower alkylsulfonyl, trifluoromethyl and cyano, additionally or especially from isobutyloxy and n-butyloxy, as indicated above in the general definitions, $A_1$ is a bivalent residue of a hydrophobic α-amino acid, as indicated above under the general definitions, bonded N-terminally to the group —C=O and C-terminally to $A_2$, $A_2$ is a bivalent residue of a hydrophobic α-amino acid, preferably as defined above under the general definitions, bonded N-terminally to $A_1$ and C-terminally to the radical $NR_4R_5$, the said amino acid residues being in the (D)- or (L)-form, preferably in the (L)-form, with the exception of phenylalanine which is in the (L)- or the (D)-form, especially $A_1$ and $A_2$ form a bivalent residue of a dipeptide of the formula Val-Phe, Ile-Phe, Val-Cha, Ile-Cha, Ile-Gly, Val-Val, Val-Gly, Val-(p-F-Phe), Val-Tyr, Val-(p-CH$_3$O-Phe), Val-(p-BzlOPhe), Val-Ile, Val-Ala, Val-Leu or Gly-(p-F-Phe), or (additionally or especially) phenylglycyl-(p-CH$_3$O-Phe), Val-(4-isobutyloxy-Phe) or Val-(4-n-butyloxy-Phe); wherein the amino acids are in the (D)- or (L)-form, especially in the (L)-form, with the exception of CL)-Val-Phe in which Phe is in the (L)- or (D)-form; or $A_1$ and $A_2$ together form a bivalent residue of a dipeptide consisting of two hydrophobic α-amino acids, preferably two of those mentioned above under the general definitions, the central amide bond of which has been reduced and which is bonded N-terminally to the group —C=O and C-terminally to the group $NR_4R_5$, as indicated in the general definitions, for example having the formula Val(red)-Phe, and $R_4$ and $R_5$ together with the bonding nitrogen atom form thiomorpholino or morpholino, especially morpholino, or additionally or especially 2,6-dimethylmorpholino;

and alternatively or in addition thereto the compounds of formula I wherein $R_1$ is morpholinosulfonyl or N-(2-pyridylmethyl)-N-methyl-aminocarbonyl and the remaining radicals are as defined;

and the pharmaceutically acceptable salts of those compounds where salt-forming groups are present.

Greater preference is given to compounds of formula I' wherein T is pyrrolidin-2-ylcarbonyl or -3-ylcarbonyl, such as (R)- or (S)-pyrrolidin-2-ylcarbonyl ((D)- or CL)-prolyl), furan-3- or especially furan-2-ylcarbonyl, pyridyl-4-, pyridyl-3- or especially pyridyl-2-ylcarbonyl, isoquinolin-1- or especially isoquinolin-3-ylcarbonyl, pyrazin-2-ylcarbonyl, lower alkoxy-lower alkylcarbonyl, such as methoxyacetyl, n-butoxyacetyl or 3-methoxypropionyl, phenyl- or naphthyl-lower alkoxy-lower alkylcarbonyl, such as benzyloxyacetyl, α-lower alkoxy-α-phenyl-lower alkylcarbonyl, such as (R)- or (S)-α-methoxy-α-phenylacetyl, lower alkoxy-lower alkoxy-lower alkylcarbonyl, such as 2-(methoxyethoxy)acetyl, lower alkoxylower alkoxy-lower alkoxy-lower alkylcarbonyl, such as 2-(2-(methoxyethoxy)ethoxy)acetyl, o-, m- or p-chlorophenyloxy-lower alkoxy-lower alkylcarbonyl, N,N-di-lower alkylamino-lower alkoxy-lower alkylcarbonyl, such as 2-(N,N-dimethylamino)ethyloxyacetyl, 2-, 3- or 4-pyfidyl-lower alkyloxy-lower alkylcarbonyl, such as pyridin-2-ylmethoxyacetyl, phenyloxy-lower alkylcarbonyl, such as phenoxyacetyl, lower alkylthio-lower alkylcarbonyl, such as methylthioacetyl, phenyl-lower alkylthio-lower alkylcarbonyl, such as benzylthioacetyl, N,N-di-lower alkylamino-lower alkylcarbonyl, such as N,N-dimethylamino-acetyl, -3-propionyl or -4-butyryl, N-lower alkylamino-lower alkylcarbonyl, such as N-methylaminoacetyl or -3-propionyl, N-imidazol(-2-, -4- or -5-)ylmethyl-N-lower alkylamino-lower alkylcarbonyl, such as N-(imidazol-4-ylmethyl)-N-methylaminoacetyl, N-pyridin (-2-, -3- or -4-) ylmethyl-N-lower alkylamino-lower alkylcarbonyl, such as N-pyridin-2-ylmethyl-N-methylaminoacetyl, N-phenyl-lower alkoxycarbonyl-N-lower alkylamino-lower alkylcarbonyl, such as N-benzyloxycarbonyl-N-methylaminoacetyl, imidazol(-1-, -2-, -4- or -5-)yl-lower alkylcarbonyl, such as 3-(imidazol-4-yl)propionyl, N-triphenyl-lower alkylimidazol (-4- or -5-) yl-lower alkylcarbonyl, such as 3-(N-triphenylmethylimidazol-4-yl)propionyl, or pyrazol(-1-, -3-, -4- or -5-)yl-lower alkylcarbonyl, such as pyrazol-1-ylacetyl, or also halo-lower alkylbenzoyl, such as p-chloromethylbenzoyl, p-(morpholino- or thiomorpholinomethyl)benzoyl or benzoyl, or (especially) lower alkanoyloxy-lower alkylcarbonyl, such as acetyloxyacetyl, lower alkoxycarbonyl-lower alkoxy-lower alkylcarbonyl, such as methoxycarbonylmethoxy-acetyl, lower alkoxycarbonyl-lower alkylthio-lower alkylcarbonyl, such as methoxycarbonylmethylthio-acetyl, lower alkoxycarbonyl-lower alkylsulfo-lower alkylcarbonyl, such as methoxycarbonylmethylsulfoacetyl, lower alkanoyloxy-lower alkoxycarbonyl-lower alkoxy-lower alkylcarbonyl, such as pivaloyloxymethoxycarbonyl-methoxyacetyl or acetyloxymethoxycarbonylmethoxyacetyl, carboxy-lower alkoxy-lower alkylcarbonyl, such as carboxymethoxyacetyl, N-phenyl-lower alkoxycarbonylamino-lower alkylcarbonyl, such as 3-benzyloxycarbonylamino-propionyl, amino-lower alkylcarbonyl, such as 3-aminopropionyl, di-lower alkylamino-lower alkoxy-lower alkoxy-lower alkylcarbonyl, such as [2-(2-dimethylaminoethoxy)-ethoxy] -acetyl, N-phenyl-lower alkoxycarbonyl-amino-lower alkoxy-lower alkoxy-lower alkylcarbonyl, such as 2-(2-N-benzyloxycarbonylaminoethoxy)ethoxyacetyl, amino-lower alkoxy-lower alkoxy-lower alkylcarbonyl, such as 2-(2-aminoethoxy) ethoxy-acetyl, or tetrahydropyranyloxy-lower alkylcarbonyl, such as 2-(4-tetrahydropyranyloxy)-acetyl or 2(R)-, 2(S)- or also 2(R,S)-(4-tetrahydropyranyloxy) propionyl;

$R_1$ is hydrogen, tert-butoxycarbonyl, isobutyloxycarbonyl, pyridine-3-carbonyl, morpholinocarbonyl, 3-benzofuranoyl or 1,2,3,4-tetrahydroisoquinoline-3-carbonyl, or especially ethoxycarbonyl, 4-tetrahydropyranyloxycarbonyl or tetrahydrofuran-2(R or S)-yloxycarbonyl; or alternatively and in addition thereto morpholinosulfonyl, N-(2-pyridylmethyl)-N-methylaminocarbonyl;

$B_1$ is a bond (preferred) or a bivalent residue of the α-amino acid valine bonded N-terminally to $R_1$ and C-terminally to the amino group at the carbon atom carrying $R_2$-CH$_2$—, in the latter case $R_1$ preferably being hydrogen, tert-butoxycarbonyl or morpholinocarbonyl, or alternatively or in addition thereto morpholinosulfonyl or N-(2-pyridylmethyl)-N-methyl-aminocarbonyl, $R_2$ and $R_3$ are each independently of the other phenyl or cyclohexyl, those radicals being unsubstituted or substituted by from one to three, preferably one or two, radicals selected independently of one another from hydroxy, methoxy, benzyloxy, fluorine, sulfo, lower alkylsulfonyl, cyano and trifluoromethyl, and especially from isobutyloxy and n-butyloxy, $A_1$ is a bivalent residue of one of the α-amino acids glycine, valine, isoleucine mid especially leucine and phenylglycine bonded N-terminally to the group —C=O and C-terminally to $A_2$, $A_2$ is a bivalent residue of one of the α-amino acids glycine, alanine, valine, leucine, isoleucine, phenylalanine, tyrosine, cyclohexylalanine, p-methoxy-phenylalanine, p-benzyloxyphenylalanine, p-fluorophenylalanine and especially p-(isobutyloxy)- or p-(n-butyloxy)-phenylalanine bonded N-terminally to $A_1$ and C-terminally to the group $NR_4R_5$, or $A_1$ and $A_2$ together form a bivalent residue of a dipeptide having a reduced central peptide bond that consists of an N-terminal amino acid residue selected from Gly(red), Val (red) and Ile(red) and a C-terminal amino acid residue selected from glycine, phenylalanine, cyclohexylalanine, tyrosine, p-methoxy-phenylalanine and p-fluorophenylalanine, and that is bonded N-terminally to the group —C=O and C-terminally to the group $NR_4R_5$, as defined above for $A_1$ and $A_2$, and $R_4$ and $R_5$ together with the bonding nitrogen atom form thiomorpholino, morpholino or preferably 2,6-dimethylmorpholino, especially morpholino, and the pharmaceutically acceptable salts of those compounds where salt-forming groups are present.

Special preference is given to compounds of formula I' wherein T is pyrrolidin-2-ylcarbonyl or -3-ylcarbonyl, such as (R)- or (S)-pyrrolidin-2-ylcarbonyl ((D)- or (L)-prolyl), furan-3- or especially furan-2-ylcarbonyl, pyfidyl-4-, pyridyl-3- or especially pyridyl-2-ylcarbonyl, isoquinolin-1- or especially isoquinolin-3-ylcarbonyl, pyrazin-2-ylcarbonyl, lower alkoxy-lower alkylcarbonyl, such as methoxyacetyl, n-butoxyacetyl or 3-methoxypropionyl, phenyl- or naphthyl-lower alkoxy-lower alkylcarbonyl, such as benzyloxyacetyl, α-lower alkoxy-a-phenyl-lower alkylcarbonyl, such as (R)- or (S)-α-methoxy-α-phenylacetyl, lower alkoxy-lower alkoxy-lower alkylcarbonyl, such as 2-(methoxyethoxy)acetyl, lower alkoxy-lower alkoxy-lower alkoxy-lower alkylcarbonyl, such as 2-(2-(methoxyethoxy)ethoxy)acetyl, o-, m- or p-chlorophenyloxy-lower alkoxy-lower alkylcarbonyl, N,N-di-lower alkylamino-lower alkoxy-lower alkylcarbonyl, such as 2-(N,N-dimethylamino)ethyloxyacetyl, 2-, 3- or 4-pyridyl-lower alkyloxy-lower alkylcarbonyl, such as pyridin-2-ylmethoxyacetyl, phenyloxy-lower alkylcarbonyl, such as phenoxyacetyl, lower alkylthio-lower alkylcarbonyl, such as methylthioacetyl, phenyl-lower alkylthio-lower alkylcarbonyl, such as benzylthioacetyl, N,N-di-lower alkylamino-lower alkylcarbonyl, such as N,N-dimethylamino-acetyl, -3-propionyl or -4-butyryl, N-lower alkylamino-lower alkylcarbonyl, such as N-methylamino-acetyl or -3-propionyl, N-imidazol(-2-, -4- or -5-)ylmethyl-N-lower alkylamino-lower alkylcarbonyl, such as N-(imidazol-4-ylmethyl)-N-methylaminoacetyl, N-pyridin (-2-, -3- or -4-)ylmethyl-N-lower alkylamino-lower alkylcarbonyl, such as N-pyridin-2-ylmethyl-N-methylaminoacetyl, N-phenyl-lower alkoxycarbonyl-N-lower alkylamino-lower alkylcarbonyl, such as N-benzyloxycarbonyl-N-methylaminoacetyl, imidazol(-1-, -2-, -4- or -5-)yl-lower alkylcarbonyl, such as 3-(imidazol-4-yl)propionyl, N-triphenyl-lower alkylimidazol(-4- or -5-)yl-lower alkylcarbonyl, such as 3-(N-triphenylmethylimidazol-4-yl)propionyl, or pyrazol(-1-, -3-, -4- or -5-)yl-lower alkylcarbonyl, such as pyrazol-1-ylacetyl, or also halo-lower alkylbenzoyl, such as p-chloromethylbenzoyl, p-(morpholino- or thiomorpholino-methyl) benzoyl or benzoyl, $R_1$ is hydrogen, tert-butoxycarbonyl, isobutyloxycarbonyl, pyridine-3-carbonyl, morpholinocarbonyl, 3-benzofuranoyl or 1,2,3,4-tetrahydro-isoquinoline-3-carbonyl; or alternatively and in addition thereto morpholinosulfonyl or N-(2-pyridylmethyl)-N-methylaminocarbonyl, $B_1$ is a bond or a bivalent residue of the α-amino acid valine bonded N-terminally to $R_1$ and C-terminally to the amino group at the carbon atom carrying $R_2$-$CH_2$—, in the latter case $R_1$ preferably being hydrogen, tert-butoxycarbonyl or morpholinocarbonyl, or alternatively or in addition thereto morpholinosulfonyl or N-(2-pyridylmethyl)-N-methylaminocarbonyl, $R_2$ and $R_3$ are each independently of the other phenyl or cyclohexyl, those radicals being unsubstituted or substituted by one or two radicals selected independently of one another from hydroxy, methoxy, benzyloxy, fluorine, sulfo, lower alkylsulfonyl, cyano and tri-fluoromethyl, $A_1$ is a bivalent residue of one of the α-amino acids glycine, valine and isoleucine bonded N-terminally to the group —C=O and C-terminally to $A_2$, $A_2$ is a bivalent residue of one of the α-amino acids glycine, alanine, valine, leucine, isoleucine, phenylalanine, tyrosine, cyclohexylalanine, p-methoxy-phenylalanine, p-benzyloxyphenylalanine and p-fluorophenylalanine bonded N-terminally to $A_1$ and C-terminally to the group $NR_4R_5$, or $A_1$ and $A_2$ together form a bivalent residue of a dipeptide having a reduced central peptide bond that consists of an N-terminal amino acid residue selected from Gly(red), Val (red) and Ile(red) and a C-terminal amino acid residue selected from glycine, phenylalanine, cyclohexylalanine, tyrosine, p-methoxy-phenylalanine and p-fluorophenylalanine, and that is bonded N-terminally to the group —C=O and C-terminally to the group $NR_4R_5$, as defined above for $A_1$ and $A_2$, and $R_4$ and $R_5$ together with the bonding nitrogen atom form thiomorpholino or morpholino, especially morpholino, and the pharmaceutically acceptable salts of those compounds where salt-forming groups are present.

Very special preference is given to a compound of formula I' wherein T is pyrrolidin-2-ylcarbonyl or -3-ylcarbonyl, such as (R)- or (S)-pyrrolidin-2-ylcarbonyl ((D)- or (L)-prolyl), furan-3- or especially furan-2-ylcarbonyl, pyridyl-4-, pyridyl-3- or especially pyridyl-2-ylcarbonyl, isoquinolin-1 - or especially isoquinolin-3-ylcarbonyl, pyrazin-2-ylcarbonyl, lower alkoxy-lower alkylcarbonyl, such as methoxyacetyl, n-butoxy-acetyl or 3-methoxypropionyl, phenyl- or naphthyl-lower alkoxy-lower alkylcarbonyl, such as benzyloxyacetyl, el-lower alkoxy-α-phenyl-lower alkylcarbonyl, such as (R)- or (S)-α-methoxy-α-phenylacetyl, lower alkoxy-lower alkoxy-lower alkylcarbonyl, such as 2-(methoxyethoxy)acetyl, lower alkoxy-lower alkoxy-lower alkoxy-lower alkylcarbonyl, such as 2-(2-(methoxyethoxy)ethoxy)acetyl, o-, m- or p-chlorophenyloxy-lower alkoxy-lower alkylcarbonyl, N,N-di-lower alkylamino-lower alkoxy-lower alkylcarbonyl, such as 2-(N,N-dimethylamino) ethyloxyacetyl, 2-, 3- or 4-pyridyl-lower alkyloxy-lower alkylcarbonyl, such as pyridin-2-ylmethoxyacetyl, phenyloxy-lower alkylcarbonyl, such as phenoxyacetyl, lower alkylthio-lower alkylcarbonyl, such as methylthioacetyl, phenyl-lower alkylthio-lower alkylcarbonyl, such as benzylthioacetyl, N,N-di-lower alkylamino-lower alkylcarbonyl, such as N,N-dimethylamino-acetyl, -3-propionyl or -4-butyryl, N-lower alkylamino-lower alkylcarbonyl, such as N-methylamino-acetyl or -3-propionyl, N-imidazol(-2-, -4- or -5-)ylmethyl-N-lower alkylamino-lower alkylcarbonyl, such as N-(imidazol-4-ylmethyl)-N-methylaminoacetyl, N-pyridin (-2-, -3- or-4-)ylmethyl-N-lower alkylamino-lower alkylcarbonyl, such as N-pyridin-2-ylmethyl-N-methylaminoacetyl, N-phenyl-lower alkoxycarbonyl-N-lower alkylamino-lower alkylcarbonyl, such as N-benzyloxycarbonyl-N-methylaminoacetyl, imidazol(-1-, -2-, -4- or-5-)yl-lower alkylcarbonyl, such as 3-(imidazol-4-yl)propionyl, N-triphenyl-lower alkylimidazol(-4- or -5-)-yl-lower alkylcarbonyl, such as 3-(N-triphenylmethylimidazol-4-yl)propionyl, or pyrazol-(-1-, -3-, -4- or -5-)yl-lower alkylcarbonyl, such as pyrazol-1-ylacetyl, or also halo-lower alkylbenzoyl, such as p-chloromethylbenzoyl, p-(morpholino- or thiomorpholino-methyl)-benzoyl or benzoyl, $R_1$ is tert-butoxycarbonyl, $R_2$ is phenyl, cyclohexyl, p-hydroxyphenyl, o-, m- or p-methoxyphenyl, p-benzyloxyphenyl, o-, m- or p-fluorophenyl, p-trifluoromethylphenyl or o-, m- or p-cyanophenyl, especially phenyl, p-hydroxyphenyl, p-methoxyphenyl, p-benzyloxyphenyl, p-fluorophenyl or p-trifluoromethylphenyl, $R_3$ independently of $R_2$ has one of the definitions given for $R_2$, $A_1$ is a bivalent residue of one of the α-amino acids glycine, (L)-valine and (L)-isoleucine bonded N-terminally to the group —C=O and C-terminally to $A_2$, $A_2$ is a bivalent residue of one of the α-amino acids glycine, alanine, valine, leucine, isoleucine, phenylalanine, tyrosine, cyclohexylalanine, p-methoxy-phenylalanine, p-benzyloxyphenylalanine or p-fluorophenylalanine bonded N-terminally to $A_1$ and C-terminally to the group $NR_4R_5$, and the radical —$NR_5R_6$ is morpholino, and salts thereof where salt-forming groups are present, or (additionally or especially) the compounds of formula I', or salts thereof, wherein T is lower alkanoyloxy-lower alkylcarbonyl, such as acetyloxyacetyl, lower alkoxycarbonyl-lower alkoxy-lower alkylcarbonyl, such as methoxycarbonylmethoxy-acetyl, lower alkoxycarbonyl-lower alkylthio-lower alkylcarbonyl, such as methoxycarbonylmethylthio-acetyl, lower alkoxycarbonyl-lower alkylsulfo-lower alkylcarbonyl, such as methoxycarbonylmethylsulfo-acetyl, lower alkanoyloxy-lower alkoxycarbonyl-lower alkoxy-lower alkylcarbonyl, such as pivaloyloxymethoxycarbonyl-methoxyacetyl or acetyloxymethoxycarbonylmethoxy-acetyl, carboxy-lower alkoxy-lower alkylcarbonyl, such as carboxymethoxyacetyl, N-phenyl-lower alkoxycarbonylamino-lower alkylcarbonyl, such as 3-benzyloxycarbonylamino-propionyl, amino-lower alkylcarbonyl, such as 3-aminopropionyl, di-lower alkylamino-lower alkoxy-lower alkoxy-lower alkylcarbonyl, such as [2-(2-dimethylaminoethoxy)-ethoxy]-acetyl, N-phenyl-lower alkoxycarbonyl-amino-lower alkoxy-lower alkoxy-lower alkylcarbonyl, such as 2-(2-N-benzyloxycarbonylaminoethoxy) ethoxy-acetyl, amino-lower alkoxy-lower alkoxy-lower alkylcarbonyl, such as 2-(2-aminoethoxy)ethoxy-acetyl, or tetrahydropyranyloxy-lower alkylcarbonyl, such as 2-(4-tetrahydropyranyloxy)-acetyl or 2(R)-, 2(S)- or also 2(R,S)-(4-tetrahydropyranyloxy)-propionyl and the remaining radicals are as defined immediately above.

Great preference is given to a compound of formula I' wherein T is an acyl radical of formula Z, as indicated above, wherein $R^z$ is hydrocarbyl wherein at least one carbon atom has been replaced by a hetero atom with the proviso that a hetero atom is not bonded directly to the carbonyl to which the radical $R^z$ is bonded, alkyl having two or more carbon atoms, lower alkenyl, lower alkynyl or aryl, preferably as defined above, especially wherein $R^z$ is heterocyclyl bonded via a ring carbon atom and selected from pyrrolyl, 2,5-dihydropyrrolyl, indolyl, indolizinyl, isoindolyl, pyrrolidinyl, such as pyrrolidin-3-yl or especially pyrrolidin-2-yl (in the (R,S)- or preferably the (R)- or (S)-configuration), hydroxypyrrolidinyl, such as 3- or especially 4-hydroxypyrrolidinyl, furyl, such as furan-3-yl or especially furan-2-yl, tetrahydrofuryl, thienyl, cyclohepta[b]pyrrolyl, imidazolyl, such as imidazol-2-yl, imidazol-3-yl or especially imidazol-5-yl, N-triphenyl-lower alkyl-imidazolyl, such as N-triphenylmethyl-imidazolyl, pyrazolyl, especially pyrazol-3-yl, oxazolyl, isoxazolyl, such as isoxazol-3-yl or -5-yl, thiazolyl, isothiazolyl, such as isothiazol-3-yl or -5-yl, triazolyl, such as 1,2,3-triazol-4- or -5-yl or 1,2,4-triazol-5-yl, tetrazolyl, pyridyl, such as pyridin-4-yl or -3-yl or especially pyridin-2-yl, quinolyl, such as quinolin-2-yl, isoquinolyl, especially isoquinolin-1-yl or -3-yl, piperidyl, especially pipericlin-2-yl, γ-pyranyl, 4,5-dihydropyranyl, 4H-chromenyl, chromanyl, γ-thiopyranyl, pyridazinyl, cinnolyl, phthalazinyl, quinazolinyl, quinoxalinyl, pyrimidinyl, pyrazinyl, phenazinyl, phenoxazinyl, phenothiazinyl, morpholinyl and thiazinyl, each of which is substituted by up to three radicals selected independently of one another from lower alkyl, phenyl-lower alkyl, diphenyl-lower alkyl, triphenyl-lower alkyl, such as triphenylmethyl, lower alkanoyl, hydroxy, lower alkoxy, phenyl-lower alkoxy, such as benzyloxy, diphenylmethoxy or triphenylmethoxy, hydroxy-lower alkyl, such as hydroxymethyl, halogen, such as fluorine, chlorine or bromine, cyano, lower alkoxycarbonyl, such as methoxy- or tert-butoxy-carbonyl, phenyl-lower alkoxycarbonyl, such as benzyloxycarbonyl and halo-lower alkyl, such as chloromethyl or trifluoromethyl, or preferably is unsubstituted, and each of which is bonded via a ring carbon atom; very special preference being given to those of the mentioned radicals which contain a ring hetero atom directly adjacent to the bonding ring carbon atom, more especially the radicals furan-2-yl, (S)- or (R)-pyrrolidin-2-yl and imidazol-4-yl, pyridin-2-yl, -3-yl or -4-yl, or isoquinolin-3-yl; or additionally or especially tetrahydropyranyl; or $R^z$ is lower alkyl (especially methyl, ethyl, n-propyl or n-butyl) which is substituted by at least one radical selected from lower alkoxy, such as methoxy, ethoxy or n-butoxy; lower alkoxy, such as methoxy, ethoxy or n-butoxy, substituted by one or two substituents, especially aryl, more especially phenyl, naphthyl, lower alkoxy, such as ethoxy or methoxy, lower alkylthio, such as methylthio or ethylthio, lower alkoxy-lower alkoxy, such as 2-methoxyethoxy, lower alkylthio-lower alkoxy, such as 2-methylthioethoxy, aryloxy or arylthio, especially phenyloxy or o-, m- or p-chlorophenyloxy, for example p-chlorophenyloxy, amino, N-lower alkylamino or N,N-di-lower alkylamino, such as 2-amino, 2-(N-lower alkyl)amino or 2-(N,N-di-lower alkyl)amino, for example 2-dimethylamino, and/or heterocyclyl as last defined for heterocyclyl $R^z$ bonded via a ring carbon atom, especially 2-, 3- or 4-pyridyl; aryloxy, especially phenyloxy; lower alkylthio, such as methylthio, ethylthio or n-butylthio; lower alkylthio, such as methylthio, ethylthio or n-butylthio, substituted by one or two substituents, especially aryl, more especially phenyl or naphthyl; arylthio, such as phenylthio; amino or amino substituted by one or two radicals selected from lower alkyl, such as methyl, heterocyclyl-lower alkyl wherein heterocyclyl is as defined for heterocyclyl $R^z$ bonded via a ring carbon atom, especially heterocyclylmethyl, such as imidazolylmethyl, for example 4-imidazolylmethyl, or pyridylmethyl, for example 2-, 3- or 4-pyridylmethyl, each bonded via a ring carbon atom, aryl-lower alkyl, such as phenyl- or naphthyl-lower alkyl, for example phenyl- or naphthyl-methyl, lower alkanoyl, such as acetyl, lower alkoxycarbonyl, such as tert-butoxycarbonyl, and aryl-lower alkoxycarbonyl, such as phenyl-lower alkoxycarbonyl, for example benzyloxycarbonyl, with especially one of the substituents of amino being lower alkyl, especially methyl, and the other being hydrogen or one of the radicals mentioned above as substituents of amino; heterocyclyl as defined above for heterocyclyl $R^z$ bonded via a ring carbon atom, especially as pyridin-2-yl, -3-yl or -4-yl; and heterocyclyl-lower alkyl wherein lower alkyl is preferably methyl, 1- or 2-ethyl or 3-propyl and wherein heterocyclyl is as defined above for heterocyclyl $R^z$ bonded via a ring carbon atom but may also be bonded via a ring nitrogen atom, especially imidazol-1-yl, imidazol-2-yl, imidazol-5-yl or more especially imidazol-4-yl, N-triphenyl-lower alkylimidazolyl, such as N-triphenylmethyl-imidazol-5-yl or especially -4-yl, or pyrazolyl, such as pyrazol-1-yl, -3-yl, -4-yl or o5-yl; or (additionally or preferably) lower alkoxycarbonyl, such as methoxycarbonyl; lower alkanoyloxy-lower alkoxycarbonyl, such as pivaloyloxymethoxycarbonyl or acetyloxymethoxycarbonyl; carboxy; phenyl-lower alkoxycarbonylamino-lower alkoxy, such as 2-(benzyloxycarbonylamino)-ethoxy; amino-lower alkoxy, such as 2-aminoethoxy; di-lower alkylamino-lower alkoxy, such as 2-(dimethylamino)-ethoxy; or N,N-di-lower alkylamino-lower alkoxy, such as 2-(di-methylamino)-ethoxy; lower alkoxycarbonyl-lower alkylsulfo, such as methoxycarbonyl-methylsulfo; lower alkanoyloxy, such as acetyloxy; and tetrahydropyranyloxy, such as 4-tetrahydropyranyloxy, and which may also carry as a further substituent aryl, which is as defined below; or $R^z$ is aryl, especially chlorophenyl, chloro-lower alkylphenyl, such as o-, m- or p-chloro-methylphenyl, p-morpholinomethyl-phenyl, p-thiomorpholinomethyl-phenyl, or also phenyl;

aryl in the said definitions being especially phenyl, naphthyl, such as 1- or 2-naphthyl, or fluorenyl, such as 9-fluorenyl, that is unsubstituted or substituted by up to three radicals selected independently of one another from lower alkyl, lower alkanoyl, hydroxy, lower alkoxy, phenyl-lower alkoxy, such as benzyloxy, diphenylmethoxy or triphenylmethoxy, hydroxy-lower alkyl, such as hydroxymethyl, halogen, such as fluorine, chlorine or bromine, cyano, lower alkoxycarbonyl, such as methoxy- or tert-butoxy-carbonyl, phenyl-lower alkoxycarbonyl, such as benzyloxycarbonyl, halo-lower alkyl, such as chloromethyl or trifluoromethyl, piperidinomethyl, piperazin-1-ylmethyl, 4-lower alkylpiperazin-1-yl-methyl, such as 4-methyl- or 4-ethyl-piperazin-1-ylmethyl, morpholinomethyl or thiomorpholinomethyl, and nitro, which may be present independently of one another, and being especially correspondingly substituted phenyl;

T in the most preferred form being in the form of pyrrolidin-2-ylcarbonyl or -3-ylcarbonyl, such as (R)- or (S)-pyrrolidin-2-ylcarbonyl ((D)- or (L)-prolyl), furan-3- or especially furan-2-ylcarbonyl, pyridyl-4-, pyridyl-3- or especially pyridyl-2-ylcarbonyl, isoquinolin-1- or especially isoquinolin-3-ylcarbonyl, pyrazin-2-ylcarbonyl, lower alkoxy-lower alkylcarbonyl, such as methoxyacetyl, n-butoxyacetyl or 3-methoxypropionyl, phenyl- or naphthyl-lower alkoxy-lower alkylcarbonyl, such as benzyloxyacetyl, α-lower alkoxy-α-phenyl-lower alkylcarbonyl, such as (R)- or (S)-α-methoxy-α-phenylacetyl, lower alkoxy-lower alkoxy-lower alkylcarbonyl, such as 2-(methoxyethoxy)acetyl, lower alkoxy-lower alkoxy-lower alkoxy-lower alkylcarbonyl, such as 2-(2-(methoxyethoxy)ethoxy) acetyl, o-, m- or p-chlorophenyloxy-lower alkoxy-lower alkylcarbonyl, N,N-di-lower alkylamino-lower alkoxy-lower alkylcarbonyl, such as 2-(N,N-dimethylamino)ethyloxyacetyl, 2-, 3- or 4-pyridyl-lower alkyloxy-lower alkylcarbonyl, such as pyridin-2-ylmethoxyacetyl, phenyloxy-lower alkylcarbonyl, such as phenoxyacetyl, lower alkyl-thio-lower alkylcarbonyl, such as methylthioacetyl, phenyl-lower alkylthio-lower alkylcarbonyl, such as benzylthioacetyl, N,N-di-lower alkylamino-lower alkylcarbonyl, such as N,N-dimethylamino-acetyl, -3-propionyl or -4-butyryl, N-lower alkylamino-lower alkylcarbonyl, such as N-methylamino-acetyl or -3-propionyl, N-imidazol(-2-, -4- or -5-)yl-methyl-N-lower alkylamino-lower alkylcarbonyl, such as N-(imidazol-4-ylmethyl)-N-methylaminoacetyl, N-pyridin(-2-, -3- or -4-)ylmethyl-N-lower alkylamino-lower alkylcarbonyl, such as N-pyridin-2-ylmethyl-N-methylaminoacetyl, N-phenyl-lower alkoxycarbonyl-N-lower alkylamino-lower alkylcarbonyl, such as N-benzyloxycarbonyl-N-methylaminoacetyl, imidazol(-1-, -2-, -4- or -5-)yl-lower alkylcarbonyl, such as 3-(imidazol-4-yl) propionyl, or N-triphenyl-lower alkylimidazol(-4- or -5-)yl-lower alkylcarbonyl, such as 3-(N-triphenylmethylimidazol-4-yl)propionyl, or pyrazol(-1-, -3-, -4- or -5-) yl-lower alkylcarbonyl, such as pyrazol- 1-ylacetyl, or also in the form of halo-lower alkylbenzoyl, such as p-chloromethylbenzoyl, p-(morpholino- or thiomorpholino-methyl)benzoyl or benzoyl, especially in the form of methoxyacetyl or in the form of 2-pyridylcarbonyl; or (additionally or especially) lower alkanoyloxy-lower alkylcarbonyl, such as acetyloxyacetyl, lower alkoxycarbonyl-lower alkoxy-lower alkylcarbonyl, such as methoxycarbonylmethoxy-acetyl, lower alkoxycarbonyl-lower alkylthio-lower alkylcarbonyl, such as methoxycarbonylmethylthio-acetyl, lower alkoxycarbonyl-lower alkylsulfo-lower alkylcarbonyl, such as methoxycarbonylmethylsulfo-acetyl, lower alkanoyloxy-lower alkoxycarbonyl-lower alkoxy-lower alkylcarbonyl, such as pivaloyloxymethoxycarbonyl-methoxyacetyl or acetyloxymethoxycarbonylmethoxy-acetyl, carboxy-lower alkoxy-lower alkylcarbonyl, such as carboxymethoxyacetyl, N-phenyl-lower alkoxycarbonylamino-lower alkylcarbonyl, such as 3-benzyloxycarbonylamino-propionyl, amino-lower alkylcarbonyl, such as 3-aminopropionyl, di-lower alkylamino-lower alkoxy-lower alkoxy-lower alkylcarbonyl, such as [2-(2-dimethylaminoethoxy)-ethoxy]-acetyl, N-phenyl-lower alkoxycarbonyl-aminolower alkoxy-lower alkoxy-lower alkylcarbonyl, such as 2-(2-N-benzyloxycarbonylaminoethoxy)ethoxy-acetyl, amino-lower alkoxy-lower alkoxy-lower alkylcarbonyl, such as 2-(2-aminoethoxy)ethoxy-acetyl, or tetrahydropyranyloxy-lower alkylcarbonyl, such as 2-(4-tetrahydropyranyloxy)-acetyl or 2(R)-, 2(S)- or also 2(R,S)-(4-tetrahydropyranyloxy)-propionyl;

and wherein either (especially preferred) $R_1$ is tert-butoxycarbonyl; $B_1$ is a bond; $R_2$ is phenyl; $R_3$ is phenyl; $A_1$ is the bivalent residue of (L)-valine (-(L)-Val-) bonded N-terminally to the group —C═O and C-terminally to $A_2$; $A_2$ is the bivalent residue of phenylalanine (-(L)-Phe-) bonded N-terminally to $A_1$ and C-terminally to the group —$NR_4R_5$; and $R_4$ and $R_5$ together with the bonding nitrogen atom form morpholino;

or $R_1$ is tert-butoxycarbonyl; $B_1$ is a bond; $R_2$ is phenyl; $R_3$ is p-methoxyphenyl; $A_1$ is the bivalent residue of (L)-valine (-(L)-Val-) bonded N-terminally to the group —C=O and C-terminally to $A_2$; $A_2$ is the bivalent residue of p-methoxy-phenylalanine (-(L)-(p-CH$_3$O-Phe)-) bonded N-terminally to $A_1$ and C-terminally to the group —NR$_4$R$_5$; and R$_4$ and R$_5$ together with the bonding nitrogen atom form morpholino;

or $R_1$ is tert-butoxycarbonyl; $B_1$ is a bond; $R_2$ is phenyl; $R_3$ is p-fluorophenyl; $A_1$ is the bivalent residue of (L)-valine bonded N-terminally to the group —C=O and C-terminally to $A_2$; $A_2$ is the bivalent residue of phenylalanine bonded N-terminally to $A_1$ and C-terminally to the group —NR$_4$R$_5$; and R$_4$ and R$_5$ together with the bonding nitrogen atom form morpholino;

or $R_1$ is tert-butoxycarbonyl; $B_1$ is a bond; $R_2$ is phenyl; $R_3$ is p-fluorophenyl; $A_1$ is the bivalent residue of (L)-valine bonded N-terminally to the group —C=O and C-terminally to $A_2$; $A_2$ is the bivalent residue of p-methoxy-phenylalanine bonded N-terminally to $A_1$ and C-terminally to the group —NR$_4$R$_5$; and R$_4$ and R$_5$ together with the bonding nitrogen atom form morpholino;

or (especially preferred) $R_1$ is tert-butoxycarbonyl; $B_1$ is a bond; $R_2$ is phenyl; $R_3$ is p-methoxyphenyl; Ax is the bivalent residue of (L)-valine (-(L)-Val-) bonded N-terminally to the group —C=O and C-terminally to $A_2$; $A_2$ is the bivalent residue of phenylalanine (-(L)-Phe-) bonded N-terminally to $A_1$ and C-terminally to the group —NR$_4$R$_5$; and R$_4$ and R$_5$ together with the bonding nitrogen atom form morpholino;

and pharmaceutically acceptable salts thereof where salt-forming groups are present.

Very special preference is given to a compound of formula I' wherein T is 4(S)-(2-furanylcarboxy); 4(S)-[4-(dimethyl-amino)-butyryloxy]; 4(S)-(N-Z-N-methyl-aminoacetyloxy); 4(S)-(methylamino-acetyloxy); 4(S)-[N-(imidazole-4-methyl)-N-methylaminoacetyloxy]; 4(S)-[3-(1-triphenylmethyl-imidazol-4-yl)-propionyloxy]; 4(S)-[3-(4-imidazolyl)-propionyloxy]; 4(S)-(methoxy-acetyloxy); 4(S)-(2-picolinoyl); 4(S)-(benzyl-oxy-acetyloxy); 4(S)-[(S)-α-methoxy-α-phenyl-acetyloxy]; 4(S)-[(R)-α-methoxy-α-phenyl-acetyloxy]; 4(S)-(1-pyrazolylacetyloxy); 4(S)-(isoquinoline-3-carbonyloxy); 4(S)-(pyrazinecarbonyloxy); 4(S)-(4-α-chloromethyl-benzoyloxy); 4(S)-[4-(4-morpholino) methyl-benzoyloxy]; 4(S)-(isonicotinoyloxy); 4(S)-(nicotinoyloxy); 4(S)-(3-methoxypropanoyloxy); 4(S)-[(4-chlorophenoxy)methoxyacetyloxy]; 4(S)-[2-(2-methoxyethoxy)acetyloxy]; 4(S)-(butyloxyacetyloxy); 4(S)-[2-[2-(2-methoxyethoxy)ethoxy]acetyloxy)]; 4(S)-(methoxyacetyloxy); 4(S)-(phenoxyacetyloxy); 4(S)-[(S)-α-methoxy-α-phenylacetyloxy)]; 4(S)-[(R)-α-methoxy-α-phenylacetyloxy]; (N,N-dimethyl-aminoacetyloxy); 4(S)-[N-(pyridine-2-methyl)-N-methyl-aminoacetyloxy]; 4(S)-[3-(dimethyl-amino)-propionyloxy]; 4(S)-[3-(N-Z-N-methyl-amino)-propionyloxy]; 4(S)-(3-methyl-amino-propionyloxy); 4(S)-[(dimethylaminoethoxy)-acetyloxy]; 4(S)-[(2-pyridylmethoxy)-acetyloxy]; 4(S)-(methoxy-acetyloxy); 4(S)-(pyridine-2-carboxy); 4(S)-(methylthioacetyloxy); 4(S)-(benzylthioacetyloxy); 4(S)-((L)-prolyloxy); 4(S)-((D)-prolyloxy); 4(S)-((L)-(N-Z-prolyl)oxy); 4(S)-((D)-(N-Z-prolyl)oxy); 3-(N-Z-amino)-propionyloxy; 3-amino-propionyloxy; (3-dimethylamino-propoxy)-acetyloxy; 2-(2-dimethylamino-ethoxy)-ethoxy-acetyloxy; (4-dimethylamino-butoxy)-acetyloxy; (2-benzyloxy)acetyloxy; (2-acetyloxy)acetyloxy; 2-(4-tetrahydropyranyloxy)acetyloxy; 2(R)-(4-tetrahydropyranyloxy)-propionyloxy; 2-(2-amino-ethoxy) ethoxy-acetyloxy); 2-(2-benzyloxycarbonylamino-ethoxy) ethoxy-acetyloxy; (methoxycarbonyl-methoxy)-acetyloxy; (methoxycarbonyl-methylthio)-acetyloxy; (methoxycarbonyl-methylsulfo)-acetyloxy; (pivaloyloxymethoxycarbonyl)-methoxy-acetyl; (carboxymethoxy)-acetyloxy; or (acetoxymethoxycarbonyl-methoxy)-acetyloxy; and $R_1$ is tert-butoxycarbonyl; $B_1$ is a bond; $R_2$ is phenyl; $R_3$ is phenyl; $A_1$ is the bivalent residue of (L)-valine (-(L)-Val-) bonded N-terminally to the group —C=O and C-terminally to $A_2$; $A_2$ is the bivalent residue of phenylalanine (-(L)-Phe-) bonded N-terminally to $A_1$ and C-terminally to the group —NR$_4$R$_5$; and R$_4$ and R$_5$ together with the bonding nitrogen atom form morpholino;

or the compound of formula I' wherein T is as last defined, and has especially one of the mentioned meanings, and $R_1$ is tert-butoxycarbonyl; $B_1$ is a bond; $R_2$ is phenyl; $R_3$ is p-methoxyphenyl; $A_1$ is the bivalent residue of (L)-valine (-(L)-Val-) bonded N-terminally to the group —C=O and C-terminally to $A_2$; $A_2$ is the bivalent residue of phenylalanine (-(L)-Phe-) bonded N-terminally to $A_1$ and C-terminally to the group —NR$_4$R$_5$; and R$_4$ and R$_5$ together with the bonding nitrogen atom form morpholino;

or in each case a pharmaceutically acceptable salt thereof where salt-forming groups are present.

Greater preference is given to a compound of formula I' wherein T is methoxyacetyl or pyridin-2-ylcarbonyl and either $R_1$ is tert-butoxycarbonyl; $B_1$ is a bond; $R_2$ is phenyl; $R_3$ is phenyl; $A_1$ is the bivalent residue of (L)-valine bonded N-terminally to the group —C=O and C-terminally to $A_2$; $A_2$ is the bivalent residue of phenylalanine bonded N-terminally to $A_1$ and C-terminally to the group —NR$_4$R$_5$; and R$_4$ and R$_5$ together with the bonding nitrogen atom form morpholino (especially preferred);

or $R_1$ is tert-butoxycarbonyl; $B_1$ is a bond; $R_2$ is phenyl; $R_3$ is p-methoxyphenyl; $A_1$ is the bivalent residue of (L)-valine bonded N-terminally to the group —C=O and C-terminally to $A_2$; $A_2$ is the bivalent residue of p-methoxy-phenylalanine bonded N-terminally to $A_1$ and C-terminally to the group —NR$_4$R$_5$; and R$_4$ and R$_5$ together with the bonding nitrogen atom form morpholino;

or $R_1$ is tert-butoxycarbonyl; $B_1$ is a bond; $R_2$ is phenyl; $R_3$ is p-fluorophenyl; $A_1$ is the bivalent residue of (L)-valine bonded N-terminally to the group —C=O and C-terminally to $A_2$; $A_2$ is the bivalent residue of phenylalanine bonded N-terminally to $A_1$ and C-terminally to the group —NR$_4$R$_5$; and R$_4$ and R$_5$ together with the bonding nitrogen atom form morpholino;

or $R_1$ is tert-butoxycarbonyl; $B_1$ is a bond; $R_2$ is phenyl; $R_3$ is p-fluorophenyl; $A_1$ is the bivalent residue of (L)-valine bonded N-terminally to the group —C=O and C-terminally to $A_2$; $A_2$ is the bivalent residue of p-methoxy-phenylalanine bonded N-terminally to $A_1$ and C-terminally to the group —NR$_4$R$_5$; and R$_4$ and R$_5$ together with the bonding nitrogen atom form morpholino;

or $R_1$ is tert-butoxycarbonyl; $B_1$ is a bond; $R_2$ is phenyl; $R_3$ is p-methoxyphenyl; $A_1$ is the bivalent residue of (L)-valine bonded N-terminally to the group —C=O and C-terminally to $A_2$; $A_2$ is the bivalent residue of phenylalanine bonded N-terminally to $A_1$ and C-terminally to the group —NR₄R₅; and R₄ and R₅ together with the bonding nitrogen atom form morpholino (especially preferred);
and pharmaceutically acceptable salts thereof where salt-forming groups are present.

Greatest preference is given to all compounds of formula I' or the individual compounds of formula I' mentioned in the Examples and the pharmaceutically acceptable salts thereof where salt-forming groups are present.

The compounds of formula I or their hydroxy-protected derivatives, and salts of such compounds having at least one salt-forming group, are obtained according to processes known per se, for example as follows:

a) for the preparation of compounds of the formula

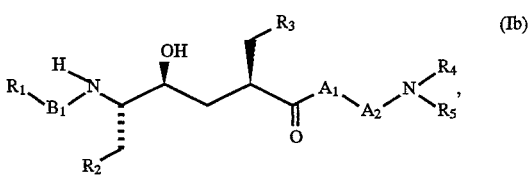
(Ib)

wherein $R_1'$ is as defined for $R_1$ in compounds of formula I, except that it is not hydrogen, the hydroxy group at the carbon atom that is vicinal to the carbon atom carrying the radical $R_2$-$CH_2$— is free or in protected form, and the other radicals are as defined for compounds of formula I, an acid of the formula $$R_1'\text{-OH} \qquad (II),$$

or a reactive acid derivative thereof, wherein $R_1'$ is as defined for $R_1$ in compounds of formula I, except that it is not hydrogen, is condensed with an amino compound of the formula

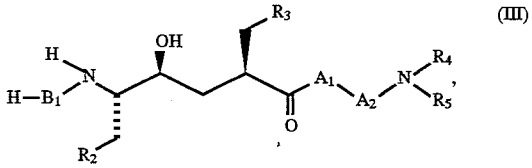
(III)

or with a reactive derivative thereof, wherein the radicals are as defined for compounds of formula I, free functional groups in the starting materials of formulae II and III, with the exception of the groups participating in the reaction, being, where appropriate, in protected form, and, if desired, protecting groups present are removed, or b) for the preparation of compounds of the formula

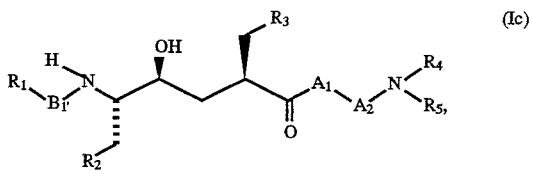
(Ic)

wherein $B_1'$ represents the same radicals as does $B_1$ in compounds of formula I, except that it is not a bond, the hydroxy group at the carbon atom that is vicinal to the carbon atom carrying the radical $R_2$-$CH_2$— is free or in protected form, and the other radicals are as defined for compounds of formula I, a carboxylic acid of the formula $$R_1\text{-}B_1'\text{-OH} \qquad (IV),$$

or a reactive acid derivative thereof, wherein $R_1$ is as defined for compounds of formula I and $B_1'$ is as last defined, is condensed with an amino compound of the formula

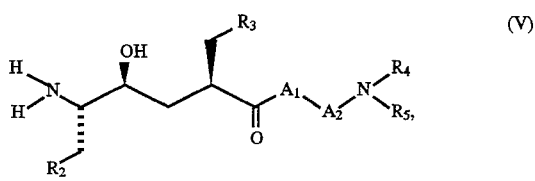
(V)

or with a reactive derivative thereof, wherein the radicals are as defined for compounds of formula I, free functional groups in the starting materials of formulae IV and V, with the exception of the groups participating in the reaction, being, where appropriate, in protected form, and, if desired, protecting groups present are removed, or c) a carboxylic acid of the formula

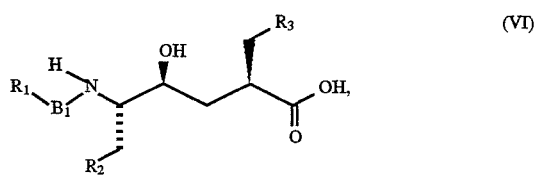
(VI)

or a reactive derivative thereof, wherein the radicals are as defined for compounds of formula I, is condensed with an amino compound of the formula

(VII)

or with a reactive derivative thereof, wherein the radicals are as defined for compounds of formula I, free functional groups in the starting materials of formulae VI and VII, with the exception of the groups participating in the reaction, being, where appropriate, in protected form and, if desired, protecting groups present are removed, or d) for the preparation of a compound of the formula

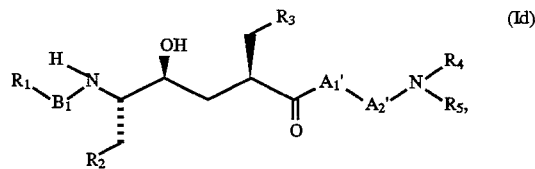
(Id)

wherein $A_1'$ and $A_2'$ are as defined for $A_1$ and $A_2$ in compounds of formula I, except that $A_1'$ is not a bond and the peptide bond between $A_1'$ and $A_2'$ is not in reduced form, the hydroxy group at the carbon atom that is vicinal to the carbon atom carrying the radical $R_2$-$CH_2$— is free or in protected form, and the other radicals are as defined for compounds of formula I, a carboxylic acid of the formula

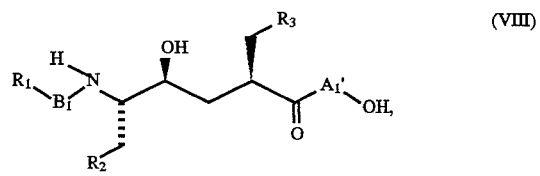
(VIII)

or a reactive derivative thereof, wherein the radicals are as last defined, is condensed with an amino compound of the formula

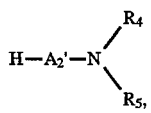 (IX)

or with a reactive derivative thereof, wherein the radicals are as last defined, free functional groups in the starting materials of formulae VIII and IX, with the exception of the groups participating in the reaction, being, where appropriate, in protected form and, if desired, protecting groups present are removed, or e) a carboxylic acid of the formula

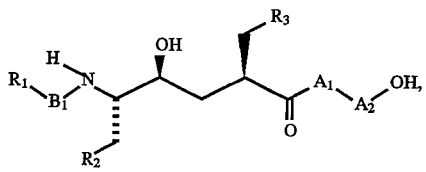 (X)

or a reactive derivative thereof, wherein the radicals are as defined for compounds of formula I, is condensed with an amino compound of the formula

 (XI)

or with a reactive derivative thereof, the radicals being as defined for compounds of formula I, free functional groups in the starting materials of formulae X and XI, with the exception of the groups participating in the reaction, being, where appropriate, in protected form and, if desired, protecting groups present are removed, or f) in a compound of formula I wherein the substituents are as defined above, provided that at least one functional group in the compound of formula I concerned is protected by protecting groups, protecting groups present are removed, and/or, if desired, a compound of formula I obtained according to any one of the above processes a) to f) that has at least one salt-forming group is converted into its salt and/or an obtainable salt is converted into the free compound or into a different salt and/or any obtainable isomeric mixtures of compounds of formula I are separated and/or a compound of formula I according to the invention is converted into a different compound of formula I according to the invention.

The compounds of formula I' and salts of those compounds having at least one salt-forming group are obtained in accordance with processes known per se, for example as follows:

aa) for the preparation of a compound of formula

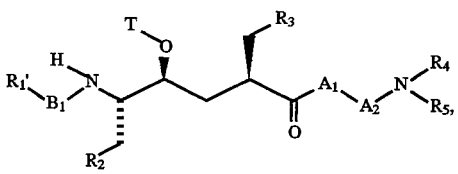 (Ib')

wherein $R_1'$ has the meanings given for $R_1$ in compounds of formula I' with the exception of hydrogen, the hydroxy group present at the carbon atom adjacent to the carbon atom carrying the radical $R_2$-$CH_2$— is in free or protected form and the remaining radicals are as defined for compounds of formula I', an acid of formula $R_1'$-OH (II), or a reactive acid derivative thereof, wherein $R_1'$ has the meanings given for $R_1$ in compounds of formula I' with the exception of hydrogen, is condensed with an amino compound of formula

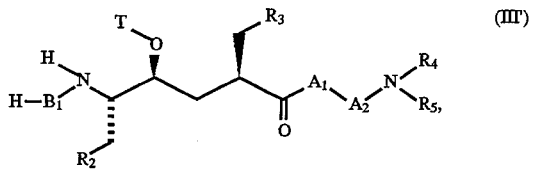 (III')

or with a reactive derivative thereof, wherein the radicals are as defined for compounds of formula I', free functional groups in the starting materials of formulae II and III', with the exception of those participating in the reaction, being if necessary in protected form, and, if desired, any protecting groups present are removed, or bb) for the preparation of a compound of formula

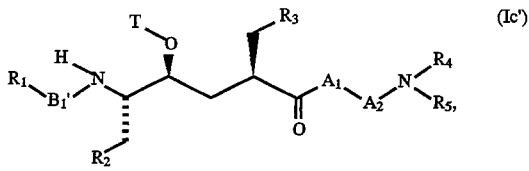 (Ic')

wherein $B_1'$ may be the same residues as $B_1$ in compounds of formula I' but may not be a bond, the hydroxy group present at the carbon atom adjacent to the carbon atom carrying the radical $R_2$-$CH_2$— is in free or protected form and the remaining radicals are as defined for compounds of formula I', a carboxylic acid of formula $R_1$-$B_1'$-OH (IV), or a reactive acid derivative thereof, wherein $R_1$ is as defined for compounds of formula I' and $B_1'$ is as last defined, is condensed with an amino compound of formula

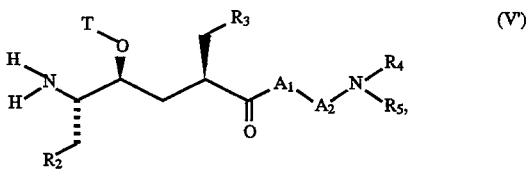 (V')

or with a reactive derivative thereof, wherein the radicals are as defined for compounds of formula I', free functional groups in the starting materials of formulae IV and V', with the exception of those participating in the reaction, being if necessary in protected form, and, if desired, any protecting groups present are removed, or cc) a carboxylic acid of formula

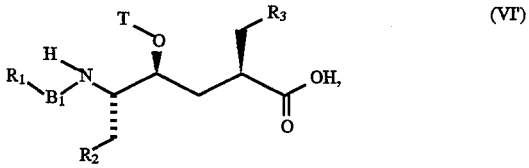 (VI')

or a reactive derivative thereof, wherein the radicals are as defined for compounds of formula I', is condensed with an amino compound of formula

 (VII)

or with a reactive derivative thereof, wherein the radicals are as defined for compounds of formula I', free functional groups in the starting materials of formulae VI' and VII, with the exception of those participating in the reaction, being if necessary in protected form, and, if desired, any protecting groups present are removed, or dd) for the preparation of a compound of formula

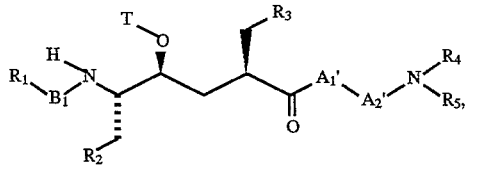

(Id')

wherein $A_1'$ and $A_2'$ are as defined for $A_1$ and $A_2$ in compounds of formula I', but $A_1'$ is not a bond and the peptide bond between $A_1'$ and $A_2'$ is not in reduced form, the hydroxy group present at the carbon atom adjacent to the carbon atom carrying the radical $R_2$-$CH_2$— is in free or protected form and the remaining radicals are as defined for compounds of formula I', a carboxylic acid of formula

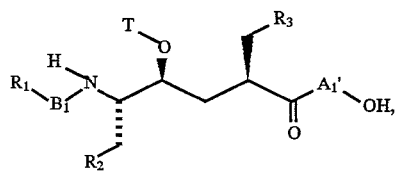

(VIII')

or a reactive derivative thereof, wherein the radicals are as last defined, is condensed with an amino compound of formula

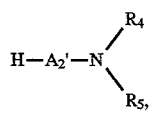

(IX)

or with a reactive derivative thereof, wherein the radicals are as last defined, free functional groups in the starting materials of formulae VIII' and IX, with the exception of those participating in the reaction, being if necessary in protected form, and, if desired, any protecting groups present are removed, or ee) a carboxylic acid of formula

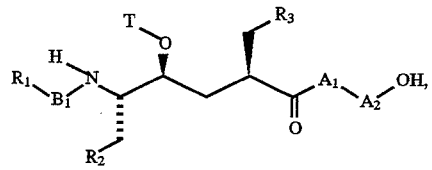

(X')

or a reactive derivative thereof, wherein the radicals are as defined for compounds of formula I', is condensed with an amino compound of formula

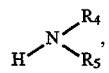

(XI)

or with a reactive derivative thereof, wherein the radicals are as defined for compounds of formula I', free functional groups in the starting materials of formulae X' and XI, with the exception of those participating in the reaction, being if necessary in protected form, and, if desired, any protecting groups present are removed, or ff) in a compound of formula I' wherein the substituents are as defined above with the proviso that in the compound of formula I' in question at least one functional group is protected by protecting groups, the protecting groups are removed, or gg) a compound of formula I

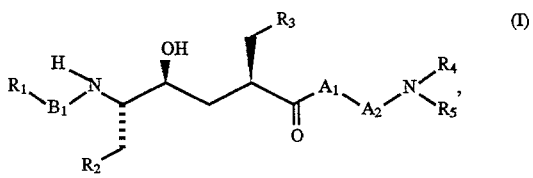

(I)

wherein the radicals are as defined for compounds of formula I', is reacted with a carboxylic acid of formula XXV

T-OH (XXV), wherein T is as defined for compounds of formula I', or with a reactive acid derivative thereof, free functional groups in the starting materials of formulae XXV and I, with the exception of those participating in the reaction, being if necessary in protected form, and, if desired, any protecting groups present are removed, or hh) for the preparation of a compound of formula I' wherein T is a radical of formula Z
wherein $R^z$ is lower alkyl substituted by etherified or esterified hydroxy or mercapto, by unsubstituted or substituted amino or by heterocyclyl bonded via nitrogen, and the remaining radicals are as defined for compounds of formula I', a compound of formula

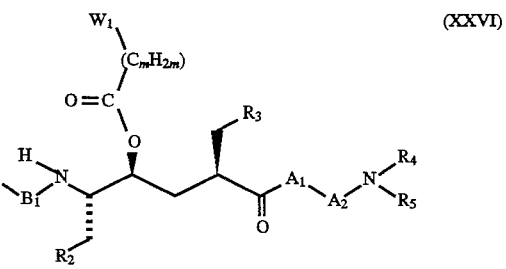

(XXVI)

wherein $W_1$ is a leaving group, -$(C_mH_{2m})$- is a lower alkylene radical (m is from 1 to 7) and the remaining radicals are as defined for compounds of formula I', is reacted with a compound of formula

L-H (XXVII), wherein L is etherified or esterified hydroxy or mercapto, unsubstituted or substituted amino, or heterocyclyl bonded via nitrogen, or with a reactive derivative thereof, free functional groups in the staffing materials of formulae XXVI and XXVII, with the exception of those participating in the reaction, being if necessary in protected form, and, if desired, any protecting groups present are removed, and/or, if desired, a compound of formula I' obtainable in accordance with any one of the above processes a) to h) having at least one salt-forming group is converted into its salt and/or an obtainable salt is convened into the free compound or into a different salt and/or isomeric mixtures of compounds of formula I' which may be obtainable are separated and/or a compound of formula I' according to the invention is convened into a different compound of formula I' according to the invention.

The above-defined processes are described in detail below:

Process a) and aa) (Formation of an amide bond)

In starting materials of formulae II, III and III', functional groups, with the exception of groups that are intended to participate in the reaction or that do not react under the reaction conditions, are protected independently of one another by protecting groups.

Protecting groups for functional groups in starting materials the reaction of which is to be avoided, especially carboxy, amino, hydroxy, mercapto and sulfo groups, include especially those protecting groups (conventional protecting groups) which are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis, etc.. In certain cases the protecting groups can additionally cause the reactions to proceed selectively, for example stereoselectively. It is characteristic of protecting groups that they can be removed easily, i.e. without undesired secondary reactions taking place, for example by solvolysis, reduction, photolysis, and also enzymatically, for example also under physiological conditions. Protecting groups may also be present in the end products, however. Compounds of formula I' or I having protected functional groups may have greater metabolic stability or pharmacodynamic properties that are better in some other way than the corresponding compounds having free functional groups.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides", Volume 3 (E. Gross and J. Meienhofer, eds.), Academic Press, London and New York 1981, in "Methoden der organischen Chemie", Houben-Weyl, 4th edition, Volume 15/I, Georg Thieme Verlag, Stuttgart 1974, in H.-D. Jakubke and H. Jescheit, "Aminosäuren, Peptide, Proteine" ("Amino acids, peptides, proteins"), Verlag Chemie, Weinheim, Deerfield Beach and Basle 1982, and in Jochen Lehmann, "Chemie der Kohlenhydrate: Monosaccharide und Derivate" ("The Chemistry of Carbohydrates: monosaccharides and derivatives"), Georg Thieme Verlag, Stuttgart 1974.

A carboxy group is protected, for example, in the form of an ester group which can be cleaved selectively under mild conditions. A carboxy group protected in esterified form is esterified especially by a lower alkyl group that is preferably branched in the 1-position of the lower alkyl group or substituted in the 1- or 2-position of the lower alkyl group by suitable substituents.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, ten-lower alkoxycarbonyl, for example tert-butoxycarbonyl.

A protected carboxy group esterified by a lower alkyl group that is substituted in the 1- or 2-position of the lower alkyl group by suitable substituents is, for example, arylmethoxycarbonyl having one or two aryl radicals, wherein aryl is phenyl that is unsubstituted or mono-, di- or tri-substituted, for example, by lower alkyl, for example tea-lower alkyl, such as tert-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di(4-methoxyphenyl)methoxycarbonyl, and also carboxy esterified by a lower alkyl group, the lower alkyl group being substituted in the 1-or 2-position by suitable substituents, such as 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl wherein the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, as well as 2-(tri-substituted silyl)-lower alkoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen and/or by nitro, for example lower alkyl, phenyl-lower alkyl, cycloalkyl or phenyl each of which is unsubstituted or substituted as above, for example 2-tri-lower alkylsilyl-lower alkoxycarbonyl, such as 2-ui-lower alkylsilylethoxycarbonyl, for example 2-trimethylsilylethoxycarbonyl or 2-(di-n-butyl-methyl-silyl)-ethoxycarbonyl, or 2-tdarylsilylethoxycarbonyl, such as triphenylsilylethoxycarbonyl.

A carboxy group may also be protected in the form of an organic silyloxycarbonyl group. An organic silyloxycarbonyl group is, for example, a tri-lower alkylsilyloxycarbonyl group, for example trimethylsilyloxycarbonyl. The silicon atom of the silyloxycarbonyl group can also be substituted by two lower alkyl groups, for example methyl groups, and by an amino group or carboxy group of a second molecule of formula I or I'. Compounds having such protecting groups can be prepared, for example, using dimethylchlorosilane as silylating agent.

A carboxy group may also be protected in the form of an internal ester with a hydroxy group present in the molecule suitably spaced from the carboxy group, for example in the γ-position with respect to the carboxy group, that is to say in the form of a lactone, preferably a γ-lactone.

A protected carboxy group is preferably tert-lower alkoxycarbonyl, for example tert-butoxycarbonyl, benzyloxycarbonyl, 4-nitrobenzyloxycarbonyl, 9-fluorenylmethoxycarbonyl or diphenylmethoxycarbonyl, or a carboxy group protected in the form of a lactone, especially a γ-lactone.

A protected amino group may be protected by an amino-protecting group, for example in the form of an acylamino, arylmethylamino, etherified mercaptoamino, 2-acyl-lower alk-1-enylamino or silylamino group or in the form of an azido group.

In an acylamino group, acyl is, for example, the acyl radical of an organic carboxylic acid having, for example, up to 18 carbon atoms, especially an unsubstituted or substituted, for example halo- or aryl-substituted, lower alkanecarboxylic acid or an unsubstituted or substituted, for example halo-, lower alkoxy- or nitro-substituted, benzoic acid, or, preferably, of a carbonic acid semiester. Such acyl groups are preferably lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloro-acetyl, unsubstituted or substituted, for example halo-, lower alkoxy- or nitro-substituted, benzoyl, such as benzoyl, 4-chlorobenzoyl, 4-methoxybenzoyl or 4-nitrobenzoyl, lower alkoxycarbonyl, preferably lower alkoxycarbonyl that is branched in the 1-position of the lower alkyl radical or suitably substituted in the 1- or 2-position, for example tert-lower alkoxycarbonyl, such as tert-butoxycarbonyl, arylmethoxycarbonyl having one, two or three aryl radicals which are phenyl that is unsubstituted or mono- or polysubstituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl, 9-fluorenylmethoxycarbonyl or di(4-methoxyphenyl) methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(trisubstituted silyl)-lower alkoxycarbonyl, for example 2-trilower alkylsilyl-lower alkoxycarbonyl, such as 2-trimethylsilylethoxycarbonyl or 2-(di-n-butylmethylsilyl)-ethoxycarbonyl, or triarylsilyl-lower alkoxycarbonyl, for example 2-tri-phenylsilylethoxycarbonyl.

In an arylmethylamino group, for example a mono-, di- or especially tri-arylmethylamino group, the aryl radicals are especially unsubstituted or substituted phenyl radicals. Such groups are, for example, benzyl-, diphenylmethyl- or especially trityl-amino.

In an etherified mercaptoamino group the mercapto group is especially in the form of substituted arylthio or aryl-lower alkylthio, wherein aryl is, for example, phenyl that is unsubstituted or substituted, for example, by lower alkyl, such as methyl or tert-butyl, lower alkoxy, such as methoxy, halogen, such as chlorine, and/or by nitro, for example 4-nitrophenylthio.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-lower alk-1-en-2-yl, for example 1-lower alkanoyl-prop-1-en-2-yl, such as 1-acetyl-prop-1-en-2-yl, or lower alkoxycarbonyl-lower alk-1-en-2-yl, for example lower alkoxycarbonyl-prop-1-en-2-yl, such as 1-ethoxycarbonyl-prop-1-en-2-yl.

A silylamino group is, for example, a ui-lower alkylsilylamino group, for example trimethylsilylamino or tert-butyldimethylsilylamino. The silicon atom of the silylamino group can also be substituted by only two lower alkyl groups, for example methyl groups, and by the amino group or carboxy group of a second molecule of formula I or I'. Compounds having such protecting groups can be prepared, for example, using the corresponding chlorosilanes, such as dimethylchlorosilane, as silylating agents.

An amino group can also be protected by conversion into the protonated form; suitable corresponding anions are especially those of strong inorganic acids, such as sulfuric acid, phosphoric acid or hydrohalic acids, for example the chlorine or bromine anion, or of organic sulfonic acids, such as p-toluenesulfonic acid.

Preferred amino-protecting groups are lower alkoxycarbonyl, phenyl-lower alkoxycarbonyl, fluorenyl-lower alkoxycarbonyl, 2-lower alkanoyl-lower alk-1-en-2-yl and lower alkoxycarbonyl-lower alk-1-en-2-yl, especially tert-butoxycarbonyl and benzyloxycarbonyl.

A hydroxy group can be protected, for example, by an acyl group, for example lower alkanoyl that is unsubstituted or substituted by halogen, such as chlorine, such as acetyl or 2,2-dichloroacetyl, or especially by an acyl radical of a carbonic acid semiester mentioned for protected amino groups. A hydroxy group can also be protected by tri-lower alkylsilyl, for example trimethylsilyl, triisopropylsilyl or tert-butyl-dimethylsilyl, a readily removable etherifying group, for example an alkyl group, such as tert-lower alkyl, for example tert-butyl, an oxa- or a thia-aliphatic or -cycloaliphatic, especially 2-oxa- or 2-thia-aliphatic or -cycloaliphatic, hydrocarbon radical, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, such as 2-tetrahydrofuryl or 2-tetrahydropyranyl, or a corresponding thia analogue, and also by 1-phenyl-lower alkyl, such as benzyl, diphenylmethyl or trityl, wherein the phenyl radicals can be substituted, for example, by halogen, for example chlorine, lower alkoxy, for example methoxy, and/ or by nitro. A preferred hydroxy-protecting group is, for example, 2,2,2-trichloroethoxycarbonyl, 4-nitrobenzyloxycarbonyl, diphenylmethoxycarbonyl, benzyl or trityl.

Two hydroxy groups, especially adjacent hydroxy groups, occurring in a molecule, or a hydroxy group and an amino group that are adjacent to one another, can be protected, for example, by bivalent protecting groups, such as a methylene group that is preferably substituted, for example, by one or two lower alkyl radicals or by oxo, for example unsubstituted or substituted alkylidene, for example lower alkylidene, such as isopropylidene, cycloalkylidene, such as cyclohexylidene, a carbonyl group or benzylidene.

A hydroxy group adjacent to a carboxy group can be protected by the formation of an internal ester (tactone), especially a γ-lactone.

Preferably a protected hydroxy group is protected by tri-lower alkylsilyl or in the form of a lactone, especially by tert-butyl-dimethyl-silyl or in the form of a γ-lactone.

A mercapto group, for example in cysteine, can be protected especially by S-alkylation with unsubstituted or substituted alkyl radicals, by silylation, by thioacetal formation, by S-acylation or by the formation of asymmetric disulfide groupings. Preferred mercapto-protecting groups are, for example, benzyl that is unsubstituted or substituted in the phenyl radical, for example by methoxy or by nitro, such as 4-methoxybenzyl, diphenylmethyl that is unsubstituted or substituted in the phenyl radical, for example by methoxy, such as di(4-methoxyphenyl)methyl, triphenylmethyl, pyfidyldiphenylmethyl, trimethylsilyl, benzylthiomethyl, tetrahydropyranyl, acylaminomethyl, such as acetamidomethyl, iso-butyrylacetamidomethyl or 2-chloroacetamidomethyl, benzoyl, benzyloxycarbonyl or alkyl-, especially lower alkyl-aminocarbonyl, such as ethylaminocarbonyl, and also lower alkylthio, such as S-ethylthio or S-tert-butylthio, or S-sulfo.

A sulfo group can be protected, for example, by lower alkyl, for example methyl or ethyl, by phenyl or in the form of a sulfonamide, for example in the form of an imidazolide.

In the context of this Application, a protecting group, for example a carboxy-protecting group, is to be understood as being expressly also a polymeric carder that is bonded in a readily removable manner to the functional group, for example the carboxy group, to be protected, for example a carrier suitable for the Merrifield synthesis. Such a suitable polymeric carrier is especially a polystyrene resin, weakly cross-linked by copolymerisation with divinylbenzene, that carries bridge members suitable for reversible bonding.

The acids of formula II are carboxylic acids or sulfonic acids.

The carboxylic acids of formula II either contain a free carboxy group or are in the form of a reactive derivative, for example in the form of an activated ester derived from the free carboxy compound, in the form of a reactive anhydride, or in the form of a reactive cyclic amide. The reactive derivatives may also be formed in situ.

Activated esters of compounds of formula II having a carboxy group are especially esters unsaturated at the linking carbon atom of the esterifying radical, for example of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters substituted by electron-attracting substituents (obtainable, for example, by treatment of the corresponding acid with a suitably substituted phenol, for example 4-nitrophenol, 4-methylsulfonylphenol, 2,4,5-tri-chlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide, 1-hydroxybenzotdazole or 3-hydroxy-3,4-dihydro-1,2,3-benzotriazin-4-one, for example by the anhydride or carbodiimide method; activated N-hydroxy esters method). Internal esters, for example γ-lactones, can also be used.

Anhydrides of acids may be symmetric or preferably mixed anhydrideof those acids, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiesters, for example carbonic acid lower alkyl semiesters (obtainable, for example, by treatment of the corresponding acid with chloroformic acid lower alkyl esters or with a 1-lower alkoxycarbonyl-2-lower alkoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate or by reaction of alkylphosphoric acid amides in the presence of sulfonic acid anhydrides and/or racemisation-reducing additives, such as N-hydroxybenzotriazole, or in the presence of cyanophosphonic acid diethyl ester) or with phosphorous acid derivatives, or anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as a lower alkane- or aryl-, for example methane- or p-toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric arthydrides method).

Suitable cyclic amides are especially amides having five-membered diazacycles of aromatic character, such as amides with imidazoles, for example imidazole (obtainable, for example, by treatment of the corresponding acid with N,N'-carbonyldiimidazole; imidazole method), or pyrazole, for example 3,5-dimethylpyrazole (obtainable, for example, via the acid hydrazide by treatment with acetylacetone; pyrazolide method).

As mentioned, derivatives of carboxylic acids that are used as acylating agents may also be formed in situ. For example, N,N'-disubstituted amidino esters may be formed in situ by reacting, for example in the presence of a suitable base, such as triethylamine, a mixture of the starting material of formula III or III' and the acid of formula II used as acylating agent, in the presence of a suitable N,N'-disubstituted carbodiimide, for example N,N'-cyclohexylcarbodiimide. In addition, amino or amido esters of the acids used as acylating agents may be formed in the presence of the starting material of formula III or III' to be acylated, by reacting a mixture of the corresponding acid and amino starting materials in the presence of an N,N'-disubstituted carbodiimide, for example N,N'-dicyclohexylcarbodiimide, and of an N-hydroxyamine or N-hydroxyamide, for example N-hydroxysuccinimide, where appropriate in the presence of a suitable base, for example 4-dimethylamino-pyridine. Moreover, activation in situ can be achieved by reaction with N,N,N',N'-tetraalkyluronium compounds, such as 0-benzotriazol-1-yl-N,N,N',N'-tetramethyluronium hexafluorophosphate. Finally, phosphoric acid anhydrides of the carboxylic acids of formula II can be prepared in situ by reacting an alkylphosphoric acid amide, such as hexamethylphosphoric acid triamide, in the presence of a sulfonic acid anhydride, such as 4-toluenesulfonic acid anhydride, with a salt, such as a tetrafluoroborate, for example sodium tetrafluoroborate, or with another derivative of hexamethylphosphoric acid triamide, such as benzotriazol-1-yl-oxy-tris(dimethylamino) phosphonium hexafluoride, preferably in the presence of a racemisation-reducing additive, such as N-hydroxybenzotriazole.

The amino group of compounds of formula III or III' that participates in the reaction preferably carries at least one reactive hydrogen atom, especially when the carboxy group reacting therewith is present in reactive form; it may, however, itself have been derivatised, for example by reaction with a phosphite, such as diethylchlorophosphite, 1,2-phenylenechlorophosphite, ethyl dichlorophosphite, ethylenechlorophosphite or tetraethylpyrophosphite. A derivative of such a compound having an amino group is, for example, also a carbamic acid halide, the amino group that participates in the reaction being substituted by halocarbonyl, for example chlorocarbonyl.

Condensation to form an amide bond can be carried out in a manner known per se, for example as described in standard works, such as Houben-Weyl, "Methoden der organischen Chemie", 4th edition, Volume 15/II (1974), Volume IX (1955), Volume E 11 (1985), Georg Thieme Verlag, Stuttgart, "The Peptides" (E. Gross and J. Meienhofer, eds.), Volumes 1 and 2, Academic Press, London and New York, 1979/1980, or M. Bodansky, "Principles of Peptide Synthesis", Springer-Verlag, Berlin 1984.

The condensation of a free carboxylic acid with the corresponding amine can be carded out preferably in the presence of one of the customary condensation agents. Customary condensation agents are, for example, carbodiimides, for example diethyl-, dipropyl-, N-ethyl-N'-(3-dimethylaminopropyl)-carbodiimide or especially dicyclohexylcarbodiimide, also suitable carbonyl compounds, for example carbonylimidazole, 1,2-oxazolium compounds, for example 2-ethyl-5-phenyl-1,2-oxazolium 3'-sulfonate and 2-tert-butyl-5-methylisoxazolium perchlorate, or a suitable acylamino compound, for example 2-ethoxy-1-ethoxycarbonyl-1,2-dihydroquinoline, N,N,N',N'-tetraalkyluronium compounds, such as O-benzotriazol-1-yl-N,N,N',N'-tetramethyluronium hexafluorophosphate, also activated phosphoric acid derivatives, for example diphenylphosphoryl azide, diethylphosphoryl cyanide, phenyl-N-phenylphosphoroamidochloridate, bis(2-oxo-3-oxazolidinyl)phosphinic acid chloride or 1-benzotriazolyloxy-tris(dimethylamino)phosphonium hexafluorophosphate.

In a manner analogous to the types of reaction mentioned for condensation for the carboxylic acids of formula II, in the condensation the sulfonic acids of formula II having a terminal sulfonyl group may also be reacted with compounds of formula III or III' to form the corresponding sulfonamides of formula Ib or Ib'.

For example, it is possible to use activated sulfonic acid esters, for example the corresponding aryl esters, such as phenyl esters, especially those substituted by nitro groups, it being possible for the amine component of formula Ib or Ib' also to be used in the form of an alkali metal amide, for example an alkali metal arylamide, such as sodium anilineamide, or an alkali metal salt of nitrogen-containing heterocycles, for example potassium pyrrolide.

It is also possible to use reactive anhydrides, such as the corresponding symmetric acid anhydrides (which can be prepared, for example, by reaction of the alkylsulfonic acid silver salts with alkylsulfonyl chlorides) or, preferably, the corresponding asymmetric acid anhydrides, for example anhydrides with inorganic acids, such as sulfonyl halides, especially sulfonyl chlorides (obtainable, for example, by reaction of the corresponding sulfonic acids with inorganic acid chlorides, for example thionyl chloride, sulfuryl chloride or phosphorus pentachloride), with organic carboxylic acids (obtainable, for example, by treatment of a sulfonic acid halide with the salt of a carboxylic acid, such as an alkali metal salt, analogously to the above-mentioned method for the preparation of mixed acid anhydrides), or azides (obtainable, for example, from a corresponding sulfonic acid chloride and sodium azide or via the corresponding hydrazide and treatment thereof with nitrous acid analogously to the above-mentioned azide method).

If desired, an organic base may be added, for example a tri-lower alkylamine having bulky radicals, such as ethyl diisopropylamine, and/or a heterocyclic base, for example pyridine, 4-dimethylaminopyridine or preferably N-methylmorpholine.

The condensation of activated esters, reactive anhydrides or reactive cyclic amides with the corresponding amines is customarily carded out in the presence of an organic base, for example simple tri-lower alkylamines, for example triethylamine or tributylamine, or one of the above-mentioned organic bases. If desired, a condensation agent is additionally used, for example as described for free carboxylic acids.

The condensation of acid anhydrides with amines can be effected, for example, in the presence of inorganic carbonates, for example ammonium or alkali metal carbonates or hydrogen carbonates, such as sodium or potassium carbonate or hydrogen carbonate (usually together with a sulfate), while the reaction of sulfonic acid halides, such as sulfonic acid chlorides, can be carried out in the presence of hydroxides, for example alkali metal hydroxides, such as sodium hydroxide or potassium hydroxide.

Carboxylic acid chlorides, for example the chlorocarbonic acid derivatives derived from the acid of formula II, are condensed with the corresponding amines preferably in the presence of an organic amine, for example the above-mentioned tri-lower alkylamines or heterocyclic bases, where appropriate in the presence of a hydrogen sulfate.

The condensation is preferably carried out in an inert, aprotic, preferably anhydrous, solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, as appropriate at reduced or elevated temperature, for example in a temperature range of from approximately −40° C. to approximately +100° C., preferably from approximately −10° C. to approximately +50° C., and without an inert gas or under an inert gas atmosphere, for example a nitrogen or argon atmosphere.

Aqueous, for example alcoholic, solvents, for example ethanol, or aromatic solvents, for example benzene or toluene, may also be used. When alkali metal hydroxides are present as bases, acetone can also be added where appropriate.

The condensation can also be carried out in accordance with the technique known as solid-phase synthesis which originates from R. Merrifield and is described, for example, in Angew. Chem. 97, 801–812 (1985), Naturwissenschaften 71,252–258 (1984) or in R. A. Houghten, Proc. Natl. Acad. Sci. USA 82, 5131–5135 (1985).

The freeing of functional groups protected by protecting groups in the resulting compounds of formula I or I' having protected functions is effected in accordance with one or more of the methods mentioned under Process f) and ff).

Process b) and bb)(Formation of an amide bond)

In starting materials of formulae IV, V and V', functional groups, with the exception of the groups that are intended to participate in the reaction or that do not react under the reaction conditions, are protected independently of one another by protecting groups.

The protecting groups, the free carboxylic acids and the reactive derivatives thereof, the free amines and the reactive derivatives thereof and the processes used for condensation are entirely analogous to those described under Process a) or aa) for the formation of an amide bond starting from compounds of formulae II, III and III' except that carboxylic acids of formula IV are used instead of those of formula II and amino compounds of formula V or V' are used instead of those of formula III or III'.

The freeing of functional groups protected by protecting groups in the resulting compounds of formula I or I' having protected functions is effected in accordance with one or more of the methods mentioned under Process f) or ff). Process c) and cc) (Formation of an amide bond) In starting materials of formulae VI, VI' and VII, functional groups, with the exception of the groups that are intended to participate in the reaction or that do not react under the reaction conditions, are protected independently of one another by protecting groups. The protecting groups, the free carboxylic acids and the reactive derivatives thereof, the free amines and the reactive derivatives thereof and the processes used for condensation are entirely analogous to those described under Process a) for the formation of an amide bond starting from compounds of formulae II, III and III' except that carboxylic acids of formula VI or VI' are used instead of those of formula II and amino compounds of formula VII are used instead of those of formula III or III'.

The freeing of functional groups protected by protecting groups in the resulting compounds of formula I or I' having protected functions is effected in accordance with one or more of the methods mentioned under Process f) or ff).

Process d) and dd) (Formation of an amide bond)

In starting materials of formulae VIII, VIII' and IX, functional groups, with the exception of the groups that are intended to participate in the reaction or that do not react under the reaction conditions, are protected independently of one another by protecting groups.

The protecting groups, the free carboxylic acids and the reactive derivatives thereof, the free amines and the reactive derivatives thereof and the processes used for condensation are entirely analogous to those described under Process a) for the formation of an amide bond starting from compounds of formulae II, III and III' except that carboxylic acids of formula VIII or VIII' are used instead of those of formula II and amino compounds of formula IX are used instead of those of formula III or III'.

The freeing of functional groups protected by protecting groups in the resulting compounds of formula I or I' having protected functions is effected in accordance with one or more of the methods mentioned under Process f) or ff).

Process e) and ee) (Formation of an amide bond)

In starting materials of formulae X, X' and XI, functional groups, with the exception of the groups that are intended to participate in the reaction or that do not react under the reaction conditions, are protected independently of one another by protecting groups.

The protecting groups, the free carboxylic acids and the reactive derivatives thereof, the free amines and the reactive derivatives thereof and the processes used for condensation are entirely analogous to those described under Process a) for the formation of an amide bond starting from compounds of formulae II, III and III' except that carboxylic acids of formula X or X' are used instead of those of formula II and amino compounds of formula XI are used instead of those of formula III or III'.

A reactive derivative of such a compound of formula XI having an amino group is, for example, also an isocyanate in which the amino group participating in the reaction has been modified in the form of an isocyanate group, in that case there being obtainable only compounds of formula I or I' that carry a hydrogen atom at the nitrogen atom of the amide group formed by the reaction.

The freeing of functional groups protected by protecting groups in the resulting compounds of formula I or I' having protected functions is effected in accordance with one or more of the methods mentioned under Process f) or ff).

Process f) and ff) (Removal of protecting groups)

The removal of protecting groups that are not constituents of the desired end product of formula I or I', for example the carboxy-, amino-, hydroxy-, mercapto- and/or sulfo-protecting groups, is effected in a manner known per se, for example by means of solvolysis, especially hydrolysis, alcoholysis or acidolysis, or by means of reduction, especially hydrogenolysis or by means of other reducing agents, as well as photolysis, as appropriate stepwise or simultaneously, it being possible also to use enzymatic methods. The removal of the protecting groups is described, for example, in the standard works mentioned hereinabove in the section relating to protecting groups.

For example, protected carboxy, for example tert-lower alkoxycarbonyl, lower alkoxy-carbonyl substituted in the 2-position by a trisubstituted silyl group or in the 1-position by lower alkoxy or by lower alkylthio, or unsubstituted or substituted diphenylmethoxycarbonyl can be converted into free carboxy by treatment with a suitable acid, such as formic acid, hydrogen chloride or trifluoroacetic acid, where appropriate with the addition of a nucleophilic compound, such as phenol or anisole. Unsubstituted or substituted benzyloxycarbonyl can be freed, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can be converted into free carboxy also by reduction, for example by treatment with an alkali metal dithionite, such as sodium dithionite, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can be cleaved also by treatment with a nucleophilic, preferably salt-forming, reagent, such as sodium thiophenolate or sodium iodide. 2-(tri-substituted silyl)-lower alkoxycarbonyl, such as 2-tri-lower alkylsilyl-lower alkoxycarbonyl, can also be converted into free carboxy by treatment with a salt of hydrofluoric acid that yields the fluoride anion, such as an alkali metal fluoride, for example sodium or potassium fluoride, where appropriate in the presence of a macrocyclic polyether ("crown ether"), or with a fluoride of an organic quaternary base, such as term-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example uimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases, for example esterified arginine or lysine, such as lysine methyl ester, using trypsin. Carboxy protected in the form of an internal ester, such as in the form of γ-lactone, can be freed by hydrolysis in the presence of a hydroxide-containing base, such as an alkaline earth metal hydroxide or, especially, an alkali metal hydroxide, for example NaOH, KOH or LiOH, more especially LiOH, the correspondingly protected hydroxy group being freed at the same time.

A protected amino group is freed in a manner known per se and, according to the nature of the protecting groups, in various ways, preferably by solvolysis or reduction. Lower alkoxycarbonylamino, such as tert-butoxycarbonylamino, can be cleaved in the presence of acids, for example mineral acids, for example a hydrogen halide, such as hydrogen chloride or hydrogen bromide, especially hydrogen bromide, or sulfuric or phosphoric acid, preferably hydrogen chloride, in polar solvents, such as water or a carboxylic acid, such as acetic acid, or ethers, preferably cyclic ethers, such as dioxane; 2-halo-lower alkoxycarbonylamino (where appropriate after conversion of a 2-bromo-lower alkoxycarbonylamino group into a 2-iodo-lower alkoxycarbonylamino group), aroylmethoxy-carbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-(tri-substituted silyl)-lower alkoxycarbonylamino, such as 2-tri-lower alkylsilyl-lower alkoxycarbonylamino, can be cleaved by treatment with a suitable acid, for example formic acid or trifluoroacetic acid, for example in a halogenated hydrocarbon, such as methylene chloride or chloroform (especially when hydroxy protected by benzyl is not to be freed at the same time); unsubstituted or substituted benzyloxycarbonylamino can be cleaved, for example, by means of hydrogenolysis, i.e. by treatment with hydrogen in the presence of a suitable hydrogenation catalyst, such as a palladium catalyst, for example bonded to a carder, such as carbon, preferably in polar solvents, such as di-lower alkyl-lower alkanoylamides, for example dimethylformamide, ethers, such as cyclic ethers, for example dioxane, esters, such as lower alkanoic acid lower alkyl esters, for example ethyl acetate, or alcohols, such as methanol, ethanol or propanol, with methanol being especially preferred, preferably approximately at room temperature; unsubstituted or substituted triarylmethylamino or formylamino can be cleaved, for example, by treatment with an acid, such as a mineral acid, for example hydrochloric acid, or an organic acid, for example formic, acetic or tri-fluoroacetic acid, where appropriate in the presence of water, and triphenylmethylamino can be cleaved especially by hydrogenolysis with a noble metal or noble metal oxide as catalyst, such as platinum, palladium or, especially, palladium hydroxide, the catalyst preferably being bonded to a carrier, such as carbon, silica gel or aluminium oxide, in inert solvents, such as an ether, preferably a lower alkyl-lower alkanoate, such as ethyl acetate, at temperatures of from 20° to 80° C., especially from 50° to 70° C., if necessary under elevated pressure, for example approximately from 1 to 10 bar; and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis, such as alcoholysis or hydrolysis, of the resulting substitution product. An amino group protected by 2-(tri-substituted silyl)-lower alkoxycarbonyl, such as 2-tri-lower alkylsilyl-lower alkoxycarbonyl, can be converted into the free amino group also by treatment with a salt of hydrofluoric acid that yields fluoride anions, as indicated above in connection with the freeing of a correspondingly protected carboxy group. Likewise, silyl, such as trimethylsilyl (*or tert-butyldimethylsilyl), bonded directly to a hetero atom, such as nitrogen, can be removed using fluoride ions, preferably with a fluoride of an organic quaternary nitrogen base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide, or especially an ether, such as tetrahydrofuran, at temperatures of from 0° to 50° C., especially at about room temperature.

Amino protected in the form of an azido group is convened into free amino, for example, by reduction, for example by catalytic hydrogenation with hydrogen in the presence of a hydrogenation catalyst, such as platinum oxide, palladium or Raney nickel, by reduction using mercapto compounds, such as dithiothreitol or mercaptoethanol, or by treatment with zinc in the presence of an acid, such as acetic acid. The catalytic hydrogenation is preferably carded out in an inert solvent, such as a halogenated hydrocarbon, for example methylene chloride, or in water or in a mixture of water and an organic solvent, such as an alcohol or dioxane, at approximately from 20° C. to 25° C., or with cooling or heating.

A hydroxy or mercapto group protected by a suitable acyl group, by a tri-lower alkylsilyl group or by unsubstituted or substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group protected by tert-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. A hydroxy group protected by benzyloxy is freed, for example, by hydrogenolysis, that is to say by treatment with hydrogen in the presence of a suitable hydrogenation catalyst, such as a palladium catalyst, for example bonded to a carrier, such as carbon, preferably in polar solvents, such as di-lower alkyl-lower alkanoylamides, for example dimethylformamide, ethers, such as cyclic ethers, for example dioxane, esters, such as lower alkylalkanoates, for example ethyl acetate, or alcohols, such as methanol, ethanol or propanol, with methanol being especially preferred, preferably at about room temperature. Mercapto protected by pyridyldiphenylmethyl can be freed, for example, using mercury(II) salts at pH 2–6 or by zinc/acetic acid or by electrolytic reduction; acetamidomethyl and isobutyrylamidomethyl can be freed, for example, by reaction with mercury(II) salts at pH 2–6; 2-chloroacetamidomethyl can be freed, for example, using 1-piperidinothiocarboxamide; and S-ethylthio, S-tert-butylthio and S-sulfo can be freed, for example, by thiolysis with thiophenol, thioglycolic acid, sodium thiophenolate or 1,4-dithiothreitol. Two hydroxy groups or an adjacent amino and hydroxy group which are protected together by means of a bivalent protecting group, preferably, for example, by a methylene group mono- or di-substituted by lower alkyl, such as lower alkylidene, for example isopropylidene, cycloalkylidene, for example cyclohexylidene, or benzylidene, can be freed by acid solvolysis, especially in the presence of a mineral acid or a strong organic acid. A tri-lower alkylsilyl group is likewise removed by acidolysis, for example by a mineral acid, preferably hydrofluoric acid, or a strong carboxylic acid. 2-halo-lower alkoxycarbonyl is removed using the above-mentioned reducing agents, for example a reducing metal, such as zinc, reducing metal salts, such as chromium(II) salts, or using sulfur compounds, for example sodium dithionite or preferably sodium sulfide and carbon disulfide. Esterified hydroxy groups, for example lower alkanoyloxy, such as acetyloxy, can also be freed by esterases, and acylated amino can be freed, for example, by suitable peptidases.

A sulfo group protected in the form of a sulfonic acid ester or sulfonamide is freed, for example, by acid hydrolysis, for example in the presence of a mineral acid, or preferably by basic hydrolysis, for example with an alkali metal hydroxide or alkali metal carbonate, for example sodium carbonate.

The temperatures for the freeing of the protected functional groups are preferably from −80° to 100° C., especially from −20° to 50° C., for example from 10° to 35° C., such as in the region of room temperature.

When several protected functional groups are present, if desired the protecting groups can be so selected that more than one such group can be removed simultaneously, for example by acidolysis, such as by treatment with trifluoroacetic acid, or with hydrogen and a hydrogenation catalyst, such as a palladium-on-carbon catalyst. Conversely, the groups can also be so selected that they cannot all be removed simultaneously, but rather in a desired sequence, the corresponding intermediates being obtained.

Process gg) (Formation of a carboxylic acid ester)

The acylation of the hydroxy group is effected, for example, in a manner known per se using an acid of formula XXV as defined above wherein T is as defined with the exception of unsubstituted or substituted aminocarbonyl, or a reactive derivative of a compound of formula XXV wherein T is as defined for compounds of formula I. A suitable reactive derivative is, for example, a carboxylic acid of formula XXV'

$$T\text{-}Z_1 \qquad (XXV')$$

wherein T is one of the radicals defined above for compounds of formula I', preferably one of the radicals mentioned with the exception of unsubstituted or substituted amino-carbonyl, and wherein $Z_1$ is reactively activated hydroxy (the compound of formula XXV' therefore contains, instead of a hydroxy function bonded to the carbonyl group, reactively activated hydroxy, preferably as defined below). The free carboxylic acid of formula XXV can be activated, especially also in situ, for example, by strong acids, such as a hydrohalic, sulfuric, sulfonic or carboxylic acid, or acidic ion exchangers, for example by hydrochloric, hydrobromic or hydriodic acid, sulfuric acid, an unsubstituted or substituted, for example halo-substituted, alkanecarboxylic acid, or by an acid of formula XXV, preferably with an excess of the acid of formula XXV, if necessary with the binding of the resulting water of reaction by water-binding agents, with removal of the water of reaction by azeotropic distillation or with extractive esterification, by acid anhydrides, especially inorganic or more especially organic acid anhydrides, for example carboxylic acid anhydrides, such as lower alkanecarboxylic acid anhydrides (with the exception of formic acid anhydride), for example acetic anhydride, or by suitable activating or coupling reagents of the type mentioned below. $T\text{-}Z_1$ may especially also be a carboxylic acid azide ($Z_1=$ azido; obtainable, for example, by reaction of a corresponding acid ester via the corresponding hydrazide and treatment thereof with nitrous acid); a carboxylic acid halide ($Z_1=$ halogen, especially chlorine or bromine), especially an acid chloride or bromide, obtainable, for example, by reaction with organic acid halides, especially with oxalyl dihalides, such as oxalyl dichloride, with inorganic acid halides, for example with acid halides of phosphorus or sulfur, such as phosphorus trichloride, phosphorus tribromide, phosphorus pentachloride, phosphorus pentabromide, phosphorus oxychloride, phosphorus oxybromide, thionyl chloride or thionyl bromide, or especially under mild conditions with tetra-lower alkyl-α-halo-enamines, for example tetramethyl-α-halo-enamines, especially 1-chloro-N,N,2-trimethyl-1-propenamine (preferably by reaction under an inert gas, such as nitrogen, in inert solvents, especially chlorinated hydrocarbons, such as methylene chloride or chloroform, or ethers, such as diethyl ether, dioxane or tetrahydrofuran, or mixtures thereof, at preferred temperatures of from −78° to 50° C., especially from −60° to 30° C., for example from −10° C. to room temperature (cf. Devos, A., et al., J. C. S. Chem. Commun. 1979, 1180–1181, and Haveaux, B., et al., Org. Synth. 59, 26 (1980)), it being possible for the resulting acid halide, for example the acid chloride of formula XXV' wherein $Z_1$ is chlorine, also to be used further directly in situ, for example by reaction with the compound of formula I in the presence of tertiary nitrogen bases, such as pyridine or 4-dimethylaminopyridine (DMAP, which is preferably added in catalytic amounts) or both of those bases, at preferred temperatures of from −20° to 50° C., especially from 10° C. to 40° C; an activated ester wherein $Z_1$ is the radical of an alcohol having electron-attracting substituents, especially cyanomethoxy or aryloxy wherein aryl is preferably phenyl or naphthyl that is mono- or poly-substituted by halogen, nitro and/or by cyano, for example nitrophenoxy, such as 4-nitrophenoxy or 2,4-dinitrophenoxy, or polyhalophenoxy, such as pentachlorophenoxy; or a symmetrical or, preferably, asymmetrical acid anhydride which can be obtained, for example, by the action of a salt, for example an alkali metal salt, of an acid of formula XXV or its reaction partner, preferably a lower alkanecarboxylic acid, such as acetic acid, such as the sodium or potassium salt, on a complementary acid halide, especially, in the case of the reaction with a salt of a carboxylic acid of formula XXV, a carboxylic acid halide, for example chloride, such as acetyl chloride, and, in the case of the reaction of a carboxylic acid halide of formula XXV' wherein $Z_1$ is halogen, for example chlorine or bromine, with a salt of a lower alkanecarboxylic acid, especially sodium or potassium acetate. There may be used as activating and coupling reagents for activating carboxylic acids of formula XXV in situ also carbodiimides, for example N,N'-di-CFC$_4$alkyl- or N,N'-di-C$_1$–C$_7$cycloalkyl-carbodiimide, such as diisopropylcarbodiimide or N,N'-dicyclohexylcarbodiimide, advantageously with the addition of an activating catalyst, such as N-hydroxysuccinimide or unsubstituted or substituted, for example halo-, $C_1$–$C_7$alkyl- or $C_1$–$C_7$alkoxy-substituted, N-hydroxy-benzotriazole or N-hydroxy-5-norbornene-2,3-dicarboxamide, $C_1$–$C_4$alkyl haloformate, for example isobutyl chloroformate, suitable carbonyl compounds, for example N,N-carbonyldiimidazole, suitable 1,2-oxazolium compounds, for example 2-ethyl-5-phenyl-1,2-oxazolium 3'-sulfonate or 2-tert-butyl-5-methyl-isoxazolium perchlorate, suitable acylamino compounds, for example 2-ethoxy-1-ethoxycarbonyl-1,2-dihydroquinoline, or suitable phosphoryl cyanamides or azides, for example diethylphosphoryl cyanamide or diphenylphosphoryl azide, also triphenylphosphine disulfide or 1-CFC$_4$alkyl-2-halopyridinium halides, for example 1-methyl-2-chloropyridinium iodide.

If two free carboxy groups are present in the compound of formula XXV it is also possible for an internal anhydride to be present as activated acid derivative.

$Z_1$ is preferably halogen, such as chlorine or bromine, and also acyloxy, for example lower alkanoyloxy, such as acetyloxy.

The reaction with an acid halide, such as an acid chloride, of formula XXV' ($Z_1$=Cl) is carried out especially in an ether, such as dioxane, tetrahydrofuran, or a nitrile, such as acetonitrile, or mixtures thereof, in the presence or absence of pyridine and in the absence or, preferably, in the presence of tertiary nitrogen bases, such as 4-dimethylaminopyridine, ethyl diisopropylamine, triethylamine or mixtures of two or more of those bases, with or without a protective gas, such as argon, at temperatures of from 0° to 80° C. or the reflux temperature, for example from room temperature to 50° C. or the reflux temperature if that is lower than 50° C.

For the specific case where $R^z$ in formula I' is unsubstituted or substituted amino there are suitable for the introduction of the corresponding radical T (unsubstituted or substituted aminocarbonyl) in the reaction with compounds of formula I especially the compounds of formula XXV' wherein $Z_1$ is halogen, such as chlorine, and wherein T is unsubstituted or substituted aminocarbonyl, which can be prepared, for example, by reaction of the complementary amines, for example unsubstituted or substituted alkylamines, aryl-lower alkylamines or arylamines, as defined for unsubstituted or substituted amino $R^z$, with phosgene or analogues thereof that contain instead of chlorine other halogen atoms, especially bromine, preferably in the presence of tertiary nitrogen bases, such as pyridine or triethylamine, and in inert solvents, for example chlorinated hydrocarbons, such as methylene chloride or chloroform, ethers, such as diethyl ether, tetrahydrofuran or dioxane, or carboxylic acid amides, such as dimethylformamide. Also suitable are corresponding N-carbonylazolides of formula XXV' ($Z_1$=N-containing heterocycle, such as 1-imidazolido) which are obtained, for example, by reaction with the corresponding N,N'-carbonyldiazolides, such as N,N'-carbonyldiimidazole, under conditions as just described for phosgene and analogues having other halogen atoms. The reaction of compounds of formula I with the corresponding compounds of formula XXV' is then likewise carried out under those conditions (cf. Staab, H. A., Angew. Chemie 74, 407 (1962)).

For the specific case of the introduction of aminocarbonyl T or an N-monosubstituted aminocarbonyl group T there is suitable as activated acid derivative especially the corresponding isocyanate of formula XXV''

$$Q\text{-}N\text{=}C\text{=}O \qquad (XXV'')$$

wherein Q is an amino-protecting group, for example trihaloacetyl, such as trifluoro- or trichloro-acetyl, or one of the unsubstituted or substituted lower alkyl radicals or aryl radicals mentioned above in the definition of unsubstituted or substituted amino $R^z$ wherein the amino group carries a substituent, it being possible, when Q is an amino-protecting group, to obtain after the reaction with the compound of formula I the corresponding compound of formula I' wherein $R_5$ is free aminocarbonyloxy by removal of the protecting group Q, as described for the freeing of amino protected by acyl under Process f), especially by acid hydrolysis, or, when Q is one of the mentioned substituted or unsubstituted lower alkyl radicals or aryl radicals, a corresponding compound of formula I containing aminocarbonyl T monosubstituted at the nitrogen atom. Both aminocarbonyl and N-monosubstituted aminocarbonyl T can be converted into N-disubstituted aminocarbonyl T by alkylation with a further unsubstituted or substituted lower alkyl radical using suitable starting materials and conditions analogous to those described below under "Additional Process Steps".

The mentioned reactions can be carried out under reaction conditions known per se, at customary temperatures, in the presence or, especially when lower alkanoyl anhydrides are used to activate the carboxylic acid of formula XXV, in the absence of inert solvents or diluents, for example in acid amides, for example carboxylic acid amides, such as dimethylformamide, dimethylacetamide or 1,3-dimethyl-3,4,5,6-tetrahydro-2(1H)-pyrimidinone (DMPU), or amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, acid anhydrides, such as acetic anhydride, esters, such as ethyl acetate, bisalkane sulfines, such as dimethyl sulfoxide, nitrogen heterocycles, such as pyridine, or mixtures of those solvents, especially in anhydrous solvents or solvent mixtures, it being possible to select for the above-mentioned reactions the particular solvents that are suitable in each case, there being used, as appropriate and expedient, salts of the compounds used, especially metal salts of carboxylic acids that are used, such as the alkali metal or alkaline earth metal salts, for example sodium or potassium salts, in the absence or the presence of catalysts, such as dimethylaminopyridine, condensation agents or neutralising agents, such as tertiary nitrogen bases, for example pyridine, triethylamine, N-methylmorpholine, dimethylaminopyridine or ethyl diisopropylamine, and, depending on the nature of the reaction and/or the reactants, under atmospheric pressure or in a closed vessel, under normal pressure or under elevated pressure, for example at the pressure produced in the reaction mixture under the reaction conditions in a closed tube, and/or in an inert atmosphere, for example under an argon or nitrogen atmosphere. Preference is given to reaction conditions that are mentioned specifically in any particular case or, especially, that are analogous to those mentioned in the Examples. The course of the reaction is advantageously monitored using customary methods of analysis, especially using thin-layer chromatography. From those reaction conditions it is possible to select the reaction conditions that are suitable for each of the reactions described in this text, reaction conditions that are specifically mentioned being especially preferred.

The reaction according to the invention is preferably carried out under mild conditions, especially at temperatures of from −10° to 60° C., for example from 0° to room temperature or at slightly elevated temperatures up to about 50° C., for example approximately from 0° to 40° C. Both in the case of the reaction with a carboxylic acid halide of formula XXV' wherein $Z_1$ is halogen, such as chlorine or bromine, and in the case of the reaction with an anhydride, especially a symmetrical anhydride ($Z_1$=O—T), the corresponding compound of formula XXV' (halide and T—O—T, respectively) is used especially in an approximately equimolar amount in relation to the compound of formula I or in excess, for example from 0.95 to 10 times the molar amount, preferably from 1.05 to 5 times the molar amount.

In starting materials of formulae I, XXV, XXV' and XXV'', functional groups, with the exception of groups that are intended to participate in the reaction or that do not react under the reaction conditions, are protected independently of one another by protecting groups.

The protecting groups are entirely analogous to those described under Process a) and aa) for the formation of an amide bond starting from compounds of formulae II and III or III'. The freeing of functional groups protected by protecting groups in the resulting compounds of formula I' having protected functions is effected in accordance with one or more of the methods mentioned under Process ff).

Process hh) (Nucleophilic substitution)

In starting materials of formulae XXVI and XXII, functional groups, with the exception of groups that are intended to participate in the reaction or that do not react under the reaction conditions, are protected independently of one another by protecting groups.

The protecting groups are entirely analogous to those described under Process a) and aa) for the formation of an amide bond starting from compounds of formulae II and III or III'.

A leaving group $W_1$ is especially a nucleofugal leaving group selected from hydroxy esterified by a strong inorganic or organic acid, such as hydroxy esterified by a mineral acid, for example a hydrohalic acid, such as hydrochloric acid, hydrobromic acid or hydriodic acid, or by a strong organic sulfonic acid, such as a lower alkanesulfonic acid that is unsubstituted or substituted, for example by halogen, such as fluorine, or an aromatic sulfonic acid, for example a benzenesulfonic acid that is unsubstituted or substituted by lower alkyl, such as methyl, halogen, such as bromine, and/or by nitro, for example a methanesulfonic acid, p-bromotoluenesulfonic acid or p-toluenesulfonic acid, and hydroxy esterified by hydrazoic acid.

The reaction between a compound of formula XXVI and a compound of formula XXVII wherein L is etherified or esterified hydroxy or mercapto is preferably carried out in the presence of a base, for example a hydroxide-containing base, such as a metal hydroxide, for example an alkali metal hydroxide, such as sodium or potassium hydroxide, or especially a metal carbonate or hydrogen carbonate, such as sodium or potassium carbonate or sodium or potassium hydrogen carbonate, there also being suitable in those cases, in addition to the solvents mentioned hereinbelow, preferably ketones, such as lower alkanones, or aqueous and protic solvents, or especially with the use of a metal alcoholate or thiolate as activated compound of formula XXVII or with the preparation thereof in situ in the presence of a strong base, for example an alkali metal hydride, such as sodium hydride, or in the presence of an alkali metal, such as sodium, in the absence or presence of a suitable solvent, especially an aprotic solvent, for example DMPU, an ether, such as diethyl ether, dioxane or tetrahydrofuran, or a carboxylic acid amide, such as dimethylformamide, at temperatures of from 0° C. to the reflux temperature, especially from 20° C. to the reflux temperature, if necessary under a protective gas, such as nitrogen or argon.

In the case of the reaction of compounds of formula XXVII wherein L is unsubstituted or substituted amino or is heterocyclyl bonded via nitrogen, the reaction is preferably carried out in the absence of a base or in the presence of a sterically hindered nitrogen base, especially a tertiary nitrogen base, such as 4-dimethylaminopyridine, pyridine or triethylamine, in an aqueous or non-aqueous solvent, such as an aqueous or non-aqueous alcohol, for example ethanol or methanol, esters, such as diethyl esters, ethers, such as diethyl ether, dioxane or tetrahydrofuran, carboxylic acid amides, such as dimethylformamide, or acetonitrile, at temperatures of from 0° C. to the reflux temperature, especially from 20° to 100° C.

Depending on the reaction conditions, the substitution can take place in the form of a first-order or second-order nucleophilic substitution.

The freeing of functional groups protected by protecting groups in the resulting compounds of formula I' having protected functions is effected in accordance with one or more of the methods mentioned under Process f) and ff).

Additional Process Steps

In the additional process steps, which are optional, functional groups of the starting compounds that are not intended to take part in the reaction may be unprotected or may be in protected form, for example they may be protected by one or more of the protecting groups mentioned above under Process a) and aa). The protecting groups may be retained in the end products or some or all of them may be removed in accordance with one of the methods mentioned under Process f) and ff).

Salts of compounds of formula I or I' having at least one salt-forming group may be prepared in a manner known per se. For example, salts of compounds of formula I or I' having acid groups may be formed, for example, by treatment with metal compounds, such as alkali metal salts of suitable organic carboxylic acids, for example the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I or I' are obtained in customary manner, for example by treatment with an acid or a suitable anion exchange reagent. Internal salts of compounds of formula I or I' containing acid and basic salt-forming groups, for example a free carboxy group and a free amino group, may be formed, for example, by the neutralisation of salts, such as acid addition salts, to the isoelectric point, for example with weak bases, or by treatment with ion exchangers.

Salts can be converted in customary manner into the free compounds; metal and ammonium salts can be converted, for example, by treatment with suitable acids or acidic ion exchangers, and acid addition salts, for example, by treatment with a suitable basic agent or basic ion exchangers.

Stereoisomeric mixtures of compounds of formula I or I', that is to say mixtures of diastereoisomers and/or enantiomers, such as, for example, racemic mixtures, can be separated into the corresponding isomers in a manner known per se by suitable separating processes. For example, mixtures of diastereoisomers can be separated into the individual diastereoisomers by fractional crystallisation, chromatography, solvent partition etc. Racemates can be separated from one another, after conversion of the optical antipodes into diastereoisomers for example by reaction with optically active compounds, for example optically active acids or bases, by chromatography on column materials covered with optically active compounds or by enzymatic methods, for example by selective reaction of only one of the two enantiomers. This separation can be carded out either at the stage of one of the starting materials or with the compounds of formula I or I' themselves.

In an obtainable compound of formula I' wherein T is a radical of formula Z wherein $R^z$ is phenyl- or naphthyl-methoxycarbonyl-substituted amino or further imino, for example in amino-lower alkyl N-substituted by those radicals or amino-lower alkyl N,N-disubstituted by phenyl- or naphthyl-methoxycarbonyl and by lower alkyl, also in a broader sense in N-phenyl- or naphthyl-methoxycarbonyl-pyrrolidin-2-yl or -amino-lower alkoxy-lower alkoxy-lower alkyl, the amino or imino group in the radical T in question can be converted into the corresponding amino- or N-lower alkylamino-lower alkylcarbonyl group by removal of phenyl- or naphthyl-lower alkoxycarbonyl, for example by hydrogenolysis, that is to say by treatment with hydrogen in the presence of a suitable hydrogenation catalyst, such as a palladium catalyst, for example bonded to a carder, such as carbon, preferably in polar solvents, such as di-lower alkyl-lower alkanoylamides, for example dimethylformamide, ethers, such as cyclic ethers, for example dioxane, esters, such as lower alkanoic acid lower alkyl esters, for example ethyl acetate, or alcohols, such as methanol or ethanol, especially at room temperature.

By reductive amination it is possible to convert amino-lower alkyl $R^z$ mono-N-substituted by heterocyclyl-lower alkyl, such as imidazolylmethyl or pyridylmethyl, each bonded via a ring carbon atom, by aryl-lower alkyl, such as phenyl- or naphthyl-lower alkyl, or especially by lower alkyl, as a constituent of T in a compound of formula I' into lower alkyl $R^z$ N,N-disubstituted by an additional radical selected from heterocyclyl-lower alkyl, such as imidazolyl-methyl or pyridylmethyl, each bonded via a ring carbon atom, and aryl-lower alkyl, such as phenyl- or naphthyl-lower alkyl. The reaction between a corresponding mono-N-substituted compound of formula I' and a corresponding heterocyclyl- or aryl-lower alkyl-ketone or lower alkanealdehyde is carded out with catalytic hydrogenation, for example in the presence of a noble metal catalyst, such as platinum or especially palladium, bonded to a carrier, preferably carbon, or a heavy metal catalyst, such as Raney nickel, at normal pressures or at pressures of from 1 to 100 bar, preferably in the presence of a noble metal catalyst at approximately normal pressure, in organic solvents, for example alcohols, such as ethanol or especially methanol, in the absence or, preferably, in the presence of a carboxylic acid, such as a lower alkanoic acid, for example acetic acid, at preferred temperatures of from 0° to 50° C., for example at room temperature, or with reduction by means of a complex boron hydride, such as sodium cyanoborohydride.

In a compound of formula I' wherein T is N-triphenylmethyl-imidazolyl-lower alkyl-carbonyl, the triphenylmethyl radical can be removed, as described under Process f), yielding the corresponding compound of formula I' wherein T is imidazol(-2-, -4- or -5-) yl.

In a compound of formula I or I' wherein one or more of the radicals $R_2$, $R_3$ and $A_2$ is substituted by benzyloxy, the benzyloxy radical can be removed, as described under Process f), yielding the corresponding compounds of formula I or I' containing hydroxy in the place of benzyloxy.

In an obtainable compound of formula I wherein the hydroxy group bonded to the carbon atom that is vicinal to the carbon atom carrying the radical $R_2$-$CH_2$— is free, the free hydroxy group can be converted into a protected hydroxy group by introducing a protecting group, as described above under Process a), for example it can be convened into an esterified hydroxy group, for example into lower alkanoyloxy, such as acetoxy. The esterification is carded out analogously to the condensation to form amides mentioned under Process a), a hydroxy group reacting instead of the amino component. The reaction is carded out preferably under conditions analogous to those mentioned under process a), especially using a lower alkanoyl anhydride, for example acetic anhydride, to form the corresponding lower alkanoyloxy group, in an organic solvent, for example a cyclic ether, such as tetrahydrofuran, in the presence of a cyclic tertiary amine, such as dimethylaminopyridine, and/or a tri-lower alkylamine, such as triethylamine, at temperatures of from 0° C. to the boiling point of the reaction mixtures, especially from 10° to 30° C.

In an obtainable compound of formula I or I', an amino or carboxamide group can be substituted, a carboxy group present in free or reactive form can be esterified or amidated or an esterified or amidated carboxy group can be converted into a free carboxy group.

The substitution of a carboxamide group or of another primary or secondary amino group, for example for the formation of the carbamoyl derivatives mono- or di-lower alkylcarbamoyl and mono- or di-hydroxy-lower alkylcarbamoyl mentioned above as a substituent of thiomorpholino or morpholino formed by $R_4$ and $R_5$ together with the bonding nitrogen atom, or with the formation of the above-mentioned derivatives of the substituent amino at thiomorpholino or morpholino formed by $R_4$ and $R_5$ together with the bonding nitrogen atom, or for the formation of N,N-disubstituted amino $R^z$ in compounds of formula I' wherein the nitrogen of the amino groups to be reacted is bonded to hydrogen, is effected, for example, by alkylation.

Suitable agents for alkylating a carboxamide group in a compound of formula I or I' are, for example, diazo compounds, for example diazomethane. Diazomethane can be decomposed in an inert solvent, the free methylene formed reacting with the carboxamide group in the compound of formula I or I'. The decomposition of diazomethane is carded out preferably catalytically, for example in the presence of a noble metal in finely divided form, for example copper, or a noble metal salt, for example copper(I) chloride or copper(II) sulfate.

Alkylating agents are also mentioned in German Offenlegungsschrift 2 331 133, for example alkyl halides, sulfonic acid esters, Meerwein salts or 1-substituted 3-aryltriazenes, which can be reacted under the conditions mentioned therein with a compound of formula I or I' containing a carboxamide group.

Further alkylating agents are selected from corresponding alkyl compounds that carry a substituent X wherein X is a leaving group. A leaving group is especially a nucleofugal leaving group selected from hydroxy esterified by a strong inorganic or organic acid, such as hydroxy esterified by a mineral acid, for example a hydrohalic acid, such as hydrochloric, hydrobromic or hydriodic acid, or by a strong organic sulfonic acid, such as an unsubstituted or substituted, for example halo-substituted, such as fluoro-substituted, lower alkanesulfonic acid, or an aromatic sulfonic acid, for example a benzenesulfonic acid that is unsubstituted or substituted by lower alkyl, such as methyl, by halogen, such as bromine, and/or by nitro, for example a methanesulfonic, trimethanesulfonic or p-toluenesulfonic acid, and hydroxy esterified by hydrazoic acid.

The reaction can be carried out under the conditions of a first-order or second-order nucleophilic substitution.

For example, one of the compounds containing a substituent X wherein X is a leaving group with high polarisability of the electron shell, for example bromine or iodine, can be reacted in a polar aprotic solvent, for example acetone, acetonitrile, nitromethane, dimethyl sulfoxide or dimethylformamide. The substitution reaction is carried out if desired at reduced or elevated temperature, for example in a temperature range of from approximately −40° to approximately 100° C., preferably from approximately −10° to approximately 50° C., and if desired under an inert gas, for example under a nitrogen or argon atmosphere.

For the esterification or amidation of a carboxy group in a compound of formula I or I', for example for the amidation of a free carboxy group of an amino acid, such as Glu or Asp, with ammonia, or of a free carboxy group at thiomorpholino or morpholino formed by $R_4$ and $R_5$ together with the bonding nitrogen atom, if desired the free acid can be used or the free acid can be converted into one of the abovementioned reactive derivatives and reacted with an alcohol, with ammonia, or with a primary, or secondary amine, or, in the case of esterification, the free acid or a reactive salt, for example the caesium salt, can be reacted with a reactive derivative of an alcohol. For example the caesium salt of a carboxylic acid can be reacted with a halide or sulfonic acid ester corresponding to the alcohol. The esterification of the carboxy group can also be carded out with other customary alkylating agents, for example with diazomethane, alkyl halides, sulfonic acid esters, Meerwein salts or 1-substituted 3-aryltriazenes, etc.

For the conversion of an esterified or amidated carboxy group into the free carboxy group it is possible to use one of the methods described above for the removal of carboxy-protecting groups or, if desired, alkaline hydrolysis under customary reaction conditions, such as those mentioned in Organikum, 17th edition, VEB Deutscher Verlag der Wissenschaften, Berlin 1988.

In a compound of formula I or I', an esterified carboxy group can be converted into an unsubstituted or substituted carboxamide group by aminolysis with ammonia or with a primary or secondary amine. The aminolysis can be carried out in accordance with the customary reaction conditions, such as those mentioned for such reactions in Organikum, 15th edition, VEB Deutscher Verlag der Wissenschaften, Berlin (East) 1976.

A free amino group present in a compound of formula I or I' can be acylated, for example to introduce one of the radicals mentioned for $R_1$ other than hydrogen. The acylation is carded out in accordance with the methods mentioned above under Process a) or one of the methods mentioned for protecting groups or, for example, according to one of the processes mentioned in Organikum, 17th edition, VEB Deutscher Verlag der Wissenschaften, Berlin (East) 1988.

In an obtainable compound of formula I or I' wherein the substituents are as defined and at least one free hydroxy group is present and the remaining functional groups are in protected form, the free hydroxy group, for example the hydroxy group at thiomorpholino or morpholino formed by $R_4$ and $R_5$ together with the bonding nitrogen atom, can be acylated or etherified.

The acylation can be carried out with acylating reagents according to one of the methods mentioned under Processes a) to e) or gg) or according to one of the methods mentioned for protecting groups or according to one of the processes mentioned in Organikum, 17th edition, VEB Deutscher Verlag der Wissenschaften, Berlin (East) 1988.

The etherification can be carried out with the abovementioned alkylating agents and under the same reaction conditions, for example with diazomethane, alkyl halides, sulfonic acid esters, Meerwein salts, 1-substituted 3-aryltriazenes, etc.. Preference is given to the reaction with corresponding alkyl halides, such as lower alkyl iodides or bromides, in the presence of caesium carbonate in suitable solvents or solvent mixtures, for example in N,N-di-lower alkyl-lower alkanoylamides, such as dimethylformamide or dimethylacetamide, or ethers, such as dioxane, or mixtures thereof, at temperatures of from 0° to the reflux temperature, preferably from 30° to 60° C., for example at about 50° C.

In a compound of formula I or I', any groups that correspond to protecting groups, and also suitable radicals $R_1$ other than hydrogen can be removed in accordance with one of the methods mentioned under Process f) and ff), especially by hydrolysis, for example in the presence of bases, such as alkali metal or alkaline earth metal hydroxides, for example sodium hydroxide, or acids, such as organic acids or mineral acids, for example a hydrogen halide, such as hydrogen chloride. The hydrolysis is effected under the customary conditions, for example in aqueous solution or in anhydrous solvents, especially in ethers, such as dioxane, at temperatures of from −50° C. to the reflux temperature of the reaction mixture in question, for example from 0° to 50° C., preferably in the presence of a protective gas, such as argon or nitrogen, or furthermore by hydrogenolysis (for example in the case of benzyloxycarbonyl radicals), preferably in polar solvents, such as alcohols, for example methanol or ethanol, or esters, such as lower alkyl-lower alkanoates, for example ethyl acetate, at the last-mentioned temperatures and in the presence of suitable hydrogenation catalysts, such as a palladium catalyst, which is preferably bonded to a carrier, such as carbon.

In a compound of formula I or I' wherein at least one of the radicals $R_2$ and $R_3$ is a phenyl group and/or one or more of the radicals $B_1$, $A_1$ and $A_2$ is phenylalanine, it being possible for each of the phenyl radicals to be substituted, as described above, the corresponding phenyl radical(s) can be reduced, for example hydrogenated, selectively to (a) corresponding cyclohexyl radical(s). The hydrogenation is preferably carried out in the presence of a catalyst that allows the selective hydrogenation of double bonds in the presence of peptide bonds, especially a catalyst comprising heavy metal oxides, such as a Rh(III)/Pt(VI) oxide catalyst according to Nishimura (S. Nishimura, Bull. Chem. Soc. Japan 33,566 (1960)), in suitable solvents, especially water, alcohols, such as methanol or ethanol, esters, such as ethyl acetate, or ethers, such as dioxane, for example in methanol, at temperatures of from 0 to 150° C., preferably from 10° to 50° C., for example at room temperature, and at hydrogen pressures of from 1 to 50 bar, for example at normal pressure.

Pharmaceutical Compositions:

The invention relates also to pharmaceutical compositions comprising compounds of formula I or I'.

The pharmacologically acceptable compounds of the present invention may be used, for example, in the preparation of pharmaceutical compositions that comprise an effective amount of the active ingredient together or in admixture with a significant amount of inorganic or organic, solid or liquid, pharmaceutically acceptable carriers.

The pharmaceutical compositions according to the invention are compositions for enteral, such as nasal, buccal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carder. The dose of the active ingredient depends on the species of warm-blooded animal, body weight, age and individual condition, individual pharmacokinetic data, the disease to be treated and the mode of administration.

The invention relates also to pharmaceutical compositions and a method for treating diseases caused by retroviruses, for example AIDS or the preliminary stages thereof, especially when HIV-2 or more especially HIV-1 is the cause of the disease, preferably wherein a compound of formula I or I' according to the invention is present in an amount that is therapeutically effective against retroviral diseases, such as AIDS and the preliminary stages thereof, in a pharmaceutical composition that is suitable for administration to a warm-blooded animal, especially a human being, for the treatment of a retroviral disease, such as AIDS, or wherein a therapeutically effective amount of a compound of formula I or I' according to the invention is administered in a treatment method to a warm-blooded animal, for example a human being, who on account of one of the mentioned diseases, especially AIDS, requires such treatment, in an amount that is therapeutically effective against retrovital diseases, such as AIDS and the preliminary stages thereof. The dose to be administered to warm-blooded animals, for example human beings of approximately 70 kg body weight, is from approximately 3 mg to approximately 10 g, preferably from approximately 40 mg to approximately 4 g, for example approximately from 300 mg to 1.5 g per person per day, divided preferably into 1 to 3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions or dispersions, and especially isotonic aqueous solutions, dispersions or suspensions, are preferably used, it being possible, for example in the case of lyophilised compositions that comprise the active ingredient alone or together with a carder, for example mannitol, for such solutions, dispersions or suspensions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semisynthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Pads), "Miglyol 812" (triglyceride of saturated fatty acids with a chain length of $C_8$ to $C_{12}$, H üls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules, or by preparing dispersions, preferably with phospholipids, which are introduced into vials. It is also possible for the active ingredients to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and also soft, sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil, fatty acid esters or lower alkylene glycols, such as 1,2-propylene glycol monolaurate (mixture of the two constitutional isomers; Gattefossé S. A., Saint Priest, France), ®Gelucire (glycerides and partial polyglycerides of fatty acid; Gattefossé S. A., Saint Priest, France) or liquid polyethylene glycols, such as PEG 300, it likewise being possible for stabilisers and/or antibacterial agents to be added. Dyes or pigments may be added to the tablets or dragée coatings or to the capsule casings, for example for identification purposes or to indicate different doses of active ingredient. Especially preferred as pharmaceutical compositions are phospholipid-stabilised dispersions of the active ingredient, preferably for oral administration, comprising a) a phospholipid or several phospholipids of the formula

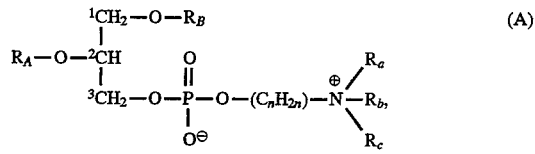

wherein $R_A$ is $C_{10-20}$acyl, $R_B$ is hydrogen or $C_{10-20}$acyl, $R_a$, $R_b$ and $R_c$ are hydrogen or $C_{1-4}$alkyl and n is an integer from two to four, if desired b) a further phospholipid or several further phospholipids c) the active ingredient and d) a pharmaceutically acceptable carrier liquid and, if desired, further excipients and/or preservatives.

The process for the preparation of those dispersions is as follows: a solution or suspension of components a) and c) or a), b) and c), but preferably of a) and b) in a ratio by weight of from 20:1 to 1:5, especially from 5:1 to 1:1, is converted into a dispersion by dilution with water and the organic solvent is then removed, for example by centrifugation, gel filtration, ultrafiltration or especially by dialysis, for example tangential dialysis, preferably against water, and then, preferably after the addition of excipients or preservatives and if necessary with the establishment of an acceptable pH value by the addition of pharmaceutically acceptable buffers, such as phosphate salts or organic acids (pure or dissolved in water), such as acetic acid or citric acid, preferably from pH 3 to 6, for example pH 4–5, the dispersion obtained is concentrated (unless it already has the correct active ingredient concentration) preferably to an active ingredient concentration of from 2 to 30 mg/ml, especially from 10 to 20 mg/ml, concentration preferably being effected in accordance with the methods last mentioned for the removal of an organic solvent, especially by ultrafiltration, for example using an apparatus for carrying out tangential dialysis and ultrafiltration.

The phospholipid-stabilised dispersion that can be prepared in accordance with that process is stable for at least several hours at room temperature, is reproducible as regards the proportions of the components and is toxicologically acceptable and is therefore especially suitable for oral administration to human beings.

The size of the particles obtained in the dispersion is variable and is preferably from approximately $1.0 \times 10^{-8}$ to approximately $1.0 \times 10^{-5}$ m, especially from approximately $10^{-7}$ to approximately $2 \times 10^{-6}$ m.

The nomenclature for the phospholipids of formula A and the numbering of the carbon atoms are in accordance with the recommendations of the IUPAC-IUB Commission on Biochemical Nomenclature (CBN) (sn-nomenclature, stereospecific numbering) given in the Eur. J. of Biochem. 79, 11–21 (1977) "Nomenclature of Lipids".

In a phospholipid of formula A, $R_A$ and $R_B$ having the definitions $C_{10-20}$acyl are preferably straight-chained $C_{10-20}$alkanoyl having an even number of carbon atoms and straight-chained $C_{10-20}$alkenoyl having a double bond and an even number of carbon atoms.

Straight-chained $C_{10-20}$alkanoyl $R_A$ and $R_B$ having an even number of carbon atoms are, for example, n-dodecanoyl, n-tetradecanoyl, n-hexadecanoyl or n-octadecanoyl. Straight-chained $C_{10-20}$alkenoyl $R_A$ and $R_B$ having a double bond and an even number of carbon atoms are, for example, 6-cis-, 6-trans-, 9-cis- or 9-trans-dodecenoyl, -tetra-decenoyl, -hexadecenoyl, -octadecenoyl or -icosenoyl, especially 9-cis-octadecenoyl (oleoyl).

In a phospholipid of formula A, n is an integer from two to four, preferably two. The group of the formula -$(C_nH_{2n})$- is unbranched or branched alkylene, for example 1,1-ethylene, 1,1-, 1,2- or 1,3-propylene or 1,2-, 1,3- or 1,4-butylene. 1,2-Ethylene (n=2) is preferred.

Phospholipids of formula A are, for example, naturally occurring cephalins wherein $R_a$, $R_b$ and $R_c$ are hydrogen, or naturally occurring lecithin s wherein $R_a$, $R_b$ and $R_c$ are methyl, for example cephalin or lecithin from soybeans, bovine brain, bovine liver or hen's eggs having different or identical acyl groups $R_A$ and $R_B$ or mixtures thereof.

Synthetic, substantially pure phospholipids of formula A having different or identical acyl groups $R_A$ and $R_B$ are preferred.

The term "synthetic" phospholipid of formula A defines phospholipids that have a uniform composition as regards $R_A$ and $R_B$. Such synthetic phospholipids are preferably the lecithins and cephalins defined below, the acyl groups $R_A$ and $R_B$ of which have a defined structure and are derived from a defined fatty acid having a degree of purity higher than approximately 95%. $R_A$ and $R_n$ may be identical or different and may be unsaturated or saturated. $R_A$ is preferably saturated, for example n-hexadecanoyl, and $R_a$ is preferably unsaturated, for example 9-cis-octadecenoyl (=oleoyl).

The term "naturally occurring" phospholipids of formula A defines phospholipids that do not have a uniform composition as regards $R_A$ and $R_B$. Such natural phospholipids are likewise lecithins and cephalins the acyl groups $R_A$ and $R_B$ of which are structurally undefinable and are derived from naturally occurring fatty acid mixtures.

The term "substantially pure" phospholipid defines a degree of purity of more than 70% (by weight) of the phospholipid of formula A, which can be established by suitable determination methods, for example by paper chromatography.

Special preference is given to synthetic, substantially pure phospholipids of formula A wherein $R_A$ is straight-chained $C_{10-20}$alkanoyl having an even number of carbon atoms and $R_b$ is straight-chained $C_{10-20}$alkenoyl having a double bond and an even number of carbon atoms. $R_a$, $R_b$ and $R_c$ are methyl and n is two.

In an especially preferred phospholipid of formula A, $R_A$ is n-dodecanoyl, n-tetradecanoyl, n-hexadecanoyl or n-octadecanoyl and $R_B$ is 9-cis-dodecenoyl, 9-cis-tetradecenoyl, 9-cis-hexadecenoyl, 9-cis-octadecenoyl or 9-cis-icosenoyl. $R_a$, $R_b$ and $R_c$ are methyl and n is two.

A very especially preferred phospholipid of formula A is synthetic 1-n-hexadecanoyl-2-(9-cis-octadecenoyl)-3-sn-phosphatidyl choline having a purity of more than 95%.

Preferred natural, substantially pure phospholipids of formula A are especially lecithin (L-α-phosphatidyl choline) from soybeans or hen's eggs.

The names given in brackets are also customarily used for the acyl radicals in the phospholipids of formula A: 9-cis-dodecenoyl (lauroleoyl), 9-cis-tetradecenoyl (myristoleoyl), 9-cis-hexadecenoyl (palmitoleoyl), 6-cis-octadecenoyl (petroseloyl), 6-trans-octadecenoyl (petroselaidoyl), 9-cis-octadecenoyl (oleoyl), 9-trans-octadecenoyl (elaidoyl), 11-cis-octadecenoyl (vaccenoyl), 9-cis-icosenoyl (gadoleoyl), n-dodecanoyl (lauroyl), n-teuradecanoyl (myristoyl), n-hexadecanoyl (palmitoyl), n-octadecanoyl (stearoyl), n-icosanoyl (arachidoyl).

Other phospholipids are preferably esters of phosphatidic acid (3-sn-phosphatidic acid) with the mentioned acyl radicals, such as phosphatidyl serine and phosphatidyl ethanolmine.

Sparingly soluble active ingredients may also be present in the form of water-soluble, pharmaceutically acceptable salts, as defined above.

The carrier liquid d) comprises the components a), b) and c) or a) and c) as liposomes in such a manner that for a period of from several days up to several weeks no solids or solid aggregates, such as micelies, re-form and the liquid comprising the said components is administrable, preferably orally, if necessary after filtration.

The carrier liquid d) may comprise pharmaceutically acceptable, non-toxic excipients, for example water-soluble excipients that are suitable for producing isotonic conditions, for example ionic additives, such as sodium chloride, or non-ionic additives (structure formers), such as sorbitol, mannitol or glucose, or water-soluble stabilisers for the liposome dispersion, such as lactose, fructose or sucrose.

In addition to the water-soluble excipients, the carrier liquid may also comprise emulsifiers, wetting agents or surfactants that can be used for liquid pharmaceutical formulations, especially emulsifiers, such as oleic acid, non-ionic surfactants of the fatty acid polyhydroxy alcohol ester type, such as sorbitan monolaurate, monooleate, monostearate or monopalmitate, sorbitan tristearate or trioleate, polyoxyethylene adducts of fatty acid polyhydroxy alcohol esters, such as polyoxyethylene sorbitan monolaurate, monooleate, monostearate, monopalmitate, tristearate or trioleate, polyethylene glycol fatty acid esters, such as polyoxyethyl stearate, polyethylene glycol-400-stearate, polyethylene glycol-2000-stearate, especially ethylene oxide/propylene oxide block polymers of the Pluronic® type (Wyandotte Chem. Corp.) or the Synperonic® type (ICI).

Preferred preservatives are, for example, antioxidants, such as ascorbic acid, or microbicides, such as sorbic acid or benzoic acid.

Starting materials:

The present invention relates also to novel starting materials and/or intermediates and to processes for their preparation. The starting materials used and the reaction conditions selected are preferably those which result in the compounds described as being preferred.

All starting materials can preferably be prepared analogously to the processes mentioned in the Examples.

In the preparation of all starting materials, free functional groups that are not intended to participate in the reaction in question, may be unprotected or may be in protected form, for example they may be protected by the protecting groups mentioned above under Process a) and aa). If necessary, the functional groups that are not intended to participate in the reaction are always in protected form (cf. for example the protection of compounds of formula XXI in the reaction, for example, to form compounds of formula XXII', see below, at the carboxy group that is not to be reacted, in order to avoid lactonisation). Those protecting groups can be removed at suitable times by the reactions described under Process f) and ff). The compounds having salt-forming groups can also be used in the form of salts, and at any stage salts can be formed or converted into the free compounds again.

In the formulae, unless the stereochemistry of asymmetric carbon atoms is defined directly by the choice of corresponding bond symbols, the configuration of asymmetric carbon atoms is indicated by the configuration symbol which is selected from (S), (R) and (S,R).

The carboxylic or sulfonic acids of formula II, or reactive derivatives thereof, are known and are commercially available or can be prepared in accordance with processes known per se.

The compounds of formula III or III' are known or can be prepared in accordance with processes known per se. They can be obtained, for example, from compounds of formula

(XII)

wherein $R_2$ is as defined for compounds of formula I or I' and Pa is an amino-protecting group, especially lower alkoxycarbonyl, such as tert-butoxycarbonyl, or phenyl-lower alkoxycarbonyl, such as benzyloxycarbonyl, (or further analogues thereof containing hydrogen in place of Pa, which can then be protected subsequently), by reduction to a compound of formula

(XIII)

(or further an analogue having hydrogen in place of Pa) wherein the radicals are as last defined.

The reduction of amino acid derivatives of formula XII to the corresponding aldehydes XIII is effected, for example, by reduction to the corresponding alcohols and subsequent oxidation to the aldehydes of formula XIII.

The reduction to the alcohols is effected especially by hydrogenation of the corresponding acid halides or other activated carboxylic acid derivatives mentioned under Process a), or by reaction of activated carboxylic acid derivatives of compounds of formula XII, especially anhydrides with organic carboxylic acids, preferably those of haloformic acid esters, such as chloroformic acid isobutyl ester, (which are preferably obtained by reaction of compounds of formula XII in the presence of basic amines, for example tri-lower alkylamines, such as triethylamine, in organic solvents, such as cyclic ethers, for example dioxane, at temperatures of from −50° to 80° C., preferably from 0° to 50° C.) with complex hydrides, such as alkali metal borohydrides, for example sodium borohydride, in aqueous solution in the presence or absence of the organic solvents last used, at temperatures of from −50° to 80° C., preferably from 0° to 50° C. The subsequent oxidation of the resulting alcohols is preferably effected with those oxidising agents which selectively convert the hydroxy group into an aldehyde group, for example chromic acid or derivatives thereof, such as pyridinium chromate or tert-butyl chromate, dichromate/sulfuric acid, sulfur trioxide in the presence of heterocyclic bases, such as pyridine/$SO_3$ (preferably dissolved in di-lower alkyl sulfoxides, such as dimethyl sulfoxide; or also aromatic solvents, such as toluene, or mixtures of those solvents), also nitric acid, pyrolusite or selenium dioxide, in water, aqueous or organic solvents, such as halogenated solvents, for example methylene chloride, carboxylic acid amides, such as dimethylformamide, and/or cyclic ethers, such as tetrahydrofuran, in the presence or absence of basic amines, for example tri-lower alkylamines, such as triethylamine, at temperatures of from −70° to 100° C., preferably from −70° to −50° C. or from −10° to 50° C., for example as described in European Patent Application EP-A-0 236 734.

Direct reduction of the compounds of formula XII to the aldehydes is also possible, for example by hydrogenation in the presence of a partially poisoned palladium catalyst or by reduction of the corresponding amino acid esters, for example the lower alkyl esters, such as ethyl esters, with complex hydrides, for example boron hydrides, such as sodium borohydride, or preferably aluminium hydrides, for example lithium aluminium hydride, lithium tri(tert-butoxy) aluminium hydride or especially diisobutylaluminium hydride, in non-polar solvents, for example in hydrocarbons or aromatic solvents, such as toluene, at from −100° to 0° C., preferably from −70 to −30° C., and subsequent reaction to form the corresponding semicarbazones, for example with the corresponding acid salts of semicarbazones, such as semicarbazide hydrochloride, in aqueous solvent systems, such as alcohol/water, for example ethanol/water, at temperatures of from −20° to 60° C., preferably from 10° to 30° C., and reaction of the resulting semicarbazone with a reactive aldehyde, for example formaldehyde, in an inert solvent, for example a polar organic solvent, for example a carboxylic acid amide, such as dimethylformamide, at temperatures of from −30° to 60° C., preferably from 0° to 30° C., and then with an acid, for example a strong mineral acid, such as a hydrogen halide, in aqueous solution, if desired in the presence of the solvent previously used, at temperatures of from −40° to 50° C., preferably from −10° to 30° C. The corresponding esters are obtained by reaction of the amino acids with the corresponding alcohols, for example ethanol, analogously to the conditions used in the condensation under Process b), for example by reaction with inorganic acid halides, such as thionyl chloride, in organic solvent mixtures, such as mixtures of aromatic and alcoholic solvents, for example toluene and ethanol, at temperatures of from −50° to 50° C., preferably from −10° to 20° C.

The preparation of compounds of formula XIII is carried out in an especially preferred manner under conditions analogous to the reaction conditions mentioned in J. Org. Chem. 47, 3016 (1982), J. Org. Chem. 43, 3624 (1978) or J. Org. Chem. 51, 3921 (1986).

For the synthesis of a compound of formula III or III', a compound of formula XIII is then reacted with a reactive tetraalkylsilane, preferably a halomethyl-tri-lower alkylsilane, such as chloromethyltrimethylsilane, in an inert solvent, for example an ether, such as diethyl ether, a cyclic ether, such as dioxane, or an ester, such as ethyl acetate, at temperatures of from −100° to 50° C., preferably from −65° to 40° C., there being obtained compounds of formula

wherein $R_6$, $R_7$ and $R_8$ are lower alkyl, for example methyl, and the remaining radicals are as last defined; the resulting compounds are converted in the presence of a Lewis acid, such as boron trifluoride ethyl etherate, in an inert solvent, especially a halogenated hydrocarbon, such as methylene chloride or chloroform, with subsequent aftertreatment with an aqueous base, for example sodium hydroxide solution, at temperatures of from −30° to 80° C., especially from 0° to 50° C., with elimination and protecting group removal, into an olefinic compound of formula

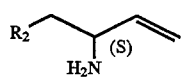

wherein $R_2$ is as defined for compounds of formula I or I'; an amino-protecting group Pa is re-introduced into the corresponding olefin, as described under Process a) for the introduction of amino-protecting groups, especially with the aid of an acid anhydride in a chlorinated hydrocarbon, such as methylene chloride or chloroform, at temperatures of from −50° to 80° C., especially from 0° to 35° C., there being obtained a protected aminoolefin of formula

in which the radicals are as last defined; the double bond is converted into an oxirane, preferably stereoselectively using peroxides, especially peroxycarboxylic acids, for example haloperbenzoic acid, such as m-chloroperbenzoic acid, in an inert organic solvent, preferably a halogenated hydrocarbon, such as methylene chloride or chloroform, at temperatures of from −50° to 60° C., especially from −10° to 25° C., and, if necessary, diastereoisomers are separated, there being obtained an epoxide of formula

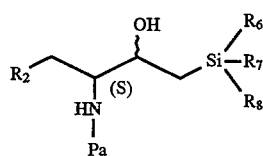

in which the radicals are as last defined; a suitable malonic acid diester, for example malonic acid dimethyl ester or malonic acid diethyl ester, is added to the olefins in question, for example by activation of the methylene group of the malonic acid diester by means of an alkali metal, for example sodium, in a polar anhydrous solvent, such as an alcohol, for example methanol or ethanol, at temperatures of from −50° to 80° C., especially from 0° to 35° C., and the solution is treated with an acid, such as a carboxylic acid, for example citric acid, them being obtained a lactone of formula

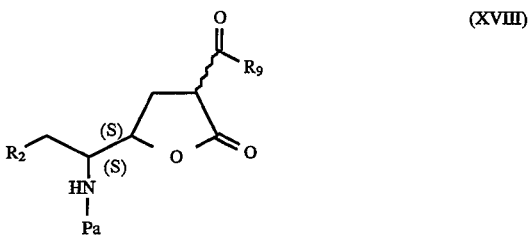

wherein $R_9$ is lower alkoxy, for example methoxy or ethoxy, and the remaining radicals are as last defined; if desired, in those compounds in which $R_2$ is phenyl that is unsubstituted or substituted as described for compounds of formula I or I', that radical is reduced to cyclohexyl, especially by hydrogenation, preferably in the presence of catalysts, such as noble metal oxides, for example mixtures of Rh(III)/Pt (VI) oxides (in accordance with Nishimura), preferably in polar solvents, such as alcohols, for example methanol, at normal pressure or at up to 5 bar, preferably at normal pressure, at temperatures of from −20° to 50° C., preferably from 10° to 35° C; a compound of formula XVIII obtained directly or after hydrogenation is reacted with a reagent that introduces the radical $R_3$-$CH_2$—, for example of the formula $R_3$-$CH_2$—W wherein $R_3$ is as defined for compounds of formula I or I' and W is a nucleofugal leaving group selected from hydroxy esterified by a strong inorganic or organic acid, such as hydroxy esterified by a mineral acid, for example a hydrohalic acid, such as hydrochloric, hydrobromic or hydriodic acid, or by a strong organic sulfonic acid, such as an unsubstituted or substituted, for example halo'substituted, such as fluoro-substituted, lower alkanesulfonic acid or an aromatic sulfonic acid, for example benzenesulfonic acid that is unsubstituted or substituted by lower alkyl, such as methyl, halogen, such as bromine, and/or by nitro, for example a methanesulfonic, trimethanesulfonic or p-toluenesulfonic acid, and hydroxy esterified by hydrazoic acid, especially bromide, in an anhydrous polar solvent, for example an alcohol, such as ethanol, in the presence of an alkali metal, for example sodium, at temperatures of from −50° to 80° C., preferably from 0° to 35° C., yielding a compound of formula

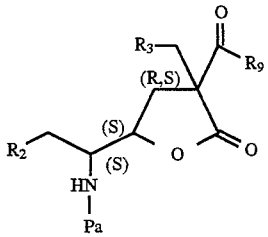
(XIX)

wherein the radicals are as last defined; the compound of formula XIX is hydrolysed and decarboxylated, for example by hydrolysis by means of a base, such as an alkali metal hydroxide, for example lithium hydroxide or sodium hydroxide, at temperatures of from −50° to 80° C., preferably approximately from 0° to 35° C., in an organic solvent, for example an ether, such as dimethoxyethane, or an alcohol, such as ethanol, and subsequent decarboxylation by heating in an inert solvent, preferably a hydrocarbon, for example an aromatic hydrocarbon, such as toluene, at temperatures of from 40° to 120° C., preferably from 70° to 120° C., there being obtained a compound of formula

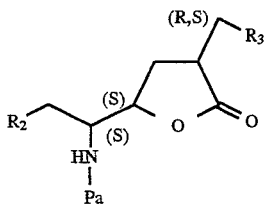
(XX)

wherein the radicals are at last defined; the resulting (R,S,S)- and (S,S,S)-isomers are separated by column chromatography, and the (R,S,S)-isomer is used further and, for the purpose of opening the lactone ring, is reacted with a base, such as an alkali metal hydroxide, for example lithium hydroxide or also sodium hydroxide, in an inert solvent, such as an ether, for example dimethoxyethane, or also an alcohol, such as ethanol, yielding a compound of formula

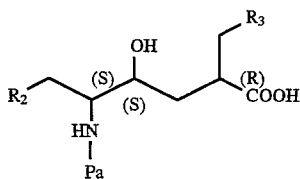
(XXI)

wherein the radicals are as last defined; there is introduced into the resulting compound a hydroxy-protecting group Py, for example one of the hydroxy-protecting groups mentioned under Process a) under the conditions mentioned therein, especially a tri-lower alkylsilyl group with the aid of the corresponding halo-tri-lower alkylsilane, for example tert-butyldimethylchlorosilane, in a polar solvent, such as a di-lower alkyl-lower alkanoyl-amide, such as dimethylformamide, in the presence of a sterically hindered amino compound, such as a cyclic amine, for example imidazole, at temperatures of from −50° to 80° C., preferably from 0° to 35° C., yielding a compound of formula

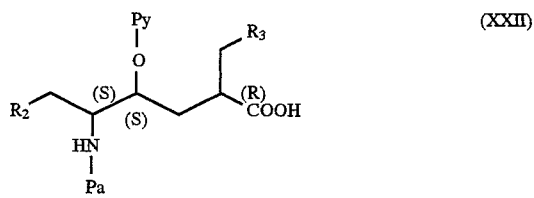
(XXII)

wherein the radicals are as last defined; or is acylated directly with a compound of formula XXV or with a reactive derivative thereof, as defined above, with the introduction of the radical T, as described above under Process gg), there being obtained the corresponding compound of formula

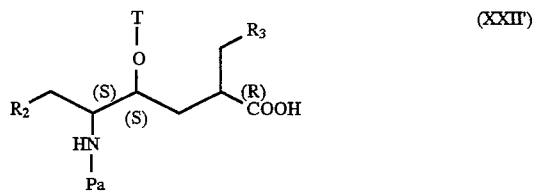
(XXII')

which contains the radical T in place of Py and in which the remaining radicals are as defined; and a compound of formula III or III' having the radicals indicated under Process a) is prepared from a compound of formula XXII or XXII', for example by condensation with a compound of formula VII wherein the radicals are as defined under Process c), under the conditions indicated for Process a), especially by in situ reaction in the presence of a condensation agent, such as benzotriazol-1-yl-oxy-bis(dimethylamino)phosphonium hexafluorophosphate or O-benzotriazol-1-yl-N,N,N',N'-tetramethyluronium hexafluorophosphate, a sterically hindered amine, such as N-methylmorpholine, and a compound hindering racemisation, such as 1-hydroxybenzotriazole, in a polar solvent, preferably an acid amide, for example a di-lower alkylamino-lower alkanoylamide, such as dimethylformamide, at temperatures of from −50° to 80° C., especially from 0° to 35° C., and by subsequent protecting group removal of Pa, as described under Process f), provided Pa is not a radical corresponding to the residue H-B$_1$- as defined above for compounds of formula I or I' with the exception of a bond, condensation with a compound of the formula H-B$_1$'-OH wherein B$_1$' is as defined under Process b), under the last-mentioned condensation conditions and finally removal of Py (only in the case of a compound of formula XXII) and/or further protecting groups, as described under Process f), and if necessary (in the case of a compound having a free hydroxy group prepared from a compound of formula XXII) the introduction of T, as described under Process gg). For the preparation of a compound of formula III or III' there is also possible successive condensation of a compound of formula XXII or XXII' with compounds that introduce the residues -B$_1$-, -A$_1$-, -A$_2$-, A$_2$-, A$_2$-NR$_4$R$_5$ and/or —NR$_4$R$_5$ of the compound of formula VII, under conditions analogous to those mentioned for Process a), and when a compound of formula XXII is used for the preparation of a compound of formula III' the protecting group Py is removed according to one of the methods described under Process f) and the radical T must then be introduced using a compound of formula XXV or a reactive derivative thereof under the reaction conditions mentioned for Process gg).

The route from an above-mentioned compound of formula XVIII to a compound of formula XX may also be as follows:

Hydrolysis of a racemic compound of formula XVIII (which can be prepared from the racemate of a compound of formula XVI via the corresponding racemate of a compound of formula XVII) and decarboxylation under conditions analogous to those employed for the hydrolysis and decarboxylation of compounds of formula XIX result in a compound which is analogous to the compound of formula XIX but in which the radicals $R_3-CH_2-$ and $R_9-(C=O)-$ are absent and which is in the form of a racemate; that compound is then reacted with a compound of the formula $R_3-CH_2-W$, as defined below of formula XVIII, wherein W is one of the nucleofugal leaving groups mentioned there, especially halogen, such as bromine or chlorine, by deprotonation in the presence of a strong base, such as an alkali metal bis(tri-lower alkylsilyl)amide, for example lithium bis(trimethylsilyl)amide, followed by alkylation with the compound of the formula $R_3-CH_2-W$ (preferably yielding the $1'(S),3(R)-(R_3-CH_2-),5(S)-$ and the $1'(R),3(S)-(R_3-CH_2-),5(R)-$compound of formula XX, that is to say a racemate).

The afore-mentioned compounds of formula XV can also be in the (R,S)-configuration at the carbon atom carrying the radical $—NH_2$ instead of in the (S)-configuration shown, and the compounds of formulae XII, XIII, XIV and especially those of formulae XVI, XVII, XVIII, XIX, XX, XXI and/or XXII can also be in the (R,S)-configuration at the carbon atom carrying the radical Pa-NH- instead of in the (S)-configuration. The afore-mentioned compounds of formulae XVI, XVII and XVIII can also be in the form of racemates, that is to say the optical antipodes of the formulae shown are also possible. It is possible to obtain from those racemates, for example, corresponding compounds of formula VI' (for example racemates if $R_1$ and $T_1$ do not contain centres of asymmetry) so that in this manner a compound of formula I' can be obtained wherein either the carbon atom carrying $R'TCH_2-$ is in the (S)-configuration, the carbon atom carrying T—O— is in the (S)-configuration and the carbon atom carrying $R_3-CH_2-$ is in the (R)-configuration (2R,4S,5S), or the mentioned carbon atoms have the opposite configuration (2S,4R,5R); or mixtures of compounds of formula VI' or I' having those two configurations may also be obtained. Corresponding racemic mixtures or mixtures of diastereoisomers can (preferably) be separated into the individual isomers at any stage.

A compound of formula XX wherein the radicals are as defined is also prepared from a compound of formula XIII wherein the radicals are as defined, by reacting an aldehyde of formula XIII with a 2-halopropionic acid ester, especially a 2-iodopropionic acid ester, such as 2-iodopropionic acid ethyl ester, there being obtained a compound of formula

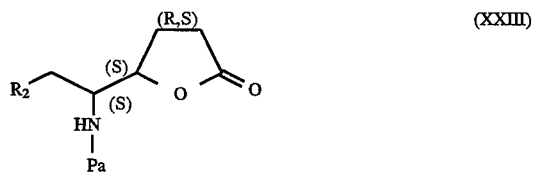

(XXIII)

wherein the radicals are as defined and wherein the carbon atom carrying the radical Pa-NH— may alternatively also be in the (R,S)-configuration.

The reaction is carded out first with the formation of the homoenolate of the 2-halopropionic acid ester in the presence of a mixture of Zn/Cu in a di-lower alkyl-lower alkanoylamide, such as dimethylacetamide, at temperatures of from 0° to 100° C., especially from 20° to 80° C. In a further batch, preferably under protective gas, such as nitrogen or argon, a titanium tetrahalide, such as titanium tetrachloride, is added to a tetra-lower alkyl orthotitanate, such as tetraisopropyl orthotitanate, in an aromatic solvent, such as toluene or xylene, in the presence of a halogenated hydrocarbon, such as methylene chloride, and the mixture is stirred at from 0° to 50° C., especially from 20° to 30° C., there being formed the corresponding dihalotitanium di-lower alkanolate or preferably the wihalotitanium lower alkanolate, especially trichlorotitanium diisopropanolate. The zinc homo-enolate solution is added dropwise thereto at temperatures of from –50° to 0° C., especially from –40° to –25° C., and then the aldehyde of formula XIII in a halogenated hydrocarbon, for example methylene chloride, is added dropwise, the reaction taking place at from –50° to 30° C., preferably approximately from –20° to 5° C., with the formation of an ester, especially an ethyl ester, of the compound of formula XXIII. That ester is then hydrolysed to form the compound of formula XIII, as defined above, preferably in an organic solvent, such as an aromatic compound, for example in toluene or xylene, in the presence of an acid, such as a carboxylic acid, for example acetic acid, at temperatures of from 20° C. to the boiling point of the reaction mixture, especially from 70° to 100° C. If necessary, diastereoisomers are separated, for example by chromatography, for example on silica gel with an organic solvent mixture, such as a mixture of alkane and ester, such as lower alkane and lower alkyl-lower alkanoyl ester, such as hexane/ethyl acetate.

From the compound of formula XXIII, the corresponding compound of formula XX is then obtained by deprotonation with a strong base, yielding the carbanion which is formed at the a-carbon atom adjacent to the oxo group of the lactone, and by subsequent nucleophilic substitution of the radical W of a compound of the formula $R_3-CH_2-W$ wherein $R_3$ and W are as defined above for the preparation of compounds of formula XIX (W is especially bromo), the reaction preferably resulting stereoselectively in the (R)-configuration at the carbon atom carrying the radical $R_3-CH_2-$ in the compound of formula XX. The reaction with the strong base, especially with an alkali metal organosilicon amide compound, for example an alkali metal bis(tri-lower alkylsilyl)amide, such as lithium bis(trimethylsilyl)amide, or with an alkali metal di-lower alkylamide, such as lithium diisopropylamide, is preferably carded out in an inert organic solvent, especially an ether, for example a cyclic ether, such as tetrahydrofuran, or 1,3-dimethyl-3,4,5,6-tetrahydro-2(1H)-pyrimidinone (DMPU), or mixtures of those solvents, at temperatures of from –100° to 0° C., preferably from –78° to –50° C., and the nucleophilic substitution is effected in situ by the addition of the compound of the formula $R_3-CH_2-W$, in the same solvent at temperatures of from –100° to 0° C., preferably from –60° to –40° C.

A compound of formula XV wherein the radicals are as defined and wherein preferably the carbon atom carrying the group $—NH_2$ is in the (R,S)-configuration can also be obtained by converting a formic acid ester, for example a formic acid lower alkyl ester, such as formic acid ethyl ester, by reaction with allylamine at temperatures of from 20° to 70° C., especially from 50° to 60° C., into formic acid allylamide. That amide is then dehydrated under protective gas, such as nitrogen or argon, preferably with an acid halide, such as phosphorus oxychloride, phosgene or especially an organic sulfonic acid halide, for example an arylsulfonic acid chloride, such as toluenesulfonic acid chloride, in the presence of a base, for example a tri-lower alkylamine, such as triethylamine, or especially a mono- or bi-cyclic amine, such as pyridine or quinoline, at temperatures of from 50° to 100° C., especially from approximately 80° to approximately 100° C. An allyl isocyanide is formed which is converted by reaction with an organolithium salt, for example lower alkyllithium, such as n-butyllithium, into the corresponding lithium salt, the reaction preferably being carried out in an inert organic solvent, especially an ether, such as dioxane or diethyl ether, or an alkane, for example hexane, or a mixture of those solvents, at temperatures of from −120° to −50° C., especially approximately from −100° to −90° C. The lithium salt formed is then reacted in situ with a compound of the formula $R_2$-$CH_2$—W wherein $R_2$ is as defined for compounds of formula I or I' and W is as defined above for compounds of the formula $R_3$-$CH_2$—W, especially bromine, preferably by the dropwise addition of $R_2$-$CH_2$—W in an organic solvent, for example an ether, such as tetrahydrofuran, at the temperatures last mentioned and with subsequent heating at from 0° to 50° C., preferably from 20° to 30° C., yielding an isocyanide of formula

(XXIV)

wherein the radicals are as defined. The compound of formula XXIV is then hydrolysed, preferably in an aqueous solution to which an acid has been added, for example in an aqueous hydrohalic acid, such as hydrochloric acid, especially in concentrated hydrochloric acid, at temperatures of from −20° to 30° C., especially approximately from 0° to 10° C., yielding the compound of formula XV wherein the radicals are as last defined and wherein the carbon atom carrying the group -$NH_2$ is preferably in the (R,S)-configuration.

Compounds of formula IV are known or can be prepared in accordance with processes known per se, for example by condensation of carboxylic or sulfonic acids of formula II, or reactive derivatives thereof, with amino compounds of the formula H-$B_1$'-OH wherein $B_1$' is as defined for compounds of formula IV, the condensation being carded out as last described, or in the case of compounds of formula II wherein $R_1$' is N-(heterocyclyl-lower alkyl)-N-lower alkylaminocarbonyl, such as N-(2-pyridylmethyl)-N-methyl-aminocarbonyl, analogously to EP 0 402 646 of 19.12.1990, Example 218.

A compound of formula V or V' is prepared, for example, from a compound of formula XXII or XXII' by condensation with a compound of formula VII or successive condensation with compounds (for example H-$A_1$'-OH, H-$A_2$'-OH, H-$A_1$-$A_2$-OH or the compound of formula XI, wherein the residues are in each case as defined above) that correspond to fragments of the compound of formula VII. The condensation conditions are analogous to those described for the preparation of the compounds of formula III or III'; when a compound of formula XXII is used, for the preparation of a compound of formula V' T can then be introduced by reaction with a compound of formula XXV or with a reactive derivative thereof, as defined under Process gg), under the conditions mentioned for Process gg).

A compound of formula VI or VI' is prepared, for example, from an amino compound of formula XXII or XXII', for example by the introduction of a carboxy-protecting group, as described under Process a), and removal of the protecting group Pa, as described under Process f), by condensation with a carboxylic acid of the formula $R_1$-$B_1$-OH wherein the radicals are as defined for compounds of formula I or I'. When a compound of formula XXII is used for the synthesis of a compound of the formula VI', T is then introduced by reaction with a compound of formula XXV or with a reactive derivative thereof, as defined under Process gg), under the conditions mentioned for Process gg).

A compound of formula VII is prepared, for example, from the corresponding amino acid H-$A_1$'-OH or H-$A_2$'-OH or the peptide H-$A_1$-$A_2$-OH and the amine components of formula XI, wherein the radicals are in each case as defined above, by condensation analogously to the process described under Process a). For the preparation of a compound having a reduced peptide bond between $A_1$ and $A_2$, the peptide bond between $A_1$ and $A_2$ can be reduced, preferably at the dipeptide stage, for example with hydrogen in the presence of heavy metal or noble metal catalysts, such as platinum or palladium, optionally on carriers, such as activated carbon, or by means of complex hydrides, preferably complex hydrides, for example lithium aluminium hydride or diisoamyl borane in polar solvents, such as alcohols, for example ethanol, or ethers, such as cyclic ethers, for example tetrahydrofuran, at temperatures of from 0° to 150° C., preferably from 20° C. to the boiling point of the reaction mixture in question. The amine of formula XI is known or is prepared in accordance with methods known per se.

A compound of formula VIII or VIII' can be prepared, for example, from a compound of formula VI or VI' by condensation with an amino acid that introduces the residue $A_1$'. The reaction is carried out analogously to the conditions described under Process a).

A compound of formula IX is prepared, for example, from an amino acid H-$A_2$'-OH, wherein $A_2$' is as defined under Process d), and an amine of formula XI wherein the radicals are as defined for compounds of formula I, by condensation.

A compound of formula X or X' is prepared, for example, from a compound of formula VI or VI' and from the corresponding amino acid H-$A_1$'-OH or H-$A_2$'-OH or the peptide H-AFA$_2$-OH wherein the residues are in each case as defined above, by condensation analogously to the process described under Process a). For the preparation of a compound having a reduced peptide bond between $A_1$ and $A_2$, the peptide bond between $A_1$ and $A_2$ is reduced, preferably at the dipeptide stage, for example with hydrogen in the presence of heavy metal or noble metal catalysts, such as platinum or palladium, optionally on carriers, such as activated carbon, or by means of complex hydrides, preferably complex hydrides, such as lithium aluminium hydride or diisoamyl borane in polar solvents, such as alcohols, for example ethanol, or ethers, such as cyclic ethers, for example tetrahydrofuran, at temperatures of from 0° to 150° C., preferably from 20° C. to the boiling point of the reaction mixture.

The amine of formula XI is known and is commercially available or is prepared in accordance with methods known per se.

Compounds of formula XXV are known or can be prepared in accordance with processes known per se, or they are commercially available.

There may be mentioned by way of example the preparation of a compound of formula XXV wherein T is arylcarbonyl substituted by heterocyclyl-lower alkyl wherein heterocyclyl is bonded via a ring nitrogen atom, which is preferably effected by reaction of a halo-lower alkyl-substituted, such as chloro- or bromo-methyl-substituted, arylcarboxylic acid, such as chloromethylbenzoic acid or bromomethylbenzoic acid, with a corresponding heterocyclic nitrogen base, such as piperdine, piperazine, 1-lower alkylpiperazine or especially morpholine or thiomorpholine, with nucleophilic substitution of the halogen atom.

Compounds of formula I can be prepared in accordance with the processes given in the European Patent Application having the publication number EP 0 532 466 (published on Mar. 17, 1993; an English language equivalent has been applied for, for example, in South Africa). That European Patent Application is therefore included in this text by reference.

The following Examples serve to illustrate the invention but do not limit the scope thereof in any way.

Temperatures are given in degrees Celsius (° C.). If no temperature is indicated, the reaction takes place at room temperature. The $R_f$ values, which indicate the relationship between the distance the particular substance concerned has migrated and the migration distance of the solvent front, are determined on silica gel thin-layer plates by thin-layer chromatography (TLC) in the following solvent systems:

| A | hexane/ethyl acetate | 1:1 |
|---|---|---|
| B | ethyl acetate | — |
| C | hexane/ethyl acetate | 4:1 |
| D | hexane/ethyl acetate | 2:1 |
| E | hexane/ethyl acetate | 3:1 |
| F | methylene chloride/methanol | 9:1 |
| G | chloroform/methanol/water/glacial acetic acid | 85:13:1.5:0.5 |
| H | ethyl acetate/methanol | 9:1 |
| I | hexane/ethyl acetate | 1:2 |
| J | chloroform/methanol/acetic acid/water | 75:27:5:0.5 |
| K | ethyl acetate/acetic acid | 19:1 |
| L | methylene chloride/methanol | 7:3 |
| M | methylene chloride/ether | 49:1 |
| N | methylenechloride/ether | 3:1 |
| O | ethyl acetate/THF | 9:1 |
| P | hexane/ethyl acetate | 8:1 |
| Q | methylene chloride/hexane/ether | 10:10:1 |
| R | methanol | — |
| S | ethyl acetate/hexane | 3:1 |
| T | ethyl acetate/ethanol | 97:3 |
| U | THF/ethyl acetate | 3:1 |
| V | methylene chloride/THF | 2:1 |
| W | methylene chloride/<sup>i</sup>propanol/methanol/triethylamine | 8:3:3:1 |
| X | acetonitrile/ethyl acetate | 1:1 |
| Y | ethyl acetate/ethanol | 95:5 |
| Z | methylene chloride/methanol | 12:1 |
| A' | methylene chloride/diethyl ether | 1:1 |
| B' | methylene chloride/tetrahydrofuran | 4:1 |
| C' | methylene chloride/tetrahydrofuran | 1:1 |

The above-mentioned letter codes for TLC systems are also used in some cases to indicate the eluants in column chromatography.

The abbreviation "$R_f(A)$" denotes, for example, that the $R_f$ value was determined in solvent system A. The ratio of solvents to one another is always indicated in parts by volume (v/v). In the definition of the eluant systems for column chromatography, the ratios of the solvents used are also given in parts by volume (v/v).

The other shortened names and abbreviations used have the following meanings:

| abs. | absolute |
|---|---|
| Anal. | elemental analysis |
| atm | physical atmospheres (pressure unit) - 1 atm corresponds to 1.013 bar |
| Boc | tert-butoxycarbonyl |
| BOP | benzotriazol-1-yloxy-tris(dimethyl- |

-continued

| brine | saturated sodium chloride solution |
|---|---|
| | amino)phosphonium hexafluorophosphate |
| calc. | calculated |
| DCC | dicyclohexylcarbodiimide |
| DMF | dimethylformamide |
| DMSO | dimethyl sulfoxide |
| ether | diethyl ether |
| ethyl acetate | acetic acid ethyl ester |
| FAB-MS | fast-atom-bombardment mass spectroscopy |
| h | hour(s) |
| HBTU | O-benzotriazol-1-yl-N,N,N',N'-tetramethyluronium hexafluorophosphate |
| HOBt | 1-hydroxybenzotriazole |
| IR | infrared spectroscopy |
| min | minute(s) |
| m.p. | melting point |
| NMM | N-methylmorpholine |
| org. | organic |
| Pd/C | palladium on activated carbon (catalyst) |
| RT | room temperature |
| TBAF | tetrabutylammonium fluoride (trihydrate) |
| TLC | thin-layer chromatography |
| Z | benzyloxycarbonyl |

Mass spectroscopic measurements are obtained in accordance with the "fast-atom-bombardment" (FAB-MS) method. The mass data relate to the protonated molecule ion $(M+H)^+$.

The values for IR spectra are indicated in $cm^{-1}$, and the solvent is given in round brackets.

The abbreviations customarily used in peptide chemistry are used to denote bivalent radicals of natural α-amino acids. The configuration at the α-carbon atom is indicated by prefixing (L)- or (D)-. Cha- is cyclohexylalanyl, -(p-F-Phe)- is phenylalanyl that is substituted in the p-position of the phenyl ring by fluorine, -(p-CH$_3$O-Phe)- is phenylalanyl that is substituted in the p-position of the phenyl ring by a methoxy group, -(p-BzlOPhe)- denotes phenylalanyl substituted in the p-position by a benzyloxy group, -(p-CN-Phe)- is phenylalanyl that is substituted in the p-position of the phenyl ring by a cyano group, -(4-n-butyloxy-Phe)- denotes phenylalanyl substituted in the p-position of the phenyl ring by n-butoxy and (4-isobutyloxy-Phe)- denotes phenylalanyl substituted in the p-position of the phenyl ring by isobutoxy.

HPLC-gradients:

I 20%→100% a) in b) for 20 min.

II 20%→100% a) in b) for 35 min.

III 20%→100% a) in b) for 30 min.

IV 20% →100% a) in b) for 20 min and then 100% a) for 8 min.

Eluant a): acetonitrile+0.05% TFA; eluant b): water+ 0.05% TFA. Column (250×4.6 mm) filled with "Reversed-Phase" material C$_{18}$-Nucleosil® (5 gm mean particle size, silica gel covalently derivatised with octadecylsilanes, Macherey & Nagel, Düren, Federal Republic of Germany). Detection by UV absorption at 215 nm. The retention times ($t_{Ret}$) are given in minutes. Flow rate 1 ml/min.

The following shortened names for radicals are defined by the corresponding formula drawings and names:

The residue with the abbreviation -Phe[C]Phe- denotes the divalent residue of 5(S)-amino-2(R)-benzyl-4(S)-hydroxy-6-phenylhexanoic acid and has the formula

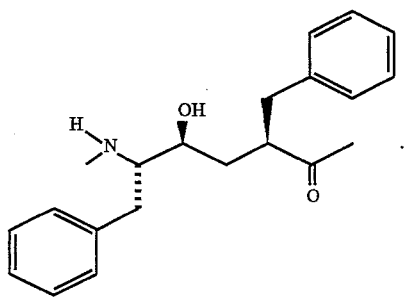

The residue with the abbreviation -Cha[C](p-CN)Phe- denotes the divalent residue of 5(S)-amino-2(R)-(p-cyanophenylmethyl)-6-cyclohexyl-4(S)-hydroxyhexanoic acid and has the formula

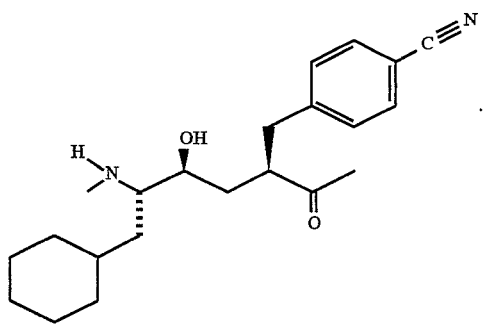

The residue with the abbreviation -Cha[C]Cha- denotes the divalent residue of 5(S)-amino-6-cyclohexyl-2(R)-cyclohexylmethyl-4(S)-hydroxyhexanoic acid and has the formula

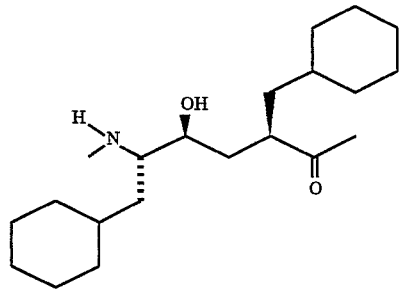

The residue with the abbreviation -Cha[C](p-F)Phe- denotes the divalent residue of 5(S)-amino-6-cyclohexyl-2(R)-(p-fluorophenylmethyl)-4(S)-hydroxyhexanoic acid and has the formula

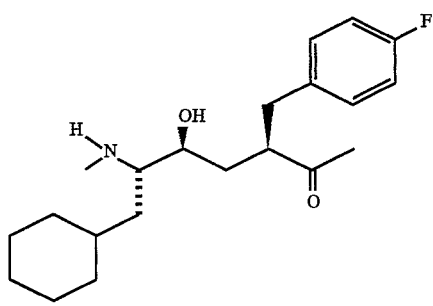

The residue with the abbreviation -(p-F)Phe[C]Phe- denotes the divalent residue of 5(S)-amino-2(R)-benzyl-6-(p-fluorophenyl)-4(S)-hydroxyhexanoic acid and has the formula

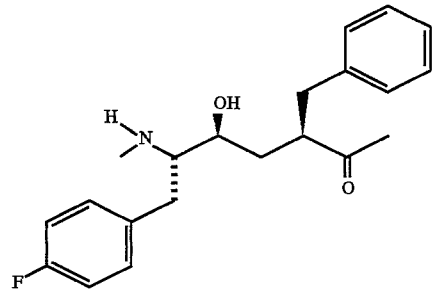

The further formulae of central building blocks shown below correspond to the following abbreviations, which are used in the Examples which follow.

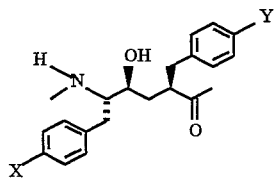
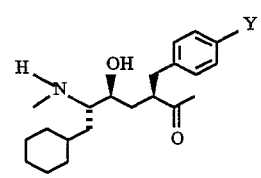

|  | X | Y |  | Y |
|---|---|---|---|---|
| —Phe[C](p-F)Phe— | H | F |  |  |
| —Phe[C](p-CN)Phe— | H | CN | —Cha[C](p-CH₃O)Phe— | CH₃O |
| —Phe[C](p-CH₃O)Phe— | H | CH₃O | —Cha[C](p-CF₃)Phe— | CF₃ |
| —Phe[C](p-CF₃)Phe— | H | CF₃ | —Cha[C](p-Bzlo)Phe— | C₆H₅—CH₂—O |
| -(p-F)Phe[C](p-F)Phe— | F | F | —Cha[C]Tyr— | OH |
| -(p-F)Phe[C](p-CN)Phe— | F | CN |  |  |
| —Tyr[C]Tyr— | OH | OH |  |  |

-continued

| | X | Y |
|---|---|---|
| —Tyr[C]Phe— | OH | H |
| —Phe[C]Tyr— | H | OH |
| -(p-BzlO)Phe[C](p-BzlO)Phe— | C₆H₅CH₂O | C₆H₅CH₂O |
| -(p-BzlO)Phe[C]Phe— | C₆H₅CH₂O | H |
| —Phe[C](BzlO)Phe— | H | C₆H₅CH₂O |
| -(p-CH₃O)Phe[C](p-CH₃O)Phe— | CH₃—O | CH₃—O |
| -(p-CH₃O)Phe[C]Phe— | CH₃—O | H |
| -(p-CH₃O)Phe[C](p-BzlO)Phe— | CH₃—O | C₆H₅CH₂O |
| -(p-CH₃O)Phe[C]Tyr— | CH₃—O | OH |

Accordingly, -Phe[C](p-F)Phe- corresponds to the divalent residue of 5(S)-amino-2(R)-(p-fluorophenylmethyl)-4(S)-hydroxy-6-phenylhexanoic acid; -Phe[C](p-CN)Phe- corresponds to the divalent residue of 5(S)-amino-2(R)-(p-cyanophenylmethyl)-4(S)-hydroxy-6-phenylhexanoic acid; -Phe[C](p-CH₃O)Phe- corresponds to the divalent residue of 5(S)-amino-4(S)-hydroxy-2(R)-(p-methoxyphenylmethyl)-6-phenylhexanoic acid; -Phe[C](p-CF₃)Phe- corresponds to the divalent residue of 5(S)-amino-4(S)-hydroxy-6-phenyl-2(R)-(p-trifluoromethylphenylmethyl)-hexanoic acid;

(p-F)Phe[C](p-F)Phe- corresponds to the divalent residue of 5(S)-amino-6-(p-fluorophenyl)-2(R)-(p-fluomphenylmethyl)-4(S)-hydroxyhexanoic acid;

(p-F)Phe[C](p-CN)Phe- corresponds to the divalent residue of 5(S)-amino-2(R)-(p-cyanophenylmethyl)-6-(p-fluorophenyl)-4(S)-hydroxyhexanoic acid; -Cha[C](p-CH₃O)Phe-corresponds to the divalent residue of 5(S)-amino-2(R)-(p-methoxyphenylmethyl)-6-cyclohexyl-4(S)-hydroxyhexanoic acid; -Cha[C](p-CF₃)Phe- corresponds to the divalent residue of 5 (S)-amino-6-cyclohexyl-4(S)-hydroxy-2(R)-(p-trifluoromethylphenylmethyl)hexanoic acid; -Tyr[C]Tyr- corresponds to the divalent residue of 5(S)-amino-4(S)-hydroxy-6-(p-hydroxyphenyl)-2(R)-(p-hydroxyphenylmethyl)-hexanoic acid; -Phe[C]Tyr- corresponds to the divalent residue of 5(S)-amino-4(S)-hydroxy-2(R)-(p-hydroxyphenylmethyl)-6-phenylhexanoic acid; -Tyr[C]Phe- corresponds to the divalent residue of 5(S)-amino-4(S)-hydroxy-6-(p-hydroxyphenyl)-2(R)-benzylhexanoic acid;

(p-BzlO)Phe[C](p-BzlO)Phe- corresponds to the divalent residue of 5(S)-amino-6-(p-benzyloxyphenyl)-2(R)-(p-benzyloxyphenylmethyl)-4(S)-hydroxyhexanoic acid;

(p-BzlO)Phe[C]Phe- corresponds to the divalent residue of 5(S)-amino-6-(p-benzyloxyphenyl)-4(S)-hydroxy-2(R)-benzylhexanoic acid; -Phe[C](p-BzlO)Phe- corresponds to the divalent residue of 5(S)-amino-2(R)-(p-benzyloxyphenylmethyl)-4(S)-hydroxy-6-phenylhexanoic acid; -(p-CH₃O)Phe[C](p-CH₃O)Phe- corresponds to the divalent residue of 5(S)-amino-4(S)-hydroxy-6-(p-methoxyphenyl)-2(R)-(p-methoxyphenylmethyl)-hexanoic acid; -(p-CH₃O)Phe[C]Phe- corresponds to the divalent residue of 5(S)-amino-4(S)-hydroxy-6-(p-methoxyphenyl)-2(R)-phenylmethylhexanoic acid;

(p-CH30-)Phe[C](p-BzlO)Phe- corresponds to the divalent residue of 5(S)-amino-2(R)-(p-benzyloxyphenylmethyl)-4(S)-hydroxy-6-(p-methoxyphenyl)-hexanoic acid; and (p-CH₃O)Phe[C]Tyr- corresponds to the divalent residue of 5(S)amino-4(S)-hydroxy-2(R)-(p-hydroxyphenylmethyl)-6-(p-methoxyphenyl)-hexanoic acid.

Cha[C](p-BzlO)Phe- denotes the divalent residue of 5(S)-amino-2(R)-(p-benzyloxybenzyl)-6-cyclohexyl-2(R)-4(S)-hydroxyhexanoic acid; -Cha[C]Tyr- accordingly denotes the divalent residue of 5(S)-amino-6-cyclohexyl-4(S)-hydroxy-2(R)-(4-hydroxybenzyl) hexanoic acid.

-(p-F)Phe[C](p-CF₃)Phe—

| | Y |
|---|---|
| —(CF₃)Phe[C]Phe— | H |
| —(CF₃)Phe[C](p-F)Phe— | F |
| —(CF₃)Phe[C](p-CF₃)Phe— | CF₃ |

The residue -(p-F)Phe[C](p-CF$_3$)Phe- accordingly corresponds to the divalent residue of (S)-amino-4(S)-hydroxy-6-(p-fluorophenyl)-2(R)-(p-trifluoromethylphenylmethyl) hexanoic acid.

The symbol (±) is intended to indicate that the residues -(CF$_3$)Phe[C]Phe-, (CF$_3$)Phe[C](p-F)Phe- and -(CF$_3$)Phe[C](p-CF$_3$)Phe-, which correspond to the divalent residues of 5-amino-2-phenyl-4-hydroxy-6-(p-trifluoromethylphenylmethyl)-hexanoic acid, 5-amino-2-(p-fluorophenylmethyl)-4-hydroxy-6-(p-trifluoromethylphenyl)-hexanoic acid and 5-amino-2-(p-trifluoromethylphenylmethyl)-4-hydroxy-6-(p-trifluoromethylphenyl)-hexanoic acid, may be present in the corresponding Examples in the form of a mixture of the 2(R),4(S),5(S)-isomer with the 2(S),4(R),5(R)-isomer.

Further meanings of corresponding divalent residues are as follows:

Phe[C](m-CN)Phe- denotes the divalent residue of 5(S)-amino-2(R)-(m-cyanophenylmethyl)-4(S)-hydroxy-6-phenylhexanoic acid;

Phe[C](o-CN)Phe- denotes the divalent residue of 5(S)-amino-2(R)-(m-cyanophenylmethyl)-4(S)-hydroxy-6-phenylhexanoic acid;

Phe[C](o-F)Phe- denotes the divalent residue of 5(S)-amino-2(R)-(o-fluorophenylmethyl)-4(S)-hydroxy-6-phenylhexanoic acid;

Phe[C](m-F)Phe- denotes the divalent residue of 5(S)-amino-2(R)-(m-fluorophenylmethyl)-4(S)-hydroxy-6-phenylhexanoic acid;

(p-CH$_3$O)Phe[C](3-CH$_3$O)Phe- denotes the divalent residue of 5(S)-amino-2(R)-(m-methoxyphenylmethyl)-4(S)-hydroxy-6-(p-methoxyphenyl)-hexanoic acid;

(p-CH$_3$O)Phe[C](2-CH$_3$O)Phe- denotes the divalent residue of 5(S)-amino-2(R)-(o-methoxyphenylmethyl)-4(S)-hydroxy-6-(p-methoxyphenyl)-hexanoic acid;

Phe[C](3-CH$_3$O)Phe- denotes the divalent residue of 5(S)-amino-2(R)-(m-methoxyphenylmethyl)-4(S)-hydroxy-6-phenylhexanoic acid; and Phe[C](2-CH$_3$O)Phe- denotes the divalent residue of 5(S)-amino-2(R)-(o-methoxyphenylmethyl)-4(S)-hydroxy-6-phenylhexanoic acid.

Finally,

Phe[C](p-isobutyloxy)Phe- corresponds to the divalent residue of 5(S)-amino-4(S)-hydroxy-2(R)-(p-isobutyloxybenzyl)-6-phenyl-hexanoic acid;

Phe[C](3,4-dimethoxy)Phe- corresponds to the divalent residue of 5(S)-amino-2(R)-(3,4-dimethoxybenzyl)-4(S)-hydroxy-6-phenyl-hexanoic acid;

Phe[C](3,4,5-trimethoxy)Phe- corresponds to the divalent residue of 5(S)-amino-4(S)-hydroxy-6-phenyl-2(R)-(3,4,5-trimethoxybenzyl)-hexanoic acid; and Phe[C](2,3,4-trimethoxy)Phe- corresponds to the divalent residue of 5(S)-amino-4(S)-hydroxy-6-phenyl-2(R)-(2,3,4-trimethoxybenzyl)-hexanoic acid.

EXAMPLE 1

Boc-Cha[C](p-F)Phe-(L)-Val-(L)-Phe-morpholin-4-ylamide 116 mg of TBAF are added to a solution of 160 mg of 5(S)-Boc-amino-4(S)-tert-butyldimethylsilyloxy)-6-cyclohexyl-2(R)-(p-fluorophenylmethyl)-hexanoyl-(L)-Val-(L)-Phe-morpholin-4-ylamide in 1.8 ml of abs. DMF and the reaction mixture is then stirred for 4.5 h at RT. The colourless solution is poured onto 50 ml of water and extracted four times with ethyl acetate. The combined extracts are washed twice with 25 ml of sodium hydrogen carbonate solution each time, twice with water and once with brine and then dried over sodium sulfate. After concentrating the solvent by evaporation, the residue is crystallised from diisopropyl ether to yield the title compound. TLC R$_f$(I)= 0.14; FAB-MS (M+H)$^+$=753.

The starting material is prepared as follows:

1 a) N-3(S)-(Boc-amino)-2(R,S)-hydroxy-4-phenyl-1-trimethylsilylbutane 24.7 g of magnesium are introduced into 100 ml of abs. ether and, over the course of 35 min, a small amount of iodine and, at the same time, 132.5 ml of chloromethyltrimethylsilane and 300 ml of ether are added, the temperature being maintained at 38° C. by means of an ice bath. The resulting reaction mixture is then stirred for 1.5 h at RT. After cooling to −60° C., a suspension of 48.6 g of N-Boc-phenylalaninal (preparation: D. J. Kempf, J. Org. Chem. 51, 3921 (1986)) in 1.1 liter of ether is added over the course of 40 min. The reaction mixture is heated to RT over the course of 90 min and is stirred for a further 0 min at that temperature. It is then poured onto 2 liters of ice-water and 1.5 liters of 0% aqueous citric acid. The separated aqueous phase is extracted twice with 500 ml of ether each time. All of the ether extracts are washed with 500 ml of a 10% citric acid solution and twice with brine. After drying over sodium sulfate, concentration is carded out in vacuo and the resulting title compound is used further without additional purification. TLC R$_f$ (C)=0.6; FAB-MS (M+H)$^+$=338.

1 b) 1-Phenyl-3-buten-2(S)-amine 5.6 ml of an approximately 48% solution of boron trifluoride ethyl etherate are added at 5° C. over the course of 10 min to a solution of 18.8 g of n-3(S)-(Boc-amino)-2-(R,S)-hydroxy-4-phenyl-1-trimethylsilylbutane in 420 ml of methylene chloride. The reaction mixture is then stirred for 16 h at RT and cooled to 10° C., and 276 ml of a 4 N sodium hydroxide solution are added over the course of 20 min. The aqueous phase is separated off and extracted twice with 400 ml of methylene chloride each time. The combined organic extracts are washed with brine and dried over sodium sulfate. The title product is used further without additional purification. TLC R$_f$ (G)=0.15; IR (methylene chloride) (cm$^{-1}$): 3370, 3020, 2920, 1640, 1605.

1 c) N-Boc-1-phenyl-3-buten-2(S)-amine 21.5 g of 1-phenyl-3-buten-2(S)-amine are dissolved in 500 ml of abs. methylene chloride, and a solution of 38.3 g of Boc-anhydride in 250 ml of methylene chloride is added dropwise thereto. After stirring for 1.5 h at RT, the batch is concentrated to 100 ml, then diluted with 1.5 liters of ether and washed in succession twice with 400 ml of 10% citric acid each time, once with 400 ml of water, once with 400 ml of saturated aqueous sodium hydrogen carbonate solution and twice with brine, and dried over sodium sulfate. After concentrating the solvent by evaporation, purification is effected by column chromatography (SiO$_2$, hexane/ethyl acetate: 95/5 to 80/20) and the title compound is recrystallised from hexane. M.p. 67°–68° C.; TLC R$_f$(C)=0.4; FAB-MS (M+H)$^+$=248.

1d) 2(R)-[1(S)-(Boc-amino)-2-phenylethyl]-oxirane

A solution of 9.74 g of m-chloroperbenzoic acid in 50 ml of methylene chloride is added over the course of 15 min at from 0° to 5° C. to a solution of 1.45 g of N-Boc-1-phenyl-3-buten-2(S)-amine in 20 ml of methylene chloride. The batch is stirred for 18 h at that same temperature and is then stirred for a further 8 h, with heating to RT, to complete the reaction and poured onto ice-cold 10% sodium carbonate solution. The aqueous phase is extracted three times with ether. The combined organic phases are washed in succession three times with 10% sodium sulfite solution, three times with saturated sodium hydrogen carbonate solution, with sodium thiosulfate solution and with brine and dried over sodium sulfate. After concentrating the solvents, the title compound is purified by column chromatography (SiO$_2$, hexane/ethyl acetate: 4/1) and recrystallised from hexane. M.p. 51°–52° C.; TLC R$_f$(C)=0.33; FAB-MS (M+H)+=264.

1e) 5(S)-[1(S)-(Boc-amino)-2-phenylethyl]-3(R,S)-ethoxycarbonyl-dihydrofuran-2-(3H)-one 3.4 g of sodium are added in portions to a solution of 26 ml of malonic acid diethyl ester in 260 ml of abs. ethanol. When the sodium has been consumed (approximately 1.5 h) a solution of 13 g of 2(R)-[1(S)-(Boc-amino)-2-phenylethyl]-oxirane in 100 ml of ethanol is added dropwise over the course of 10 min. After stirring for 5 h at RT, the reaction mixture is poured onto 1.5 liters of ice-water and adjusted to pH 4 with 10% citric acid. After extracting four times with ether, the combined organic phases are washed in succession twice with saturated aqueous sodium hydrogen carbonate solution, once with brine, again with saturated aqueous sodium hydrogen carbonate solution, with water and again with brine. After concentrating the solvent, the title compound is obtained by column chromatography (SiO$_2$, hexane/ethyl acetate: 4/1). TLC R$_f$(C)=0.22; FAB-MS (M+H)$^+$=378.

1 f) 5(S)-[1(S)-Boc-amino)-2-cyclohexylethyl]-3(R,S)-ethoxycarbonyl-dihydrofuran-2-(3H)-one 10 g of 5(S)-[1(S)-(Boc-amino)-2-phenylethyl]-3(R,S)-ethoxycarbonyl-dihydrofuran-2-(3H)-one in 100 ml of ethanol are hydrogenated with 1 g of Nishimura catalyst (Rh(III) and Pt(VI) oxide (monohydrate, Degussa)) for 2 h under normal pressure (approximately 1 atm). The catalyst is filtered off through Celite (diatomaceous earth, Sigma, Switzerland) and washed with ethanol and the filtrate is concentrated by evaporation. TLC R$_f$(C)=0.23.

1 g) 5(S)-[1(S)-(Boc-amino)-2-cyclohexylethyl]-3(R,S)-ethoxycarbonyl-3-(p-fluorophenylmethyl)-dihydrofuran-2-(3H)-one 10.2 g of 5(S)-[1(S)-(Boc-amino)-2-cyclohexylethyl]-3(R,S)-ethoxycarbonyl-dihydrofuran-2-(3H)-one are reacted at RT with 5.39 g of p-fluorobenzyl bromide (Fluka, Buchs, Switzerland) and 0.68 g of sodium in 180 ml of ethanol. Because, according to TLC, not all of the lactone has reacted after 1.5 h, a further 0.2 g of sodium and 0.7 g of p-fluorobenzyl bromide are added. After 16 h, the batch is poured onto a mixture of 10% citric acid and ice and extracted 3 times with ether. The organic phases are washed twice with water and twice with brine, dried with Na$_2$SO$_4$ and concentrated by evaporation. After the addition of hexane/ethyl acetate, some of the oily crude product crystallises out under the effect of ultrasound to give the title compound (ratio of diastereoisomers 4:1). Column chromatography (SiO$_2$, hexane/ethyl acetate 4:1) of the mother liquor yields more title compound (ratio of diastereoisomers approximately 1:4). TLC R$_f$(C)=0.29; FAB-MS (M+H)$^+$=492.

1 h) 5(S)-[1(S)-(Boc-amino)-2-cyclohexylethyl]-3(R)-(n-fluorophenylmethyl)-dihydrofuran-2-(3H)-one and 5(S)-[1(S)-(Boc-amino)-2-cyclohexylethyl]-3(S)-(p-fluorophenylmethyl)-dihydrofuran-2-(3H)-one 91 ml of 1 M lithium hydroxide solution are added dropwise at RT over the course of 5 min to 10.3 g of 5(S)-[1(S)-(Boc-amino)-2-cyclohexylethyl]-3(R,S)-ethoxycarbonyl-3-(p-fluorophenylmethyl)-dihydrofuran-2-(3H)-one (ratio of diastereoisomers approximately 1:1) in 174 ml of 1,2-dimethoxyethane and the batch is stirred for 15 h at RT. After concentrating the solvent by evaporation, the resulting residue is poured onto 500 ml of 10% citric acid and extracted three times with ether. The combined ether phases are washed once with brine and dried over sodium sulfate. After concentrating the solvent by evaporation, the crude carboxylic acid is obtained which is converted into a mixture of the title compounds by means of subsequent decarboxylation by heating for 9 hours at 90° C. in 450 ml of toluene. Column chromatography (SiO$_2$, hexane/ethyl acetate 9:1→4:1) yields first the 3(R)-epimer [TLC R$_f$(E)= 0.45], followed by the 3(S)-epimer [TLC R$_f$(E)=0.41].

1 i) 5(S)-(Boc-amino)-4(S)-hydroxy-6-cyclohexyl-2(R)-(p-fluorophenylmethyl)-hexanoic acid 19.6 ml of 1 M lithium hydroxide solution are added dropwise at from 20° to 25° C. over the course of 2 min to 2.05 g of 5(S)-[1(S)-(Boc-amino)-2-cyclohexylethyl]-3(R)-(p-fluorophenylmethyl)-dihydrofuran-2-(3H)-one in 78 ml of dimethoxyethane and 39 ml of water.

After stirring for 3 h at RT, the batch is concentrated under reduced pressure and the residue is taken up in 100 ml of saturated aqueous ammonium chloride solution and 5 ml of 10% of citric acid and extracted four times with methylene chloride. The combined organic phases are washed with brine and dried over sodium sulfate. Concentration yields the title compound in the form of a foam which is used in the next stage without further purification.

1 j) 5(S)-(Boc-amino)-4(S)-(tert-butyldimethylsilyloxy)-6-cyclohexyl-2(R)-(p-fluorophenylmethyl)-hexanoic acid A solution of 2.01 g of 5(S)-(Boc-amino)-4(S)-hydroxy-6-cyclohexyl-2(R)-(p-fluorophenylmethyl)-hexanoic acid in 6.4 ml of DMF is stirred for 18 h at RT with 2.73 g of imidazole and 3.39 g of tert-butyldimethylchlorosilane. The reaction mixture is then poured onto ice-water and extracted with 3 portions of ethyl acetate. The combined organic phases are washed with 10% citric acid solution, water and brine, dried with sodium sulfate and concentrated by evaporation to yield an oil. The oil is dissolved in 68 ml of methanol and 23 ml of THF, a solution of 4.1 g of potassium carbonate in 23 ml of water is added at RT and the batch is stirred for 1 h and finally partially concentrated by evaporation at RT. The aqueous residue is poured onto 10% citric acid solution and ice and extracted 3 times with ethyl acetate. The organic phases are washed twice with water and twice with brine, dried with sodium sulfate and concentrated by evaporation. Column chromatography (SiO$_2$, hexane/ethyl acetate 5:1→2:1) yields the title compound: TLC R$_f$(E)=0.2; FAB-MS (M+H)$^+$=552.

1 k) 5(S)-(Boc-amino)-4(S)-(tert-butyldimethylsilyloxy)-6-cyclohexyl-2(R)-(p-fluorophenylmethyl)-hexanoyl-(L)-Val-Phe-morpholin-4-ylamide A solution of 102 mg of 5(S)-(Boc-amino)-4(S)-(tert-butyldimethylsilyloxy)-6-cyclohexyl-2(R)-(p-fluorophenylmethyl)-hexanoic acid, 90 mg of BOP and 27 mg of HOBT is stirred for 30 min at RT in approximately 2 ml of DMF, and then 74 mg of H-(L)-Val-(L)-Phe-morpholin-4-ylamide are added [for preparation, see under 1 l) to 1 o)]. After 16 h at RT, the batch is concentrated by evaporation, the residue is partitioned between 3 portions of ethyl acetate, water, sat. sodium hydrogen carbonate solution, water and brine, and the organic phases are dried with sodium sulfate and concentrated by evaporation. The title compound is obtained in the form of a crude product; TLC R$_f$(I)=0.57; FAB-MS (M+H)$^+$=867.

1 l) Z-(L)-Phe-morpholin-4-ylamide

A solution of 4.49 g of Z-(L)-Phe-OH in 190 ml of methylene chloride is cooled to 0° C. and 3.09 g of DCC are added. After stirring for 20 min at 0° C., a solution of 1.31 ml of morpholine in 10 ml of methylene chloride is added dropwise over the course of 15 min. The reaction mixture is stirred for a further 24 h at RT and, after filtering off the precipitated dicyclohexylurea, washing is carried out in succession with methylene chloride, aqueous sodium hydrogen carbonate solution and brine. After drying over sodium sulfate and concentrating, the crude title compound is obtained and is recrystallised from ether. TLC $R_f(B)=0.55$.

1 m) H-(L)-Phe-morpholin-4-ylamide

A solution of 5.5 g of Z-(L)-Phe-morpholin-4-ylamide with 1.5 g of 10% Pd/C in 150 ml of methanol is converted into the title compound by hydrogenolysis for 1 h at RT with the calculated amount of hydrogen. After filtering off the catalyst, the filtrate is concentrated and, after dilution with ethyl acetate, the resulting solution is washed with a saturated sodium hydrogen carbonate solution, dried over sodium sulfate and concentrated under reduced pressure. Column chromatography (analogous to Example 1 o)) yields the title compound in pure form. TLC $R_f(F)=0.3$.

1 n) Z-(L)-Val-(L)-Phe-morpholin-4-ylamide 1.75 g of DCC are added to a solution of 2.14 g of Z-(L)-Val-OH in 80 ml of abs. ice-cooled methylene chloride and, after stirring for 20 min at that temperature, a solution of 2 g of H-(L)-Phe-morpholin-4-ylamide is added dropwise over the course of 15 min. The reaction mixture is stirred for a further 24 h at RT and the resulting urea is filtered off. The filtrate is washed in succession with aqueous sodium hydrogen carbonate solution and brine and, after drying over sodium sulfate, is concentrated. Stirring with ether and filtering off the insoluble residue yields, after concentration, the title compound, which is further processed without additional purification. TLC $R_f(F)=0.7$.

1 o) H-(L)-Val-(L)-Phe-morpholin-4-ylamide

Analogously to Example 1 m), 3.9 g of Z-(L)-Val-(L)-Phe-morpholin-4-ylamide is converted, by hydrogenolysis over 0.5 g of 10% Pd/C in 150 ml of methanol, into the crude title compound which is purified by column chromatography (SiO$_2$, methylene chloride to methylene chloride/methanol: 97.5 to 2.5 (v/v)). TLC $R_f(F)=0.4$.

EXAMPLE 2

Boc-Phe[C]Phe-(L)-Val-(L)-Phe-morpholin-4-ylamide

Analogously to Example 1, 330.3 mg of 5(S)-Boc-amino-4(S)-(tert-butyldimethylsilyloxy)-6-phenyl-2 (R)-phenylmethylhexanoyl-(L)-Val-(L)-Phe-morpholin-4-ylamide in 3 ml of abs. DMF are convened with 247.2 mg of TBAF into the title compound, which recrystallises from hexane. TLC $R_f(B)=0.5$; FAB-MS $(M+H)^+=729$.

The starting material is prepared as follows:

2 a) 5(S)-[(1(S)-(Boc-amino)-2-phenylethyl]-3(R,S)-ethoxycarbonyl-3-phenylmethyldihydrofuran-2-(3H)-one A solution of 23.8 g of 5 (S)-[1(S)-(Boc-amino)-2-phenylethyl]-3(R,S)-ethoxycarbonyl-dihydrofuran-2-(3H)-one in 410 ml of abs. ethanol and 14.4 ml of benzyl bromide is added to a solution of 2.76 g of sodium in 410 ml of abs. ethanol. The reaction mixture is stirred under argon for 18 h at RT and then poured onto a mixture of ice and 10% citric acid. After extracting three times with ether, the combined organic extracts are washed with water and brine and dried over sodium sulfate. Concentration yields the title compound in the form of a colourless oil which is used in the next stage without additional purification. TLC $R_f(C)=0.4$; FAB-MS $(M+H)^+=468$.

2 b) 5(S)-[1(S)-(Boc-amino)-2-phenylethyl]-3(R)-phenylmethyl-dihydrofuran-2-(3H)-one and 5(S)-[1(S)-(Boc-amino)-2-phenylethyl]-3(S)-phenylmethyl-dihydrofuran-2-(3H)-one 81.4 ml of a 1 M aqueous lithium hydroxide solution are added dropwise at RT over the course of 5 min to a solution of 10 g of 5(S)-[(1(S)-(Boc-amino)-2-phenylethyl]-3(R,S)-ethoxycarbonyl-3-phenylmethyl-dihydrofuran-2-(3H)-one in 175 ml of dimethoxyethane. The batch is then stirred for 15 h at RT and, after concentrating the solvent by evaporation, the resulting residue is poured onto 500 ml of 10% citric acid and extracted three times with ether. The combined ether phases are washed once with brine and dried over sodium sulfate. Concentration of the solvent by evaporation yields 9.8 g of the crude carboxylic acid which is decarboxylated to form the title product by heating for 14 hours at 90° C. in 450 ml of toluene. The title product is purified by column chromatography (hexane/ethyl acetate: 9/1) to yield first 5(S)-[1(S)-(Boc-amino)-2-phenylethyl]-3 (R)-phenylmethyl-di-hydrofuran-2-(3H)-one [TLC $R_f(C)=0.3$; FAB-MS $(M+H)+=396$] and then 5(S)-[1(S)-(Boc-amino)-2-phenylethyl]-3(S)-phenylmethyl-dihydrofuran-2-(3H)-one [TLC $R_f(C)=0.25$; FAB-MS $(M+H)^+=396$].

2 c) 5(S)-(Boc-amino)-4(S)-hydroxy-6-phenyl-2(R)-phenyimethylhexanoic acid 176 ml of a 1 M lithium hydroxide solution are added dropwise at 20° C. over the course of 10 min to a solution of 17.6 g of 5(S)-[1(S)-(Boc-amino)-2-phenylethyl]-3(R)-phenylmethyl-dihydrofuran-2-(3H)-one in 710 ml of ethylene glycol dimethyl ether and 352 ml of water. The reaction mixture is then stirred at RT for 1.5 h and the solvent is concentrated by evaporation. The residue is poured onto 1 liter of cold 10% citric acid and the acidic solution is extracted three times with 800 ml of ethyl acetate each time. The combined extracts are washed first with 800 ml of water and then with 800 ml of brine. After drying the organic solution over sodium sulfate, the solvent is distilled off. The crude title compound is used in the next stage without further purification. FAB-MS $(M+H)^+=414$.

2 d) 5(S)-(Boc-amino)-4(S)-(tert-butyldimethylsilyloxy)-6-phenyl-2(R)-phenylmethyl-hexanoic acid 8 g of imidazole and 10 g of tert-butyldimethylchlorosilane are added, with stirring, to a solution of 6.35 g of 5(S)-(Boc-amino)-4(S)-hydroxy-6-phenyl-2(R)-phenylmethylhexanoic acid in 90 ml of DMF. After stirring for 18 h at RT, the clear yellow solution is poured onto ice-water and extracted three times with 250 ml of ethyl acetate each time. The combined extracts are washed in succession three times with 10% citric acid, once with water, three times with aqueous saturated sodium hydrogen carbonate solution, once with water and finally with brine. After drying over sodium sulfate, the solvent is concentrated by evaporation and the resulting tert-butyl dimethyl silyl ether (13.5 g) is dissolved in 53 ml of THF and treated with 53 ml of acetic acid and 20 ml of water. After stirring for 3 h at RT, the batch is poured into water and extracted three times with ether. The collected ether extracts are washed twice with water and once with brine and dried over sodium sulfate. After concentration, the crude product is purified by column chromatography (SiO$_2$, hexane/ethyl acetate 3.5/1.5) to yield the title compound. TLC $R_f(D)=0.37$; FAB-MS $(M+H)+=528$.

2 e) 5(S)-(Boc-amino)-4(S)-(tert-butyldimethylsilyloxy)-6-phenyl-2(R)-phenylmethylhexanoyl-(L)-Val-(L)-Phe-morpholin-4-ylamide Analogously to Example 1 k), 250 mg of 5(S)-(Boc-amino)-4(S)-tert-butyldimethylsilyloxy-6-phenyl-2(R)-phenylmethylhexanoic acid in 3 ml of DMF are converted into the title compound with 230.5 mg of BOP, 70.4 mg of HOBT, 182.6 ml of N-methylmorpholine and 189.5 mg of H-Val-Phe-morpholin-4-ylamide. TLC R$_f$(A)=0.24. FAB-MS (M+H)+=843.

Note: the 5(S)-[1(S)-(Boc-amino)-2-phenylethyl]-3(R)-phenylmethyl-dihydrofuran-2-(3H)-one mentioned as first compound in Example 2b) is prepared preferably as follows (method of preparation that is suitable also for larger amounts):

i) 5(S)-[1(S)-(Boc-amino)-2-phenylethyl]-dihydrofuran-2-(3H)-one (A. E. DeCamp, A. T. Kawaguchi, R. P. Volante, and I. Shinkai, Tetrahedron Lett. 32, 1867 (1991)). Under a nitrogen atmosphere, 173 g of Zn/Cu (preparation: R. D. Smith, H. E. Simmons, W. E. Parham, M. D. Bhavsar, Org. Synth., Coll. Vol 5,855 (1973)) and 280 ml of dimethylacetamide are added to a solution of 375 g (1.65 mol) of 3-iodopropionic acid ethyl ester [Example 21 D) l)a)] in 1700 ml toluene and the mixture is stirred vigorously for 1 h at RT and then for 4 h at 80° C. (→zinc homoenolate solution). In a second apparatus (nitrogen atmosphere), 127 ml (1.14 mol) of titanium tetrachloride are added to a solution of 122 ml (0.40 mol) of tetraisopropyl orthotitanate in 350 ml of toluene and 1900 ml of methylene chloride with slight cooling at an internal temperature of from 15 to 25° C., and the mixture is stirred for 15 min at RT (→yellow solution) and cooled to −40° C. (→partial crystallisation of the trichlorotitanium isopropanolate). The zinc homoenolate solution, cooled to RT, is filtered under an argon atmosphere through a G3 glass frit and added dropwise to the trichlorotitanium isopropanolate, the temperature being maintained at from −30° C. to −25° C. (→deep red solution), and the mixture is stirred for 5 min at −25° C. and cooled to −40° C. Subsequently a solution of 233 g (0.85 mol) of N-Boc-phenylalaninal (preparation: D. J. Kempf, J. Org. Chem. 51, 3921 (1986), then crystailisation from hexane (0° C., approximately 18 h), washing with cold hexane, drying) in 1500 ml of methylene chloride is added dropwise and the mixture is stirred for 15 h at from −22 to −18° C. and finally for 1 h at 0° C. The reaction mixture is taken up in 10 l of ice-water and 12 l of tert-butyl methyl ether and stirred vigorously for from 7 to 10 min. The aqueous phase is removed and extracted twice with 10 l of ether each time; the organic phases are washed with 8 l of water, 8 l of sat. sodium hydrogen carbonate solution, 8 l of water and 5 l of brine, dried with sodium sulfate and concentrated by evaporation (→crystalline 5(S)-(Boc-amino)-4(S)-hydroxy-6-phenylhexanoic acid ethyl ester). The above intermediate is heated for 2.5 h at 100° C. in 6500 ml of toluene and 230 ml of acetic acid under an argon atmosphere. The cooled reaction mixture is poured, with stirring, onto 6 l of ice-water, the aqueous phase is removed and extracted twice with 2000 ml of toluene each time, and the organic phases are washed with 5 l of sat. sodium hydrogen carbonate solution, 5 l of 40% sodium hydrogen sulfite solution, 4 l of water and 4 l of brine and dried with sodium sulfate. Concentration of the organic phases by evaporation to a residue of approximately 300 g and the addition of 800 ml of hexane (stirred for several hours to complete the reaction) yields crystalline lactone, which according to HPLC contains approximately 10% of the (5R) epimer (TLC R$_f$(E)= 0.08; t$_{Ret}$(II)=18.8 min). That material is used in the next step. The pure title compound may be obtained by column chromatography (SiO$_2$, hexane/ethyl acetate 2:1): TLC R$_f$(E)=0.14; t$_{Ret}$(II)-19.2 min; [α]$^D$=17.7° (c=1; ethanol).

ii) 5(S)-[1(S)-(Boc-amino)-2-phenylethyl]-3(R)-phenylmethyldihydrofuran-2-(3H)-one (A. K. Ghosh, S. P. McKee, and W. J. Thompson, J. Org. Chem. 56, 6500 (1991)). Under a nitrogen atmosphere, a solution of 1943 g (6.32 mol) of 5(S)-[1(S)-(Boc-amino)-2-phenylethyl]-dihydrofuran-2-(3H)-one in 12.0 l of THF and 1.9 l of 1,3-dimethyl-3,4,5,6-tetrahydro-2(1H)-pyrimidinone is cooled to −75° C., at an internal temperature of below −70° C. 14000 ml of lithium bis(trimethylsilyl) amide (IM) in THF (Aldrich) are added, and the mixture is then stirred for 20 min at −75° C. Over a period of 1 h, 835 ml (7.00 mol) of benzyl bromide are added thereto, the internal temperature not being allowed to exceed −70° C., and the mixture is stirred for 30 min at −75° C. to complete the reaction. There are then added to the clear solution at from −75 to −70° C. 2320 ml of propionic acid (90 min) followed by 2320 ml of water (1 h), the temperature being allowed to rise to −10° C. The reaction mixture is poured onto 30 l of ethyl acetate and 35 l of 10% citric acid solution, and the aqueous phase is removed and re-extracted twice with 10 l of ethyl acetate each time. The organic phases are washed three times with 12 l of sat. sodium bicarbonate solution each time, with 20 l of brine and twice with 20 l of water each time, and concentrated, and the oily residue is taken up in 10 l of toluene and concentrated by evaporation to a residual volume of approximately 5 l. Filtration of the evaporation residue through 4 kg of Merck silica gel (0.063–0.200 mm), subsequent washing with toluene and crystallisation of the crude product from hexane (4 l of hexane/kg of crude product) yields the title compound: TLC R$_f$(D)=0.54; FAB-MS (M+H)$^+$=414.

EXAMPLE 3

Boc-Cha[C](p-CN)Phe-(L)-Val-(L)-Phe-morpholin-4-ylamide

Analogously to Example 1, 185 mg of 5(S)-(Boc-amino)-4(S)-(tert-butyldimethylsilyloxy)-6-cyclohexyl-2(R)-(p-cyanophenylmethyl)-hexanoyl(L)-Val-(L)-Phe-morphoin-4-ylamide are converted into the title compound with 133 mg of TBAF in 2.5 ml of abs. DMF. TLC R$_f$(B)=0.33; FAB-MS (M+H)+=760.

The starting material is prepared as follows:

3 a) 5(S)-[1(S)-(Boc-amino)-2-cyclohexylethyl]-3-methoxycarbonyl-dihydrofuran-2-(3H)-one 2.5 g of 5(S)-[1(S)-(Boc-amino)-2-phenylethyl]-3-ethoxycarbonyl-dihydrofuran-2-(3H)-one (Example 1 e)) are hydrogenated in 50 ml of methanol over 250 mg of Rh(III) and Pt(VI) oxide (monohydrate) (Nishimura catalyst, Degussa) for 2 h at RT and under normal pressure (approximately 1 atm). After filtering off and then washing the catalyst with methanol, concentration is carried out and the title compound is obtained in pure form by column chromatography (SiO$_2$, hexane/ethyl acetate: 3/1 (v/v)). TLC R$_f$(E)=0.2; FAB-MS (M+H)$^+$=370.

3 b) 5(S)-[1(S)-(Boc-amino)-2-cyclohexylethyl]-3(R,S)-methoxycarbonyl-3-(p-cyanophenylmethyl)-dihydrofuran-2-(3H)-one Analogously to Example 1 g), 2.25 g of 5 (S)-[1(S)-(Boc-amino)-2-cyclohexylethyl]-3(R,S)-methoxycarbonyl-dihydrofuran-2-(3H)-one are converted into the title compound with 1.32 g of p-cyanobenzyl bromide (Fluka, Buchs, Switzerland) and 156 mg of sodium in methanol. After working up, the title compound is obtained. TLC R$_f$(E)= 0.27.

3 c) 5(S)-[1(S)-(Boc-amino)-2-cyclohexylethyl]-3(R)-(o-cyanophenylmethyl)-dihydrofuran-2-(3H)-one and 5(S)-[1

(S)-(Boc-amino)-2-cyclohexylethyl]-3(S)-(O-cyanophenylmethyl)-dihydrofuran-2-(3H)-one Analogously to Example 1 h), 2.95 g of 5(S)-[1(S)-(Boc-amino)-2-cyclohexylethyl]-3-methoxycarbonyl-(p-cyanophenylmethyl)-dihydrofuran-2-(3H)-one in 55 ml of 1,2-dimethoxyethane are converted into the corresponding carboxylic acid with 24.4 ml of 1 M lithium hydroxide solution and then converted into the title compound by subsequent decarboxylation by heating in 130 ml of toluene. Separation by column chromatography (SiO$_2$, hexane/ethyl acetate: 4/1 to 3.5/1.5 (v/v)) yields first the 3(R)-form of the title compound, which crystallises from ether/hexane [m.p. 106°–108° C., TLC R$_f$(A)=0.53; FAB-MS (M+H)$^+$=427] and then the 3(S)-form of the title compound [TLC R$_f$(A)= 0.47; FAB-MS (M+H)+=427].

3 d) 5(S)-(Boc-amino)-4(S)-hydroxy-6-cyclohexyl-2(R)-(o-cyanophenylmethyl)hexanoic acid 7 ml of a 1 M lithium hydroxide solution are added dropwise at from 20° to 25° C. over the course of 2 min to a solution of 550 mg of 5(S)-[1(S)-(Boc-amino)-2-cyclohexylethyl]-3(R)-(p-cyanophenylmethyl)-dihydrofuran-2-(3H)-one in 20 ml of 1,2-dimethoxyethane and 14 ml of water. After stirring for 2 h at RT, the batch is concentrated under reduced pressure and the residue is taken up in 100 ml of saturated aqueous ammonium chloride solution and 5 ml of 10% citric acid and extracted four times with methylene chloride. The combined organic phases are washed with brine and dried over sodium sulfate. Concentration yields the title compound. TLC R$_f$(F)=0.4.

3 e) 5(S)-(Boc-amino)-4(S)-(tert-butyldimethylsilyloxy)-6-cyclohexyl-2(R)-(p-cyanophenylmethyl)-hexanoic acid 1.18 g of tert-butyldimethylchlorosilane and imidazole are added, with stirring, to 790 mg of 5 (S)-(Boc-amino)-4(S)-hydroxy-6-cyclohexyl-2(R)-(p-cyanophenylmethyl)-hexanoic acid in approximately 10 ml of DMF. After stirring for 18 h at RT, the clear yellow solution is poured onto ice-water and extracted three times with 250 ml of ethyl acetate each time. The combined extracts are washed in succession three times with 10% citric acid, once with water, three times with aqueous saturated sodium hydrogen carbonate solution, once with water and finally with brine. After drying over sodium sulfate, the solvent is concentrated by evaporation and the resulting tert-butyl dimethyl silyl ether (13.5 g) is dissolved in 53 ml of THF and treated with 53 ml of acetic acid and 20 ml of water. After stirring for 3 h at RT, the batch is poured onto water and extracted three times with ether. The collected ether extracts are washed twice with water and once with brine and dried over sodium sulfate. After concentration, the crude product is subjected to a final purification which is carried out by column chromatography (SiO$_2$, hexane/ethyl acetate: 3/1 to 1/1 (v/v)). The title compound is obtained. TLC R$_f$(A)=0.42; IR (methylene chloride) (cm$^4$) 2856, 2230, 1711, 1609, 1449.

3 f) 5(S)-(Boc-amino)-4(S)-(tert-butyldimethylsilyloxy)-6-cyclohexyl-2(R)-(p-cyanophenylmethyl)-hexanoyl-(L)-Val-(L)-Phe-morpholin-4-ylamide Analogously to Example 1 k), 138 mg of 5(S)-(Boc-amino)-4(S)-(tert-butyldimethylsilyloxy)-6-cyclohexyl-2 (R)-(p-cyanophenylmethyl)-hexanoic acid are converted into the title compound with 122 mg of BOP, 37 mg of HOBT, 0.069 ml of N-methylmorpholine and 100 mg of H-(L)-Val-(L)-Phe-morpholin-4-ylamide in 3 ml of DMF. Purification is effected by column chromatography (SiO$_2$, hexane/ethyl acetate: 1/1 (v/v)) to yield the pure title product. TLC R$_f$(A)=0.25; FAB-MS (M+H)+=874.

EXAMPLE 4

H-Phe[C]Phe-(L)-Val-(L)-Phe-morpholin-4-ylamide 20 ml of trifluoroacetic acid are added at 5° C. over the course of 3 min to a solution of 1.048 g of Boc-Phe[C]Phe-(L)-Val-(L)-Phe-morpholin-4-ylamide (Example 2) in 20 ml of abs. methylene chloride. After stirring for a further 90 min at RT, the batch is concentrated by evaporation, 150 ml of saturated aqueous sodium hydrogen carbonate solution are added to the residue and extraction is carried out three times with ethyl acetate. The combined extracts are washed in succession with 100 ml of water, 100 ml of saturated sodium hydrogen carbonate solution, 100 ml of water and with brine. After drying over sodium sulfate, the solvent is concentrated by evaporation and the crude product is purified by column chromatography (SiO$_2$, methylene chloride/methanol/ammonia: 95/5/0.1 to 90/10/0.1 (v/v)) to yield the title compound. TLC R$_f$(G)=0.33; FAB-MS (M+H)$^+$=629.

EXAMPLE 5

3-Benzofuranoyl-Phe[C]Phe-(L)-Val-(L)-Phe-morpholin-4-ylamide 93 mg of BOP, 29 mg of HOBT and 0.044 ml of N-methylmorpholine are added in succession to a solution of 30.9 mg of benzofuran-3-carboxylic acid (preparation according to Chin-Hsing Chou et al., J. Org. Chem. 51, 420814 4212, 1986) in 3 ml of DMF and then the batch is stirred for 30 min at RT. After the addition of 100 mg of H-Phe[C]Phe-(L)-Val-(L)-Phe-morpholin-1-ylamide (Example 4) the batch is stirred for a further 3 hours at RT and then poured onto 100 ml of water. After extracting three times with 50 ml of ethyl acetate each time, the combined organic phases are washed in succession with 100 ml of water, 100 ml of saturated sodium hydrogen carbonate solution, 100 ml of water and 100 ml of brine. After drying over sodium sulfate and concentrating by evaporation, the residue is digested with ether, and the title compound, which is obtained in the form of a solid, is dried. TLC R$_f$(G)=0.73; FAB-MS (M+H)$^+$=773.

EXAMPLE 6

Nicotinoyl-Phe[C]Phe-(L)-Val-(L)-Phe-morpholin-4-ylamide

Analogously to Example 5, 23.5 mg of nicotinic acid in 3 ml of DMF are converted into the title compound with 93 mg of BOP, 29 mg of HOBT, 0.044 ml of N-methylmorpholine and 100 mg of H-Phe[C]Phe-(L)-Val-(L)-Phe-morpholin-1-ylamide. After crystallisation from ether and drying, the pure title compound is obtained. TLC R$_f$(G)=0.57; FAB-MS (M+H)+=734.

EXAMPLE 7

Morpholinocarbonyl-Val-Phe[C]Phe-(L)-Val-(L)-Phe-morpholin-4-yl-amide

Analogously to Example 5, 44 mg of N-morpholinocarbonyl-(L)-Val in 3 ml of DMF are converted into the title compound with 93 mg of BOP, 29 mg of HOBT, 0.044 ml of N-methylmorpholine and 100 mg of H-Phe[C]Phe-(L)-Val-(L)-Phe-morpholin-4-ylamide (Example 4). Crystallisation from ether and drying yields the title compound. TLC R$_f$(G)=0.5; FAB-MS (M+H)+= 841.5.

7 a) N-Chlorocarbonylmorpholine

Over the course of 5 min at RT, 180 ml of a 20% phosgene solution in toluene, and then, over the course of 10 min with cooling to from 5° to 10° C., a solution of 18 ml of morpholine in 180 ml of toluene are added to 180 ml of toluene. The white suspension is stirred for 1 h at RT and for a further 2 h under a stream of nitrogen. After filtering off the solid with suction and then washing it with toluene, the filtrate is concentrated by evaporation. The resulting title compound is processed further without additional purification. IR (CH$_2$Cl$_2$): 1730, 1400, 1205 cm$^{-1}$.

7 b) N-Morpholinocarbonyl-(L)-Val-benzyl ester 15 g of the p-toluenesulfonic acid salt of (L)-valine benzyl ester (Fluka, Buchs, Switzerland) and 15.4 ml of N-ethyldiisopropylamine are added to 3 ml of N-chlorocarbonylmorpholine in 210 ml of CH$_2$Cl2. After stirring for 16 h at RT, a further 1.5 ml and, after 23 h, a further 0.8 ml, of N-chlorocarbonylmorpholine are added. After a total of 39 hours, the reaction mixture is concentrated, diluted with ethyl acetate and washed in succession twice with 1 N hydrochloric acid, once with water, once with saturated aqueous sodium hydrogen carbonate solution and twice with brine. After drying over sodium sulfate, the batch is concentrated under reduced pressure. The crude product is purified by column chromatography (SiO$_2$, ethyl acetate) to obtain the title compound. TLC R$_f$(B)=0.5.

7 c) N-Morpholinocarbonyl-(L)-Val

A solution of 9.7 g of N-morpholinocarbonyl-(L)-Val-benzyl ester in 300 ml of ethyl acetate is hydrogenated for 3 h at RT in the presence of 2 g of 10% Pd/C and under normal pressure. After filtering off and then washing the catalyst with ethyl acetate, the mother liquor is concentrated. The residue is taken up in ethyl acetate, filtered over Hyflo Super Cel® (kieselguhr, Fluka, Buchs, Switzerland) and concentrated under reduced pressure. The resulting title compound is further processed without additional purification.

EXAMPLE 8

Boc-Cha[C]Cha-(L)-Val-(L)-Cha-morpholin-4-ylamide

Analogously to Example 3 a), 100 mg of Boc-Phe[C]Phe-CL)-Val-(L)-Phe-morpholin-4-ylamide (Example 2) in 30 ml of methanol are hydrogenated over a period of 4 h at RT in the presence of 40 mg of Nishimura catalyst. After filtering off the catalyst and concentrating, the residue is recrystallised from hexane and purified by column chromatography (SiO$_2$, hexane/ethyl acetate: ½ (v/v)) to yield the title compound. TLC R$_f$(I)=0.5; FAB-MS (M+H)$^+$=747.

EXAMPLE 9

Boc-Cha[C](p-F)Phe-(L)-Val-(L)-(p-F-Phe)-morpholin-4-ylamide

Analogously to Example 1), 0.18 g of 5(S)-(Boc-amino)-4(S)-(tert-butyldimethylsilyloxy)-6-cyclohexyl-2(R)-(p-fluorophenylmethyl)-hexanoyl-(L)-Val-(L)-(p-F-Phe)-morpholin-4-ylamide is converted into the title compound with 114 mg of TBAF in 1.8 ml of DMF: TLC R$_f$(B)=0.44; FAB-MS (M+H)$^+$=771.

The starting material is prepared as follows:

9 a) Z-(L)-p-fluorophenylalanine

2 N NaOH is added to a solution of 5.0 g of H-(L)-(p-F-Phe)-OH [(L)-p-fluorophenylalanine (Fluka, Buchs, Switzerland)] in 55 ml of THF and 20 ml of H20 until a pH of approximately 10 is obtained. 4.66 g of chloroformic acid benzyl ester are added dropwise to the resulting suspension and then the batch is stirred for 4 h at RT; the pH is maintained at approximately 10 by the addition of 2 N NaOH. The reaction mixture is concentrated by evaporation and the residue is partitioned between ethyl acetate, 10% citric acid solution and brine and dried with Na$_2$SO$_4$. Column chromatography (SiO$_2$, dichloromethane/-methanol 7:3) yields the pure title compound: TLC R$_f$(K)=0.50.

9 b) Z-(L)-(O-F-Phe)-morpholin-4-ylamide

Analogously to Example 11), 9.01 g of Z-(L)-(p-F-Phe)-OH and 2.38 g of morpholine in 350 ml of dichloromethane are converted into the title compound with 5.62 g of DCC, the title compound being obtained in pure form after column chromatography (SiO$_2$, ethyl acetate): TLC R$_f$(B)=0.6.

9 c) H-(L)-(p-F-Phe)-morpholin-4-ylamide

Analogously to Example 1 m), 0.90 g of Z-(L)-(p-F-Phe)-morpholin-4-ylamide in 50 ml of MeOH is converted into the title compound by hydrogenolysis with 0.2 g of 10% Pd/C: TLC R$_f$(L)=0.4.

9 d) Z-(L)-Val-(L)-(p-F-Phe)-morpholin-4-ylamide

Analogously to Example 1 n), 1.36 g of H-(L)-(p-F-Phe)-morpholino4-ylamide and 1.36 g of Z-(L)-Val in 70 ml of dichloromethane are converted into the title compound with 1.11 g of DCC: TLC R$_f$(B)=0.55.

9 e) H-(L)-Val-(L)-(p-F-Phe)-morpholin-4-ylamide

Analogously to Example 1 m), 2.80 g of Z-(L)-Val-(L)-(p-F-Phe)-morpholin-4-ylamide in 150 ml of MeOH are converted into the title compound by hydrogenolysis with 0.6 g of 10% Pd/C, the title compound being obtained in pure form after column chromatography (SiO$_2$, dichloromethane/methanol 9:1): TLC R$_f$(F)=0.44; FAB-MS (M+H)$^+$=352.

9 f) 5(S)-(Boc-amino)-4(S)-(tert-butyldimethyisilyloxy)-6-cyclohexyl-2(R)-(D-fluorophenylmethyl)-hexanoyl-(L)-Val-(L)-(p-F-Phe)-morpholin-4-ylamide 76 mg of HBTU are added to a solution of 100 mg of 5(S)-(Boc-amino)-4(S)-(tert-butyldimethylsilyloxy)-6-cyclohexyl-2(R)-(p-fluorophenylmethyl)-hexanoic acid (Example 1 j)) and 70.3 mg of H-(L)-Val-(L)-(p-F-Phe)-morpholin-4-ylamide in 1.7 ml of NMM/CH$_3$CN 0.25 M (0.25 M NMM in CH$_3$CN). After 16 h at RT, the batch is concentrated by evaporation. The residue is partitioned between 3 portions of ethyl acetate, water, 2 portions of 10% citric acid solution, water, 2 portions of saturated sodium hydrogen carbonate solution, water and finally brine, and the organic phases are dried with sodium sulfate and concentrated by evaporation to yield the title compound: TLC R$_f$(A)=0.20; FAB-MS (M+H)$^+$=885.

EXAMPLE 10

Boc-Cha[C](D-F)Phe-(L)-Val-(L)-(0-CH$_3$O-Phe)-morpholin-4-ylamide

Analogously to Example 1), 0.18 g of 5(S)-(Boc-amino)-4(S)-(tert-butyldimethylsilyloxy)-6-cyclohexyl-2(R)-(p-fluorophenylmethyl)-hexanoyl-(L)-Val-(L)-(p-CH$_3$O)Phe-morpholin-4-ylamide is converted into the title compound with 114 mg of TBAF in 1.8 ml of DMF: TLC R$_f$(B)=0.40; FAB-MS (M+H)$^+$=783.

The starting material is prepared as follows:

10 a) Z-(DL)-p-methoxyphenylalanine

Analogously to Example 9 a), 2.5 g of DL-p-methoxyphenylalanine (Bachem, Bubendorf, Switzerland) in 64 ml of THF and 17.9 ml of H$_2$O are reacted with 2.3 g of chloroformic acid benzyl ester, the pH being maintained at approximately 10 by the addition of 1 N Na$_2$CO$_3$ solution. The reaction mixture is concentrated by evaporation and the residue is partitioned between ethyl acetate and dilute hydrochloric acid and brine to yield the title compound: TLC R$_f$(B)=0.3; IR (CH$_2$Cl$_2$): 1720, 1612, 1513 cm$^{-1}$.

10 b) Z-(DL)-(p-CH$_3$O-Phe)-morpholin-4-ylamide

Analogously to Example 11), 2.4 g of Z-(DL)-(p-CH$_3$O-Phe)-OH (Z-(DL)-p-methoxyphenylalanine) in 36 ml of methylene chloride and 0.63 g of morpholine in 36 ml of methylene chloride are reacted with 1.5 g of DCC to form the title compound: TLC $R_f(B)$=0.5; IR ($CH_2Cl_2$): 1720, 1641, 1612, 1512 $cm^{-1}$.

10 c) H-(DL)-(p-$CH_3$O-Phe)-morpholin-4-ylamide

Analogously to Example 1 m), 3.8 g of Z-(DL)-(p-$CH_3$O-Phe)-morpholin-4-ylamide in 70 ml of methanol are converted into the title compound by hydrogenolysis with 0.8 g of 0% Pd/C, the title compound being obtained in pure form after column chromatography ($SiO_2$, methylene chloride/methanol 9:1): TLC $R_f(F)$=0.3; IR ($CH_2Cl_2$): 1642, 1613, 514, 1463, 1443.

10 d) Z-(L)-Val-(DL)-(p-$CH_3$O-Phe)-morpholin-4-ylamide

Analogously to Example 1 n), 1.80 g of Z-(L)-Val-OH in 40 ml of methylene chloride and 1.90 g of H-(DL)-(p-$CH_3$O-Phe)-morpholin-4-ylamide in 40 ml of methylene chloride are reacted with 1.48 g of DCC to form the title compound: TLC $R_f(B)$=0.12; IR ($CH_2Cl_2$): 1722, 1674, 1643, 1612, 1512, 1465, 1443.

10 e) H-(L)-Val-(L)-(p-$CH_3$O-Phe)-morpholin-4-ylamide and H-(L)-Val-(D)-(p-$CH_3$O-Phe)-morpholin-4-ylamide Analogously to Example 1 m), 3.6 g of Z-(L)-Val-(DL)-(p-$CH_3$O-Phe)-morpholin-4-ylamide in 150 ml of MeOH are converted into a mixture of the title compounds by hydrogenolysis with 0.6 g of 10% Pd/C. Column chromatography ($SiO_2$, dichloromethane→dichloromethane/methanol 19:1→, dichloromethane/methanol 9:1) yields first a fraction which, according to amino acid analysis by means of GC on a Chirasil-L-Val column 0l. Bayer, Z. Naturforschung, B 1983, 38, 1281) contains H-(L)-Val-(L)-(p-$CH_3$O-Phe)-morpholin-4-ylamide {TLC $R_f(F)$=0.52; FAB-MS $(M+H)^+$=364; GC $T_{Ret}$ [(p-$CH_3$O-Phe) derivative] =27.65 min}, followed by a fraction containing the epimer H-(L)-Val-(D)-(p-$CH_3$O-Phe)-morpholin-4-ylamide {TLC $R_f(F)$=0.37; GC $T_{Ret}$ [(p-$CH_3$O)Phe derivative]=27.26 min}.

10 f) 5(S)-(Boc-amino)-4(S)-(tert-butyldimethylsilyloxy)-6-cyclohexyl-2(R)-(p-fluorophenylmethyl)-hexanoyl-CL)-Val-(L)-(p-$CH_3$O-Phe)-morpholin-4-ylamide Analogously to Example 9 f), 100 mg of 5(S)-(Boc-amino)-4(S)-(tert-butyldimethylsilyloxy)-6-cyclohexyl-2(R)-(p-fluorophenylmethyl)-hexanoic acid (Example 1 j)) and 72.7 mg of H-(L)-Val-(L)-(p-$CH_3$O-Phe)-morpholin-4-ylamide in 1.7 ml of NMM/$CH_3$CN 0.25 M and 1 ml of DMF are reacted with 76 mg of HBTU to form the title compound: TLC $R_f(A)$=0.18; FAB-MS $(M+H)^+$=897.

EXAMPLE 11

Boc-Cha[C](D-F)Phe-(L)-Val-(L)-Cha-morpholin-4-ylamide

Analogously to Example 1), 0.16 g of 5(S)-(Boc-amino)-4(S)-(tert-butyldimethylsilyloxy)-6-cyclohexyl-2(R)-p-fluorophenylmethyl)-hexanoyl-(L)-Val-(L)-Cha-morpholin-4-ylamide is converted into the title compound with 114 mg of TBAF in 1.8 ml of DMF: TLC $R_f(B)$=0.49; FAB-MS (M+H)+=759.

The starting material is prepared as follows:

11 a) H-(L)-Val-(L)-Cha-morpholin-4-ylamide

Analogously to Example 3 a), 1.0 g of H-(L)-Val-(L)-Phe-morpholin-4-ylamide (Example 1 o)) in 25 ml of methanol is hydrogenated with 0.15 g of Nishimura catalyst to form the title compound which is obtained in pure form by column chromatography ($SiO_2$, methylene chloride→methylene chloride/methanol 40:1) and digestion with hexane: TLC $R_f(F)$=0.50; FAB-MS (M+H)+=340; IR ($CH_2Cl_2$): 1645, 1509, 1463, 1449.

11 b) 5(S)-(Boc-amino)-4(S)-(tert-butyldimethylsilyloxy)-6-cyclohexyl-2(R)-(p-fluorophenylmethyl)-hexanoyl-(L)-Val-(L)-Cha-morpholin-4-ylamide Analogously to Example 9 f), 100 mg of 5(S)-(Boc-amino)-4(S)-(tert-butyldimethylsilyloxy)-6-cyclohexyl-2(R)-(p-fluorophenylmethyl)-hexanoic acid (Example 1 j)) and 67.9 mg of H-(L)-Val-(L)-Cha-morpholin-4-ylamide in 1.7 ml of NMM/$CH_3$CN 0.25 M are reacted with 76 mg of HBTU to form the title compound: TLC $R_f(A)$=0.47; FAB-MS $(M+H)^+$=873.

EXAMPLE 12

1,2,3,4-tetrahydroisoquinoline-3(S)-carbonyl-Val-Phe[C]Phe-(L)-Val-(L)-Phe-morpholin-4-ylamide Analogously to Example 4), 242 mg of N-Boc-1,2,3,4-tetrahydroisoquinoline-3(S)-carbonyl-Val-Phe[C]Phe-(L)-Val-(L)-Phe-morpholin-4-ylamide in 8 ml of methylene chloride are cleaved with 8 ml of trifluoroacetic acid to form the title compound: TLC $R_f(J)$=0.5; FAB-MS (M+H)+= 887.5; IR (KBr): 1639, 1531, 1495, 1453.

The starting material is prepared as follows:

12 a) N-Boc-1,2,3,4-tetrahydroisoquinoline-3(S)-carboxylic acid 20 g of 1,2,3,4-tetrahydroisoquinoline-3(S)-carboxylic acid (for preparation see: P. L. Julian, W. J. Karpel, A. Magnani and E. W. Meyer, J. Am. Chem. Soc. 1948, 70, 180, except that (L)-β-phenylalanine is used as starting material), 233.6 g of potassium carbonate and 37 g of Boc-anhydride are stirred for 4 h at RT in 400 ml of dioxane/water 1:1. The reaction mixture is acidified with dilute HCl to pH 2 and extracted three times with ethyl acetate. After washing the organic phases with 1 N potassium hydrogen sulfate solution, water and brine, drying with $Na_2SO_4$, concentrating by evaporation and crystallising from methylene chloride/hexane, the title compound is obtained: TLC $R_f(C)$=0.2; $[α]_D$=16 (c=1, MeOH).

12 b) N-Boc-1,2,3,4-tetrahydroisoquinoline-3(S)-carbonyl-L-Val-benzyl ester

Under a $N_2$ atmosphere, 6.47 g of N-Boc-1,2,3,4-tetrahydroisoquinoline-3(S)-carboxylic acid in 70 ml of methylene chloride are converted into the corresponding acid chloride at 0° C. with 4.7 g of 1-chloro-N,N,2-trimethylprop-1-enylamine (Haveaux, B., Dekoker, A., Rens, M., Sidani, A. R., Toye, J. and Ghosez, L., Org. Synth. 59, 26–34) and, after 15 min, 9.0 g of Hünig base and a solution of 6.83 g of L-Val-benzyl ester-HCl in 54 ml of methylene chloride are added thereto. After 15 min at 0° C. and 16 h at RT, the reaction mixture is washed with 10% citric acid solution, water, sat. sodium carbonate solution, water and brine. The aqueous phases are extracted with 2 portions of methylene chloride and the combined organic phases are dried with sodium sulfate and concentrated by evaporation. Because, according to $^1$H-NMR, some of the Boc-protecting group has been lost in the course of the reaction, the crude product is further reacted with 6.8 g of Boc-anhydride in 160 ml of methylene chloride and 2.7 g of Htinig base. Column chromatography ($SiO_2$, hexane/ethyl acetate 3:1) yields the pure title compound: TLC $R_f(E)$= 0.15.

12 c) N-Boc-1,2,3,4-tetrahydroisoquinoline-3(S)-carbonyl-L-Val

Analogously to Example 7 c), 1.97 g of N-Boc-1,2,3,4-tetrahydroisoquinoline-3(S)-carbonyl-L-Val-benzyl ester in 50 ml of ethyl acetate are hydrogenated with 0.4 g of 10% Pd/C to form the title compound, which is used in the next stage without further purification: TLC $R_f(J)$=0.53; FAB-MS (M+H)+=377.

12 d) N-Boc-1,2,3,4-tetrahydroisoquinoline-3(S)-carbonyl-Val-Phe[C]Phe-(L)-Val-(L)-Phe-morpholin-4-ylamide Analogously to Example 5), 180 mg of N-Boc-1,2,3,4-tetrahydroisoquinoline-3(S)-carbonyl-L-Val in 4 ml of DMF are reacted with 232 mg of BOP, 71 mg of HOBT, 0.11 ml of NMM and a solution of 250 mg of H-Phe[C]Phe-(L)-Val-(L)-Phe-morpholin-4-ylamide (Example 4) in 2 ml of DMF. Column chromatography (SiO₂, ethyl acetate) yields the title compound which, according to amino acid analysis (GC, Chirasil-L-Val: (E. Bayer, Z. Naturforschung, B 1983, 38, 1281)) contains an epimer (approximately 14% D-Val content) as a secondary product: TLC $R_f(B)$=0.4; FAB-MS (M+H)+=987; IR (KBr): 1697, 1643, 1523, 1496.

EXAMPLE 13

Boc-Phe[C]Phe-(L)-Val-(L)-(p-F-Phe)-morpholin-4-ylamide

Analogously to Example 1), 375 mg of 5(S)-(Boc-amino)-4(S)-(tert-butyldimethylsilyloxy)-6.phenyl-2(R)-phenylmethylhexanoyl-(L)-Val-(L)-(p-F-Phe)-morpholin-4-ylamide in 7 ml of DMF are desilylated with 275 mg of TBAF to form the title compound which, after crystallisation from diethyl ether/hexane, is obtained in pure form: TLC $R_f(3)$=0.50; FAB-MS (M+H)+=747.

The starting material is prepared as follows:

13 a) 5(S)-(Boc-amino)-4(S)-(tert-butyldimethyisilyloxy)-6-Phenyl-2(R)-phenylmethylhexanoyl-(L)-Val-(L)-(p-F-Phe)-morpholin-4-ylamide Analogously to Example 1 k), 250 mg of 5(S)-(Boc-amino)-4(S)-(tert-butyldimethylsilyloxy)-6-phenyl-2(R)-phenylmethylhexanoic acid (Example 2 d)) in 5 ml of DMF are reacted with 230.6 mg of BOP, 70.4 mg of HOBT, 130 µl of NMM and 199.7 mg of H-(L)-Val-(L)-(p-F)Phe-morpholin-4-ylamide (for preparation see Example 9 e)) dissolved in 2 ml of DMF. Column chromatography (SiO₂, ethyl acetate/hexane 2:1) yields the title compound: TLC $R_f(I)$=0.43; FAB-MS (M+H)⁺=861.

EXAMPLE 14

Boc-Phe[C]Phe-(L)-Val-(L)-(p-CH₃O-Phe)-morpholin-4-ylamide Analogously to Example 1), 283 mg of 5(S)-(Boc-amino)-4(S)-(tert-butyldimethylsilyloxy)-6-phenyl-2(R)-phenylmethylhexanoyl-(L)-Val-(L)-(p-CH₃O)Phe-morpholin-4-yl-amide in 7 ml of DMF are desilylated with 204.5 mg of TBAF to form the title compound which, after digestion with diethyl ether/hexane and column chromatography (SiO₂, ethyl acetate) is obtained in pure form: TLC $R_f(B)$=0.37; FAB-MS (M+H)+=759.

The starting material is prepared as follows:

14 a) 5(S)-(Boc-amino)-4(S)-(tert-butyldimethylsilyloxy)-6-phenyl-2(R)-phenylmethylhexanoyl-(L)-Val-(L)-(p-CH₃O-Phe)-morpholin-4-ylamide Analogously to Example 1 k), 250 mg of 5(S)-(Boc-amino)-4(S)-(tert-butyldimethylsilyloxy)-6-phenyl-2(R)-phenylmethylhexanoic acid (Example 2 d)) in 5 ml of DMF are reacted with 230.6 mg of BOP, 70.4 mg of HOBT, 130 gl of NMM and 206.6 mg of H-(L)-Val-(L)-(P-CH₃O)Phe-morpholin-4-ylamide (for preparation see Example 10 e)) dissolved in 2 ml of DMF. Column chromatography (SiO₂, ethyl acetate/hexane 2: 1) yields the title compound: TLC $R_f(I)$=0.37; FAB-MS (M+H)+=873.

EXAMPLE 15

Boc-Phe[C]Phe-(L)-Val-(L)-Cha-morpholin-4-ylamide

Analogously to Example 1), 430 mg of 5(S)-(Boc-amino)-4(S)-(tert-butyldimethylsilyloxy)-6-phenyl-2(R)-phenylmethylhexanoyl-(L)-Val-(L)-Cha-morpholin-4-ylamide in 5 ml of DMF are desilylated with 320 mg of TBAF to form the title compound which, after column chromatography (SiO₂, ethyl acetate) and digestion with hexane, is obtained in pure form: TLC $R_f(F)$=0.51; FAB-MS (M+H)+=735.

The starting material is prepared as follows:

15 a) 5(S)-(Boc-amino)-4(S)-(tert-butyldimethylsilyloxy)-6-phenyl-2(R)-phenylmethylhexanoyl-(L)-Val-(L)-Cha-morpholin-4-ylamide Analogously to Example 1 k), 300 mg of 5(S)-(Boc-amino)-4(S)-(tert-butyldimethylsilyloxy)-6-phenyl-2(R)-phenylmethylhexanoic acid (Example 2 d)) in 3 ml of DMF are reacted with 277 mg of BOP, 84.5 mg of HOBT, 0.22 ml of NMM and 231 mg of H-(L)-Val-(L)-Cha-morpholin-4-ylamide (for preparation see Example 11 a)) dissolved in 2 ml of DMF. Column chromatography (SiO₂, ethyl acetate/hexane 1:1) yields the title compound: TLC $R_f(A)$=0.28; FAB-MS (M+H)⁺=849.

EXAMPLE 16

Boc-Phe[C]Phe-(L)-Ile-(L)-Phe-morpholin-4-ylamide

Analogously to Example 1), 329.8 mg of 5(S)-(Boc-amino)-4(S)-(tert-butyldimethylsilyloxy)-6-phenyl-2(R)-phenylmethylhexanoyl-(L)-Ile-(L)-phe-morpholin-4-ylamide in 5 ml of DMF are desilylated with 242.7 mg of TBAF to form the title compound which, after digestion with hexane, is obtained in pure form: TLC $R_f(B)$=0.57; FAB-MS (M+H)⁺=743.

The starting material is prepared as follows:

16 a) Z-(L)-Ile-(L)-Phe-morpholin-4-ylamide

Analogously to Example 1 n), 294 mg of Z-(L)-Ile in 10 ml of dichloromethane are converted with 229 mg of DCC and 260 mg of H-(L)-Phe-morpholin-4-ylamide (Example 1 m)) into the title compound, which, after column chromatography (SiO₂, ethyl acetate/hexane 1:1), is obtained in pure form: TLC $R_f(A)$=0.43; FAB-MS (M+H)⁺=482.

16 b) H-(L)-Ile-(L)-Phe-morpholin-4-ylamide

Analogously to Example 1 m), 0.38 g of Z-(L)-Ile-(L)-Phe-morpholin-4-ylamide in 15 ml of MeOH is converted by hydrogenolysis with 0.12 g of 10% Pd/C into the title compound which, after column chromatography (SiO₂, dichloromethane/methanol 9:1), is obtained in pure form: TLC $R_f(F)$=0.5; FAB-MS (M+H)⁺=348.

16 c) 5(S)-(Boc-amino)-4(S)-(tert-butyldimethylsilyloxy)-6-phenyl-2(R)-phenylmethylhexanoyl-CL)-Ile-(L)-Phe-morpholin-4-ylamide Analogously to Example 1 k), 240.5 mg of 5(S)-(Boc-amino)-4(S)-(tert-butyldimethylsilyloxy)-6-phenyl-2(R)-phenylmethylhexanoic acid (Example 2 d)) in 5 ml of DMF are reacted with 242 mg of BOP, 73.8 mg of HOBT, 125.5 µl of NMM and 190 mg of H-(L)-Ile-(L)-Phe-morpholin-4-ylamide. Column chromatography (SiO₂, ethyl acetate/hexane 1:1) yields the title compound: TLC $R_f(A)$=0.21; FAB-MS (M+H)⁺=857.

EXAMPLE 17

Boc-Phe[C]Phe-(L)-Val-Gly-morpholin-4-ylamide

Analogously to Example 1), 343.7 mg of 5(S)-(Boc-amino)-4(S)-(tert-butyldimethylsilyloxy)-6-phenyl-2(R)-phenylmethylhexanoyl-(L)-Val-Gly-morpholin-4-ylamide in 5 ml of DMF are desilylated with 282.7 mg of TBAF to form the title compound which is finally digested with diethyl ether: TLC $R_f(B)$=0.23; FAB-MS (M+H)⁺=639.

The starting material is prepared as follows:

17 a) Z-Gly-morpholin-4-ylamide

Analogously to Example 11), 8.37 g of Z-Gly-OH in 500 ml of dichloromethane are convened into the title compound with 8.25 g of DCC and 3.49 ml of morpholine: TLC $R_f(B)$=0.28.

17 b) H-Gly-morpholin-4-ylamide

Analogously to Example 1 m), 10.8 g of Z-Gly-morpholin-4-ylamide in 600 ml of MeOH are converted by hydrogenolysis with 3 g of 10% Pd/C into the title compound which, after filtering off the catalyst and concentrating the filtrate by evaporation, is used directly in the next stage: TLC $R_f(F)$=0.2; IR ($CH_2Cl_2$): 1654, 1461, 1440.

17 c) Z-(L)-Val-Gly-morpholin-4-ylamide

Analogously to Example 1 n), 2.51 g of Z-(L)-Val in 75 ml of dichloromethane are converted into the title compound with 2.06 g of DCC and 1.44 g of H-Gly-morpholin-4-ylamide: TLC $R_f(B)$=0.21.

17 d) H-(L)-Val-Gly-morpholin-4-ylamide

Analogously to Example 1 m), 3.7 g of Z-(L)-Val-Gly-morpholin-4-ylamide in 160 ml of MeOH are converted by hydrogenolysis with 0.6 g of 10% Pd/C into the title compound which, after filtering off the catalyst and column chromatography ($SiO_2$, dichloromethane/methanol 9:1→4:1) is obtained in pure form: TLC $R_f(F)$=0.23; FAB-MS $(M+H)^+$=244; IR ($CH_2Cl_2$): 1650, 1508, 1467, 1439.

17 e) 5(S)-(Boc-amino)-4(S)-(tert-butyldimethylsilyloxy)-6-phenyl-2(R)-phenylmethylhexanoyl-(L)-Val-Gly-morpholin-4-ylamide Analogously to Example 1 k), 300 mg of 5(S)-(Boc-amino)-4(S)-(tert-butyldimethylsilyloxy)-6-phenyl-2(R)-phenylmethylhexanoic acid (Example 2 d)) in 5 ml of DMF are reacted with 302 mg of BOP, 92.1 mg of HOBT, 156.5 μl of NMM and 175.5 mg of H-(L)-Val-Gly-morpholin-4-ylamide. Column chromatography ($SiO_2$, ethyl acetate/hexane 1:9→ethyl acetate) yields the title compound: TLC $R_f(B)$=0.44; FAB-MS $(M+H)^+$=753.

EXAMPLE 18

Boc-Phe[C]Phe-(L)-Ile-Gly-morpholin-4-ylamide

Analogously to Example 1), 362.4 mg of 5(S)-(Boc-amino)-4(S)-(tert-butyldimethylsilyloxy)-6-phenyl-2(R)-phenylmethylhexanoyl-(L)-Ile-Gly-morpholin-4-ylamide in 5 ml of DMF are desilylated with 292.7 mg of TBAF to form the title compound which is finally digested with diethyl ether: TLC $R_f(B)$=0.30; FAB-MS $(M+H)^+$=653.

The starting material is prepared as follows:

18 a) Z-(L)-Ile-Gly-morpholin-4-ylamide

Analogously to Example 1 n), 2.65 g of Z-(L)-Ile in 75 ml of dichloromethane are reacted with 2.06 g of DCC and 1.44 g of H-Gly-morpholin-4-ylamide (Example 17 b)). After digestion with diethyl ether the title compound is obtained: TLC $R_f(F)$=0.7.

18 b) H-(L)-Ile-Gly-morpholin-4-ylamide

Analogously to Example 1 m), 3.2 g of Z-(L)-Ile-Gly-morpholin-4-ylamide in 160 ml of MeOH are converted by hydrogenolysis with 0.6 g of 10% Pd/C into the title compound which, after filtering off the catalyst and column chromatography ($SiO_2$, dichloromethane/methanol 9:1), is obtained in pure form: TLC $R_f(F)$=0.3; FAB-MS $(M+H)^+$=258; IR ($CH_2Cl_2$): 1653, 1510, 1467, 1439.

18 c) 5(S)-(Boc-amino)-4(S)-(tert-butyldimethylsilyloxy)-6-1phenyl-2(R)-phenylmethylhexanoyl-(L)-Ile-Gly-morpholin-4-ylamide Analogously to Example 1 k), 300 mg of 5(S)-(Boc-amino)-4(S)-(tert-butyldimethylsilyloxy)-6-phenyl-2(R)-phenylmethylhexanoic acid (Example 2 d)) in 5 ml of DMF are reacted with 301.8 mg of BOP, 92.1 mg of HOBT, 156.5 gl of NMM and 185 mg of H-(L)-Ile-Gly-morpholin-4-ylamide. Column chromatography ($SiO_2$, ethyl acetate/hexane 9:1) yields the title compound: TLC $R_f(B)$=0.40; FAB-MS $(M+H)^+$=767.

EXAMPLE 19

Boc-Phe[C]Phe-(L)-Val-(L)-Val-morpholin-4-ylamide

Analogously to Example 1 ), 416 mg of 5 (S)-(Boc-amino)-4(S)-(tert-butyldimethylsilyloxy)-6-phenyl-2(R)-phenylmethylhexanoyl-(L)-Val-(L)-Val-morpholin-4-ylamide in 10 ml of DMF are desilylated with 330 mg of TBAF to form the title compound which is finally digested with diethyl ether: TLC $R_f(B)$=0.39; FAB-MS $(M+H)^+$=681.

The starting material is prepared as follows:

19 a) Z-(L)-Val-(L)-Val-morpholin-4-ylamide

Analogously to Example 11), 2.0 g of Z-(L)-Val-(L)-Val-OH (Bachere, Bubendoff, Switzerland) in 50 ml of dichloromethane are converted into the title compound with 1.17 g of DCC and 0.96 ml of morpholine dissolved in 50 ml of dichloromethane: TLC $R_f(B)$=0.5.

19 b) H-(L)-Val-(L)-Val-morpholin-4-ylamide

Analogously to Example 1 m), 2.3 g of Z-(L)-Val-(L)-Val-morpholin-4-ylamide in 220 ml of MeOH are converted by hydrogenolysis with 0.5 g of 10% Pd/C into the title compound which, after filtering off the catalyst and column chromatography ($SiO_2$, dichloromethane→dichloromethane/methanol 19:1→9:1) and stirring in diethyl ether/hexane, is obtained in pure form: TLC $R_f(F)$=0.74; FAB-MS $(M+H)^+$=286; IR ($CH_2Cl_2$): 1642, 1507, 1461, 1440.

19 c) 5(S)-(Boc-amino)-4(S)-(tert-butyidimethylsilyloxy)-6-phenyl-2(R)-phenylmethylhexanoyl-(L)-Val-(L)-Val-morpholin-4-ylamide Analogously to Example 1 k), 300 mg of 5(S)-(Boc-amino)-4(S)-(tert-butyldimethylsilyloxy)-6-phenyl-2(R)-phenylmethylhexanoic acid (Example 2 d)) in 5 ml of DMF are reacted with 277 mg of BOP, 84.5 mg of HOBT, 156.5 gl of NMM and 194.6 mg of H-(L)-Val-(L)-Val-morpholin-4-ylamide. Column chromatography ($SiO_2$, ethyl acetate/hexane 2: 1) yields the title compound: TLC $R_f(I)$=0.27; FAB-MS $(M+H)^+$=795.

EXAMPLE 20

Boc-Phe[C]Phe-(L)-Val-(L)-Phe-thiomorpholin-4-ylamide

Analogously to Example 1), 484 mg of 5(S)-(Boc-amino)-4(S)-(tert-butyldimethylsilyloxy)-6-phenyl-2(R)-phenylmethylhexanoyl-(L)-Val-(L)-Phe-thiomorpholin-4-ylamide in 5 ml of DMF are desilylated with 356 mg of TBAF. Column chromatography ($SiO_2$, ethyl acetate/hexane 2: 1) and digestion with hexane yields the title compound: TLC $R_f(I)$=0.31; FAB-MS $(M+H)^+$=745.

The starting material is prepared as follows:

20 a) Z-(L)-Val-(L)-Phe-thiomorpholin-4-ylamide

Analogously to Example 11), 1.99 g of Z-(L)-Val-(L)-Phe-OH (Bachere, Bubendoff, Switzerland) in 40 ml of dichloromethane are reacted with 1.03 g of DCC and a solution of 0.52 g of thiomorpholine in 40 ml of dichloromethane to form the title compound which, after extraction, is obtained in the form of an oil: TLC $R_f(F)$=0.8; IR ($CH_2Cl_2$): 1725, 1675, 1642, 1499, 1465, 1454.

20 b) H-(L)-Val-(L)-Phe-thiomorpholin-4-ylamide 45 ml of HBr/acetic acid 33% (Fluka, Buchs, Switzerland) are added, while cooling with ice, to 2 g of Z-(L)-Val-(L)-Phe-thiomorpholin-4-ylamide and the reaction mixture is stirred for 1.5 h at RT. It is then concentrated by evaporation, the residue is partitioned between 3 portions of ethyl acetate, sat. sodium hydrogen carbonate solution, water and brine, and the organic phases are dried with $Na_2SO_4$ and concentrated by evaporation. Column chromatography ($SiO_2$, methylene chloride/methanol 9:1) yields first the title compound, followed by a secondary product, presumably an epimer: TLC $R_f(F)=0.56$; FAB-MS $(M+H)^+$ =350; IR ($CH_2Cl_2$): 1641, 1502, 1463, 1454, 1448; amino acid analysis {GC, Chirasil-L-Val column (E. Bayer, Z. Naturforschung, B 1983, 38, 1281 )}: $T_{Ret.}${(L)-Val derivative}=8.36 min (ee≦99%), $T_{Ret.}${(L)-Phe derivative}=22.73 min (ee=94%).

20 c) 5(S)-(Boc-amino)-4(S)-(tert-butyldimethylsilyloxy)-6-phenyl-2(R)-phenylmethylhexanoyl-(L)-Val-(L)-Phe-thiomorpholin-4-ylamide Analogously to Example 1 k), 300 mg of 5(S)-(Boc-amino)-4(S)-(tert-butyldimethylsilyloxy)-6-phenyl-2 (R)-phenylmethylhexanoic acid (Example 2 d)) in 5 ml of DMF are reacted with 277 mg of BOP, 84.5 mg of HOBT, 219 gl of NMM and 238.4 mg of H-(L)-Val-(L)-Phe-thiomorpholin-4-ylamide dissolved in 3 ml of DMF. Column chromatography ($SiO_2$, ethyl acetate/hexane 1:1) yields the title compound: TLC $R_f(A)=0.43$; FAB-MS $(M+H)^+$= 859.

EXAMPLE 21

In a manner analogous to that described in any one of the above Examples, or in the manner indicated in detail hereinafter, the following compounds are obtained:

A)

1) One of the compounds mentioned hereinafter under B) to J) in which -morpholin-4-ylamide is replaced by the radical -thiomorpholin-4-ylamide;

B)

1) Boc-(p-F)Phe[C](D-F)Phe-(L)-Val-(L)-Phe-morpholin-4-ylamide

Analogously to Example 1), 83 mg of 5(S)-(Boc-amino)-4(S)-(tert-butyldimethylsilyloxy)-6-(p-fluorophenyl)-2(R)-(p-fluorophenylmethyl)-hexanoyl-(L)-Val-(L)-Phe-morpholin-4-ylamide are converted into the title compound with 60 mg of TBAF in 0.95 ml of DMF: FAB-MS $(M+H)^+$=765.

The starting material is prepared as follows:

1) a) N-Boc-(p-fluorophenylalanine):

In 0.4 liter of dioxane/water 1:1, 20 g (109 mmol) of p-fluorophenylalanine (Fluka; Buchs/Switzerland) are reacted with 35.5 g (163 mmol) of Boc-anhydride and 150 g (1.09 mol) of potassium carbonate. After 4 h, the reaction mixture is acidified with citric acid solution and extracted with 3 portions of ethyl acetate. The organic phases are washed with 10% citric acid, water and brine, dried with sodium sulfate and concentrated by evaporation. The residue is dissolved in a small amount of methylene chloride and crystallisation is carried out by the addition of hexane to yield the title compound.

1) b) N-Boc-(p-fluorophenylalaninol):

At from –5° C. to –10° C., 9.66 ml (69 mmol) of triethylamine are added to a solution of 17.9 g (63 mmol) of N-Boc-(p-fluorophenylaianine) in 73 ml of abs. THF, and a solution of 9.05 ml (69 mmol) of chloroformic acid isobutyl ester in 44 ml of abs. THF is added dropwise thereto. After stirring for 0.5 h at RT, the precipitate formed is filtered off with suction. The filtrate is added dropwise, with cooling, to 4.77 g (126 mmol) of sodium borohydride in 28 ml of water. After stirring for 4 h at RT, the batch is acidified with 10% citric acid, some of the THF is evaporated off in a rotary evaporator and the residue is partitioned between 3 portions of ethyl acetate, 2 potions of 2 N sodium hydroxide solution, water, saturated sodium hydrogen carbonate solution and brine. The organic phases are dried with sodium sulfate and concentrated by evaporation and, after dissolving in a small amount of methylene chloride and crystallising by the addition of hexane, the title compound is obtained: TLC $R_f(A)=0.36$; $^1$H-NMR (200 MHz, $CD_3OD$): 7.24 (dd, 8 and 5 Hz, 2 H), 6.98 (t, 8 Hz, 2 H), 3.73 (m, 1 H), 3.47 (d, 5 Hz, 2 H), 2.88 (dd, 13 and 6 Hz, 1 H), 2.62 (dd, 13 and 8 Hz, 1 H), 1.36 (s, 9 H).

1) c) N-Boc-(p-fluorophenylalaninal):

4.44 ml (62.4 mmol) of DMSO dissolved in 76 ml of methylene chloride are added dropwise under a $N_2$ atmosphere to a solution, cooled to –60° C., of 4.0 ml (46.8 mmol) of oxalyl chloride in 44 ml of methylene chloride. After stirring for 15 min, 8.4 g (31.2 mmol) of N-Boc-(p-fluorophenylalaninol) in the form of a solution in 185 ml of methylene chloride/THF 1:1 are added to the clear reaction solution (→precipitation) and then the batch is stirred for 25 min. 17.3 ml (124.8 mmol) of triethylamine dissolved in 38 ml of methylene chloride are then added. After stirring for 30 rain, 278 ml of a 20% potassium hydrogen sulfate solution are added dropwise, followed by 220 ml of hexane. The batch is allowed to warm up to RT, and the aqueous phase is separated off and extracted with 2 portions of ether. After washing the organic phases with saturated sodium hydrogen carbonate solution, water and brine, drying with sodium sulfate and concentrating by evaporation, the title compound is obtained and is used in the next stage without further purification: 1H-NMR (200 MHz, $CDCl_3$): 9.63 (s, 1 H), 6.9–7.2 (2m, 4 H), 5.04 (m, 1 H), 4.42 (m, 1 H), 3.10 (m, 2 H), 1.43 (s, 9 H).

1) d) 5(S)-[1(S)-(Boc-amino)-2-(p-fluorophenyl)ethyl]-dihydrofuran-2-(3H)-one

Analogously to Example 21 D) 1) b), the Zn homoenolate is formed from 16.7 g of 2-iodopropionic acid ethyl ester in 124 ml of toluene, 8.1 g of Zn/Cu and 12.4 ml of dimethylacetamide. The Zn homoenolate is transferred by means of a cannula to the trichlorotitanium isopropanolate, which has been cooled to from –40° C. to –25° C. (prepared from 5.11 ml of tetraisopropyl orthotitanate and 5.71 ml of titanium tetrachloride in 16 ml of toluene and 8.5 ml of methylene chloride). The batch is heated for 5 min at –25° C. and then cooled to –40° C. again. A solution of 9.28 g of N-Boc-(p-fluorophenylalaninal) in 33 ml of methylene chloride is then added dropwise and the batch is subsequently stirred for 15 h at approximately –20° C. and finally for 1 h at 0° C. The reaction mixture is poured onto 0.4 kg of ice-water and 0.55 liter of tert-butyl methyl ether and stirred vigorously for 10 min. The aqueous phase is separated off and extracted with 2 portions of ether, and the organic phases are washed with water, saturated sodium hydrogen carbonate solution, water and brine, dried with sodium sulfate and concentrated by evaporation to yield crystalline 5(S)-(Boc-amino)-4(S)-hydroxy-6-(p-fluorophenyl)-hexanoic acid ethyl ester as an intermediate which is heated for 2 h at 100° C. in 244 ml of toluene and 7.3 ml of acetic acid. 0.5 liter of water is added to the cooled reaction mixture and the aqueous phase is separated off and extracted with 2 portions of ether, and the org. phases are washed with saturated sodium hydrogen carbonate solution, water and brine, dried with sodium sulfate and concentrated by evaporation. Column chromatography (SiO$_2$, hexane/ethyl acetate 2: 1) yields the pure title compound: TLC R$_f$(D)=0.22; FAB-MS (M+H)$^+$=324. [α]$^D$=20.7° (c=1; ethanol).

1) e) 5(S)-[1(S)-(Boc-amino)-2-(p-fluorophenyl)ethyl]-3 (R)-(p-fluoro-phenylmethyl)-dihydrofuran-2-(3H)-one Analogously to Example 21 D) 1) c), 1.0 g of 5(S)-[1(S)-(Boc-amino)-2-(p-fluorophenyl)ethyl]-dihydrofuran-2-(3H)-one dissolved in 7.9 ml of THF is deprotonated with 6.05 ml of lithium bis(trimethylsilyl)amide 1 M in THF and alkylated with 0.673 g of p-fluorobenzyl bromide at –75° C. (1 h). Column chromatography (SiO$_2$, methylene chloride/ether 49:1) yields the pure title compound: TLC R$_f$(M)= 0.17; $^1$H-NMR (200 MHz, CDCl$_3$): 7.19–7.05 and 7.04–6.88 (2m, per 4 H), 4.50 (d, 10 Hz, HN), 4.11 (m, 1 H), 3.87 (qm, approximately 8 Hz, 1 H), 3.1–2.7 (m, 5 H), 2.33–2.14 and 2.02–1.85 (2 m, per 1 H), 1.35 (s, 9 H).

1) f) 5(S)-(Boc-amino)-4(S)-hydroxy-6-(p-fluorophenyl)-2(R)-(p-fluorophenylmethyl)-hexanoic acid Analogously to Example 1 i), 790 mg of 5(S)-[1(S)-(Boc-amino)-2-(p-fluorophenyl) ethyl]-3(R)-(p-fluorophenylmethyl)-dihydrofuran-2-(3H)-one in 9 ml of dimethoxyethane and 15 ml of water are hydrolysed with 7.3 ml of 1 M lithium hydroxide solution to form the title compound which is used further directly.

1) g) 5(S)-(Boc-amino)-4(S)-(tert-butyldimethylsilyloxy)-6-(p-fluorophenyl)-2(R)-(p-fluorophenylmethyl)-hexanoic acid Analogously to Example 1 j), 956 mg of 5(S)-(Boc-amino)-4(S)-hydroxy-6-(p-fluorophenyl)-2(R)-(p-fluorophenylmethyl)-hexanoic acid in 2.3 ml of DMF are silylated with 1.47 g of tert-butyldimethylchlorosilane and 1.19 g of imidazole. Hydrolysis of the silyl ester function with 1.76 g of potassium carbonate in 50 ml of methanol/THF/water 3:1:1 yields, after column chromatography (SiO$_2$, hexane/ethyl acetate 2:1 ), the title compound: TLC R$_f$(D)=0.13; FAB-MS (M+H)$^+$=564.

1) h) 5(S)-(Boc-amino)-4(S)-(tert-butyldimethylsilyloxy)-6-(p-fluorophenyl)-2(R)-(O-fluorolphenylmethyl)-hexanoyl-(L)-Val-(L)-Phe-morpholin-4-ylamide Analogously to Example 9 f), 110 mg of 5(S)-(Boc-amino)-4(S)-(tert-butyldimethylsilyloxy)-6-(p-fluorophenyl)-2(R)-(p-fluorophenylmethyl)-hexanoic acid and 71.5 mg of H-(L)-Val-(L)-Phe-morpholin-4-ylamide (Example 1 o)) in 1.83 ml of NMM/CH$_3$CN 0.25 M are reacted with 81.5 mg of HBTU. The pure title compound is obtained after column chromatography (SiO$_2$, m ethylene chloride/ether 3: 1 ): TLC R$_f$(N )=0.14; FAB-MS (M+H)$^+$=879.

2) Boc-(p-F)Phe[C](p-F)Phe-(L)-Val-(L)-(p-F-Phe)-morpholin-4-ylamide

Analogously to Example 1 ), 150 mg of 5(S)-(Boc-amino)-4(S)-(tert-butyldimethylsilyloxy)-6-(p-fluorophenyl)-2(R)-(p-fluorophenylmethyl)-hexanoyl-(L)-Val-(L)-(p-F-Phe)-morpholin-4-ylamide are converted into the title compound with 105 mg of TBAF in 2.5 ml of DMF: FAB-MS (M+H)$^+$=783.

The starting material is prepared as follows:

2) a) 5(S)-(Boc-amino)-4(S)-(tert-butyldimethylsilyloxy)-6-(p-fluorophenyl)-2 (R)-(p-fluorophenylmethyl)-hexanoyl-(L)-Val-(L)-(p-F-Phe)-morpholin-4-ylamide Analogously to Example 9 f), 100 mg of 5(S)-(Boc-amino)-4(S)-(tert-butyldimethylsilyloxy)-6-(p-fluorophenyl)-2(R)-(p-fluorophenylmethyl)-hexanoic acid [Example 21 B) 1) g)] and 68.5 mg of H-(L)-Val-(L)-(p-F-Phe)-morpholin-4-ylamide (Example 9 e)) in 1.67 ml of NMM/CH$_3$CN 0.25 M are reacted with 74 mg of HBTU to form the title compound: TLC R$_f$(A)=0.17; FAB-MS (M+H)$^+$=897.

3) Boc-(p-F)Phe[C](p-F)Phe-(L)-Val-(L)-(p-CH$_3$O-Phe)-morpholin-4-ylamide

Analogously to Example 1), 126 mg of 5(S)-(Boc-amino)-4(S)-(tert-butyldimethylsilyloxy)-6-(p-fluorophenyl)-2(R)-(p-fluorophenylmethyl)-hexanoyl-(L)-Val-(L)-(p-CH$_3$O-Phe)-morpholin-4-ylamide are converted into the title compound with 87 mg of TBAF in 2 ml of DMF: FAB-MS (M+H)$^+$=795.

The starting material is prepared as follows:

3) a) 5(S)-(Boc-amino)-4(S)-(tert-butyldimethylsilyloxy)-6-(p-fluorophenyl)-2(R)-(p-fluorophenylmethyl)-hexanoyl-(L)-Val-(L)-(p-CH$_3$O-Phe)-morpholin-4-ylamide Analogously to Example 9 f), 80 mg of 5(S)-(Boc-amino)-4(S)-(tert-butyldimethylsilyloxy)-6-(p-fluorophenyl)-2(R)-(p-fluorophenylmethyl)-hexanoic acid [Example 21 B) 1) g)]and 56.7 mg of H-(L)-Val-(L)-(p-CH$_3$O-Phe)morpholin-4-ylamide (Example 10e)) in 1.3 ml of NMM/CH$_3$CN 0.25 M are reacted with 59.2 mg of HBTU to form the title compound: FAB-MS (M+H)$^+$=909.

4) Boc-(p-F)Phe[C](O-F)Phe-(L)-Val-(L)-Cha-morpholin-4-ylamide

Analogously to Example 1), 230 mg of 5(S)-(Boc-amino)-4(S)-(tert-butyldimethylsilyloxy)-6-(p-fluorophenyl)-2(R)-(p-fluorophenylmethyl)-hexanoyl-(L)-Val-(L)-Cha-morpholin-4-ylamide are converted into the title compound with 164 mg of TBAF in 3.8 ml of DMF: FAB-MS (M+H)$^+$=771.

The starting material is prepared as follows: 4) a) 5(S)-(Boc-amino)-4(S)-(tert-butyldimethylsilyloxy)-6-(p-fluorophenyl)-2(R )-(p-fluoronhenylmethyl)-hexanoyl-(L)-Val-(L)-Cha-morpholin-4-ylamide Analogously to Example 9 f), 150 mg of 5(S)-(Boc-amino)-4(S)-(tert-butyldimethylsilyloxy)-6-(p-fluorophenyl)-2(R)-(p-fluorophenylmethyl)-hexanoic acid [Example 21 B) 1) g)]and 99.4 mg of H-(L)-Val-(L)-Cha-morpholin-4-ylamide (Example 11 a)) in 2.4 ml of NMM/CH$_3$CN 0.25 M are reacted with 111 mg of HBTU to form the title compound: FAB-MS (M+H)$^+$=885.

5) Boc-(p-F)Phe[C](p-F)Phe-(L)-Ile-(L)-Phe-morpholin-4-ylamide

C)

1) Boc-(p-F)Phe[C](p-CN)Phe-(L)-Val-(L)-Phe-morpholin-4-ylamide

2) Boc-(p-F)Phe[C](p-CN)Phe-(L)-Val-(L)-(p-F-Phe)-morpholin-4-ylamide

3) Boc-(p-F)Phe[C](p-CN)Phe-(L)-Val-(L)-(p-CH$_3$O-Phe)-morpholin-4-yl-amide

4) Boc-(p-F)Phe[C](p-CN)Phe-(L)-Val-(L)-Cha-morpholin-4-ylamide

5) Boc-(p-F)Phe[C](p-CN)Phe-(L)-Ile-(L)-Phe-morpholin-4-ylamide

D)

1) Boc-Phe[C](p-F)Phe-(L)-Val-(L)-Phe-morpholin-4-ylamide

Analogously to Example 1), 0.31 g of 5(S)-(Boc-amino)-4(S)-(tert-butyl-dimethylsilyloxy)-6-phenyl-2(R)-(p-fluorophenylmethyl)-hexanoyl- (L)-Val-(L)-Phe-morpholin-4-ylamide is deprotected with 226 mg of TBAF in 3.0 ml of DMF to form the title compound which, after column chromatography (SiO$_2$, ethyl acetate), is obtained in pure form: TLC R$_f$(B)=0.55; FAB-MS (M+H)$^+$=747.

The starting material is prepared as follows:

1) a) 2-Iodopropionic acid ethyl ester

A suspension of 170 ml of 2-bromopropionic acid ethyl ester (Fluka; Buchs/Switzerland) and 950 g of sodium iodide in 1.8 liters of acetone is stirred for 20 h at 60° C. The reaction mixture is filtered, the filtrate is partially concentrated by evaporation, poured onto approximately 2.5 liters of ether, washed with 1.0 liter of 1% sodium thiosulfate solution and finally with brine, dried with sodium sulfate and concentrated by evaporation. Distillation (83° C.; 20 mbar) yields the pure title compound: MS (M)$^+$=228; $^1$H-NMR (200 MHz, CDCl$_3$): 4.17 (q, 7 Hz, 2 H), 3.34 and 2.97 (21, 7 Hz, 2x 2H), 1.28 (t, 7 Hz, 3 H).

1) b) 5(S)-[1(S)-(Boc-amino)-2-phenylethyl]-dihydrofuran-2-(3H)-one (Analogously to A. E. DeCamp, A. T. Kawaguchi, R. P. Volante, and I. Shinkai, Tetrahedron Lett. 32, 1867 (1991)). Under a N$_2$ atmosphere, 8.03 g of Zn/Cu (preparation: R. D. Smith, H. E. Simmons, W. E. Parham, M. D. Bhavsar, Org. Synth., Coll. Vol 5, 855 (1973)) and 12.96 ml of dimethylacetamide are added to a solution of 17.4 g of 2-iodopropionic acid ethyl ester in 130 ml of toluene and then the batch is stirred vigorously for 1 h at RT and for 4 h at 80° C. (→Zn homoenolate solution). In a second apparatus, (N$_2$ atmosphere), 5.90 ml (53.8 mmol) of titanium tetrachloride are added, with slight cooling, to a solution of 5.58 ml (18.9 mmol) of tetraisopropyl orthotitanate in 16.4 ml of toluene and 91.8 ml of methylene chloride. The batch is stirred for 15 min at RT (→yellow solution) and cooled to −40° C. (→partial crystallisation of the trichlorotitanium isopropanolate). Using a cannula, the Zn homoenolate solution, which has cooled to RT, is decanted from the metallic solid and is added dropwise to the trichlorotitanium iso-propanolate, the temperature being maintained at from −40° C. to −30° C. (→dark red solution), and then the batch is heated at −25° C. for 5 min and cooled again to −40° C. A solution of 9.0 g of N-Boc-phenylalaninal (preparation: D. J. Kempf, J. Org. Chem. 51, 3921 (1986)) in 32.8 ml of methylene chloride is then added dropwise thereto and the batch is subsequently stirred for 15 h at approximately −20° C. and finally for 1 h at 0° C. The reaction mixture is poured onto 0.5 kg of ice-water and 0.5 liter of ether and stirred vigorously for 10 min. The aqueous phase is separated off and extracted with 2 portions of ether; the organic phases are washed with 2 portions of water, saturated sodium hydrogen carbonate solution and brine, dried with sodium sulfate and concentrated by evaporation to yield crystalline 5(S)-(Boc-amino)-4(S)-hydroxy-6-phenylhexanoic acid ethyl ester as intermediate. This intermediate is heated for 2.5 h at 80° C. in 295 ml of toluene and 9 ml of acetic acid. 0.5 liter of water is added to the reaction mixture, the aqueous phase is separated off and extracted with 2 portions of ether, the organic phases are washed with saturated sodium hydrogen carbonate solution, water and brine and dried with sodium sulfate. Partial concentration of the organic phases by evaporation and the addition of hexane yields the crystalline title compound which, according to analysis, contains approximately 10% (4R)-epimer (TLC R$_f$(E)=0.08). Column chromatography (SiO$_2$, hexane/ethyl acetate 2:1) yields the pure title compound: TLC R$_f$(E)= 0.14; [a]D=17.7° (c=1; ethanol).

1) c) 5(S)-[1(S)-(Boc-amino)-2-phenylethyl]-3(R)-(O-fluorophenylmethyl)-dihydrofuran-2-(3H)-one (Analogously to A. K. Ghosh, S. P. McKee, and W. J. Thompson, J. Org. Chem. 56, 6500 (1991)). 1.92 ml of lithium bis(trimethylsilyl)amide 1 M in THF (Aldrich) are added at −75° C. under a N2 atmosphere to a solution of 300 mg (0.982 mmol) of 5(S)-[1(S)-(Boc-amino)-2-phenylethyl]-dihydrofuran-2-(3H)-one in 6 ml of THF and the batch is then stirred for 15 min at that temperature. 132 gl (1.077 mmol) of p-fluorobenzyl bromide (Fluka; Buchs/ Switzerland) are then added dropwise and the batch is stirred for 30 min at −50° C. to complete the reaction. After cooling to −75° C. again, 0.3 ml of propionic acid and then 0.3 ml of water are added. The batch is heated to 0° C., diluted with ethyl acetate, washed with 10% citric acid solution, saturated sodium hydrogen carbonate solution and brine, dried over sodium sulfate and concentrated by evaporation. Column chromatography (SiO$_2$, hexane/ethyl acetate 4:1) yields the pure title compound: TLC R$_f$(D)=0.54; FAB-MS (M+H)$^+$=414.

1) d) 5(S)-(Boc-amino)-4(S)-hydroxy-6-phenyl-2(R)-(p-fluorophenylmethyl)-hexanoic acid Analogously to Example 1 i), 1.46 g of 5(S)-[1(S)-(Boc-amino)-2-phenylethyl]-3(R)-(p-fluorophenylmethyl)-dihydrofuran-2-(3H)-one in 57 ml of dimethoxyethane and 29 ml of water are hydrolysed with 14.1 ml of 1 M lithium hydroxide solution to form the title compound which is further used without additional purification.

1) e) 5(S)-(Boc-amino)-4(S)-(tert-butyldimethylsilyloxy)-6-phenyl-2(R)-(p-fluorophenylmethyl)-hexanoic acid Analogously to Example 1 j), 0.9 g of 5(S)-(Boc-amino)-4(S)-hydroxy-6-phenyl-2(R)-(p-fluorophenylmethyl)-hexanoic acid in 4 ml of DMF is silylated with 1.49 g of tert-butyldimethylchlorosilane and 1.2 g of imidazole. Hydrolysis of the silyl ester function with 1.9 g of potassium carbonate in 50 ml of methanol/THF/water 3:1:1 yields, after acidification with citric acid solution and extraction with ethyl acetate, the title compound: TLC R$_f$(D)=0.2.

1) f) 5(S)-(Boc-amino)-4(S)-(tert-butyldimethylsilyloxy)-6-phenyl-2(R)-(p-fluorophenylmethyl)-hexanoyl-(L)-Val-(L)-Phe-morpholin-4-ylamide Analogously to Example 9 f), 200 mg of 5(S)-(Boc-amino)-4(S)-(tert-butyldimethylsilyloxy)-6-phenyl-2(R)-(p-fluorophenylmethyl)-hexanoic acid and 134 mg of H-(L)-Val-(L)-Phe-morpholin-4-ylamide (Example 1 o)) in 3.6 ml of NMM/CH$_3$CN 0.25 M are reacted with 153 mg of HBTU. Crystallisation from hexane yields the pure title compound: TLC R$_f$(A)=0.25.

2) Boc-Phe[C](p-F)Phe-(L)-Val-(L)-(p-F-Phe)-morpholin-4-ylamide

Analogously to Example 1 ), 350 mg (0.395 mmol) of 5(S)-(Boc-amino)-4(S)-(tert-butyldimethylsilyloxy)-6-phenyl-2(R)-(p-fluorophenylmethyl)hexanoyl-(L)-Val-(L)-(p-F-Phe)-morpholin-4-ylamide are deprotected with 374 mg (1.19 mmol) of TBAF in 3 ml of DMF to yield the title compound: t$_{Ret}$(II)=23.3 min; FAB-MS (M+H)$^+$=765.

The starting material is prepared as follows:

2) a) 5(S)-(Boc-amino)-4(S)-(tert-butyldimethylsilyloxy)-6-phenyl-2(R)-(p-fluorophenylmethyl)-hexanoyl-(L)-Val-(L)-(p-F-Phe)-morpholin-4-ylamide Analogously to Example 9f), 265 mg (0.485 mmol) of 5(S)-(Boc-amino)-4(S)-(tert-butyldimethylsilyloxy)-6-phenyl-2(R)-(p-fluorophenylmethyl)hexanoic acid [(Example 21 D) 1)e)] and 188 mg (0.53 mmol) of H-(L)-Val-(L)-(p-F-Phe)-morpholin-4-ylamide (Example 9e) in 4.6 ml of NMM/CH$_3$CN 0.25 M are reacted with 202.6 mg (0.53 mmol) of HBTU: TLC R$_f$(D)=0.28; t$_{Ret}$(II)=33.4 min.

3) Boc-Phe[C](p-F)Phe-(L)-Val-(L)-(p-CH$_3$O-Phe) morpholin-4-ylamide

Analogously to Example 1), 280 mg (0.312 mmol) of 5(S)-(Boc-amino)-4(S)-(tert-butyldimethylsilyloxy)-6-phenyl-2(R)-(p-fluorophenylmethyl)hexanoyl-(L)-Val-(L)-(p-CH$_3$O-Phe)-morpholin-4-ylamide are deprotected with 295 mg (0.94 mmol) of TBAF in 3 ml of DMF to yield the title compound. Column chromatography (SiO$_2$, ethyl acetate/hexane 4:1→ethyl acetate) yields the pure title compound: TLC R$_f$(B)=0.56; t$_{Ret}$(II)=23.1 min; FAB-MS (M+H)$^+$=777.

The starting material is prepared as follows:

3) a) 5(S)-(Boc-amino)-4(S)-(tert-butyldimethylsilyloxy)-6-phenyl-2(R)-(p-fluorophenylmethyl)-hexanoyl-(L)-Val-(L)-(p-CH₃O-Phe)-morpholin-4-ylamide Analogously to Example 9f), 200 mg (0.366 mmol) of 5(S)-(Boc-amino)-4(S)-(tert-butyldimethylsilyloxy)-6-phenyl-2(R)-(p-fluorophenylmethyl)-hexanoic acid [Example 21 D) 1)e)]and 146 mg (0.402 mmol) of H-(L)-Val-(L)-(p-CH₃O-Phe)-morpholin-4-ylamide (Example 10e) in 3.6 ml of NMM/CH₃CN 0.25 M are reacted with 153 mg (0.402 mmol) of HBTU: TLC R$_f$(D)=0.22; t$_{Ret}$(II)=33.1 min.

4) Boc-Phe[C](p-F)Phe-(L)-Val-(L)-Cha-morpholin-4-ylamide

Analogously to Example I), 120 mg of 5(S)-(Boc-amino)-4(S)-(tert-butyldimethylsilyloxy)-6-phenyl-2(R)-(p-fluorophenylmethyl)-hexanoyl-CL)-Val-(L)-Cha-morpholin-4-ylamide are deprotected with 87 mg of TBAF in 1.4 ml of DMF to form the title compound: TLC R$_f$(B)=0.61; FAB-MS (M+H)⁺=753.

The starting material is prepared as follows:

4) a) 5(S)-(Boc-amino)-4(S)-(tert-butyldimethylsilyloxy)-6-phenyl-2(R)-(p-fluorophenylmethyl)-hexanoyl-(L)-Val-(L)-Cha-morpholin-4-ylamide Analogously to Example 9 f), 100 mg of 5(S)-(Boc-amino)-4(S)-(tert-butyldimethylsilyloxy)-6-phenyl-2(R)-(p-fluorophenylmethyl)-hexanoic acid [Example 21 D) 1) e)]and 68 mg of H-(L)-Val-(L)-Cha-morpholin-4-yl-amide (Example 1 la)) in 1.8 ml of NMM/CH₃CN 0.25 M are reacted with 76.4 mg of HBTU: TLC R$_f$(A)=0.50.

5) Boc-Phe[C](p-F)Phe-(L)-Ile-(L)-Phe-morpholin-4-ylamide

Analogously to Example 1), 220 mg (0.251 mmol) of 5(S)-(Boc-amino)-4(S)-(tert-butyldimethylsilyloxy)-6-phenyl-2(R)-(p-fluorophenylmethyl)hexanoyl-(L)-Ile-(L)-Phe-morpholin-4-ylamide are deprotected with 240 mg (0.75 mmol) of TBAF in 3 ml of DMF to yield the title compound. Column chromatography (SiO₂, ethyl acetate/ THF 9:1 ) yields the pure title compound: TLC R$_f$(O)=0.3; t$_{Ret}$(II)=23.9 min; FAB-MS (M+H)⁺=761.

The starting material is prepared as follows:

5) a) 5(S)-(Boc-amino)-4(S)-(tert-butyldimethylsilyloxy)-6-phenyl-2(R)-(p-fluorophenylmethyl)-hexanoyl-(L)-Ile-(L)-Phe-morpholin-4-ylamide Analogously to Example 9f), 200 mg (0.366 mmol) of 5(S)-(Boc-amino)-4(S)-(tert-butyldimethylsilyloxy)-6-phenyl-2(R)-(p-fluorophenylmethyl)-hexanoic acid [Example 21 D) 1)e)]and 140 mg (0.403 mmol) of H-(L)-Ile-(L)-Phe-morpholin-4-ylamide (Example 16b) in 3.5 ml of NMM/CH₃CN 0.25 M are reacted with 153 mg (0.40 mmol) of HBTU: TLC R$_f$(D)=0.16; t$_{Ret}$(II)=34.4 min.

E)

1) Boc-Phe[C](O-CN)Phe-(L)-Val-(L)-Phe-morpholin-4-ylamide

Analogously to Example 1), 60 mg of 5(S)-(Boc-amino)-4(S)-(tert-butyldimethylsilyloxy)-6-phenyl-2(R)-(p-cyanophenylmethyl)-hexanoyl-(L)-Val-(L)-Phe-morpholin-4-ylamide are deprotected with 64.3 mg of TBAF in 1.0 ml of DMF to form the title compound. Column chromatography (SiO₂, ethyl acetate) yields the pure title compound: TLC R$_f$(B)=0.26; FAB-MS (M+H)⁺=754.

The starting material is prepared as follows:

1) a) 5(S)-[1(S)-(Boc-amino)-2-phenylethyl]-3(R)-(p-cyanophenylmethyl)-dihydrofuran-2-(3H)-one Analogously to Example 21 D) 1) c), 1.5 g of 5(S)-[1(S)-(Boc-amino)-2-phenylethyl]-dihydrofuran-2-(3H)-one [Example 21 D) 1) b)]dissolved in 32 ml of THF are deprotonated with 9.8 ml of lithium bis(trimethylsilyl)amide 1 M in THF and alkylated with 1.0 g of 4-bromomethylbenzonitrile (Fluka; Buchs/Switzerland) dissolved in 3 ml of THF. Column chromatography (SiO₂, hexane/ethyl acetate 1:1) yields the pure title compound: TLC R$_f$(D)=0.33.

1) b) 5(S)-(Boc-amino)-4(S)-hydroxy-6-phenyl-2(R)-(O-cyanophenylmethyl)-hexanoic acid Analogously to Example 1 i), 0.50 g of 5(S)-[1(S)-(Boc-amino)-2-phenylethyl]-3(R)-(p-cyanophenylmethyl)-dihydrofuran-2-(3H)-one in 19 ml of dimethoxyethane and 10 ml of water is hydrolysed with 4.8 ml of 1 M lithium hydroxide solution to form the title compound: TLC R$_f$(F)=0.3.

1) c) 5(S)-(Boc-amino)-4(S)-(tert-butyldimethylsilyloxy)-6-phenyl-2(R)-(p-cyanophenylmethyl)-hexanoic acid Analogously to Example 1 j), 0.62 g of 5(S)-(Boc-amino)-4(S)-hydroxy-6-phenyl-2(R)-(p-cyanophenylmethyl)-hexanoic acid in 6.2 ml of DMF is silylated with 0.98 g of tert-butyldimethylchlorosilane and 0.79 g of imidazole. Hydrolysis of the silyl ester function with 1.2 g of potassium carbonate in 31 ml of methanol/THF/water 3:1:1 yields, after acidification with citric acid solution and extraction with ethyl acetate, the title compound: TLC R$_f$(D)=0.29; FAB-MS (M+H)⁺=553.

1) d) 5(S)-(Boc-amino)-4(S)-(tert-butyldimethylsilyloxy)-6-phenyl-2(R)-(n-cyanophenylmethyl)-hexanoyl-(L)-Val-(L)-Phe-morpholin-4-ylamide Analogously to Example 9 f), 72 mg of 5(S)-(Boc-amino)-4(S)-(tert-butyldimethylsilyloxy)-6-phenyl-2(R)-(p-cyanophenylmethyl)-hexanoic acid and 43.3 mg of H-(L)-Val-(L)-Phe-morpholin-4-ylamide (Example 1 o)) in 1.14 ml of NMM/CH₃CN 0.25 M are reacted with 50 mg of HBTU to form the title compound: TLC R$_f$(A)=0.19.

2) Boc-Phe[C](p-CN)Phe-(L)-Val-(L)-(p-F-Phe)-morpholin-4-ylamide

3) Boc-Phe[C](p-CN)Phe-(L)-Val-(L)-(p-CH₃O-Phe)-morpholin-4-ylamide

4) Boc-Phe[C](p-CN)Phe-(L)-Val-(L)-Cha-morpholin-4-ylamide

5) Boc-Phe[C](p-CN)Phe-(L)-Ile-(L)-Phe-morpholin-4-ylamide

Analogously to Example 1), 510 mg of 5(S)-(Boc-amino)-4(S)-(tert-butyldimethylsilyloxy)-6-phenyl-2(R)-(p-cyanophenylmethyl)-hexanoyl-(L)-Ile-(L)-Phe-morpholin-4-ylamide are desilylated with 362.3 mg of TBAF in 10 ml of DMF. The reaction mixture is poured onto ice-water and extracted with 3 portions of methylene chloride, and the organic phases are washed with saturated sodium hydrogen carbonate solution, water and brine, dried with sodium sulfate and concentrated by evaporation. Column chromatography (SiO₂, ethyl acetate) yields the pure title compound: TLC R$_f$(B)=0.51; FAB-MS (M+H)⁺=768.

The starting material is prepared as follows:

5) a) 5(S)-(Boc-amino)-4(S)-(tert-butyldimethylsilyloxy)-6-phenyl-2(R)-(O-cyanophenylmethyl)-hexanoyl-(L)-Ile-(L)-Phe-morpholin-4-ylamide Analogously to Example 9 f), 360 mg of 5(S)-(Boc-amino)-4(S)-(tert-butyldimethylsilyloxy)-6-phenyl-2(R)-(p-cyanophenylmethyl)-hexanoic acid [Example 21 E) 1) d)]and 253 mg of H-(L)-Ile-(L)-Phe-morpholin-4-yl-amide (Example 16 b)) in 6.36 ml of NMM/CH₃CN 0.25 M are reacted with 276 mg of HBTU. Partitioning of the residue of concentration by evaporation between methylene chloride, 10% citric acid solution, water, saturated sodium hydrogen carbonate solution, water and brine, drying the organic phases with sodium sulfate and concentration by evaporation yields the title compound: TLC R$_f$(D)=0.07.

F)

1) Boc-Phe[C](O-CH₃O)Phe-(L)-Val-(L)-Phe-morpholin-4-ylamide

Analogously to Example 1), 417 mg (0.48 mmol) of 5(S)-(Boc-amino)-4(S)-(tert-butyldimethylsilyloxy)-6-phenyl-2(R)-(p-methoxyphenylmethyl)hexanoyl-(L)-Val-(L)-Phe-morpholin-4-ylamide are deprotected with 301 mg (0.95 mmol) of TBAF in 5 ml of DMF to yield the title compound: TLC R$_f$(F)=0.4; t$_{Ref}$(I)=15.8 min; FAB-MS (M+H)⁺=759.

The starting material is prepared as follows:

1) a) p-Methoxybenzyl iodide

A solution of 1.7 ml (12.8 mmol) of 4-methoxybenzyl chloride (Fluka; Buchs/Switzerland) in 25 ml of acetone is stirred at RT with 9.4 g (62.6 mmol) of sodium iodide. A gas chromatogram of the reaction mixture after 90 min indicates complete reaction, and the reaction mixture is therefore poured onto ether and washed with 10% sodium thiosulfate solution and brine. The organic phase is dried with Na₂SO4 and concentrated by evaporation to yield the title compound: ¹H-NMR (200 MHz, CD3OD: 3.78 (s, 3 H), 4.54 (s, 2 H), 6.8–6.95 and 7.2–7.4 (2 m, each 2 H).

1) b) 5(S)-[1(S)-(Boc-amino)-2-phenylethyl]-3(R)-(p-methoxyphenylmethyl)-dihydrofuran-2-(3H)-one Analogously to Example 21 D) 1)c), 2.98 g (9.74 mmol) of S(S)-[1(S)-(Boc-amino)-2-phenylethyl]-dihydrofuran-2-(3H)-one [Example 21 D) 1)b)] dissolved in 40 ml of THF are deprotonated at −75° C. with 19.5 ml of lithium bis (trimethylsilyl)amide 1 M in THF and alkylated with 2.9 g (11.7 mmol) of p-methoxybenzyl iodide in 20 ml of THF (45 min). Column chromatography(SiO₂, hexane/ethyl acetate 2:1) and digestion from DIPE yields the pure tire compound: TLC R$_f$(D)-0.32; t$_{Ref}$(I)=16.7 min.

1) c) 5(S)-(Boc-amino)-4(S)-hydroxy-6-phenyl-2(R)-(p-methoxyphenylmethyl)-hexanoic acid Analogously to Example 1i), 1.7 g (3.99 mmol) of 5(S)-[1(S)-(Boc-amino)-2-phenylethyl]-3(R)-(p-methoxyphenylmethyl)-dihydrofuran-2-(3H)-one in 43 ml of dimethoxyethane and 11 ml of water are hydrolysed with 16 ml of 1 M lithium hydroxide solution. Stirring in ether yields the pure title compound: TLC R$_f$(F)=0.53; t$_{Ref}$(I)=14.2 min; FAB-MS (M+Na)⁺=466.

1) d) 5(S)-(Boc-amino)-4(S)-(tert-butyldimethylsilyloxy)-6-phenyl-2(R)-(p-methoxyphenylmethyl)-hexanoic acid Analogously to Example 1 j), 0.93 g (2.10 mmol) of 5(S)-(Boc-amino)-4(S)-hydroxy-6-phenyl-2(R)-(p-methoxyphenylmethyl)-hexanoic acid in 20 ml of DMF are silylated with 1.4 g (9.64 mmol) of tert-butyldimethylchlorosilane and 1.17 g (17.2 mmol) of imidazole. The silyl ester function is hydrolysed with 1.7 g of potassium carbonate in methanol (23 ml)/THF (7 ml)/water (7 ml) and the crude product is stirred in hexane to yield the title compound: t$_{Ref}$(I)=20.6 min; FAB-MS (M+H)⁺=558.

1) e) 5(S)-(Boc-amino)-4(S)-(tert-butyldimethylsilyloxy)-6-phenyl-2(R)-(p-methoxyphenylmethyl)-hexanoyl-(L)-Val-(L)-Phe-morpholin-4-ylamide Analogously to Example 9f), 300 mg (0.537 mmol) of 5(S)-(Boc-amino)-4(S)-(tert-butyldimethylsilyloxy)-6-phenyl-2(R)-(p-methoxyphenylmethyl)-hexanoic acid and 197 mg (0.59 mmol) of H-(L)-Val-(L)-Phe-morpholin-4-ylamide (Example 1o) in 5.2 ml of NMM/CH₃CN 0.25 M are reacted with 224 mg (0.59 mmol) of HBTU: t$_{Ref}$(I)=22.1 min; FAB-MS (M+H)⁺=873.

2) Boc-Phe[C](p-CH₃O)Phe-(L)-Val-(L)-(p-F-Phe)-morpholin-4-ylamide

3) Boc-Phe[C](p-CH₃O)Phe-(L)-Val-(L)-(p-CH₃O-Phe)-morpholin-4-yl-amide

Analogously to Example 1), 200 mg (0.22 mmol) of 5(S)-(Boc-amino)-4(S)-(tert-butyldimethylsilyloxy)-6-phenyl-2(R)-(p-methoxyphenylmethyl)-hexanoyl-(L)-Val-(L)-(p-CH₃O-Phe)-morpholin-4-ylamide are deprotected with 210 mg (0.66 mmol) of TBAF in 3 ml of DMF to yield the title compound. Column chromatography (SiO₂, methylene chloride/methanol 19:1) yields the pure title compound: TLC R$_f$(F)=0.66; t$_{Ref}$(II)=22.5 min; FAB-MS (M+H)⁺=789.

The starting material is prepared as follows:

3) a) 5(S)-(Boc-amino)-4(S)-(tert-butyldimethylsilyloxy)-6-phenyl-2(R)-(p-methoxyphenylmethyl)-hexanoyl-CL)-Val-(L)-(p-CH₃O-Phe)-morpholin-4-ylamide Analogously to Example 9f), 200 mg (0.358 mmol) of 5(S)-(Boc-amino)-4(S)-(tert-butyldimethylsilyloxy)-6-phenyl-2(R)-(p-methoxyphenylmethyl)-hexanoic acid and 143 mg (0.39 mmol) of H-(L)-Val-(L)-(p-CH₃O-Phe)-morpholin-4-ylamide (Example 10e) in 3.6 ml of NMM/CH₃CN 0.25 M are reacted with 149 mg (0.39 mmol) of HBTU: t$_{Ref}$(II)=33.2 min.

4) Boc-Phe[C](p-CH₃O)Phe-(L)-Val-(L)-Cha-morpholin-4-ylamide

5) Boc-Phe[C](p-CH₃O)Phe-(L)-Ile-(L)-Phe-morpholin-4-ylamide

G)

1) Boc-Phe[C](p-CF₃)Phe-(L)-Val-(L)-Phe-morpholin-4-ylamide

Analogously to Example 1), 120 mg (0.13 mmol) of 5(S)-(Boc-amino)-4(S)-(tert-butyldimethylsilyloxy)-6-phenyl-2(R)-(p-trifluoromethylphenylmethyl)-hexanoyl-(L)-Val-(L)-Phe-morpholin-4-ylamide are deprotected with 124 mg (0.39 mmol) of TBAF in 3 ml of DMF to yield the title compound. Precipitation with DIPE from a concentrated solution in DMF yields the pure title compound: t$_{Ref}$(II)=24.7 min; FAB-MS (M+H)⁺=797.

The starting material is prepared as follows:

1) a) 5(S)-[1(S)-(Boc-amino)-2-phenyl-ethyl]-3(R)-(p-trifluoromethylphenylmethyl)-dihydrofuran-2-(3H)-one Analogously to Example 21 D) 1)c), 1.0 g (3.26 mmol) of 5(S)-[1(S)-(Boc-amino)-2-phenylethyl]-dihydrofuran-2-(3H)-one [Example 21 D) 1)b)] dissolved in 20 ml of THF are deprotonated at −75° C. with 6.5 ml of lithium bis (trimethylsilyl)amide 1 M in THF and alkylated starting at −75° C. with 0.93 g (3.91 mmol) of p-trifluoromethylbenzyl bromide (Fluka; Buchs/Switzerland) (warming up during 45 min up to −60° C.). Column chromatography (SiO₂, hexane/ethyl acetate 2:1 ) yields the pure title compound: TLC R$_f$(D)=0.4; t$_{Ref}$(II)=27.0 min; FAB-MS (M+H-butene)⁺=408.

1) b) 5(S)-(Boc-amino)-4(S)-hydroxy-6-phenyl-2(R)-(p-trifluoromethylphenylmethyl)-hexanoic acid Analogously to Example 1i), 4.3 g (9.3 mmol) of 5(S)-[1(S)-(Boc-amino)-2-phenylethyl]-3(R)-(p-uifluoromethylphenylmethyl)-dihydrofuran-2-(3H)-one in 100 ml of dimethoxyethane und 25 ml of water are hydrolysed with 37 ml of 1 M lithium hydroxide solution to yield the title compound: TLC R$_f$(H)=0.68; t$_{Ref}$(II)=22.5 min.

1) c) 5(S)-(Boc-amino)-4(S)-(tert-butyldimethylsilyloxy)-6-phenyl-2(R)-(p-trifluoromethylphenylmethyl)-hexanoic acid Analogously to Example 1 j), 3.2 g (6.65 mmol) of 5(S)-(Boc-amino)-4(S)-hydroxy-6-phenyl-2(R)-(p-trifluoromethylphenylmethyl)-hexanoic acid in 25 ml of DMF are silylated with 4.6 g (30.6 mmol) of tert-butyl-dimethylchlorosilane and 3.7 g (54.5 mmol) of imidazole. Hydrolysis of the silyl ester function with 5.5 g of potassium carbonate in methanol (75 ml)/THF (22 ml)/water (12 ml) yields the title compound: t$_{Ref}$(II)=32.7 min.

1) d) 5(S)-(Boc-amino)-4(S)-(tert-butyldimethylsilyloxy)-6-phenyl-2(R)-(p-trifluoromethylphenylmethyl)-hexanoyl-(L)-Val-(L)-Phe-morpholin-4-ylamide Analogously to Example 9f), 200 mg (0.335 mmol) of 5(S)-(Boc-amino)-(S)-(tert-butyldimethylsilyloxy)-6-phenyl-2(R)-(p-trifluoromethylphenylmethyl)-hexanoic and 123 mg (0.369 mmol) of H-(L)-Val-(L)-Phe-morpholin-4-ylamide (Example 1o) in 3.2 ml of NMM/CH$_3$CN 0.25 M are reacted with 140 mg (0.37 mmol) of HBTU: $t_{Ref}$(II)=34.8 min.

2) Boc-Phe[C](p-CF$_3$)Phe-(L)-Val-(L)-(p-F-Phe)-morpholin-4-ylamide

3) Boc-Phe[C](p-CF$_3$)Phe-(L)-Val-(L)-(p-CH$_3$O-Phe)-morpholin-4-ylamide

4) Boc-Phe[C](p-CF$_3$)Phe-(L)-Val-(L)-Cha-morpholin-4-ylamide

5) Boc-Phe[C](p-CF$_3$)Phe-(L)-Ile-(L)-Phe-morpholin-4-ylamide

H)
1) Boc-Cha[C](p-CN)Phe-(L)-Val-(L)-(p-F-Phe)-morpholin-4-ylamide

2) Boc-Cha[C](p-CN)Phe-(L)-Val-(L)-(p-CH$_3$O-Phe)-morpholin-4-ylamide

3) Boc-Cha[C](p-CN)Phe-(L)-Val-(L)-Cha-morpholin-4-ylamide

4) Boc-Cha[C](p-CN)Phe-(L)-Ile-(L)-Phe-morpholin-4-ylamide

I)
1) Boc-Cha[C](p-CH$_3$O)Phe-(L)-Val-(L)-Phe-morpholin-4-ylamide

2) Boc-Cha[C](p-CH$_3$O)Phe-(L)-Val-(L)-(p-F-Phe)-morpholin-4-ylamide

3) Boc-Cha[C](p-CH$_3$O)Phe-(L)-Val-(L)-(p-CH$_3$O-Phe)-morpholin-4-yl-amide

4) Boc-Cha[C](p-CH$_3$O)Phe-(L)-Val-(L)-Cha-morpholin-4-ylamide

5) Boc-Cha[C](p-CH$_3$O)Phe-(L)-Ile-(L)-Phe-morpholin-4-ylamide

J)
1) Boc-Cha[C](p-CF$_3$)Phe-(L)-Val-(L)-Phe-morpholin-4-ylamide

2) Boc-Cha[C](p-CF$_3$)Phe-(L)-Val-(L)-(p-F-Phe)-morpholin-4-ylamide

3) Boc-Cha[C](p-CF$_3$)Phe-(L)-Val-(L)-(p-CH$_3$O-Phe)-morpholin-4-ylamide

4) Boc-Cha[C](p-CF$_3$)Phe-(L)-Val-(L)-Cha-morpholin-4-ylamide

5) Boc-Cha[C](p-CF$_3$)Phe-(L)-Ile-(L)-Phe-morpholin-4-ylamide

EXAMPLE 22

Analogously to any one of the above-mentioned Examples, or in the manner indicated in detail, there are prepared by selecting appropriate starting materials:

A) Boc-(L)-Val-Phe[C]Phe-(L)-Val-(L)-Phe-morpholin-4-ylamide;

B) H-(L)-Val-Phe[C]Phe-CL)-Val-(L)-Phe-morpholin-4-ylamide;

C) Boc-Cha[C](p-F)Phe-(L)-Ile-(L)-Phe-morpholin-4-ylamide

Analogously to Example 1), 0.15 g of 5(S)-(Boc-amino)-4(S)-(tert-butyldimethylsilyloxy)-6-cyclohexyl-2(R)-(p-fluorophenylmethyl)-hexanoyl-(L)-Ile-(l)-Phe-morpholin-4-ylamide is converted into the title compound with 117 mg of TBAF in 1.7 ml of DMF: TLC R$_f$(I)=0.18; FAB-MS (M+H)$^+$=767.

The starting material is prepared as follows:

C) a) 5(S)-(Boc-amino)-4(S)-(tert-butyldimethylsilyloxy)-6-cyclohexyl-2(R)-(p-fluorophenylmethyl)-hexanoyl-(L)-Ile-(L)-Phe-morpholin-4-ylamide Analogously to Example 9 f), 102 mg of 5(S)-(Boc-amino)-4(S)-(tert-butyldimethylsilyloxy)-6-cyclohexyl-2(R)-(p-fluorophenylmethyl)-hexanoic acid (Example 1 j)) and 70.8 mg of H-(L)-Ile-(L)-Phe-morpholin-4-ylamide (Example 16 b)) in 1.77 ml of NMM/CH$_3$CN 0.25 M are reacted with 77.4 mg of HBTU to form the title compound: TLC R$_f$(A)=0.17; FAB-MS (M+H)$^+$=881.

D) Boc-Cha[C](p-F)Phe-(L)-Val-(L)-Cha-morpholin-4-ylamide;

E) Boc-Phe[C]Phe-(L)-Val-(D)-Phe-morpholin-4-ylamide;

F) Boc-Phe[C]Phe-(L)-Val(red)-(L)-Phe-morpholin-4-ylamide;

G) Isobutoxycarbonyl-Phe[C]Phe-(L)-Val-(L)-Phe-morpholin-4-ylamide;

H) Boc-Cha[C](p-CN)Phe-(L)-Val-(L)-Phe-thiomorpholin-4-ylamide;

I) Boc-Cha[C](p-F)Phe-(L)-Val-(L)-Phe-thiomorpholin-4-ylamide

Analogously to Example 1), 0.16 g of 5(S)-(Boc-amino)-4(S)-(tert-butyldimethylsilyloxy)-6-cyclohexyl-2(R)-(p-fluorophenylmethyl)-hexanoyl-(L)-Val-(L)-Phe-thiomorpholin-4-ylamide is converted into the title compound with 114 mg of TBAF in 1.8 ml of DMF: TLC R$_f$(I)=0.38; FAB-MS (M+H)$^+$=769.

The starting material is prepared as follows:

I) a) 5(S)-(Boc-amino)-4(S)-(tert-butyldimethylsilyloxy)-6-cyclohexyl-2(R)-(p-fluorophenylmethyl)-hexanoyl-(L)-Val-(L)-Phe-thiomorpholin-4-ylamide Analogously to Example 9 f), 100 mg of 5(S)-(Boc-amino)-4(S)-(tert-butyldimethylsilyloxy)-6-cyclohexyl-2(R)-(p-fluorophenylmethyl)-hexanoic acid (Example 1 j)) and 70 mg of H-(L)-Val-(L)-Phe-thiomorpholin-4-ylamide (Example 20 b)) in 1.7 ml of NMM/CH$_3$CN 0.25 M are reacted with 76 mg of HBTU. After 18 h at RT, some of the title compound is obtained directly from the reaction mixture by filtration. More title compound is obtained by partitioning the residue, obtained after concentrating the filtrate by evaporation, between 3 portions of ethyl acetate, water, 2 portions of 10% citric acid solution, water, 2 portions of saturated sodium hydrogen carbonate solution, water and brine, drying the organic phases with sodium sulfate and concentrating by evaporation: TLC R$_f$(A)=0.55; FAB-MS (M+H)$^+$=883.

J) The compounds of Examples 22 A) to 22 G) in which -morpholin-4-ylamide is replaced by the radical-thiomorpholin-4-ylamide.

EXAMPLE 23

The following are prepared analogously to any one of the preceding processes:

a) Boc-Phe[C]Phe-(L)-Val-(L)-Phe-(4-methylpiperazin-1-yl)-amide b) Boc-Phe[C]Phe-(L)-Val-(L)-Phe-piperidin-1-ylamide c) Boc-Phe[C]Phe-(L)-Val-(L)-Phe-pyrrolidin-1-ylamide

EXAMPLE 24

Gelatin solution

A sterile-filtered aqueous solution of any one of the compounds of formula I mentioned in the above or following Examples 1 to 23 and 33 to 41, which solution also additionally comprises 20% cyclodextrin, and a sterile gelatin solution preserved with phenol, are so mixed under aseptic conditions, with heating, that 1.0 ml of solution having the following composition is obtained:

active ingredient 3 mg gelatin 150.0 mg phenol 4.7 mg dist. water with 20% cyclodextrin 1.0 ml

EXAMPLE 25

Sterile dry substance for injection 5 mg of any one of the compounds of formula I mentioned in the above and following Examples 1 to 23 and 33 to 41 are dissolved as active ingredient in 1 ml of an aqueous solution with 20 mg of mannitol and 20% cyclodextrin as solubilisers. The solution is sterile-filtered and introduced under aseptic conditions into a 2 ml-ampoule, deep-frozen and lyophilised. Before use, the lyophilisate is dissolved in 1 ml of distilled water or 1 ml of physiological saline solution. The solution is administered intramuscularly or intravenously. The formulation can also be introduced into double-chamber syringe ampoules.

EXAMPLE 26

Nasal spray 500 mg of finely ground (<5.0 μm) powder of any one of the compounds of formula I mentioned in the above or following Examples 1 to 23 and 33 to 41 are suspended as active ingredient in a mixture of 3.5 ml of Myglyol 812® and 0.08 g of benzyl alcohol. The suspension is introduced into a container having a metering valve. 5.0 g of Freon 12® are introduced into the container through the valve under pressure. The "Freon" is dissolved in the Myglyol-benzyl alcohol mixture by shaking. The spray container contains approximately 100 individual doses which can be administered individually.

EXAMPLE 27

Film-coated tablets

The following constituents are processed for the preparation of 10 000 tablets each containing 100 mg of active ingredient:

active ingredient 1000 g corn starch 680 g colloidal silica 200 g magnesium stearate 20 g stearic acid 50 g sodium carboxymethyl starch 250 g water quantum satis A mixture of any one of the compounds of formula I mentioned in the above or following Examples 1 to 23 and 33 to 41, as active ingredient, 50 g of corn starch and colloidal silica are processed with starch paste consisting of 250 g of corn starch and 2.2 kg of demineralised water to form a moist mass which is forced through a sieve having a mesh size of 3 mm and dried at 45° for 30 min in a fluidised bed drier. The dried granules are forced through a sieve having a mesh size of 1 mm, mixed with a previously sieved mixture (1 mm sieve) of 330 g of corn starch, the magnesium stearate, the stearic acid and the sodium carboxymethyl starch and compressed to form slightly convex tablets.

EXAMPLE 28

Orally administrable dispersion 1

625 mg of any one of the compounds of formula I mentioned in the above or following Examples I to 23 and 33 to 41, for example Boc-Phe[C]Phe-(L)-Val-(L)-Phe-morpholin-4-ylamide, as active ingredient, and 625 mg of POPC (1-palmitoyl-2-oleoyl-phosphatidylcholine=1-hexadecanoyl-2-(9-cis-octadecenoyl)-3-sn-phosphatidylcholine) are dissolved in 25 ml of ethanol. The solution is diluted with 10 times the amount of water. For that purpose, the ethanolic solution is added dropwise at room temperature at a rate of 10 ml/min to the mount of water provided. The ethanol is removed from the mixture by tangential dialysis (cross flow filtration) against 1750 ml of water (system: Minitan®, 700 cm$^2$ polyether sulfone membrane having an exclusion limit of 100 kD, manufactured by Millipore (USA)). Using the same system, the mixture is concentrated to 15 mg of active ingredient by ultrafiltration. After the addition of 1.24 mg/ml of citric acid and 1.24 mg/ml of disodium hydrogen phosphate•2 H$_2$O to adjust the pH to 4.2, and of 1 mg/ml of sorbic acid as antimicrobial preservative, the dispersion is again concentrated to 15 mg/ml and introduced into small bottles, for example having a capacity of 20 ml. The dispersion particles have a diameter of from 0.1 to 2 gm. They are stable for at least six months at from +2° to 8° C. and are suitable for oral administration.

EXAMPLE 29

Orally administrable dispersion 2

The preparation is carded out analogously to Example 28 except that 25 mg of active ingredient and 50 mg of POPC are used to prepare the ethanolic solution.

EXAMPLE 30

Orally administrable dispersion 3

The preparation is carded out analogously to Example 28 except that 25 mg of active ingredient and 125 mg of POPC are used to prepare the ethanolic solution.

EXAMPLE 31

Orally administrable dispersion 4

The preparation is carded out analogously to Example 28 except that 50 mg of active ingredient and 50 mg of POPC are used to prepare the ethanolic solution.

EXAMPLE 32

Orally administrable dispersion 5

The preparation is carried out analogously to any one of Examples 28 to 31 except that active ingredient and phosphatidylcholine from soya or phosphatidylcholine from egg yolk (70 –100% pure) are used instead of POPC to prepare the ethanolic solution. If desired, an antioxidant, such as ascorbic acid, is added at a concentration of 5 mg/ml.

EXAMPLE 33

Boc-(p-F)Phe[C](p-CF$_3$)Phe-(L)-Val-(L)-Phe-morpholin-4-ylamide

Analogously to Example 1), 265 mg of 5(S)-(Boc-amino) 4(S)-(tert-butyldimethylsilyloxy)-6- (p-fluorophenyl)-2(R)-(p-trifluoromethylphenylmethyl)-hexanoyl-(L)-Val-(L)-Phe-morpholin-4-ylamide are converted into the title compound with 180 mg of TBAF in 4.2 ml of DMF: TLC R$_f$(I)=0.3; FAB-MS (M+H)$^+$=815.

The starting material is prepared as follows:

33a) 5(S)-[1(S)-(Boc-amino)-2-(o-fluorophenyl)ethyl]-3 (R)-(D-trifluoromethylphenylmethyl)-dihydrofuran-2-(3H) -one Analogously to Example 21 D) 1) c), 1.0 g of 5(S)-[1(S) -(Boc-amino)-2-(p-fluorophenyl)ethyl]-dihydrofuran-2-

(3H)-one dissolved in 6.3 ml of THF is deprotonated with 6.05 ml of lithium bis(trimethylsilyl)amide 1 M in THF and alkylated with 0.739 g of p-trifluoromethylbenzyl bromide (Fluka; Buchs/Switzerland) at −75° C. (40 min). Column chromatography (SiO$_2$, hexane/ethyl acetate 2: 1) yields the pure title compound: TLC R$_f$(D)=0.48; FAB-MS (M+H)$^+$= 482.

33b) 5(S)-(Boc-amino)-4(S)-hydroxy-6-(p-fluorophenyl)-2(R)-(p-trifluoromethylphenylmethyl)-hexanoic acid Analogously to Example 1 i), 1.05 g of 5(S)-[1(S)-(Boc-amino)-2-(p-fluorophenyl)ethyl]-3(R)-(p-trifluoromethylphenylmethyl)-dihydrofuran-2-(3H)-one in 35.5 ml of dimethoxyethane and 17.9 ml of water are hydrolysed with 8.7 ml of 1 M lithium hydroxide solution to form the title compound which is used further directly.

33c) 5(S)-(Boc-amino)-4(S)-(tert-butyldimethylsilyloxy)-6-(p-fluorophenyl)-2(R)-(p-trifluoromethylphenylmethyl)-hexanoic acid Analogously to Example 1 j), 1.06 g of 5(S)-(Boc-amino)-4(S)-hydroxy-6-(p-fluorophenyl)-2(R)-(p-trifluoromethylphenylmethyl)-hexanoic acid in 2.3 ml of DMF are silylated with 1.47 g of tert-butyldimethylchlorosilane and 1.18 g of imidazole. Hydrolysis of the silyl ester function with 1.76 g of potassium carbonate in 50 ml of methanol/THF/water 3:1:1 yields, after column chromatography (SiO$_2$, hexane/ethyl acetate 2: 1), the title compound: TLC R$_f$(D)=0.15; $^1$H-NMR (200 MHz, CD$_3$OD): 7.59 and 7.39 (2d, 8 Hz, per 2 H), 7.19 and 6.98 (2 m, per 2 H), 6.47 and 5.90 (d, approximately 9 Hz, together 1 H), 3.9–3.65 (m, 2 H), 3.15–2.8 (m, 4 H), 2.53–2.37, 2.07–1.9 and 1.6–1.4 (3 m, per 1 H), 1.37–1.22 (m, 9 H), 0.94 (s, 9 H), 0.2–0.1 (m, 6 H).

33d) 5(S)-(Boc-amino)-4(S)-(tert-butyldimethylsilyloxy)-6-(p-fluorophenyl)-2(R)-(p-trifluoromethylphenylmethyl)-hexanoyl-(L)-Val-(L)-Phe-morpholin-4-ylamide Analogously to Example 9 f), 180 mg of 5(S)-(Boc-amino)-4(S)-(tert-butyldimethylsilyloxy)-6-(p-fluorophenyl)-2(R)-(p-trifluoromethylphenylmethyl)-hexanoic acid and 107.5 mg of H-(L)-Val-(L)-Phe-morpholin-4-ylamide (Example 1 o)) in 2.8 ml of NMM/CH$_3$CN 0.25 M are reacted with 122 mg of HBTU: FAB-MS (M+H)$^+$=929.

EXAMPLE 34

Boc-(p-F)Phe[C](p-CF$_3$)Phe-(L)-Val-(L)-(p-F-Phe)-morpholin-4-yl-amide

Analogously to Example 1), 270 mg of 5(S)-(Boc-amino)-4(S)-(tert-butyldimethylsilyloxy)-6-(p-fluorophenyl)-2(R)-(p-trifluoromethylphenylmethyl)-haxanoly-(L)-Val-(L)-(p-F-Phe)-morpholin-4-ylamide are converted into the title compound with 180 mg of TBAF in 4.2 ml of DMF: TLC R$_f$(I)=0.2; FAB-MS (M+H)$^+$=833.

The starting material is prepared as follows:

34a) 5(S)-(Boc-amino)-4(S)-(tert-butyldimethylsilyloxy)-6-(p-fluorophenyl)-2(R)-(D-trifluoromethylphenylmethyl)-hexanoyl-(L)-Val-(L)-(p-F-Phe)-morpholin-4-yl-amide Analogously to Example 9 f), 180 mg of 5(S)-(Boc-amino)-4(S)-(tert-butyldimethylsilyloxy)-6-(p-fluorophenyl)-2(R)-(p-trifluoromethylphenylmethyl)-hexanoic acid (Example 33c) and 113.2 mg of H-(L)-Val-(L)-(p-F-Phe)-morpholin-4-ylamide (Example 9 e)) in 2.8 ml of NMM/CH$_3$CN 0.25 M are reacted with 122 mg of HBTU: FAB-MS (M+H)$^+$=947.

EXAMPLE 35

Boc-(p-F)Phe[C](p-CF$_3$)Phe-(L)-Val-(L)-(p-CH$_3$O-Phe)-morpholin-4-yl-amide

Analogously to Example 1), 193 mg of 5(S)-(Boc-amino)-4(S)-(tert-butyldimethylsilyloxy)-6-(p-fluorophenyl)-2(R)-(p-trifluoromethylphenylmethyl)-hexanoyl-(L)-Val-(L)-(p-CH$_3$O-Phe)-morpholin-4-ylamide are converted into the title compound with 127 mg of TBAF in 3 ml of DMF: TLC R$_f$(I)=0.47; FAB-MS (M+H)$^+$=845.

The starting material is prepared as follows:

35a) 5(S)-(Boc-amino)-4(S)-(tert-butyldimethylsilyloxy)-6-(p-fluorophenyl)-2(R)(-(p-trifluoromethylphenylmethyl)-hexanoyl-(L)-Val-(L)-(p-CH$_3$O-PHe)-morpholin-4-yl-amide Analogously to Example 9 f), 180 mg of 5(S)-(Boc-amino)-4(S)-(tert-butyldimethylsilyloxy)-6-(p-fluorophenyl)-2(R)-(p-trifluoromethylphenylmethyl)-hexanoic acid (Example 33c) and 117.2 mg of H-(L)-Val-(L)-(p-CH$_3$O-Phe)-morpholin-4-ylamide (Example 10 e)) in 2.8 ml of NMM/CH$_3$CN 0.25 M are reacted with 122 mg of HBTU: FAB-MS (M+H)$^+$=959.

EXAMPLE 36

Morpholinosulfonyl-(L)-Val-Phe[C]Phe-CL)-Val-(L)-Phe-morpholin-4-ylamide

Analogously to Example 5), 102 mg of N-morpholinosulfonyl-(L)-Val in 4 ml of DMF are activated with 186 mg of BOP, 57 mg of HOBT and 0.09 ml of NMM and reacted with 200. mg of H-Phe[C]Phe-(L)-Val-(L)-Phe-morpholin-4-ylamide (Example 4) in 1 ml of DMF to form the title compound. The reaction mixture is poured into water, extracted with a large amount of ethyl acetate (poorly soluble) and washed with water, saturated sodium hydrogen carbonate solution, water and brine. The crude product is stirred in ether to yield the pure title compound: FAB-MS (M+H)$^+$=877.

The starting material is prepared as follows:

36a) N-Chlorosulfonylmorpholine

With intensive cooling, 32.7 ml of sulfuryl chloride are added at approximately 0° C. to 23.5 ml of morpholine. The suspension is then carefully heated to 60° C., causing the onset of hydrogen chloride evolution. After 5 h at 60° C., the evolution of hydrogen chloride is complete. The cooled brown reaction mixture is poured onto ice, and the precipitating oil is extracted with ether, washed with water, 5% sodium hydrogen carbonate solution and water and dried with sodium sulfate. The organic phases are concentrated by evaporation and distilled at elevated temperature and reduced pressure (90° C.; 1 mbar) to yield the title compound: $^1$H-NMR (200 MHz, DMSO-d6): 3.80 and 3.29 (2t, 5 Hz, per 4 H).

36b) N-Morpholinosulfonyl-(L)-Val 2 g of (L)-valine dissolved in 50 ml of 1 N NaOH are added dropwise to 6.3 g of N-chlorosulfonylmorpholine in 20 ml of THF and the batch is stirred for 17 h at RT to complete the reaction. 15 ml of 1 N NaOH are added to the yellow emulsion and the batch is extracted with ether. The aqueous phase is acidified with 2 N HCl and extracted with ethyl acetate. The ethyl acetate phase is dried with sodium sulfate and concentrated by evaporation. According to the 1H-NMR spectrum, crystallisation from ether yields a secondary product. The pure title compound is obtained from the residue, resulting from concentration of the filtrate by evaporation, by crystallisation from hexane: TLC $R_f(f)$= 0.25.

EXAMPLE 37

Morpholinosulfonyl-Phe[C]Phe-(L)-Val-(L)-Phe-morpholin-4-ylamide 0.132 ml of triethylamine and 71 mg of N-chlorosulfonylmorpholine (Example 36a) in 1 ml of DMF are added to a solution of 200 mg of H-Phe[C]Phe-(L)-Val-CL)-Phe-morpholin-4-ylamide (Example 4) in 5 ml of DMF. Because, after 2 h at RT, there is still a large amount of H-Phe[C]Phe-(L)-Val-CL)-Phe-morpholin-4-ylamide present according to TLC, another 71 mg of N-chlorosulfonylmorpholine are added. After 18 h, the batch is poured into water, extracted with 3 portions of ethyl acetate, washed with saturated sodium hydrogen carbonate solution, water and brine, dried with sodium sulfate and concentrated by evaporation. Column chromatography (SiO$_2$, methylene chloride/methanol 9:1) yields the pure title compound: TLC $R_f(F)$=0.60; FAB-MS (M+H)$^+$=778.

EXAMPLE 38

N-(N-(2-pyridylmethyl)-N-methylaminocarbonyl)-(L)-Val-Phe[C]Phe-(L)-Val-(L)-Phe-morpholin-4-ylamide Analogously to Example 5), 152 mg of N-(N-(2-pyridylmethyl)-N-methylaminocarbonyl)-(L)-valine (for preparation see EP 402 646 A 1, 19th Dec. 1990) in 5 ml of DMF are activated with 279 mg of BOP, 85 mg of HOBT and 0.132 ml of NMM and reacted with 300 mg of H-Phe[C]Phe-(L)-Val-(L)-Phe-morpholin-4-ylamide (Example 4) to form the title compound. Column chromatography (SiO$_2$, ethyl acetate/acetone 9:1→acetone) yields the pure title compound after digestion with ether: TLC $R_f(F)$=0.28; FAB-MS (M+H)$^+$=876.

EXAMPLE 39

5(S)-(Boc-amino)-4(S)-(acetoxy)-6-phenyl-2(R)-phenylmethylhexanoyl-(L)-Val-(L)-Phe-morpholin-4-ylamide 0.114 ml of triethylamine, 1 mg of dimethylaminopyridine and 0.08 ml of acetic anhydride are added to 400 mg of Boc-Phe[C]Phe-(L)-Val-(L)-Phe-morpholin-4-ylamide (Example 2) in 8 ml of THF. After 30 min at RT, the colourless solution is poured onto water and extracted with 3 portions of ethyl acetate. The organic phases are washed with water, saturated sodium hydrogen carbonate solution, water and brine, dried with sodium sulfate and concentrated by evaporation to yield the title compound which, after column chromatography (SiO$_2$, hexane/ethyl acetate 1:2), is obtained in pure form: TLC $R_f(B)$=0.59; FAB-MS (M+H)$^+$=771.

EXAMPLE 40

In a manner analogous to that described in any one of the preceding Examples, the following compounds are obtained:
A) Boc-(p-CF$_3$)Phe[C]Phe-(L)-Val-(L)-Phe-morpholin-4-ylamide
B) Boc-(p-CF$_3$)Phe[C]Phe-(L)-Val-(L)-(p-F)Phe-morpholin-4-ylamide
C) Boc-(p-CF$_3$)Phe[C]Phe-(L)-Val-(L)-(p-CH$_3$O)Phe-morpholin-4-ylamide
D) Boc-(p-CF$_3$)Phe[C]Phe-(L)-Val-(L)-Cha-morpholin-4-ylamide
E) Boc-(p-CF$_3$)Phe[C]Phe-(L)-Ile-(L)-Phe-morpholin-4-ylamide
F) Boc-(p-CF$_3$)Phe[C](V-F)Phe-(L)-Val-(L)-Phe-morpholin-4-ylamide Analogously to Example 1), 136 mg (0.146 mmol) of a mixture of 5(S)-(Boc-amino)-4(S)-(tert-butyldimethylsilyloxy)-6-(p-trifluoromethylphenyl)-2(R)-(p-fluorophenylmethyl)-hexanoyl-(L)-Val-(L)-Phe-morpholin-4-ylamide and 5(R)-(Boc-amino)-4(R)-(tert-butyldimethyl silyloxy)-6- (p-trifluoromethylphenyl)-2(S)-(p-fluorophenylmethyl)-hexanoyl-(L)-Val-(L)-Phe-morpholin-4-ylamide are deprotected with 92 mg (0.293 mmol) of TBAF in 1.5 ml of DMF to yield the title compound: $t_{Ret}(II)$=26.0 min; FAB-MS (M+H)$^+$=815.

The starting material is prepared as follows:

a) rac. N-Boc-1-(p-trifluoromethylphenyl)-3-buten-2-amine

Analogously to Example 1d), 10.5 g (48.8 mmol) of rac. 1-(p-trifluoromethylphenyl)-3-buten-2-amine (Example 40 P) c)) and 13.8 g (63.4 mmol) of Boc anhydride are reacted in 100 ml of methylene chloride. The reaction mixture is washed with 0.1 N HCl and 2 portions of brine, and the aqueous phases are extracted with 2 portions of methylene chloride. The organic phases are dried with Na$_2$SO4, concentrated by evaporation and precipitated with hexane from a concentrated solution in methylene chloride to yield the title compound: TLC $R_f(P)$=0.27; $t_{Ret}(II)$=25.5 min; Anal.: calc. C 60.94%, H 6.39%, N 4.44%, F 18.07%; found C 61.15%, H 6.43%, N 4.27%, F 18.09%.

b: 2(R)-[1(S)-(Boc-amino)-2-(p-trifluoromethylphenyl)-ethyl]-oxirane and 2(S)-[1(R)-(Boc-amino)-2-(p-trifluoromethylphenyl)-ethyl]-oxirane Analogously to Example 1d), 13.5 g (42.8 mmol) of rac. N-Boc-1-(p-trifluoromethylphenyl)-3-buten-2-amine and 36.8 g (214 mmol) of m-chloroperbenzoic acid are reacted in 284 ml of chloroform. The reaction mixture is partitioned between 3 portions of methylene chloride, 10% Na$_2$SO$_3$ solution, sat. Na$_2$CO$_3$ solution, water and brine, and column chromatography (SiO$_2$, hexane/ethyl acetate 4: 1) of the crude product yields the racemate of the title compounds: TLC $R_f(C)$-0.15; $t_{Ret}(II)$=22.9 min; Anal.: calc. C 58.00%, H 6.08%, N 4.23%, F 17.20%; found C 58.03%, H 6.33%, N 4.45%, F 17.02%.

c: 5(S)-[1(S)-(Boc-amino)-2-(p-trifluoromethylphenyl)-ethyl]-3(R,S)-carbethoxydihydrofuran-2-(3H)-one and 5(R)-[1(R)-(Boc-amino)-2-(p-trifluoromethylphenyl)-ethyl]-3 (S,R)-carbethoxydihydrofuran-2-(3H)-one Analogously to Example 1e), 9.6 g (29.0 mmol) of a mixture of 2(R)-[1(S)-(Boc-amino)-2-(p-trifluoromethylphenyl)-ethyl]-oxirane and 2(S)-[1(R)-(Boc-amino)-2-(p-trifluoromethylphenyl)-ethyl]-oxirane in 48 ml of ethanol and 5 ml of THF are reacted with sodium diethylmalonate (prepared from 153 ml of ethanol, 2 g (87 mmol) of sodium und 15.4 ml (101 mmol) of malonic acid diethyl ester). Crystallisation by the addition of hexane to a concentrated solution in ethyl acetate yields a mixture of the title compounds: TLC $R_f(D)$=0.40; $t_{Ret}(II)$=24.1 min and 24.6 min; FAB-MS (M+Na)$^+$=468.

d: 5(S)-[1(S)-(Boc-amino)-2-(p-trifluoromethylphenyl)-ethyl]-dihydrofuran-2-(3H)-one and 5(R)-[1(R)-(Boc-amino)-2-(p-trifluoromethylphenyl)-ethyl]-dihydrofuran-2-(3H)-one Analogously to Example 1h), 9.0 g (20.2 mmol) of a mixture of 5(S)-[1(S)-(Boc-amino)-2-(p-trifluoromethylphenyl)-ethyl]-3(R,S)-carbethoxydihydrofuran-2-(3H)-one and 5(R)-[1(R)-(Boc-amino)-2-(p-trifluoromethylphenyl)-ethyl]-3(S,R)-carbethoxydihydrofuran-2-(3H)-one in 166 ml of dimethoxyethane are hydrolysed with 86.9 ml of 1 N aqueous LiOH solution. Decarboxylation of the resulting carboxylic acids in 350 ml of toluene (9 h 120° C.) and crystallisation of the crude product by the addition of hexane to a concentrated solution in ethyl acetate yields the title compound in the form of a racemate: $t_{Ref}(II)=23.2$ min; Anal.: calc. C 57.90%, H 5.94%, N 3.75%, F 15.26%; found C 57.70%, H 5.78%, N 3.82%, F 15.42%.

e: 5(S)-[1(S)-(Boc-amino)-2-(p-trifluoromethylphenyl)-ethyl]-3(R)-(p-fluorophenylmethyl)-dihydrofuran-2-(3H)-one and 5(R)-[1(R)-(Boc-amino)-2-(p-trifluoromethylphenyl)-ethyl]-3(S)-(p-fluorophenylmethyl)-dihydrofuran-2-(3H)-one Analogously to Example 21 D) 1)c), 700 mg (1.88 mmol) of a mixture of 5(S)-[1(S)-(Boc-amino)-2-(p-trifluoromethylphenyl)-ethyl]-dihydrofuran-2-(3H)-one and 5(R)-[1(R)-(Boc-amino)-2-(p-trifluoromethylphenyl)-ethyl]-dihydrofuran-2-(3H)-one dissolved in 3.4 ml of THF and 0.38 ml of 1,3-dimethyl-3,4,5,6-tetrahydro-2(1H)-pyrimidinone are deprotonated at −75° C. with 3.67 ml of lithium bis(trimethylsilyl)amide 1 M in THF, and alkylated at −75° C. (40 min) with 0.242 ml (1.88 mmol) of 4-fluorobenzyl bromide (Fluka; Buchs/Switzerland). Column chromatography (SiO$_2$, hexane/ethyl acetate 2: 1) yields the title compound: TLC R$_f$(D)=0.59; $t_{Ref}(II)=26.6$ min; FAB-MS (M+H)$^+$=482.

f) (S)-(Boc-amino)-4(S)-hydroxy-6-(p-trifluoromethylphenyl)-2(R)-(p-fluorophenyl-methyl)-hexanoic acid and 5(R)-(Boc-amino)-4(R)-hydroxy-6-(p-trifluoromethylphenyl)-2(S)-(p-fluorophenylmethyl)-hexanoic acid Analogously to Example 1i), 1.1 g (2.28 mmol) of a mixture of 5(S)-[1(S)-(Boc-amino)-2-(p-trifluoromethylphenyl)-ethyl]-3(R)-(p-fluorophenylmethyl)-dihydrofuran-2-(3H)-one and 5(R)-[1(R)-(Boc-amino)-2-(p-trifluoromethylphenyl)-ethyl]-3(S)-(p-fluorophenylmethyl)-dihydrofuran-2-(3H)-one in 37 ml of dimethoxyethane and 19 ml of water are hydrolysed with 9.1 ml of 1 M lithium hydroxide solution. The reaction mixture, partially concentrated by evaporation, is poured onto a mixture of ice, 112 ml of sat. NH$_4$Cl solution, 9.4 ml of 10% citric acid solution and 46 ml of methylene chloride, and methanol is added until the precipitated solid has dissolved to give a clear solution in the 2 phases. The aqueous phase is extracted with 2 portions of methylene chloride/methanol approximately 9:1, and the organic phases are washed with brine, dried with Na$_2$SO$_4$ and concentrated by evaporation: TLC R$_f$(D)=0.15; $t_{Ref}(II)=22.7$ min.

g) 5(S)-(Boc-amino)-4(S)-(tert-butyldimethylsilyloxy)-6-(p-trifluoromethylphenyl)-2-(R)-(p-fluorophenylmethyl)-hexanoic acid and 5(R)-(Boc-amino)-4(R)-(tert-butyldimethylsiloxy)-6-(p-trifluoromethylphenyl)-2(S)-(p-fluorophenylmethyl)-hexanoic acid Analogously to Example 1 j), 1.1 g (2.20 mmol) of a mixture of 5(S)-(Boc-amino)-4(S)-hydroxy-6-(p-trifluoromethylphenyl)-2(R)-(p-fluorophenylmethyl)-hexanoic acid and 5 (R)-(Boc-amino)-4(R)-hydroxy-6-(p-trifluoromethylphenyl)-2(S)-(p-fluorophenylmethyl)-hexanoic acid in 2.4 ml of DMF are silylated with 1.52 g (10.1 mmol) of tert-butyldimethylchlorosilane and 1.2 g (18.0 mmol) of imidazole. The silyl ester function is hydrolysed with 1.8 g of potassium carbonate in 50 ml of methanol/FHF/water 3:1:1 and, after extraction and column chromatography (SiO$_2$, hexane/ethyl acetate 2:1), yields the title compound: TLC R$_f$(D)=0.16; $t_{Ref}(II)$-32.7 min; FAB-MS (M+H)$^+$=614.

h) 5(S)-(Boc-amino)-4(S)-(tert-butyldimethylsiloxy)-6-(p-trifluoromethylphenyl)-2(R)-(p-fluorophenylmethyl)-hexanoyl-(L)-Val-(L)-Phe-morpholin-4-ylamide and 5(R)-(Boc-amino)-4(R)-(tert-butyldimethylsilyloxy)-6-6-(p-trifluoromethylphenyl)-2(S)-(p-fluorophenylmethyl)-hexanoyl-(L)-Val-(L)-Phe-morpholin-4-ylamide Analogously to Example 9f), 200 mg (0.326 mmol) of a mixture of 5(S)-(Boc-amino)-4(S)-(tert-butyldimethylsilyloxy)-6-(p-trifluoromethylphenyl)-2(R)-(p-fluorophenylmethyl)-hexanoic acid and 5(R)-(Boc-amino)-4(R)-(tert-butyldimethylsilyloxy)-6-(p-trifluoromethylphenyl)-2(s)-(p-fluorophenylmethyl)-hexanoic acid and 119 mg (0.358 mmol) of H-(L)-Val-(L)-Phe-morpholin-4-ylamide (Example lo) in 3.1 ml of NMM/CH$_3$CN 0.25 M are reacted with 136 mg (0.36 mmol) of HBTU to yield the title compound: $t_{Ref}(II)=34.5$ min; FAB-MS (M+H)$^+$=929.

G) Boc-(p-CF$_3$)Phe[C](p-F)Phe-(L)-Val-(L)-(p-F)Phe-morpholin-4-ylamide

H) Boc-(p-CF$_3$)Phe[C](p-F)Phe-(L)-Val-(L)-Cha-morpholin-4-ylamide

I) Boc-(p-CF$_3$)Phe[C](p-F)Phe-(L)-Val-(L)-(P-CH$_3$O)Phe-morpholin-4-ylamide

J) Boc-(p-CF$_3$)Phe[C](p-F)Phe-(L)-Ile-(L)-Phe-morpholin-4-ylamide

K) Boc-(p-CF$_3$)Phe[C](p-CF$_3$)Phe-(L)-Val-(L)-Phe-morpholin-4-ylamide

Analogously to Example 1), 110 mg (0.112 mmol) of a mixture of 5(S)-(Boc-amino)-4(S)-(tert-butyldimethylsilyloxy)-6- (p-trifluoromethylphenyl)-2(R)-(p-uifluoromethylphenylmethyl)-hexanoyl-(L)-Val-(L)-Phe-morpholin-4-ylamide and 5(R)-(Boc-amino)-4(R)-(tert-butyldimethylsilyloxy)-6-(p-trifluoromethylphenyl)-2(S)-(p-trifluoromethylphenylmethyl)-hexanoyl-(L)-Val-(L)-Phe-morpholin-4-ylamide are deprotected with 71 mg (0.225 mmol) of TBAF in 1.1 ml of DMF to yield the title compound: $t_{Ref}(I)=18.0$.and 18.6 min (12% ); FAB-MS (M+H)$^+$=865.

The starting material is prepared as follows:

a: 5(S)-[1(S)-(Boc-amino)-2-(p-trifluoromethylphenyl)-ethyl]-3(R)-(p-trifluoromethylphenylmethyl)-dihydrofuran-2-(3H)-one and 5 (R)-[1(R)-(Boc-amino)-2-(p-trifluoromethylphenyl)-ethyl]-3(S)-(p-trifluoromethylphenylmethyl)-dihydrofuran-2-(3H)-one Analogously to Example 21 D) 1)c), 1.5 g (4.02 mmol) of a mixture of 5(S)-[1(S)-(Boc-amino)-2-(p-trifluoromethylphenyl)-ethyl]-dihydrofuran-2-(3H)-one and 5 (R)-[1(R)-(Boc-amino)-2-(p-trifluoromethylphenyl)-ethyl]-dihydrofuran-2-(3H)-one dissolved in 7.3 ml of THF and 0.81 ml of 1,3-dimethyl-3,4,5,6-tetrahydro-2(1H)-pyrimidinone are deprotonated at −75° C. with 7.86 ml of lithium bis(trimethylsilyl)amide 1M in THF and alkylated at −75° C. (40 min) with 1.01 g (4.02 mmol) of 4-trifluoromethylbenzyl bromide (Fluka; Buchs/Switzerland). Column chromatography (SiO$_2$, methylene chloride/hexane/ether 10:10:1) yields the title compound: TLC R$_f$(Q)=0.23; $t_{Ref}(II)=27.7$ min; FAB-MS (M+H-Boc)$^+$=432.

b) 5(S)-(Boc-amino)-4(S)-hydroxy-6-(p-trifluoromethylphenyl)-2(R)-(p-trifluoromethylphenylmethyl)-hexanoic acid and 5(R)-(Boc-amino)-4(R)-hydroxy-6-(p-trifluoromethylphenyl)-2(S)-(p-trifluoromethylphenylmethyl)-hexanoic acid Analogously to Example 1i), 1.43 g (2.69 mmol) of a mixture of 5(S)-[1(S)-(Boc-amino)-2-(p-trifluoromethylphenyl)-ethyl]-3(R)-(p-trifluoromethylphenylmethyl)-dihydrofuran-2-(3H)-one and 5(R)-[1(R)-(Boc-amino)-2-(p-trifluoromethylphenyl)-ethyl]-3(S)-(p-trifluoromethylphenylmethyl)-dihydrofuran-2-

(3H)-one in 43 ml of dimethoxyethane and 22 ml of water are hydrolysed with 10.7 ml of 1M lithium hydroxide solution. The reaction mixture, partially concentrated by evaporation, is poured onto a mixture of ice, 132 ml of sat. NH$_4$Cl solution, 11 ml of 10% citric acid solution and 54 ml of methylene chloride, and methanol is added until the precipitated solid has dissolved. The aqueous phase is extracted with 2 portions of methylene chloride/methanol approximately 4:1, and the organic phases are washed with brine, dried with Na$_2$SO$_4$ and concentrated by evaporation: $t_{Ref}$(II)=24.2 min; FAB-MS (M+H)$^+$=550.

c) 5(S)-(Boc-amino)-4(S)-(tert-butyldimethylsilyloxy)-6(p-trifluoromethylphenyl)-2(R)-(p-trifluoromethylphenylmethyl)-hexanoic acid and 5(R)-(Boc-amino)-4(R)-(tert-butyldimethylsilyloxy)-6-(p-trifluoromethylphenyl)-2(S)-(p-trifluoromethylphenylmethyl)-hexanoic acid Analogously to Example 1j), 1.38 g (2.51 mmol) of a mixture of 5(S)-(Boc-amino)-4(S)-hydroxy-6-(p-trifluoromethylphenyl)-2(R)-(p-trifluoromethylphenylmethyl)-hexanoic acid and 5(R)-(Boc-amino)-4(R)-hydroxy-6-(p-trifluoromethylphenyl)-2(S)-(p-trifluoromethylphenylmethyl)-hexanoic acid in 5.7 ml of DMF are silylated with 1.74 g (11.6 mmol) of tert-butyldimethylchlorosilane and 1.4 g (20.6 mmol) of imidazole. Hydrolysis of the silyl ester function with 2.1 g of potassium carbonate in 55 ml of methanol/THF/water 3:1:1 yields the title compound: TLC R$_f$(A)=0.25; $t_{Ref}$(I)=21.8 min.

d) 5(S)-(Boc-amino)-4(S)-(tert-butyldimethylsilyloxy)-6-(p-trifluoromethylphenyl)-2(R)-(p-trifluoromethylphenylmethyl)-hexanoyl-(L)-Val-(L)-Phe-morpholin-4-ylamide and 5(R)-(Boc-amino)-4(R)-(tert-butyldimethylsiloxy)-6-(p-trifluoromethylphenyl)-2(S)-(p-trifluoromethylphenylmethyl)-hexanoyl-(L)-Val-(L)-Phe-morpholin-4-ylamide Analogously to Example 9f), 200 mg (0.301 mmol) of a mixture of 5(S)-(Boc-amino)-4(S)-(tert-butyldimethylsilyloxy)-6-(p-trifluoromethylphenyl)-2(R)-(p-trifluoromethylphenylmethyl)-hexanoic acid and 5(R)-(Boc-amino)-4(R)-(tert-butyldimethylsilyloxy)-6-(p-trifluoromethylphenyl)-2(S)-(p-trifluoromethylphenylmethyl)-hexanoic acid and 110 mg (0.331 mmol) of H-(L)-Val-(L)-Phe-morpholin-4-ylamide (Example 1o) in 2.8 ml of NMM/CH$_3$CN 0.25M are reacted with 126 mg (0.33 mmol) of HBTU. In the course of the reaction, one of the diastereoisomers precipitates from the reaction mixture and can be filtered off (→5(R),4(R),2(S)). By means of extraction (analogously to Example 9f) of the mother liquor and column chromatography (SiO$_2$, hexane/ethyl acetate 1:1), the other diastereoisomer (→5(S),4(S),2(R)) can be isolated in a diastereoisomeric purity of approximately 90% (according to $^1$H-NMR spectroscopy): TLC R$_f$(A)-0.15; $t_{Ref}$(I)=23.0 min (diastereoisomer not separated); $^1$H-NMR (300 MHz, CD$_3$OD, after cristallisation (→5(R),4(R),2(S))): inter alia 0.60 (dd, (H$_3$C)$_2$CH), $^1$H-NMR (300 MHz, CD$_3$OD, after chromatography (→5(S),4(S),2(R))): inter alia 0.91 (dd, (H$_3$C)$_2$CH).

L) Boc-(p-CF$_3$)Phe[C](p-CF$_3$)Phe-(L)-Val-(L)-(p-F)Phe-morpholin-4-ylamide

M) Boc-(p-CF$_3$)Phe[C](p-CF$_3$)Phe-(L)-Ile-(L)-Phe-morpholin-4-ylamide

N) Boc-(p-CF$_3$)Phe[C](p-CF$_3$)Phe-(L)-Val-(L)-(p-CH$_3$O)Phe-morpholin-4-ylamide O) Boc-(p-CF$_3$)Phe[C](p-CF$_3$)Phe-(L)-Val-(L)-Cha-morpholin-4-ylamide P) The compounds according to the preceding Examples A) to O) in which the radical -morpholin-4-ylamide is replaced by the radical -thiomorpholin-4-ylamide.

The starting material is prepared as follows:

40a) N-Allylformamide

A solution of 300 ml of allylamine in 1288 ml of formic acid ethyl ester is heated at 60° C. for 8 h. The reaction mixture is concentrated in a rotary evaporator and the residue is distilled via a Vigreux column (77° C.; 1 mbar): $^1$H-NMR (200 MHz, CDCl$_3$): 8.2–7.95 (m, 1 H), 6.5–5.8 (sb, 1 H), 5.9–5.7 (m, 1 H), 5.3–5.05 (m, 2 H), 3.95–3.75 (m, 2 H).

40b) Allyl Isocyanide (U. Schöllkopf, R. Jentsch, K. Madawinata and R. Harms, Liebigs Ann. Chem., (1976) 2105). 517 g of quinoline and 286 g of p-toluenesulfonic acid chloride are placed under a N$_2$ atmosphere at 90° C. A vacuum of from 2 to 4 mbar is applied and 85 g of N-allylformamide are added dropwise, the resulting isocyanide being distilled off continuously into the condensation trap (acetone/dry ice) via a Vigreux column at an internal temperature of 85°–95° C. When the reaction is complete, the distillate is immediately distilled off again via a Vigreux column (N$_2$ atmosphere, normal pressure; 100° C.): $^1$H-NMR (200 MHz, CDCl$_3$): 5.9–5.7 (m, 1 H), 5.45 (d, 16 Hz, 1 H), 5.32 (d, 10 Hz, 1 H), 4.05 (m, 2 H); IR (CH$_2$Cl$_2$): 2150, 1650.

40c) rac. 1-(p-trifluoromethylphenyl)-3-buten-2-amine

Under a N$_2$ atmosphere, 4.5 g of allyl isocyanide are dissolved in 100 ml of THF/ether/pentane abs. 4:1:1 and cooled to –100° C. 42 ml of n-butyllithium (1.6M in hexane) are added dropwise at from –100° to –90° C., a yellow colouring first appearing and a solid being precipitated shortly before the end of the addition. The reaction mixture is allowed to warm up to –70° C. slowly and is then cooled to –100° C. again. At from –100° to 85° C., a solution of 16 g of p-trifluoromethylbenzyl bromide (Fluka; Buchs/Switzerland) in 10 ml of THF is added dropwise and the reaction mixture is slowly heated to RT. It is concentrated by evaporation in a rotary evaporator (80 mbar; 30 ° C.), and the residue is poured onto 150 ml of ice-water and extracted 3 times with ether. The ether phases are concentrated by evaporation; 85 ml of methanol and 17 ml of conc. hydrochloric acid are added to the brown residue at 0° C. and the mixture is left overnight in a refrigerator. The mixture is concentrated by evaporation in a rotary, evaporator and the residue is partitioned between 2×150 ml of 2M hydrochloric acid and 2 P×200 ml of ether. The combined aqueous phases are rendered alkaline with solid sodium hydroxide, with cooling, and extracted with 3 portions of ethyl acetate. The organic phases are washed with brine, dried with sodium sulfate, concentrated by evaporation and distilled in a bulb tube (0.1 mbar; 170 ° C.) to yield the pure title compound: $^1$H-NMR (200 MHz, CDCl$_3$): 7.56 and 7.32 (2d, 8 Hz, per 2 H), 5.96–5.78 (m, 1 H), 5.19–5.02 (m, 2 H), 3.68–3.55 (m, 1 H), 2.87 and 2.71 (AB×d, J$_{ab}$=13 Hz, J$_1$=6 Hz, J$_2$=8 Hz, 2 H), 1.4 (sb, 2 H).

Further reaction analogously to Examples 1d) to 1k) and 1), 9f) and 9, 10f) and 10, 15a) and 15 or 16c) and 16 leads to the compounds mentioned above under a) to o).

EXAMPLE 41

The following are prepared analogously to any one of the preceding Examples:

A) Boc-Phe[C]Phe-(L)-Val-(L)-Tyr-morpholin-4-ylamide

Analogously to Example 1), 360 mg (0.418 mmol) of 5(S)-(Boc-amino)-4(S)-(tert-butyldimethylsilyloxy)-6-phenyl-2(R)-phenylmethylhexanoyl-(L)-Val-(L)-Tyr-morpholin-4-ylamide are deprotected with 263 mg (0.84 mmol) of TBAF in 7 ml of DMF to yield the title compound: TLC R$_f$(B)=0.28; $t_{Ref}$(II)=20.1 min; FAB-MS (M+H)$^+$=745.

The starting material is prepared as follows:

a: Z-(L)-Tyr-morpholin-4-ylamide 9.08 g (44 mmol) of DCC are added to an ice-cooled suspension of 14.04 g (40 mmol) of Z-(L)-Tyr-OH in 750 ml of methylene chloride and the mixture is stirred for 20 min. Subsequently, 10.81 g (80 mmol) of HOBT and a solution of 5.23 g (60 mmol) of morpholine in 50 ml of methylene chloride are added. The mixture is stirred for 18 h at RT and then filtered. The filtrate is washed with sat. NaHCO$_3$ solution, water and brine and the aqueous phases are extracted with 2 portions of methylene chloride. The organic phases are dried with Na$_2$SO$_4$, concentrated by evaporation and subjected to column chromatography (SiO$_2$, ethyl acetate) to yield the title compound: TLC R$_f$(B)=0.39.

b: H-(L)-Tyr-morpholin-4-ylamide

A solution of 2.05 g (5.3 mmol) of Z-(L)-Tyr-morpholin-4-ylamide in 91 ml of methanol is hydrogenated for 1.5 h at RT in the presence of 0.5 g of 10% Pd/C. Filtration through ®Celite (filter aid of diatomaceous earth, John-Manville Corp.) and concentration of the filtrate by evaporation yields the title compound: TLC R$_f$(R)=0.34.

c: Z-(L)-Val-(L)-Tyr-morpholin-4-ylamide

At 0° C., 5.18 g (25 mmol) of DCC and 3.73 g (27.5 mmol) of HOBT are added to a solution of 6.3 g (25 mmol) of Z-(L)-Val-OH in 400 ml of methylene chloride and the mixture is then stirred for 20 min. A solution of 6.27 g (25 mmol) of H-(L)-Tyr-morpholin-4-ylamide in 600 ml of methylene chloride is subsequently added. After the mixture has been stirred for 18 h at RT, working up is carried out as described in Example 41 A) a): TLC R$_f$(B)=0.50.

d: H-(L)-Val-(L)-Tyr-morpholin-4-ylamide

Hydrogenation in the presence of 1 g of 10% Pd/C for 1.5 h at RT of a solution of 4.83 g (10 mmol) of Z-(L)-Val-(L)-Tyr-morpholin-4-ylamide in 182 ml of methanol, followed by filtration through ®Celite, concentration of the filtrate by evaporation and column chromatography (SiO$_2$, methylene chloride/methanol 9:1), yields the title compound: TLC R$_f$(F)=0.30; FAB-MS (M+H)$^+$=350.

e: 5(S)-(Boc-amino)-4(S)-(tert-butyldimethylsilyloxy)-6-phenyl-2(R)-phenylmethylhexanoyl-(L)-Val-(L)-Tyr-morpholin-4-ylamide Analogously to Example 1k), 300 mg (0.569 mmol) of 5(S)-(Boc-amino)-4(S)-(tert-butyldimethylsilyloxy)-6-phenyl-2(R)-phenylmethylhexanoic acid (Example 2d)) in 5 ml of DMF are activated with 277 mg (0.626 mmol) of BOP, 84.5 mg (0.625 mmol) of HOBT and 157 µl (1.42 mmol) of NMM, and reacted with 198.6 mg (0.568 mmol) of H-(L)-Val-(L)-Tyr-morpholin-4-ylamide in 2 ml of DMF (2 h RT). Column chromatography (SiO$_2$, ethyl acetate/hexane 2:1) yields the title compound: TLC R$_f$(I)=0.26; t$_{Ref}$(II)=32.2 min; FAB-MS (M+H)$^+$=859.

B) Boc-Tyr[C]Phe-(L)-Val-(L)-Phe-morpholin-4-ylamide

Hydrogenation in the presence of 82 mg of 10% Pd/C at RT of 165 mg (0.197 mmol) of Boc-(p-BzlO)Phe[C]Phe-(L)-Val-(L)-Phe-morpholin-4-ylamide (Example 46) dissolved in 12 ml of methanol, followed by filtration through ®Celite and concentration of the filtrate by evaporation, yields the title compound: t$_{Ref}$(I)=13.9 min; FAB-MS (M+H)$^+$=745.

C) Boc-Tyr[C]Phe-(L)-Val-(L)-Tyr-morpholin-4-ylamide

Hydrogenation in the presence of 120 mg of 10% Pd/C at RT of 235 mg (0.25 mmol) of Boc-(p-BzlO)Phe[C]Phe-(L)-Val-(L)-(p-BzlOPhe)-morpholin-4-ylamide (Example 47) dissolved in 30 ml of methanol, followed by filtration through ®Celite, concentration of the filtrate by evaporation and crystallisation from ethyl acetate/hexane, yields the title compound: TLC R$_f$(B)=0.43; t$_{Ref}$(I)=12.1 min; FAB-MS (M+H)$^+$=761.

D) Boc-Phe[C]Tyr-(L)-Val-(L)-Phe-morpholin-4-ylamide

Hydrogenation in the presence of 70 mg of 10% Pd/C at RT of 140 mg (0.168 mmol) of Boc-Phe[C](p-BzlO)Phe-(L)-Val-(L)-Phe-morpholin-4-ylamide (Example 44) dissolved in 10 ml of methanol, followed by filtration through ®Celite and concentration of the filtrate by evaporation, yields the title compound: t$_{Ref}$(II)=19.9 min; FAB-MS (M+H)$^+$=745.

E) Boc-Phe[C]Tyr-(L)-Val-(L)-Tyr-morpholin-4-ylamide

Hydrogenation in the presence of 75 mg of 10% Pd/C at RT of 140 mg (0.159 mmol) of Boc-Phe[C](p-BzlO)Phe-(L)-Val-(L)-(p-BzlOPhe)-morpholin-4-ylamide (Example 45) dissolved in 10 ml of methanol, followed by filtration through ®Celite and concentration of the filtrate by evaporation, yields the title compound: t$_{Ref}$(II)=17.2 min; FAB-MS (M+H)$^+$=761.

F) Boc-Tyr[C]Tyr-(L)-Val-(L)-Phe-morpholin-4-ylamide

Hydrogenation in the presence of 85 mg of 10% Pd/C at RT of 188 mg (0.178 mmol) of Boc-(p-BzlO)Phe[C](BzlO)Phe-(L)-Val-(L)-Phe-morpholin-4-ylamide (Example 48) dissolved in 20 ml of methanol, followed by filtration through ®Celite and concentration of the filtrate by evaporation, yields the title compound: TLC R$_f$(B)=0.50; t$_{Ref}$(I)=12.1 min; FAB-MS (M+H)$^+$=761.

G) Boc-Tyr[C]Tyr-(L)-Val-(L)-Tyr-morpholin-4-ylamide

Hydrogenation in the presence of 85 mg of 10% Pd/C at RT of 209 mg (0.20 mmol) of Boc-(p-BzlO)Phe[C](p-BzlO)Phe-(L)-Val-(L)-(p-BzlOPhe)-morpholin-4-ylamide (Example 49) dissolved in 20 ml of methanol, followed by filtration and concentration of the filtrate by evaporation, yields the title compound: TLC R$_f$(B)=0.15; t$_{Ref}$(I)=10.6 min; FAB-MS (M+H)$^+$=777.

H) The compounds according to the above Reference Examples A) to G), in which the radical -morpholin-4-ylamide has been replaced by the radical -thiomorpholin-4-ylamide.

EXAMPLE 42

Boc-Phe[C](o-CN)Phe-(L)-Val-(L)-Phe-morpholin-4-ylamide

Analogously to Example 1), 145 mg (0.167 mmol) of 5(S)-(Boc-amino)-4(S)-(tert-butyldimethylsilyloxy)-6-phenyl-2(R)-(o-cyanophenylmethyl)-hexanoyl-(L)-Val-(L)-Phe-morpholin-4-ylamide are deprotected with 105 mg (0.334 mmol) of TBAF in 4 ml of DMF. Precipitation with DIPE from a concentrated solution in DMF yields the pure title compound: t$_{Ref}$(I)=15.7 min; FAB-MS (M+H)$^+$=754.

The starting material is prepared as follows:

a) 5(S)-[1(S)-(Boc-amino)-2-phenylethyl]-3(R)-(o-cyanophenylmethyl)-dihydrofuran-2-(3H)-one Analogously to Example 21 D) 1)c), 2.0 g (6.55 mmol) of 5(S)-[1(S)-(Boc-amino)-2-phenylethyl]-dihydrofuran-2-(3H)-one [Example 21 D) 1)b)] dissolved in 40 ml of THF are deprotonated with 13.1 ml of lithium bis(trimethylsilyl) amide 1M in THF and alkylated (75 min) with 1.4 g (7.2 mmol) of 2-bromomethylbenzonitrile (Fluka; Buchs/Switzerland). Column chromatography (SiO$_2$, hexane/ethyl acetate 2:1) and stirring in hexane yields the pure title compound: TLC R$_f$(D)=0.45; t$_{Ref}$(I)=16.2 min.

b) 5(S)-(Boc-amino)-4(S)-hydroxy-6-phenyl-2(R)-(o-cyanophenylmethyl)-hexanoic acid Analogously to Example 1i), 1.67 g (3.97 mmol) of 5(S)-[1(S)-(Boc-amino)-2-phenylethyl]-3(R)-(o-cyanophenylmethyl)-dihydrofuran-2-(3H)-one in 37 ml of dimethoxyethane and 20 ml of water are hydrolysed with 16 ml of 1M lithium hydroxide solution to yield the title compound: t$_{Ref}$(I)=13.8 min.

c) 5(S)-(Boc-amino)-4(S)-(tert-butyldimethylsilyloxy)-6-phenyl-2(R)-(p-cyanophenylmethyl)-hexanoic acid Analogously to Example 1j), 0.85 g (1.93 mmol) of 5(S)-(Boc-amino)-4(S)-hydroxy-6-phenyl-2(R)-(o-cyanophenylmethyl)-hexanoic acid in 10 ml of DMF are silylated with 1.34 g (8.9 mmol) of tert-butyldimethylchlorosilane and 1.08 g (15.9 mmol) of imidazole. Hydrolysis of the silyl ester function with 1.6 g of potassium carbonate in 40 ml of methanol/THF/water 5:1:2, followed by column chromatography (SiO$_2$, ethyl acetate/ hexane 1:1), yields the title compound: TLC R$_f$(A)=0.4; t$_{Ref}$(I)=20.0 min.

d) 5(S)-(Boc-amino)-4(S)-(tert-butyldimethylsilyloxy)-6-phenyl-2(R)-(o-cyanophenylmethyl)-hexanoyl-(L)-Val-(L)-Phe-morpholin-4-ylamide At 5° C., 41 mg (0.20 mmol) of DCC are added to 100 mg (0.18 mmol) of 5(S)-(Boc-amino)-4(S)-(tert-butyldimethylsilyloxy)-6-phenyl-2(R)-(o-cyanophenylmethyl)-hexanoic acid in 3 ml of THF. After 10 min, 66 mg (0.20 mmol) of H-(L)-Val-(L)-Phe-morpholin-4-ylamide (Example 1o) and 27 mg (0.20 mmol) of HOBT are added and the mixture is stirred for 17 h at RT. The reaction mixture is filtered and the filtrate is partitioned between 3 portions of ethyl acetate, 10% citric acid solution, water, sat. NaHCO$_3$ solution and brine. The organic phase is dried with Na$_2$SO$_4$, concentrated by evaporation and digested in DIPE to yield the title compound: t$_{Ref}$(I)=21.8 min; FAB-MS (M+H)$^+$=868.

EXAMPLE 43

Boc-Phe[C](m-CN)Phe-(L)-Val-(L)-Phe-morpholin-4-ylamide

Analogously to Example 1), 131 mg (0.151 mmol) of 5(S)-(Boc-amino)-4(S)-(tert-butyldimethylsilyloxy)-6-phenyl-2(R)-(m-cyanophenylmethyl)-hexanoyl-(L)-Val-(L)-Phe-morpholin-4-ylamide are deprotected with 95 mg (0.301 mmol) of TBAF in 4 ml of DMF. Precipitation with DIPE from a concentrated solution in DMF yields the pure title compound: t$_{Ref}$(I)=15.7 min; FAB-MS (M+H)$^+$=754.

The starting material is prepared as follows:

a) 5(S)-[1(S)-(Boc-amino)-2-phenylethyl]-3(R)-(m-cyanophenylmethyl)-dihydrofuran-2-(3H)-one Analogously to Example 21 D) 1)c), 2.0 g (6.55 mmol) of 5(S)-[1(S)-(Boc-amino)-2-phenylethyl]-dihydrofuran-2-(3H)-one [Example 21 D) 1)b)] dissolved in 40 ml of THF are deprotonated at −75° C. with 13.1 ml of lithium bis(trimethylsilyl)amide 1M in THF and alkylated (60 min −60° C.) with 1.4 g (7.2 mmol) of 3-bromomethylbenzonitrile (Fluka; Buchs/Switzerland). Column chromatography (SiO$_2$, hexane/ethyl acetate 2:1) and stirring in hexane yields the pure title compound: TLC R$_f$(D)=0.41; t$_{Ref}$(I)=16.1 min.

b) 5(S)-(Boc-amino)-4(S)-hydroxy-6-phenyl-2(R)-(m-cyanophenylmethyl)-hexanoic acid Analogously to Example 1i), 1.6 g (3.8 mmol) of 5(S)-[1(S)-(Boc-amino)-2-phenylethyl]-3(R)-(m-cyanophenylmethyl)-dihydrofuran-2-(3H)-one in 37 ml of dimethoxyethane and 20 ml of water are hydrolysed with 15.2 ml of 1M lithium hydroxide solution to yield the title compound: t$_{Ref}$(I)=13.8 min.

c) 5(S)-(Boc-amino)-4(S)-(tert-butyldimethylsilyloxy)-6-phenyl-2(R)-(m-cyanophenylmethyl)-hexanoic acid Analogously to Example 1j), 1.4 g (3.2 mmol) of 5(S)-(Boc-amino)-4(S)-hydroxy-6-phenyl-2(R)-(m-cyanophenylmethyl)-hexanoic acid in 20 ml of DMF are silylated with 2.2 g (14.6 mmol) of tert-butyldimethylchlorosilane and 1.8 g (26 mmol) of imidazole. Hydrolysis of the silyl ester function with 2.6 g of potassium carbonate in 55 ml of methanol/THF/water 8:1:2, followed by column chromatography (SiO$_2$, ethyl acetate/ hexane 1:1), yields the title compound: TLC R$_f$(A)=0.39; t$_{Ref}$(I)=19.8 min.

d) 5(S)-(Boc-amino)-4(S)-(tert-butyldimethylsilyloxy)-6-phenyl-2(R)-(m-cyanophenylmethyl)-hexanoyl-(L)-Val-(L)-Phe-morpholin-4-ylamide Analogously to Example 42 d), 100 mg (0.18 mmol) of 5(S)-(Boc-amino)-4(S)-(tert-butyldimethylsilyloxy)-6-phenyl-2(R)-(m-cyanophenylmethyl)-hexanoic acid in 3 ml of THF are activated with 41 mg (0.20 mmol) of DCC and reacted with 66 mg (0.20 mmol) of H-(L)-Val-(L)-Phe-morpholin-4-ylamide (Example 1o) and 27 mg (0.20 mmol) of HOBT to yield the title compound: t$_{Ref}$(I)=21.5 min; FAB-MS (M+H)$^+$=868.

EXAMPLE 44

Boc-Phe[C](p-BzlO)Phe-(L)-Val-(L)-Phe-morpholin-4-ylamide

Analogously to Example 1), 560 mg (0.59 mmol) of 5(S)-(Boc-amino)-4(S)-(tert-butyldimethylsilyloxy)-6-phenyl-2(R)-(p-benzyloxyphenylmethyl)-hexanoyl-(L)-Val-(L)-Phe-morpholin-4-ylamide are deprotected with 372 mg (1.18 mmol) of TBAF in 8.4 ml of DMF to yield the title compound: t$_{Ref}$(II)=26.1 min; FAB-MS (M+H)$^+$=835.

The starting material is prepared as follows:

a) p-Benzyloxybenzyl Iodide

A solution of 1.0 g (4.3 mmol) of 4-benzyloxybenzyl chloride (Fluka; Buchs/Switzerland) in 8 ml of acetone is stirred at RT with 3.13 g (20.9 mmol) of sodium iodide. According to a gas chromatrogram, the reaction is complete after 90 min. Working up as described in Example 21 F) 1) a) yields the title compound: $^1$H-NMR (200 MHz, CDCl$_3$: 4.48 (s, 2 H), 5.06 (s, 2 H), 6.85–6.95 (m, 2 H), 7.25–7.48 (m, 7 H).

b) 5(S)-[1(S)-(Boc-amino)-2-phenylethyl]-3(R)-(p-benzyloxyphenylmethyl)-dihydrofuran-2-(3H)-one Analogously to Example 21 D) 1)c), 1.13 g (3.70 mmol) of 5(S)-[1(S)-(Boc-amino)-2-phenylethyl]-dihydrofuran-2-(3H)-one [Example 21 D) 1)b)] dissolved in 4.8 ml of THF and 0.75 ml of 1,3-dimethyl-3,4,5,6-tetrahydro-2(1H)-pyrimidinone are deprotonated at −75° C. with 7.25 ml of lithium bis(trimethylsilyl)amide 1M in THF, and alkylated (15 min) with 1.2 g (3.7 mmol) of p-benzyloxybenzyl iodide in 2 ml of THF. Column chromatography (SiO$_2$, hexane/ ethyl acetate 2:1) yields the pure title compound: TLC R$_f$(D)=0.30; t$_{Ref}$(II)=28.2 min; FAB-MS (M+H)$^+$=502.

c) 5(S)-(Boc-amino)-4(S)-hydroxy-6-phenyl-2(R)-(p-benzyloxy-phenylmethyl)-hexanoic acid Analogously to Example 1i), 1.4 g (2.79 mmol) of 5(S)-[1(S)-(Boc-amino)-2-phenylethyl]-3(R)-(p-benzyloxyphenylmethyl)-dihydrofuran-2-(3H)-one in 45 ml of dimethoxyethane and 23 ml of water are hydrolysed with 11 ml of 1M lithium hydroxide solution. The reaction mixture, partially concentrated by evaporation, is poured onto a mixture of ice, 137 ml of sat. NH$_4$Cl solution, 11 ml of 10% citric acid solution and 56 ml of methylene chloride, and methanol is added until the precipitated solid has dissolved. The aqueous phase is extracted with 2 portions of methylene chloride/methanol approximately 10:1, and the organic phases are washed with brine, dried with Na$_2$SO$_4$ and concentrated by evaporation: t$_{Ref}$(II)=24.0 min; FAB-MS (M+H)$^+$=520.

d) 5(S)-(Boc-amino)-4(S)-(tert-butyldimethylsilyloxy)-6-phenyl-2(R)-(p-benzyloxyphenylmethyl)-hexanoic acid Analogously to Example 1j), 1.4 g (2.69 mmol) of 5(S)-(Boc-amino)-4(S)-hydroxy-6-phenyl-2(R)-(p-benzyloxyphenylmethyl)-hexanoic acid in 2.9 ml of DMF are silylated with 1.87 g (12.4 mmol) of tert-butyldimethylchlorosilane and 1.5 g (22 mmol) of imidazole. Hydrolysis of the silyl ester function with 2.2 g of potassium carbonate in 63 ml of methanol/THF/water 3:1:1 and column chromatography (SiO$_2$, hexane/ethyl acetate 2:1) of the crude product yields the title compound: TLC R$_f$(D)=0.17; t$_{Ref}$(II)=33.7 min; FAB-MS (M+H)$^+$=634.

e) 5(S)-(Boc-amino)-4(S)-(tert-butyldimethylsilyloxy)-6-phenyl-2(R)-(p-benzyloxyphenylmethyl)-hexanoyl-(L)-Val-(L)-Phe-morpholin-4-ylamide Analogously to Example 9f), 400 mg (0.631 mmol) of 5(S)-(Boc-amino)-4(S)-(tert-butyldimethylsilyloxy)-6-phenyl-2(R)-(p-benzyloxyphenylmethyl)-hexanoic acid and 231 mg (0.69 mmol) of H-(L)-Val-(L)-Phe-morpholin-4-ylamide (Example 1o) in 5.7 ml of NMM/CH$_3$CN 0.25M are reacted with 263 mg (0.69 mmol) of HBTU: TLC R$_f$(A)= 0.3; t$_{Ref}$(II)=35.8 min; FAB-MS (M+H)$^+$=949.

EXAMPLE 45

Boc-Phe[C](p-BzlO)Phe-(L)-Val-(L)-(p-BzlOPhe)-morpholin-4-ylamide

Analogously to Example 1), 665 mg (0.63 mmol) of 5(S)-(Boc-amino)-4(S)-(tert-butyldimethylsilyloxy)-6-phenyl-2(R)-(p-benzyloxyphenylmethyl)-hexanoyl-(L)-Val-(L)-(p-BzlOPhe)-morpholin-4-ylamide are deprotected with 398 mg (1.26 mmol) of TBAF in 9 ml of DMF. Precipitation with DIPE from a concentrated solution in methylene chloride yields the pure title compound: t$_{Ref}$(II)=28.7 min; FAB-MS (M+H)$^+$=941.

The starting material is prepared as follows:
a: Boc-(L)-(p-BzlOPhe)-morpholin-4-ylamide 9.08 g (44 mmol) of DCC are added to an ice-cooled suspension of 14.84 g (40 mmol) of Boc-(L)-Tyr(Bzl)-OH (Bachere; Bubendorf/Switzerland) in 650 ml of methylene chloride and the mixture is stirred for 20 min. Subsequently, 10.81 g (80 mmol) of HOBT and a solution of 5.23 g (60 mmol) of morpholine in 50 ml of methylene chloride are added. After having been stirred for 18 h at RT the mixture is filtered. The filtrate is washed with sat. NaHCO$_3$ solution, water and brine and the aqueous phases are extracted with 2 portions of methylene chloride. The organic phases are concentrated by evaporation and again dissolved in a small amount of methylene chloride, the residual undissolved dicyclohexylurea is filtered off and the filtrate is concentrated by evaporation to yield the title compound: TLC R$_f$(B)=0.69.

b: H-(L)-(p-BzlOPhe)-morpholin-4-ylamide

At 0° C., 30 ml of TFA are added to a solution of 1.0 g (2.69 mmol) of Boc-(L)-(p-BzlOPhe)-morpholin-4-ylamide in 30 ml of methylene chloride. After 45 min, the solvent is evaporated off, and the residue is dissolved in ethyl acetate and washed with sat. NaHCO$_3$ solution, 2×water and brine. The aqueous phases are extracted with 2 portions of ethyl acetate. The organic phases are dried with Na$_2$SO$_4$ and concentrated by evaporation to yield the title compound: TLC R$_f$(F)=0.42.

c: Boc-(L)-Val-(L)-(p-BzlOPhe)-morpholin-4-ylamide

At 0° C., 2.68 g (13 mmol) of DCC and 1.93 g (14.3 mmol) of HOBT are added to a solution of 2.8 g (13 mmol) of Boc-(L)-Val-OH in 350 ml of methylene chloride and the mixture is then stirred for 20 min. A solution of 4.41 g (13 mmol) of H-(L)-(p-BzlOPhe)-morpholin-4-ylamide and 1.8 ml (13 mmol) of triethylamine in 250 ml of methylene chloride is then added. After stirring for 18 h at RT, working up is carried out as described in Example 41 A) a). This yields the pure title compound after column chromatography (SiO$_2$, ethyl acetate/hexane 3:1): TLC R$_f$(S)=0.50.

d: H-(L)-Val-(L)-(p-BzlOPhe)-morpholin-4-ylamide

Analogously to Example 45 b), 5.7 g (10.6 mmol) of Boc-(L)-Val-(L)-(p-BzlOPhe)-morpholin-4-ylamide in 120 ml of methylene chloride are cleaved with 120 ml of TFA to yield the title compound: TLC R$_f$(F)=0.42.

e) 5(S)-(Boc-amino)-4(S)-(tert-butyldimethylsilyloxy)-6-phenyl-2(R)-(o-benzyloxyphenylmethyl)-hexanoyl-(L)-Val-(L)-(p-BzlOPhe)-morpholin-4-ylamide Analogously to Example 9f), 400 mg (0.631 mmol) of 5(S)-(Boc-amino)-4(S)-(tert-butyldimethylsilyloxy)-6-phenyl-2(R)-(p-benzyloxyphenylmethyl)-hexanoic acid (Example 44 d)) and 305 mg (0.69 mmol) of H-(L)-Val-(L)-(p-BzlOPhe)-morpholin-4-ylamide in 5.7 ml of NMM/CH$_3$CN 0.25M are reacted with 263 mg (0.69 mmol) of HBTU: TLC R$_f$(A)=0.31; t$_{Ref}$(II)=37.1 min; FAB-MS (M+H)$^+$=1055.

EXAMPLE 46

Boc-(p-BzlO)Phe[C]Phe-(L)-Val-(L)-Phe-morpholin-4-ylamide

Analogously to Example 1), 664 mg (0.70 mmol) of 5(S)-(Boc-amino)-4(S)-(tert-butyldimethylsilyloxy)-6-(p-benzyloxyphenyl)-2(R)-(phenylmethyl)-hexanoyl-(L)-Val-(L)-Phe-morpholin-4-ylamide are deprotected with 440 mg (1.40 mmol) of TBAF in 7 ml of DMF. Crystallisation from $^i$propanol/hexane yields the pure title compound: TLC R$_f$(D) =0.32; t$_{Ref}$(I)=17.8 min; FAB-MS (M+H)$^+$=835.

The starting material is prepared as follows:
a: N-Boc-(p-benzyloxyphenylalaninol)

Analogously to Example 21 B) 1)b), 37.1 g (100 mmol) of Boc-(L)-(p-BzlOPhe)-OH (Bachem; Bubendorf/Switzerland) in 116 ml of THF are activated at from −5° C. to −10° C. with 15.33 ml (110 mmol) of triethylamine and 14.36 ml (110 mmol) of chloroformic acid isobutyl ester in 70 ml of THF. The filtered reaction mixture is introduced dropwise into 7.57 g (200 mmol) of sodium borohydride, treatment with water and digestion in hexane yield the title compound: TLC R$_f$(A)=0.50; FAB-MS (M+H)$^+$=358.

b: N-Boc-(p-benzyloxyphenylalaninal)

Analogously to Example 21 B) 1)c), a solution of 3.5 ml of (49 mmol) of DMSO in 60 ml of methylene chloride is added at −60° C. to 4.76 g (37.5 mmol) of oxalyl chloride in 33.6 ml of methylene chloride. The addition of 8.94 g (25 mmol) of N-Boc-(p-benzyloxyphenylalaninol) in 150 ml of methylene chloride, 14 ml (100 mmol) of triethylamine in 30 ml of methylene chloride and aqueous working up (extraction of the aqueous phases with ethyl acetate) yields the crystalline title compound: TLC R$_f$(A)=0.71; $^1$H-NMR (200 MHz, CDCl$_3$): 1.44 (s, 9 H), 3.06 (d, J=6 Hz, 2 H), 4.39 (m, 1 H), 6.86–6.98 and 7.03–7.15 (2m, each 2 H), 7.30–7.48 (m, 5 H), 9.62 (s, 1 H).

c: 5(S)-[1(S)-(Boc-amino)-2-(p-benzyloxyphenyl)ethyl]-dihydrofuran-2-(3H)-one

Analogously to Example 21 D) 1)b), the zinc homoenolate is formed from 7.7 ml (57.1 mmol) of 2-iodopropionic acid ethyl ester in 100 ml of toluene, 6.0 g (91.8 mmol) of Zn/Cu and 9.69 ml of dimethylacetamide. The zinc homoenolate is transferred by means of cannula to trichlorotitanium isopropanolate (prepared from 4.17 ml (14.2 mmol) of tetraisopropyl orthotitanate and 4.41 ml (40.2 mmol) of titanium tetrachloride in 12 ml of toluene and 69 ml of methylene chloride) which has been cooled to from −40° C. to −25° C. The mixture is heated for 5 min at −25° C. and cooled again to −40° C. A solution of 9.7 g (27 mmol) of N-Boc-(p-benzyloxyphenylalaninal) in 24.5 ml of methylene chloride is then added dropwise and the mixture is stirred for 15 h at approximately −20° C. and then for 1 h at 0° C. The reaction mixture is poured onto 0.4 kg of ice-water and 0.5 l of ether, and stirred vigorously for 10 min. The aqueous phase is removed and extracted with 2 portions of ether. The organic phases are washed with water, sat. sodium hydrogen carbonate solution, water and brine, dried with sodium sulfate and concentrated by evaporation (→crystalline 5(S)-(Boc-amino)-4(S)-hydroxy-6-(p-benzyloxyphenyl)-hexanoic acid ethyl ester).

The above intermediate is heated for 2.5 h at 100° C. in 220 ml of toluene and 6.73 ml of acetic acid. 0.5 l of water is added to the cooled reaction mixture, the aqueous phase is removed and extracted with 2 portions of ether, and the organic phases are washed with sat. sodium hydrogen carbonate solution, water and brine, dried with sodium sulfate and concentrated by evaporation. Crystallisation of the residue from ether/hexane yields the pure title compound: TLC $R_f(E)$=0.28; $t_{Ret}(II)$=23.5 min; $^1$H-NMR (200 MHz, CDCl$_3$): 1.40 (s, 9 H), 2.03–2.2 and 2.44–2.64 and 2.73–2.98 (3m, each 2 H), 3.95 and 4.48 (2m, each 1 H), 4.62 (d, J=9 Hz, 1 H), 6.87–6.97 and 7.09–7.21 (2m, each 2 H), 7.27–7.48 (m, 5 H).

d: 5(S)-[1(S)-(Boc-amino)-2-(p-benzyloxyphenyl)-ethyl]-3 (R)-(phenylmethyl)-dihydrofuran-2-(3H)-one Analogously to Example 21 D) 1)c), 2.47 g (6.0 mmol) of 5(S)-[1(S)-(Boc-amino)-2-(p-benzyloxyphenyl)ethyl]-dihydrofuran-2-(3H)-one dissolved in 12 ml of THF and 1.2 ml of 1,3-dimethyl-3,4,5,6-tetrahydro-2(1H)-pyrimidinone are deprotonated at −70° C. with 11.73 ml of lithium bis(trimethylsilyl)amide 1M in THF and alkylated (75 min) with 0.713 ml (6.0 mmol) of benzyl bromide in 3 ml of THF. Column chromatography (SiO$_2$, hexane/ethyl acetate 4:1→2:1) and crystallisation from ether/hexane yields the pure title compound: TLC $R_f(D)$=0.36.

e) 5(S)-(Boc-amino)-4(S)-hydroxy-6-(p-benzyloxyphenyl)-2(R)-(phenylmethyl)-hexanoic acid Analogously to Example 1i), 0.502 g (1.00 mmol) of 5(S)-[1(S)-(Boc-amino)-2-(p-benzyloxyphenyl)-ethyl]-3(R)-(phenylmethyl)-dihydrofuran-2-(3H)-one in 16 ml of dimethoxyethane and 8.6 ml of water are hydrolysed with 4 ml of 1M lithium hydroxide solution. The reaction mixture, partially concentrated by evaporation, is poured onto a mixture of ice, 49 ml of sat. NH$_4$Cl solution, 4.1 ml of 10% citric acid solution and methylene chloride, and ethanol is added until the precipitated solid has dissolved. The aqueous phase is extracted with 2 portions of methylene chloride/ethanol approximately 9:1, and the organic phases are washed with brine, dried with Na$_2$SO$_4$ and concentrated by evaporation: TLC $R_f(A)$=0.22.

f) 5(S)-(Boc-amino)-4(S)-(tert-butyldimethylsilyloxy)-6-(p-benzyloxyphenyl)-2(R)-(phenylmethyl)-hexanoic acid Analogously to Example 1j), 1.04 g (2.00 mmol) of 5(S)-(Boc-amino)-4(S)-hydroxy-6-(p-benzyloxyphenyl)-2(R)-(phenylmethyl)-hexanoic acid in 7 ml of DMF are silylated with 1.39 g (9.0 mmol) of tert-butyldimethylchlorosilane and 1.12 g (16.4 mmol) of imidazole. Hydrolysis of the silyl ester function with 1.6 g of potassium carbonate in 46 ml of methanol/THF/water 3:1:1 and column chromatography (SiO$_2$, hexane/ethyl acetate 4:1→2:1→1:2) of the crude product yields the title compound: TLC $R_f(A)$=0.69.

g) 5(S)-(Boc-amino)-4(S)-(tert-butyldimethylsilyloxy)-6-(p-benzyloxyphenyl)-2(R)-(phenylmethyl)-hexanoyl-(L)-Val-(L)-Phe-morpholin-4-ylamide Analogously to Example 9f), 126.7 mg (0.200 mmol) of 5(S)-(Boc-amino)-4(S)-(tert-butyldimethylsilyloxy)-6-(p-benzyloxyphenyl)-2(R)-(phenylmethyl)-hexanoic acid and 73.3 mg (0.22 mmol) of H-(L)-Val-(L)-Phe-morpholin-4-ylamide (Example 1o) in 1.88 ml of NMM/CH$_3$CN 0.25M are reacted with 83.4 mg (0.22 mmol) of HBTU: TLC $R_f(A)$=0.33; FAB-MS (M+H)$^+$=949.

EXAMPLE 47

Boc-(p-BzlO)Phe[C]Phe-(L)-Val-(L)-(p-BzlOPhe)-morpholin-4-ylamide

Analogously to Example 1), 788 mg (0.85 mmol) of 5(S)-(Boc-amino)-4(S)-(tert-butyldimethylsilyloxy)-6-(p-benzyloxyphenyl)-2(R)-(phenylmethyl)-hexanoyl-(L)-Val-(L)-(p-BzlOPhe)-morpholin-4-ylamide are deprotected with 534 mg (1.70 mmol) of TBAF in 8.5 ml of DMF. Crystallisation from $^i$propanol/hexane yields the pure title compound: TLC $R_f(B)$=0.51; $t_{Ret}(I)$=19.0 min; FAB-MS (M+H)$^+$=941.

The starting material is prepared as follows:

a) 5(S)-(Boc-amino)-4(S)-(tert-butyldimethylsilyloxy)-6-(p-benzyloxyphenyl)-2(R)-(phenylmethyl)-hexanoyl-(L)-Val-(L)-(p-BzlOPhe)-morpholin-4-ylamide Analogously to Example 9f), 560 mg (0.88 mmol) of 5(S)-(Boc-amino)-4(S)-(tert-butyldimethylsilyloxy)-6-(benzyloxyphenyl)-2(R)-(phenylmethyl)-hexanoic acid and 425 mg (0.968 mmol) of H-(L)-Val-(L)-(p-BzlOPhe)-morpholin-4-ylamide (Example 45 d)) in 8.27 ml of NMM/CH$_3$CN 0.25M are reacted with 366.9 mg (0.968 mmol) of HBTU: TLC $R_f(A)$=0.33; FAB-MS (M+H)$^+$=1055.

EXAMPLE 48

Boc-(p-BzlO)Phe[C](p-BzlO)Phe-(L)-Val-(L)-Phe-morpholin-4-ylamide

Analogously to Example 1), 1.10 g (1.0 mmol) of 5(S)-(Boc-amino)-4(S)-(tert-butyldimethylsilyloxy)-6-(p-benzyloxyphenyl)-2(R)-(p-benzyloxyphenylmethyl)-hexanoyl-(L)-Val-(L)-Phe-morpholin-4-ylamide are deprotected with 628 mg (2.0 mmol) of TBAF in 10 ml of DMF. Crystallisation from hot $^i$propanol yields the pure title compound: TLC $R_f(A)$=0.61; $t_{Ret}(I)$=19.1 min; FAB-MS (M+H)$^+$=941.

The starting material is prepared as follows:

a: 5(S)-[1(S)-(Boc-amino)-2-(p-benzyloxyphenyl)-ethyl]-3(R)-(p-benzyloxyphenylmethyl)-dihydrofuran-2-(3H)-one Analogously to Example 21 D) 1)c), 2.47 g (6.0 mmol) of 5(S)-[1(S)-(Boc-amino)-2-(p-benzyloxyphenyl)ethyl]-dihydrofuran-2-(3H)-one (Example 46 c)) dissolved in 12 ml of THF and 1.2 ml of 1,3-dimethyl-3,4,5,6-tetrahydro-2(1H)-pyrimidinone are deprotonated at −70° C. with 11.73 ml of lithium bis(trimethylsilyl)amide 1M in THF and alkylated (60 min) with 1.946 g (6.0 mmol) of p-benzyloxybenzyl iodide (Example 44a)) in 3 ml of THF. Column chromatography (SiO$_2$, hexane/ethyl acetate 4:1) and crystallisation from ethyl acetate/hexane yields the pure title compound: TLC $R_f(D)$=0.45; $t_{Ret}(I)$=19.9 min; FAB-MS (M+H)$^+$=608.

b) 5(S)-(Boc-amino)-4(S)-hydroxy-6-(p-benzyloxyphenyl)-2(R)-(p-benzyloxyphenylmethyl)-hexanoic acid Analogously to Example 1i), 2.7 g (4.43 mmol) of 5(S)-[1(S)-(Boc-amino)-2-(p-benzyloxyphenyl)-ethyl]-3(R)-(p-benzyloxyphenylmethyl)dihydrofuran-2-(3H)-one in 59 ml of dimethoxyethane and 31.8 ml of water are hydrolysed with 14.8 ml of 1M lithium hydroxide solution. The reaction mixture, partially concentrated by evaporation, is poured onto a mixture of ice, 181 ml of sat. NH₄Cl solution, 16.2 ml of 10% citric acid solution and 400 ml of ethyl acetate, and THF is added until the precipitated solid has dissolved. The aqueous phase is extracted with 2 portions of ethyl acetate, and the organic phases are washed with brine, dried with Na₂SO₄, concentrated by evaporation and digested in hexane: TLC R$_f$(A)=0.07.

c) 5(S)-(Boc-amino)-4(S)-(tert-butyldimethylsilyloxy)-6-(p-benzyloxyphenyl)-2(R)-(p-benzyloxyphenylmethyl)-hexanoic acid Analogously to Example 1j), 2.44 g (3.90 mmol) of 5(S)-(Boc-amino)-4(S)-hydroxy-6-(p-benzyloxyphenyl)-2(R)-(p-benzyloxyphenylmethyl)-hexanoic acid in 14 ml of DMF are silylated with 2.70 g (17.6 mmol) of tert-butyldimethylchlorosilane and 2.18 g (32 mmol) of imidazole. Hydrolysis of the silyl ester function with 3.2 g of potassium carbonate in 90 ml of methanol/THF/water 3:1:1 and column chromatography (SiO₂, hexane/ethyl acetate 2:1→1:1) of the crude product yields the title compound: TLC R$_f$(A)=0.53; FAB-MS (M+H)⁺=740.

d) 5(S)-(Boc-amino)-4(S)-(tert-butyldimethylsilyloxy)-6-(p-benzyloxyphenyl)-2(R)-(p-benzyloxyphenylmethyl)-hexanoyl-(L)-Val-(L)-Phe-morpholin-4-ylamide Analogously to Example 9f), 740 mg (1.00 mmol) of 5(S)-(Boc-amino)-4(S)-(tert-butyldimethylsilyloxy)-6-(p-benzyloxyphenyl)-2(R)-(p-benzyloxyphenylmethyl)-hexanoic acid and 367 mg (1.10 mmol) of H-(L)-Val-(L)-Phe-morpholin-4-ylamide (Example 1o) in 9.39 ml of NMM/CH₃CN 0.25M are reacted with 417 mg (1.10 mmol) of HBTU: TLC R$_f$(A)=0.27; FAB-MS (M+H)⁺=1055.

EXAMPLE 49

Boc-(p-BzlO)Phe[C](p-BzlO)Phe-(L)-Val-(L)-(p-BzlOPhe)-morpholin-4-ylamide

Analogously to Example 1), 0.85 g (0.73 mmol) of 5(S)-(Boc-amino)-4(S)-(tert-butyldimethylsilyloxy)-6-(p-benzyloxyphenyl)-2(R)-(p-benzyloxyphenylmethyl)-hexanoyl-(L)-Val-(L)-(p-BzlOPhe)-morpholin-4-ylamide are deprotected with 460 mg (1.46 mmol) of TBAF in 7.3 ml of DMF. Digestion in ethyl acetate/hexane yields the pure title compound: TLC R$_f$(B)=0.66; t$_{Ret}$(I)=20.2 min; FAB-MS (M+H)⁺=1047.

The starting material is prepared as follows:

a: 5(S)-(Boc-amino)-4(S)-(tert-butyldimethylsilyloxy)-6-(p-benzyloxyphenyl)-2(R)-(p-benzyloxyphenylmethyl)-hexanoyl-(L)-Val-(L)-(p-BzlOPhe)-morpholin-4-ylamide Analogously to Example 9f), 740 mg (1.00 mmol) of 5(S)-(Boc-amino)-4(S)-(tert-butyldimethylsilyloxy)-6-(p-benzyloxyphenyl)-2(R)-(p-benzyloxyphenylmethyl)-hexanoic acid (Example 48) and 483 mg (1.10 mmol) of H-(L)-Val-(L)-(p-BzlOPhe)-morpholin-4-ylamide (Example 45) in 9.39 ml of NMM/CH₃CN 0.25M are reacted with 417 mg (1.10 mmol) of HBTU: TLC R$_f$(A)= 0.19.

EXAMPLE 50

Boc-Phe[C](o-F)Phe-(L)-Val-(L)-Phe-morpholin-4-ylamide

Analogously to Example 1), 190 mg (0.219 mmol) of 5(S)-(Boc-amino)-4(S)-(tert-butyldimethylsilyloxy)-6-phenyl-2(R)-(o-fluorophenylmethyl)-hexanoyl-(L)-Val-(L)-Phe-morpholin-4-ylamide are deprotected with 138 mg (0.438 mmol) of TBAF in 3 ml of DMF to yield the title compound: TLC R$_f$(A)=0.23; t$_{Ret}$(I)=16.0 min; FAB-MS (M+H)⁺=747.

The starting material is prepared as follows:

a) 5(S)-[1(S)-(Boc-amino)-2-phenyl-ethyl]-3(R)-(o-fluorophenylmethyl)-dihydrofuran-2-(3H)-one Analogously to Example 21 D) 1)c), 5.0 g (16.37 mmol) of 5(S)-[1(S)-(Boc-amino)-2-phenylethyl]-dihydrofuran-2-(3H)-one [Example 21 D) 1)b)] dissolved in 75 ml of THF are deprotonated at −75° C. with 32.7 ml of lithium bis(trimethylsilyl)amide 1M in THF and alkylated starting at −75° C. with 2.1 ml (18.0 mmol) of o-fluorobenzyl bromide (Fluka; Buchs/Switzerland) (warming up during 60 min up to max. −60° C.). Column chromatography (SiO₂, hexane/ethyl acetate 3:1) yields the title compound: TLC R$_f$(D)= 0.61.

b) 5(S)-(Boc-amino)-4(S)-hydroxy-6-phenyl-2(R)-(o-fluorophenylmethyl)-hexanoic acid Analogously to Example 1i), 4.5 g (10.8 mmol) of 5(S)-[1(S)-(Boc-amino)-2-phenylethyl]-3(R)-(o-fluorophenylmethyl)-dihydrofuran-2-(3H)-one in 170 ml of dimethoxyethane are hydrolysed with 43.5 ml of 1M lithium hydroxide solution. The evaporation residue of the reaction mixture is poured onto a mixture of ice, 120 ml of sat. ammonium chloride solution and 240 ml of 10% citric acid solution, and extracted with 3 portions of methylene chloride. The organic phases are washed with water and brine, dried over Na₂SO₄ and concentrated by evaporation: t$_{Ret}$(I) =14.5 min.

c) 5(S)-(Boc-amino)-4(S)-(tert-butyldimethylsilyloxy)-6-phenyl-2(R)-(fluorophenylmethyl)-hexanoic acid Analogously to Example 1j), 1.5 g (3.47 mmol) of 5(S)-(Boc-amino)-4(S)-hydroxy-6-phenyl-2(R)-(o-fluorophenylmethyl)-hexanoic acid in 15 ml of DMF are silylated with 2.4 g (16 mmol) of tert-butyldimethylchlorosilane and 1.95 g (28.5 mmol) of imidazole. Hydrolysis of the silyl ester function with 2.8 g of potassium carbonate in 50 ml of methanol/THF/water 4:1:1 yields the title compound after column chromatography (SiO₂, hexane/ethyl acetate 2:1): TLC R$_f$(D)=0.33; t$_{Ret}$(I)= 20.7 min.

d) 5(S)-(Boc-amino)-4(S)-(tert-butyldimethylsilyloxy)-6-phenyl-2(R)-(o-fluorophenylmethyl)-hexanoyl-(L)-Val-(L)-Phe-morpholin-4-ylamide Analogously to Example 9f), 150 mg (0.27 mmol) of 5(S)-(Boc-amino)-4(S)-(tert-butyldimethylsilyloxy)-6-phenyl-2(R)-(o-fluorophenylmethyl)-hexanoic acid and 101 mg (0.30 mmol) of H-(L)-Val-(L)-Phe-morpholin-4-ylamide (Example 1o) in 2.6 ml of NMM/CH₃CN 0.25M are reacted with 115 mg (0.30 mmol) of HBTU: t$_{Ret}$(I)=22.3 min.

EXAMPLE 51

Boc-Phe[C](o-F)Phe-(L)-Val-(L)-(p-CH₃O-Phe)-morpholin-4-ylamide

Analogously to Example 1), 332 mg (0.37 mmol) of 5(S)-(Boc-amino)-4(S)-(tert-butyldimethylsilyloxy)-6-phenyl-2(R)-(o-fluorophenylmethyl)-hexanoyl-(L)-Val-(L)-(p-CH₃O-Phe)-morpholin-4-ylamide are deprotected with 350 mg (1.11 mmol) of TBAF in 3 ml of DMF. Digestion from DIPE and ether yields the title compound: TLC R$_f$(B) =0.50; t$_{Ret}$(I)=16.0 min; FAB-MS (M+H)⁺=777.

The starting material is prepared as follows:

a) 5(S)-(Boc-amino)-4(S)-(tert-butyldimethylsilyloxy)-6-phenyl-2(R)-(o-fluorophenylmethyl)-hexanoyl-(L)-Val-(L)-(p-CH₃O-Phe)-morpholin-4-ylamide Analogously to Example 9f), 205 mg (0.375 mmol) of 5(S)-(Boc-amino)-4(S)-(tert-butyldimethylsilyloxy)-6-phenyl-2(R)-(o-fluorophenylmethyl)-hexanoic acid (Example 50c) and 150 mg (0.412 mmol) of H-(L)-Val-(L)

-(p-CH₃O-Phe)-morpholin-4-ylamide (Example 1Oe) in 3.6 ml of NMM/CH₃CN 0.25M are reacted with 156 mg (0.412 mmol) of HBTU. The crude product (foam) is stirred to yield the title compound: TLC R$_f$(A)=0.16; t$_{Ret}$(I)=22.6 min.

EXAMPLE 52

Boc-Phe[C](m-F)Phe-(L)-Val-(L)-Phe-morpholin-4-ylamide

Analogously to Example 1), 181 mg (0.24 mmol) of 5(S)-(Boc-amino)-4(S)-(tert-butyldimethylsilyloxy)-6-phenyl-2(R)-(m-fluorophenylmethyl)-hexanoyl-(L)-Val-(L)-Phe-morpholin-4-ylamide are deprotected with 151 mg (0.478 mmol) of TBAF in 3 ml of DMF. Digestion in hexane yields the title compound: TLC R$_f$(A)=0.54; t$_{Ret}$(I)=16.2 min; FAB-MS (M+H)⁺=747.

The starting material is prepared as follows:

a) 5(S)-[1(S)-(Boc-amino)-2-phenylethyl]-3(R)-(m-fluorophenylmethyl)-dihydrofuran-2-(3H)-one Analogously to Example 21 D) 1)c), 5.0 g (16.37 mmol) of 5(S)-[1(S)-(Boc-amino)-2-phenylethyl]-dihydrofuran-2-(3H)-one [Example 21 D) 1)b)] dissolved in 75 ml of THF are deprotonated at −75° C. with 32.7 ml of lithium bis (trimethylsilyl)amide 1M in THF and alkylated starting at −75° C. with 3.4 g (18.0 mmol) of 3-fluorobenzyl bromide (Fluka; Buchs/Switzerland) (warming up during 60 min up to max. −50° C.). Column chromatography (SiO₂, hexane/ethyl acetate 3:1) yields the title compound: TLC R$_f$(D)=0.6; t$_{Ret}$(I)=17.2 min.

b) 5(S)-(Boc-amino)-4(S)-hydroxy-6-phenyl-2(R)-(m-fluorophenylmethyl)-hexanoic acid Analogously to Example 1i), 3.7 g (8.95 mmol) of 5(S)-[1(S)-(Boc-amino)-2-phenylethyl]-3(R)-(m-fluorophenylmethyl)-dihydrofuran-2-(3H)-one in 140 ml of dimethoxyethane are hydrolysed with 35.8 ml of 1M lithium hydroxide solution. Extraction of the evaporation residue of the reaction mixture from a mixture of ice, 120 ml of sat. ammonium chloride solution and 240 ml of 10% citric acid solution with a large amount of methylene chloride (solubility!) yields the title compound: t$_{Ret}$(I)=14.6 min.

c) 5(S)-(Boc-amino)-4(S)-(tert-butyldimethylsilyloxy)-6-phenyl-2(R)-(m-fluorophenylmethyl)-hexanoic acid Analogously to Example 1j), 2.7 g (6.25 mmol) of 5(S)-(Boc-amino)-4(S)-hydroxy-6-phenyl-2(R)-(m-fluorophenylmethyl)-hexanoic acid in 30 ml of DMF are silylated with 4.33 g (28.8 mmol) of tert-butyldimethylchlorosilane and 3.51 g (51.3 mmol) of imidazole. Hydrolysis of the silyl ester function with 5.1 g of potassium carbonate in 100 ml of methanol/THF/water 4:1:1 yields the title compound after column chromatography (SiO₂, hexane/ethyl acetate 2:1): t$_{Ret}$(I)=20.8 min.

d) 5(S)-(Boc-amino)-4(S)-(tert-butyldimethylsilyloxy)-6-phenyl-2(R)-(m-fluorophenylmethyl)-hexanoyl-(L)-Val-(L)-Phe-morpholin-4-ylamide Analogously to Example 9f), 150 mg (0.27 mmol) of 5(S)-(Boc-amino)-4(S)-(tert-butyldimethylsilyloxy)-6-phenyl-2(R)-(m-fluorophenylmethyl)-hexanoic acid and 101 mg (0.30 mmol) of H-(L)-Val-(L)-Phe-morpholin-4-ylamide (Example 1o) in 2.6 ml of NMM/CH₃CN 0.25M are reacted with 115 mg (0.30 mmol) of HBTU. Column chromatography (SiO₂, hexane/ethyl acetate 1:1) yields the title compound: TLC R$_f$(A)=0.28; t$_{Ret}$(I)=23.0 min.

EXAMPLE 53

Boc-Phe[C](m-F)Phe-(L)-Val-(L)-(p-CH₃O-Phe)-morpholin-4-ylamide

Analogously to Example 1), 336 mg (0.37 mmol) of 5(S)-(Boc-amino)-4(S)-(tert-butyldimethylsilyloxy)-6-phenyl-2(R)-(m-fluorophenylmethyl)-hexanoyl-(L)-Val-(L)-(p-CH₃O-Phe)-morpholin-4-ylamide are deprotected with 350 mg (1.12 mmol) of TBAF in 3 ml of DMF. Digestion from DIPE and ether yields the title compound: TLC R$_f$(B) =0.48; t$_{Ret}$(I)=16.1 min; FAB-MS (M+H)⁺=777.

The starting material is prepared as follows:

a) 5(S)-(Boc-amino)-4(S)-(tert-butyldimethylsilyloxy)-6-phenyl-2(R)-(m-fluorophenylmethyl)-hexanoyl-(L)-Val-(L)-(p-CH₃O-Phe)-morpholin-4-ylamide Analogously to Example 9f), 205 mg (0.375 mmol) of 5(S)-(Boc-amino)-4(S)-(tert-butyldimethylsilyloxy)-6-phenyl-2(R)-(m-fluorophenylmethyl)-hexanoic acid (Example 52c) and 150 mg (0.412 mmol) of H-(L)-Val-(L)-(p-CH₃O-Phe)-morpholin-4-ylamide (Example 1Oe) in 3.6 ml of NMM/CH₃CN (0.25M) are reacted with 156 mg (0.412 mmol) of HBTU. The crude product is stirred in an ultra-sound bath in hexane to yield the title compound: TLC R$_f$(A)=0.16; t$_{Ret}$(I)=22.5 min.

EXAMPLE 54

Boc-Phe[C]Phe-(L)-Val-(L)-Leu-morpholin-4-ylamide

Analogously to Example 1, 900 mg (1.11 mmol) of 5(S)-Boc-amino-4(S)-(tert-butyldimethylsilyloxy)-6-phenyl-2(R)-phenylmethylhexanoyl-(L)-Val-(L)-Leu-morpholin-4-ylamide are deprotected with 608 mg (1.93 mmol) of TBAF in 12 ml of DMF to yield the title compound: t$_{Ret}$(I)=16 min; FAB-MS (M+H⁺)=695.

The starting material is prepared as follows:

a) Z-(S)-Val-(L)-Leu-morpholin-4-ylamide

Analogously to Example 41 A) a), 3.98 g (10.9 mmol) of Z-(L)-Val-(L)-Leu-OH (Bachem, Switzerland) are converted into the title compound with 0.87 ml (10 mmol) of morpholine. TLC R$_f$ (methylene chloride/methanol 9:1)= 0.6.

b) H-(S)-Val-(L)-Leu-morpholin-1-ylamide

Analogously to Example 41 A) b), 4.7 g (10.9 mmol) of Z-(L)-Val-(L)-Leu-morpholin-4-ylamide are converted into the title compound by hydrogenation in the presence of 1 g of 10% Pd/C. TLC R$_f$ (methylene chloride/methanol 9:1)= 0.3: FAB-MS (M+H⁺)=300.

c) 5(S)-(Boc-amino)-4(S)-(tert-butyldimethylsilyloxy)-6-phenyl-2(R)-phenylmethylhexanoyl-(L)-Val-(L)-Leu-morpholin-4-ylamide Analogously to Example 1 k), 750 mg (1.42 mmol) of 5(S)-(Boc-amino-4(S)-(tert-butyldimethyl-silyloxy)-6-phenyl-2(R)-phenylmethylhexanoic acid and 508 mg (1.696 mmol) of H-(L)-Val-(L)-Leu-morpholin-4-ylamide are reacted in DMF: t$_{Ret}$(I)=22.4 min; FAB-MS (M+H⁺)=809.

EXAMPLE 55

Boc-Phe[C]Phe-(L)-Val-(L)-Ala-morpholin-4-ylamide

Analogously to Example 1, 623 mg (0.81 mmol) of 5(S)-(Boc-amino)-4(S)-(tert-butyldimethylsilyloxy)-6-phenyl-2(R)-phenylmethylhexanoyl-(L)-Val-(L)-Ala-morpholin-4-ylamide are deprotected with 456.5 mg (1.447 mmol) of TBAF in 11 ml of DMF to yield the title compound: t$_{Ret}$(II)=19.6 min; FAB-MS (M+H⁺)=653.

The starting material is prepared as follows:

a) Z-(L)-Val-(L)-Ala-morpholin-1-ylamide

Analogously to Example 41 A) a), 2 g (6.21 mmol) of Z-(L)-Val-(L)-Ala-OH (Bachem, Switzerland) are converted into the title compound with 0.54 ml (6.21 mmol) of morpholine. TLC R$_f$(methylene chloride/m ethanol: 9/1 )=0.61.

b) H-(L)-Val-(L)-Ala-morpholin-1-ylamide

Analogously to Example 41 A) b), 2.4 g (6.2 mmol) of Z-(L)-Val-(L)-Ala-morpholin-1-ylamide are converted into the title compound by hydrogenation in the presence of 0.4 g of 10% Pd/C. TLC $R_f$(methylene chloride/methanol: 9/1) =0.53; FAB-MS (M+H$^+$)=258.

c) 5(S)-(Boc-amino)-4(S)-(tert-butyldimethylsilyloxy)-6-phenyl-2(R)-phenylmethylhexanoyl-(L)-Val-(L)-Ala-morpholin-1-ylamide Analogously to Example 1k, 500 mg (0.947 mmol) of 5(S)-(Boc-amino)-4(S)-(tert-butyldimethylsilyloxy)-6-phenyl-2(R)-phenylmethylhexanoic acid and 292.4 mg (1.136 mmol) of H-(L)-Val-(L)-Ala-morpholin-4-ylamide are reacted in DMF: $t_{Ret}$(II)=32.4 min; FAB-MS (M+H$^+$)= 767.

EXAMPLE 56

The following compounds are prepared analogously to one of the above Examples:

A) Boc-(p-CH$_3$O)Phe[C]Phe-(L)-Val-(L)-Phe-morpholin-4-ylamide

B) Boc-(p-CH$_3$O)Phe[C](p-CH$_3$O)Phe-(L)-Val-(L)-Phe-morpholin-4-ylamide

C) Boc-(p-CH$_3$O)Phe[C](p-BzlO)Phe-(L)-Val-(L)-Phe-morpholin-4-ylamide

D) Boc-(p-CH$_3$O)Phe[C]Tyr-(L)-Val-(L)-Phe-morpholin-4-ylamide

E) Boc-(p-CH$_3$O)Phe[C]Phe-(L)-Val-(L)-(p-CH$_3$O-Phe)-morpholin-4-ylamide

F) Boc-(p-CH$_3$O)Phe[C]Phe-(L)-Val-(L)-Tyr-morpholin-4-ylamide

G) Boc-(p-CH$_3$O)Phe[C](p-CH$_3$O)Phe-(L)-Val-(L)-(p-CH$_3$O-Phe)-morpholin-4-ylamide H) Boc-(p-CH$_3$O)Phe[C](p-CH$_3$O)Phe-(L)-Val-(L)-Tyr-morpholin-4-ylamide I) Boc-(p-CH$_3$O)Phe[C](p-BzlO)Phe-(L)-Val-(L)-(p-CH$_3$O-Phe)-morpholin-4-ylamide J) Boc-(p-CH$_3$O)Phe[C](p-BzlO)Phe-(L)-Val-(L)-Tyr-morpholin-4-ylamide K) Boc-(p-CH$_3$O)Phe[C]Tyr-(L)-Val-(L)-(p-CH$_3$O-Phe)-morpholin-4-ylamide L) Boc-(p-CH$_3$O)Phe[C]Tyr-(L)-Val-(L)-Tyr-morpholin-4-ylamide M) Boc-(p-CH$_3$O)Phe[C](3-CH$_3$O)Phe-(L)-Val-(L)-Phe-morpholin-4-ylamide N) Boc-(p-CH$_3$O)Phe[C](2-CH$_3$O)Phe-(L)-Val-(L)-Phe-morpholin-4-ylamide O) Boc-Phe[C](2-CH$_3$O)Phe-(L)-Val-(L)-Phe-morpholin-4-ylamide 101.6 g of TBAF are added to a solution of 140.3 mg of 5(S)-(Boc-amino)-4(S)-(tert-butyldimethylsilyloxy)-6-phenyl-2(R)-(2-methoxyphenylmethyl)-hexanoyl-(L)-Val-(L)-Phe-morpholin-4-ylamide in 3 ml of DMF, and the reaction mixture is stirred at RT for 21 h. The faintly yellowish solution is diluted with approximately 30 ml of ethyl acetate, washed in succession once with water, once with saturated sodium bicarbonate solution and twice with brine until neutral, and dried over sodium sulfate. After removal of the solvent, the residue is purified on silica gel (eluant B) to yield the title compound. TLC $R_f$(B)=0.26. FAB-MS (M+H)$^+$=759.

The starting material is prepared as follows:

56 O) a) 2-Methoxybenzyl Chloride 16.8 ml of thionyl chloride are added dropwise over a period of approximately 30 minutes to 10 ml of 2-methoxybenzyl alcohol (Fluka, Buchs, Switzerland) and 53.76 g of diisopropylaminomethylpolystyrene (Polyhünig base; Fluka, Buchs, Switzerland; copolymer of 98% styrene and 2% divinylbenzene, diisopropylaminomethylated) in 200 ml of abs. ether. After having been stirred for a further 1.5 h at 0° C., the mixture is filtered with suction and the filtrate is concentrated in a rotary evaporator and under a high vacuum. The residue is purified by chromatography on silica gel (eluant: hexane/ethyl acetate 6:1). TLC $R_f$(C)=0.5. $^1$H-NMR (200 MHz, CDCl$_3$): 7.42–7.24 (m, 2H); 7.0–6.84 (m, 2H); 4.68 (s, 2H); 3.9 (s, 3H).

56 O) b) 2-Methoxybenzyl Iodide 9.3 g of sodium iodide are added to 2 g of 2-methoxybenzyl chloride in 22 ml of abs. acetone and the mixture is stirred overnight at RT. The reaction mixture is diluted with 250 ml of ether and washed with 10% sodium thiosulfate solution and brine. The title compound is obtained by drying over sodium sulfate and removing the solvent and is further processed without being purified. TLC $R_f$(C)=0.46. $^1$H-NMR (200 MHz, CDCl$_3$): 7.36–7.2 (m, 2H); 6.92–6.8 (m, 2H); 4.48 (s, 2H); 3.91 (s, 3H).

56 O) c) 5(S)-[1(S)-(Boc-amino)-2-phenylethyl]-3(R)-(2-methoxyphenylmethyl)-dihydro-furan-2-(3H)-one Under a nitrogen atmosphere, a solution of 1 g of 5(S)-[1(S)-(Boc-amino)-2-phenylethyl]-dihydrofuran-2-(3H)-one [for preparation see under Example 2 i)] in 4 ml of abs. THF and 0.66 ml of DMPU is cooled to –75° C., 6.42 ml of lithium bis(trimethylsilyl)amide (1M) in THF (Aldrich, Steinheim, Federal Republic of Germany) are added at an internal temperature of below –70° C., and the mixture is then stirred for 20 min at –75° C. 812 mg of 2-methoxybenzyl iodide in 2 ml of abs. THF are added dropwise to the reaction solution over a period of 10 min using a syringe, during which the internal temperature must not exceed –70° C., and the mixture is stirred for 1 h at –75° C. to complete the reaction. 1.22 ml of propionic acid followed by 1.22 ml of water are then added to the clear solution at from –75° C. to –70° C. using a syringe, the temperature rising to –30° C. The reaction mixture is subsequently diluted with 50 ml of ethyl acetate and stirred cold (ice/water cooling) for 5 min with 20 ml of 10% citric acid solution. The aqueous phase is removed, and the organic phase is washed in succession with brine, sat. sodium bicarbonate solution and again with brine. The combined aqueous phases are re-extracted twice with ethyl acetate. The combined organic phases are dried over sodium sulfate and concentrated. The title compound is obtained in the form of a brownish oil. Purification is carried out by chromatography on silica gel. Chromatography on silica gel (eluant E) yields the pure title compound. TLC $R_f$(hexane/ethyl acetate 2.5:1)=0.54. MS M$^+$=425.

56 O) d) 5(S)-(Boc-amino)-4(S)-hydroxy-6-phenyl-2(R)-(2-methoxyphenylmethyl)-hexanoic acid 4.45 ml of a 1M lithium hydroxide solution are added dropwise at RT to a solution of 474 mg of 5(S)-[1(S)-(Boc-amino)-2-phenylethyl]-3(R)-(2-methoxyphenylmethyl)-dihydrofuran-2-(3H)-one in 18 ml of dimethoxyethane and 9.07 ml of water. The reaction mixture is then stirred for 3 h at RT, diluted with ethyl acetate and THF and washed in a separating funnel with a mixture of 54.78 ml of sat. ammonium chloride solution and 4.58 ml of 10% citric acid solution, followed by brine and water, until neutral. The title compound is obtained after drying over sodium sulfate and removing the solvent and is further processed without being further purified. TLC $R_f$(hexane/ethyl acetate 2.5:1)=0.15.

56 O) e) 5(S)-(Boc-amino)-4(S)-(tert-butyldimethylsilyloxy)-6-phenyl-2(R)-(2-methoxyphenylmethyl)-hexanoic acid 614 mg of imidazole and 796 mg of tert-butyldimethylchlorosilane are added, with stirring, to a solution of 500 mg of 5(S)-(Boc-amino)-4(S)-hydroxy-6-phenyl-2(R)-(2-methoxyphenylmethyl)-hexanoic acid in 5 ml of DMF. After having been stirred for 20 h at RT, the reaction solution is poured onto ice-water and extracted with ethyl acetate. The organic phase is washed with 10% citric acid solution and brine and dried over sodium sulfate. The solvent is then concentrated by evaporation and the residue is chromatographed on silica gel (eluants E and A) to yield the title compound. $R_f$(hexane/ethyl acetate 2.5:1 )=0.12. FAB-MS (M+H)$^+$=558.

56 O) f) 5(S)-(Boc-amino)-4(S)-(tert-butyldimethylsilyloxy)-6-phenyl-2(R)-(2-methoxyphenylmethyl)-hexanoyl-(L)-Val-(L)-Phe-morpholin-4-ylamide A mixture of 100 mg of 5(S)-(Boc-amino)-4(S)-(tert-butyldimethylsilyloxy)-6-phenyl-2(R)-(2-methoxyphenylmethyl)-hexanoic acid, 74.71 mg of HBTU and 65.68 mg of H-(L)-Val-(L)-Phe-morpholin-4-ylamide [for preparation see under Example 1 o)] in 1.68 ml of a 0.25M solution of NMM in acetonitrile is stirred for 15 h at RT under argon. The solution is concentrated to dryness, and the residue is taken up in ethyl acetate and washed in succession with 10% citric acid, water, sat. sodium bicarbonate solution and brine. The title compound is obtained after drying over sodium sulfate and removing the solvent and is further processed without being purified. TLC $R_f$(A)=0.20. FAB-MS (M+H)$^+$=873.

P) Boc-Phe[C](3-CH$_3$O)Phe-(L)-Val-(L)-Phe-morpholin-4-ylamide

Analogously to Example 56 O), 356 mg of 5(S)-(Boc-amino)-4(S)-(tert-butyldimethyl-silyloxy)-6-phenyl-2(R)-(3-methoxyphenylmethyl)-hexanoyl-(L)-Val-(L)-Phe-morpholin-4-ylamide in 6.09 ml of DMF are desilylated with 206 mg of TBAF to yield the title compound: Purification is carried out by chromatography on silica gel (eluant B). TLC $R_f$(B)=0.37. FAB-MS (M+H)$^+$=759.

The starting material is prepared as follows:
56 P) a) 3-Methoxybenzyl Iodide

Analogously to Example 56 O) b), the title compound is obtained from 2 ml of 3-methoxybenzyl chloride (Fluka, Buchs, Switzerland) and 9.72 g of sodium iodide in 23 ml of abs. acetone. TLC $R_f$(hexane/ethyl acetate 2.5:1)=0.71. $^1$H-NMR (200 MHz, CDCl$_3$): 7.20 (m, 1H); 7.0–6.87 (m, 2H); 6.78 (dxd, 1H); 4.42 (s, 2H); 3.8 (s, 3H).

56 P) b) 5(S)-[1(S)-(Boc-amino)-2-phenylethyl]-3(R)-(3-methoxyphenylmethyl)-dihydro-furan-2-(3H)-one Analogously to Example 56 O) c), 1.5 g of 5(S)-[1(S)-(Boc-amino)-2-phenylethyl]-dihydrofuran-2-(3H)-one [prepared according to Example 2i)] in 3 ml of abs. THF are deprotonated (−75° C.) with 9.62 ml of lithium bis (trimethylsilyl)amide (1M in THF) and with the addition of 0.998 ml of DMPU, and alkylated with 1.22 g of 3-methoxybenzyl iodide. Chromatography on silica gel (eluant E) yields the pure title compound. TLC $R_f$(hexane/ethyl acetate 2.5:1)=0.32. FAB-MS (M+H)$^+$=426.

56 P) c) 5(S)-(Boc-amino)-4(S)-hydroxy-6-phenyl-2(R)-(3-methoxyphenylmethyl)-hexanoic acid Analogously to Example 56 O) d), 1.315 g of 5(S)-[1(S)-(Boc-amino)-2-phenylethyl]-3(R)-(3-methoxyphenylmethyl)-dihydrofuran-2-(3H)-one in 49.9 ml of dimethoxyethane and 25.16 ml of water are hydrolysed with 12.36 ml of lithium hydroxide solution 1M to yield the title compound which is directly further processed. TLC $R_f$(A)=0.09. FAB-MS (M+H)$^+$=444.

56 P) d) 5(S)-(Boc-amino)-4(S)-(tert-butyldimethylsilyloxy)-6-phenyl-2(R)-(3-methoxyphenylmethyl)-hexanoic acid Analogously to Example 56 O) e), 1.3 g of 5(S)-(Boc-amino)-4(S)-hydroxy-6-phenyl-2(R)-(3-methoxyphenylmethyl)-hexanoic acid in 13 ml of DMF are silylated with 1.987 g of tert-butyldimethylchlorosilane and 1.646 g of imidazole. Chromatography on silica gel (eluants E, D and A) yields the pure title compound. TLC $R_f$(D)=0.06. FAB-MS (M+H)$^+$=558.

56 P) e) 5(S)-(Boc-amino)-4(S)-(tert-butyldimethylsilyloxy)-6-phenyl-2(R)-(3-methoxyphenylmethyl)-hexanoyl-(L)-Val-(L)-Phe-morpholin-4-ylamide Analogously to Example 56 O) f), 192.2 mg of 5(S)-(Boc-amino)-4(S)-(tert-butyldimethylsilyloxy)-6-phenyl-2(R)-(3-methoxyphenylmethyl)-hexanoic acid and 126.4 mg of H-(L)-Val-(L)-Phe-morpholin-4-ylamide [prepared according to Example 1o)] in 3.23 ml of NMM/CH$_3$CN 0.25M are reacted with 143.7 mg of HBTU to yield the title compound. TLC $R_f$(A)=0.25. FAB-MS (M+H)$^+$=873.

Q) Boc-Phe[C](3-CH$_3$O)Phe-(L)-Val-(L)-(p-CH$_3$O-Phe)-morpholin-4-ylamide

R) Boc-Phe[C](2-CH$_3$O)Phe-(L)-Val-(L)-(p-CH$_3$O-Phe)-morpholin-4-ylamide

S) Boc-Phe[C](p-BzlO)Phe-(L)-Val-(L)-(p-CH$_3$O-Phe)-morpholin-4-ylamide

Analogously to Example 1), 345 mg (0.352 mmol) of 5(S)-(Boc-amino)-4(S)-(tert-butyldimethylsilyloxy)-6-phenyl-2(R)-[(p-benzyloxyphenyl)methyl]-hexanoyl-(L)-Val-(L)-(p-CH$_3$O-Phe)-morpholin-4-ylamide are deprotected with 222 mg (0.704 mmol) of TBAF in 5 ml of DMF. Digestion from DIPE in an ultrasound bath yields the title compound: TLC $R_f$(B)=0.28; $t_{Ret}$(I)=17.6 min; FAB-MS (M+H)$^+$=865.

The starting material is prepared as follows:
a) 5(S)-(Boc-amino)-4(S)-(tert-butyldimethylsilyloxy)-6-phenyl-2(R)-[(p-benzyloxyphenyl)methyl]hexanoyl-(L)-Val-(L)-(p-CH$_3$O-Phe)-morpholin-4-ylamide Analogously to Example 9f), 263 mg (0.415 mmol) of 5(S)-(Boc-amino)-4(S)-(tert-butyldimethylsilyloxy)-6-phenyl-2(R)-[(p-benzyloxyphenyl)methyl]-hexanoic acid (Example 44d) and 137 mg (0.377 mmol) of H-(L)-Val-(L)-(p-CH$_3$O-Phe)-morpholin-4-ylamide (Example 10e) in 3.6 ml of NMM/CH$_3$CN 0.25M are reacted with 157 mg (0.415 mmol) of HBTU to yield the title compound: $t_{Ret}$(I)=23.5 min.

EXAMPLE 57

Boc-Phe[C]Tyr-(L)-Val-(L)-(p-CH$_3$O-Phe)-morpholin-4-ylamide

Hydrogenation of 70 mg (0.081 mmol) of Boc-Phe[C](p-BzlO)Phe-(L)-Val-(L)-(p-CH$_3$O-Phe)-morpholin-4-ylamide (Example 56S)) in 8 ml of methanol in the presence of 35 mg of 10% Pd/C yields the title compound after filtration through Celite and concentration by evaporation: TLC $R_f$(B) =0.17; $t_{Ret}$(I)=14.1 min; FAB-MS (M+H)$^+$=775.

EXAMPLE 58

Boc-Phe[C](p-CN)Phe-(L)-Val-(L)-(p-CH$_3$O-Phe)-morpholin-4-ylamide

Analogously to Example 1), 322 mg (0.36 mmol) of 5(S)-(Boc-amino)-4(S)-(tert-butyldimethylsilyloxy)-6-phenyl-2(R)-(p-cyanophenylmethyl)-hexanoyl-(L)-Val-(L)-(p-CH$_3$O-Phe)-morpholin-4-ylamide are deprotected with 340 mg (1.08 mmol) of TBAF in 3 ml of DMF over a period of 19 h. Digestion of the crude product from DIPE in an ultrasound bath yields the title compound: TLC $R_f$(Y)=0.41; $t_{Ret}$(I)=15.4 min; FAB-MS (M+H)$^+$=784.

The starting material is prepared as follows:

a) 5(S)-(Boc-amino)-4(S)-(tert-butyldimethylsilyloxy)-6-phenyl-2(R)-(p-cyanophenylmethyl)-hexanoyl-(L)-Val-(L)-(p-CH₃O-Phe)-morpholin-4-ylamide Under a nitrogen atmosphere, 200 mg (0.362 mmol) of 5(S)-(Boc-amino)-4(S)-(tert-butyldimethylsilyloxy)-6-phenyl-2(R)-(p-cyanophenylmethyl)-hexanoic acid [Example 21 E)1)c)] are dissolved in 6 ml of abs. THF and, at 5° C., 82 mg (0.398 mmol) of DCC are added. After 10 min 145 mg (0.398 mmol) of H-(L)-Val-(L)-(p-CH₃O-Phe)-morpholin-4-ylamide (Example 10e) and 54 mg (0.398 mmol) of HOBT are added and the mixture is stirred for 17 h at RT. The reaction mixture is filtered, and the filtrate is taken up in ethyl acetate and washed with 10% citric acid solution, water, sat. NaHCO₃ solution and brine. The aqueous phases are extracted twice with ethyl acetate, and the organic phases are dried with Na₂SO₄, concentrated by evaporation and digested in DIPE to yield the title compound: $t_{Ref}(I)$=21.8 min; FAB-MS (M+H)⁺=898.

EXAMPLE 59

(S)-(Boc-amino)-4(S)-hydroxy-6-phenyl-2(R)-[(2,4-difluorophenyl)methyl]-hexanoyl-(L)-Val-(L)-Phe-morpholin-4-ylamide Analogously to Example 1), 264 mg (0.30 mmol) of 5(S)-(Boc-amino)-4(S)-(tert-butyldimethylsilyloxy)-6-phenyl-2(R)-[(2,4-difluorophenyl)-methyl]hexanoyl-(L)-Val-(L)-Phe-morpholin-4-ylamide are deprotected with 190 mg (0.60 mmol) of TBAF in 5 ml of DMF for 17 h. Digestion of the crude product from a small amount of methylene chloride and DIPE/hexane 3:1 in an ultrasound bath yields the title compound: TLC $R_f(B)$=0.71; $t_{Ref}(I)$=16.1 min; FAB-MS (M+H)⁺=765.

The starting material is prepared as follows:

a) 5(S)-[1(S)-(Boc-amino)-2-phenylethyl]-3(R)-[(2,4-difluorophenyl)methyl]-dihydro-furan-2-(3H)-one Analogously to Example 21 D) 1)c), 5.0 g (16.37 mmol) of 5(S)-[1(S)-(Boc-amino)-2-phenylethyl]-dihydrofuran-2-(3H)-one [Example 21 D) 1)b)] dissolved in 100 ml of THF are deprotonated at −75° C. with 32.7 ml of lithium bis(trimethylsilyl)amide 1M in THF, and alkylated starting at −75° C. with 2.51 ml (19.6 mmol) of 2,4-difluorobenzylbromide (Aldrich; Milwaukee/USA) (warming up during 2 h up to max. −60° C.). Column chromatography (SiO₂, hexane/ethyl acetate 2:1) yields the title compound: TLC $R_f(D)$=0.5; $t_{Ref}(I)$=17.2 min.

b) 5(S)-(Boc-amino)-4(S)-hydroxy-6phenyl-2(R)-[(2,4-difluorophenyl)methyl]-hexanoic acid Analogously to Example 1i), 3.1 g (7.18 mmol) of 5(S)-[1(S)-(Boc-amino)-2-phenylethyl]-3(R)-[(2,4-difluorophenyl)methyl]-dihydrofuran-2-(3H)-one in 77 ml of dimethoxyethane and 19 ml of water are hydrolysed with 28.7 ml of 1M lithium hydroxide solution (19 h RT): $t_{Ref}(I)$=14.7 min.

c) 5(S)-(Boc-amino)-4(S)-(tert-butyldimethylsilyloxy)-6-phenyl-2(R)-[(2,4-difluorophenyl)methyl]-hexanoic acid Analogously to Example 1j), 3.2 g (7.12 mmol) of 5(S)-(Boc-amino)-4(S)-hydroxy-6-phenyl-2(R)-[(2,4-difluorophenyl)methyl]-hexanoic acid in 67 ml of DMF are silylated with 4.93 g (32.7 mmol) of tert-butyldimethylchlorosilane and 3.97 g (58.4 mmol) of imidazole. Hydrolysis of the silyl ester function with 5.9 g of potassium carbonate in 77 ml of methanol, 20 ml of THF and 20 ml of water yields the title compound after column chromatography (SiO₂, hexane/ethyl acetate 2:1): TLC $R_f(D)$=0.22; $t_{Ref}(I)$=20.8 min.

d) 5(S)-(Boc-amino)-4(S)-(tert-butyldimethylsilyloxy)-6-phenyl-2(R)-[(2,4-difluorophenyl)-methyl]-hexanoyl-(L)-Val-(L)-Phe-morpholin-4-ylamide Analogously to Example 9f), 200 mg (0.35 mmol) of 5(S)-(Boc-amino)-4(S)-(tert-butyldimethylsilyloxy)-6-phenyl-2(R)-[(2,4-difluorophenyl)methyl]-hexanoic acid and 130 mg (0.39 mmol) of H-(L)-Val-(L)-Phe-morpholin-4-ylamide (Example 1o) in 3.4 ml of NMM/CH₃CN 0.25M are reacted with 148 mg (0.39 mmol) of HBTU to yield the title compound: $t_{Ref}(I)$=22.4 min.

EXAMPLE 60

Boc-Phe[C]Phe-(L)-Val-(L)-Phe-trans-(2,6)-dimethylmorpholin-4-ylamide

Analogously to Example 1, 770 mg (0.89 mmol) of 5(S)-(Boc-amino)-4(S)-(tert-butyldimethylsilyloxy)-6-phenyl-2(R)-(phenylmethyl)-hexanoyl-(L)-Val-(L)-Phe-trans-(2,6)-dimethylmorpholin-4-ylamide are deprotected with 280 mg (0.89 mmol) of TBAF in 10 ml of DMF. Digestion from DIPE and ether yields the title compound: TLC $R_f(D')$-0.26; $t_{Ref}(I)$=17.1 min.; FAB-MS(M+H)⁺=757.

The starting compound is prepared as follows:

a) 5(S)-(Boc-amino)-4(S)-(tert-butyldimethylsilyloxy)-6-phenyl-2(R)-(phenylmethyl)-hexanoyl-(L)-Val-(L)-Phe-trans-(2,6)-dimethylmorpholin-4-ylamide Analogously to Example 9f), 420 mg (0.97 mmol) of 5(S)-(Boc-amino)-4(S)-(tert-butyldimethylsilyloxy)-6-phenyl-2(R)-(phenylmethyl)-hexanoic acid (Example 50c) and 512 mg (0.97 mmol) of H-(L)-Val-(L)-Phe-trans-(2,6)-dimethylmorpholin-4-ylamide in 10 ml of NMM/CH₃CN 0.25M are reacted with 405 mg of HBTU. Chromatography on silica gel with ethyl acetate/hexane (1:1) yields the title compound: $t_{Ref}(I)$=22.9 min.

b) H-(L)-Val-(L)-Phe-trans-(2,6)-dimethylmorpholin-4-ylamide 402 mg (1.1 mmol) of HBTU are added to a solution of 400 mg (1 mmol) of Z-(L)-Phe-(L)-Val-OH and 120 mg (1 mmol) of trans-(2,6)-dimethylmorpholine in 10 ml of NMM/CH₃CN 0.25M and the mixture is stirred for 96 h at RT. The reaction mixture is diluted with ether and washed in succession with water, 10% citric acid, sat. sodium bicarbonate solution, water and sat. sodium chloride solution. The organic phases are dried over sodium sulfate and concentrated by evaporation. The residue is hydrogenated as described in Example 1 m) with Pd/C in methanol and yields the title compound in the form of an amorphous solid.

EXAMPLE 61

Boc-Phe[C](p-isobutyloxy)Phe-(L)-Val-(L)-Phe-morpholin-4-ylamide 233 mg (0.7 mmol) of caesium carbonate are added to a solution of 155 mg (0.2 mmol) of Boc-Phe[C]Tyr-(L)-Val-(L)-Phe-morpholin-4-ylamide from Example 41D in 18 ml of dioxane and the mixture is stirred for 12 h. 1.1 ml (9.4 mmol) of isobutyl iodide are added to the milky suspension and the reaction mixture is stirred for 2 h at RT and then heated for 6 h at 80° C. The reaction mixture is cooled and diluted with methylene chloride, solids are removed by filtration and the filtrate is concentrated by evaporation. The title compound is obtained after purification by chromatography on silica gel with ethyl acetate/hexane (95:5): TLC $R_f(C'')$=0.56; $t_{Ref}(I)$=18.1 min.; FAB-MS (M+H)⁺=801.

EXAMPLE 62

Boc-Phe[C](p-isobutyloxy)Phe-(L)Val-(L)-(p-isobutyloxy-Phe)-morpholin-4-ylamide

Analogously to Example 61, the title compound is obtained from 114 mg (0.14 mmol) of 5(S)-(Boc-amino)-4

(S)-hydroxy-6-phenyl-2(R)-(4-hydroxyphenylmethyl)-hexanoyl-(L)-Val-(L)-(p-isobutyloxy-Phe)-morpholin-4-ylamide, 163 mg (0.5 mmol) of caesium carbonate and 0.4 ml (3.4 mmol) of isobutyl iodide after purification by chromatography on silica gel with ethyl acetate: TLC $R_f$(C') -0.55 $t_{Ret}$(I)=20.1.;FAB-MS (M+H)$^+$=873.

The starting material is prepared as follows:
a) 5(S)-(Boc-amino)-4(S)-hydroxy-6-phenyl-2(R)-(4-hydroxyphenylmethyl)-hexanoyl-(L)-Val-(L)-(p-isobutyloxy-Phe)-morpholin-4-ylamide A solution of 408 mg (0.4 mmol) of 5(S)-(Boc-amino)-4(S)-(tert-butyldimethylsilyloxy)-6-phenyl-2(R)-(4-benzyloxyphenylmethyl)-hexanoyl-(L)-Val-(L)-(p-isobutyloxy-Phe)-morpholin-4-ylamide in 6 ml of methanol is hydrogenated for 5 h with 76 mg of Pd/C 5% in the presence of 1 atm hydrogen pressure. The catalyst is removed by filtration, the filtrate is concentrated by evaporation, and the residue is chromatographed on silica gel with ethyl acetate/methanol (19:1). In addition to 5(S)-(Boc-amino)-4(S)-(tert-butyldimethylsilyloxy)-6-phenyl-2(R)-(4-hydroxyphenylmethyl)-hexanoyl-(L)-Val-(L)-(p-isobutyloxy-Phe)-morpholin-4-ylamide obtained as a by-product, the title compound is obtained: TLC $R_f$(C')= 0.37.

b) 5(S)-(Boc-amino)-4(S)-(tert-butyldimethylsilyloxy)-6-phenyl-2-(R)-(4-benzyloxyphenylmethyl)-hexanoyl-(L)-Val-(L)-(p-isobutyloxy-Phe)-morpholin-4-ylamide Analogously to Example 9f, 291 mg (0.45 mmol) of 5(S)-(Boc-amino)-4(S)-(tert-butyldimethylsilyloxy)-6-phenyl-2(R)-(4-benzyloxyphenylmethyl)-hexanoic acid (Example 44d) and 203 mg (0.5 mmol) of H-(L)-Val-(L)-(p-isobutyloxy-Phe)-morpholin-4-ylamide (Example 70b) in 4.6 ml of NMM/CH$_3$CN 0.25M are reacted with 193 mg of HBTU: TLC $R_f$(E')=0.39; FAB-MS (M+H)$^+$=1021.

EXAMPLE 63

5(S)-[4-(Tetrahydropyranyl)oxycarbonylamino]-4(S)-hydroxy-6-phenyl-2(R)-benzylhexanoyl-(L)-Val-(L)-Phe-morpholin-4-ylamide 0.331 ml (2.38 mmol) of triethylamine are added to 500 mg (0.795 mmol) of 5(S)-(amino)-4(S)-hydroxy-6-phenyl-2(R)-benzylhexanoyl-(L)-Val-(L)-Phe-morpholin-4-ylamide and reacted, with cooling to 5° C., with 262 mg (1.59 mmol) of chloroformic acid 4-tetrahydropyranyl ester (Chemical Abstracts Registry No. 89641-80-5). After having been stirred for a further hour at RT, the reaction mixture is poured onto water and extracted 3 times with ethyl acetate. The combined organic phases are washed with water, saturated sodium bicarbonate solution and brine, dried over sodium sulfate, and then concentrated under reduced pressure. The title compound is purified by column chromatography (SiO$_2$, methylene chloride/methanol); TLC $R_f$ (B)= 0.3; $t_{Ret}$(I)=14.28 min; FAB-MS (M+H$^+$)=757.

EXAMPLE 64

5(S)-[3(S)-(Tetrahydrofuranyl)oxycarbonylamino]-4(S)-hydroxy-6-phenyl-2(R)-benzylhexanoyl-(L)-Val-(L)-Phe-morpholin-4-ylamide Analogously to Example 63, 500 mg (0.795 mmol) of 5(S)-(amino)-4(S)-hydroxy-6-phenyl-2(R)-benzylhexanoyl-(L)-Val-(L)-Phe-morpholin-4-ylamide are reacted with 363 mg (2.41 mmol) of chloroformic acid 3(S)-tetrahydrofuranyl ester. The title compound is purified by precipitation with ether; TLC $R_f$(B)=0.25; $t_{Ret}$(I)=13.86 min; FAB-MS (M+H$^+$)=743.

The starting material is prepared as follows:
a) Chloroformic Acid 3(S)-tetrahydrofuranyl Ester 14.1 ml (27.24 mmol) of a 20% solution of phosgene in toluene are added dropwise to 14 ml of toluene. After the mixture has been cooled in an ice-bath, a solution of 2 g (22.7 mmol) of (S)-(+)3-hydroxy-tetrahydrofuran (JPS CHIMIE, Bevaix, Switzerland) in a small amount of toluene is added, the mixture is then stirred for 1 h at RT, and the excess phosgene is expelled with argon. After concentration in a rotary evaporator at reduced pressure, distillation is carried out for the purpose of purification. Boiling point at 12 torr: 130° C.

EXAMPLE 65

5(S)-[3(R)-(Tetrahydrofuranyl)oxycarbonylamino]-4(S)-hydroxy-6-phenyl-2(R)-benzylhexanoyl-(L)-Val-(L)-Phe-morpholin-4-ylamide Analogously to Example 63, 500 mg (0.795 mmol) of 5(S)-(amino)-4(S)-hydroxy-6-phenyl-2(R)-benzylhexanoyl-(L)-Val-(L)-Phe-morpholin-4-ylamide are reacted with 363 mg (2.41 mmol) of chloroformic acid 3(R)-tetrahydrofuranyl ester. The title compound is purified by column chromatography (SiO$_2$, ethyl acetate to ethyl acetate/acetone: 9/1 ); TLC $R_f$(ethyl acetate/acetone: 4/1)= 0.62; $t_{Ret}$(IV)=14.06 min; FAB-MS (M+H$^+$)=743.

The starting material is prepared as follows:
a) Chloroformic Acid 3(R)-tetrahydrofuranyl Ester 12.5 ml (24.15 mmol) of a 20% solution of phosgene in toluene are cooled in an ice-bath, a solution of 1.06 g (12.03 mmol) of (R)-(+)-3-hydroxytetrahydrofuran (JPS CHIMIE, Bevaix, Switzerland) in a small amount of toluene is then added dropwise and, after the mixture has been stirred at RT for 2 h, the excess phosgene is expelled with argon. After concentration by evaporation in a rotary evaporator under reduced pressure, the crude title compound is further processed without being further purified.

EXAMPLE 66

5(S)-Ethoxycarbonylamino-4(S)-hydroxy-6-phenyl-2(R)-benzylhexanoyl-(L)-Val-(L)-Phe-morpholin-4-ylamide Analogously to Example 63, 500 mg (0.795 mmol) of 5(S)-(amino)-4(S)-hydroxy-6-phenyl-2(R)-benzylhexanoyl-(L)-Val-(L)-Phe-morpholin-4-ylamide are reacted with 0.151 ml (1.585 mmol) of chloroformic acid ethyl ester (Fluka, Buchs, Switzerland). The title compound is purified by crystallisation (ethyl acetate/ether); TLC $R_f$(B)=0.4; $t_{Ret}$(IV)=14.51 min; FAB-MS (M+H$^+$)=701.

EXAMPLE 67

5(S)-(Boc-amino)-4(S)-hydroxy-6-cyclohexyl-2(R)-(4-benzyloxyphenylmethyl)-hexanoyl-(L)-Val-(L)-Phe-morpholin-4-ylamide Analogously to Example 1, 1.45 g (1.517 mmol) of 5(S)-(Boc-amino)-4(S)-(tert-butyldimethylsilyloxy)-6-cyclohexyl-2(R)-(4-benzyloxybenzyl)-hexanoyl-(L)-Val-(L)-Phe-morpholin-4-ylamide in 12 ml of DMF are reacted with 0.958 g (3.03 mmol) of TBAF trihydrate to yield the title compound. The title compound is purified by crystallisation (hexane). TLC $R_f$ (B)=0.5; $t_{Ret}$(IV)=18.99 min; FAB-MS (M+H$^+$)=841.

The starting compounds are prepared as follows:
a) 5(S)-[1(S)-(Boc-amino)-2-cyclohexylethyl]-dihydrofuran-2-(3H)-one A solution of 5 g (16.37 mmol) of 5(S)-[1(S)-(Boc-amino)-2-phenylethyl]-dihydrofuran-2-(3H)-one in 50 ml of methanol is hydrogenated for 2 h at RT under normal pressure in the presence of 0.5 g of Nishimura catalyst. The catalyst is removed by filtration and the filtrate is then concentrated in a rotary evaporator and dried under a high vacuum. TLC $R_f$ (D)=0.5; FAB-MS (M+H$^+$)=312.

b) 5(S)-[1(S)-(Boc-amino)-2-cyclohexylethyl]-3(R)-(4-benzyloxybenzyl)-dihydrofuran-2-(3H)-one Analogously to Example 21 D) 1) c), 30.9 g (99.26 mmol) of 5(S)-[1(S)-(Boc-amino)-2-cyclohexylethyl]-dihydrofuran-2-(3H)-one are reacted with 200 ml (200 mmol) of lithium bis(trimethylsilyl)amide 1M in THF and 34 g (104.8 mmol) of 4-benzyloxybenzyl iodide to yield the title compound. The title compound is purified by column chromatography (SiO$_2$, hexane/ethyl acetate: 4/1 to 1/1) and crystallisation (hexane/ethyl acetate); TLC $R_f$ (C)=0.33; $t_{Ref}$(IV)=20.41 min; FAB-MS (M+H$^+$)=508.

c) 5(S)-(Boc-amino)-4(S)-hydroxy-6-cyclohexyl-2(R)-(4-benzyloxybenzyl)-hexanoic acid Analogously to Example 1 i), 2.4 g (4.728 mmol) of 5(S)-[1(S)-(Boc-amino)-2-cyclohexylethyl]-3(R)-(4-benzyloxybenzyl)-dihydrofuran-2-(3H)-one in 10 ml of 1,2-di-methoxyethane are reacted with 9.45 ml of 1M LiOH solution to yield the title compound, which is purified by crystallisation from hexane. TLC $R_f$ (E)=0.33; $t_{Ref}$(IV)=18 min; FAB-MS (M+H$^+$)=526.

d) 5(S)-(Boc-amino)-4(S)-(tert-butyldimethyl)silyloxy-6-cyclohexyl-2(R)-(4-benzyloxybenzyl)-hexanoic acid Analogously to Example 1 j), 28.8 g (54.8 mmol) of 5(S)-(Boc-amino)-4(S)-hydroxy-6-cyclohexyl-2(R)-(4-benzyloxybenzyl)-hexanoic acid in 288 ml of DMF are converted into the title compound with 35.8 g (237.6 mmol) of tert-butyldimethylchlorosilane and 30 g (237.6 mmol) of imidazole. The title compound is purified by column chromatography (SiO$_2$, hexane/ethyl acetate: 4/1 to 1/1); TLC $R_f$ (E)=0.33; $t_{Ref}$(IV)=23.72 min;

e) 5(S)-(Boc-amino)-4(S)-(tert-butyldimethyl)silyloxy-6-cyclohexyl-2(R)-(4-hydroxyphenylmethyl)-hexanoyl-(L)-Val-(L)-Phe-morpholin-4-ylamide 3 g (4.69 mmol) of 5(S)-(Boc-amino)-4(S)-(tert-butyldimethylsilyloxy)-6-cyclohexyl-2(R)-(4-benzyloxybenzyl)-hexanoic acid in 40 ml of DMF are cooled in an ice-bath to 5° C. with 1.91 g (5.16 mmol) of H-(L)-Val-(L)-Phe-morpholin-4-ylamide, and 0.783 ml (5.16 mmol) of DEPC and 2.3 ml (16.41 mmol) of triethylamine are added. After the mixture has been stirred for 1.5 h at RT it is poured onto water and extracted three times with ethyl acetate. The combined organic phases are washed with water, saturated sodium bicarbonate solution (twice) and brine, dried over sodium sulfate and then concentrated under reduced pressure. The title compound is purified by column chromatography (SiO$_2$, hexane/ethyl acetate: 1/1); TLC $R_f$ (A)=0.3; $t_{Ref}$(IV)=25.3 min; FAB-MS (M+H$^+$)=955.

EXAMPLE 68

5(S)-(Boc-amino)-4(S)-hydroxy-6-cyclohexyl-2(R)-(4-hydroxyphenylmethyl)-hexanoyl-(L)-Val-(L)-Phe-morpholin-4-ylamide Analogously to Example 1, 0.69 g (0.797 mmol) of 5(S)-(Boc-amino)-4(S)-(tert-butyldimethylsilyloxy)-6-cyclohexyl-2(R) -(4-hydroxyphenylmethyl)-hexanoyl-(L)-Val-(L)-Phe-morpholin-4-ylamide in 5 ml of DMF are reacted with 0.5 g (1.59 mmol) of TBAF trihydrate to yield the title compound. The title compound is purified by crystallisation (ether). $t_{Ref}$(IV)=15.52 min; FAB-MS (M+H$^+$)=751.

The starting compound is prepared as follows:
a) 5(S)-(Boc-amino)-4(S)-(tert-butyldimethyl)silyloxy-6-cyclohexyl-2(R)-(4-hydroxyphenylmethyl)-hexanoyl-(L)-Val-(L)-Phe-morpholin-4-ylamide Analogously to Example 45, 19.5 g (20.41 mmol) of 5(S)-(Boc-amino)-4(S)-hydroxy-6-cyclohexyl-2(R)-(4-benzyloxyphenylmethyl)-hexanoyl-(L)-Val-(L)-Phe-morpholin-4-ylamide (Example 67 e) in 400 ml of methanol are hydrogenated in the presence of 4 g of 10% Pd/C. The title compound obtained after working up is further reacted without additional purification; TLC $R_f$ (A) 0.28; $t_{Ref}$(IV)= 21.99 min; FAB-MS (M+H$^+$)=866.

EXAMPLE 69

5(S)-(Boc-amino)-4(S)-hydroxy-6-cyclohexyl-2(R)-(4-methoxyphenylmethyl)-hexanoyl-(L)-Val-(L)-Phe-morpholin-4-ylamide Analogously to Example 1, 3.93 g (4.469 mmol) of 5(S)-(Boc-amino)-4(S)-(tert-butyldimethylsilyloxy)-6-cyclohexyl-2(R)-(4-methoxyphenylmethyl)hexanoyl-(L)-Val-(L)-Phe-morpholin-4-ylamide in 15 ml of DMF are reacted with 2.82 g (8.94 mmol) of TBAF trihydrate to yield the title compound. The title compound is purified by precipitation (hexane). TLC $R_f$ (B)=0.64; $t_{Ref}$(IV)=17.34 min; FAB-MS (M+H$^+$)=765.

The starting compound is prepared as follows:
a) 5(S)-(Boc-amino)-4(S)-(tert-butyldimethyl)silyloxy-6-cyclohexyl-2(R)-(4-methoxyphenylmethyl)-hexanoyl-(L)-Val-(L)-Phe-morpholin-4-ylamide Analogously to Example 70 a), a solution of 4 g (4.623 mmol) of 5(S)-(Boc-amino)-4(S)-(tert-butyldimethyl)-silyloxy-6-cyclohexyl-2(R)-(4-hydroxyphenylmethyl)-hexanoyl-(L)-Val-(L)-Phe-morpholin-4-ylamide in 70 ml of dioxane is reacted with 6.02 g (18.49 mmol) of caesium carbonate and 9.1 ml (92.46 mmol) of methyl iodide. The title compound obtained after working up is further processed without being further purified. TLC $R_f$ (I)=0.36; $t_{Ref}$(IV)=24 min; FAB-MS (M+H$^+$)=880.

EXAMPLE 70

5(S)(Boc-amino)-4(S)-hydroxy-6-phenyl-2(R)-benzylhexanoyl-(L)-Val-(L)-(4-isobutyloxy-Phe)-morpholin-4-ylamide Analogously to Example 1, 201 mg (0.22 mmol) of 5(S)-(Boc-amino)-4(S)-(tert-butyldimethylsilyloxy)-6-phenyl-2(R)-benzylhexanoyl-(L)-Val-(L)-(4-isobutyloxy-Phe)-morpholin-4-ylamide are deprotected with 139 mg (0.44 mmol) of TBAF in 5 ml of DMF over a period of 18.5 h. Column chromatography (SiO$_2$, ethyl acetate/hexane: 4/1) yields the title compound: TLC $R_f$(B)=0.38; $t_{Ref}$(I)=18.3 min; FAB-MS (M+H$^+$)=801.

The starting compounds are prepared as follows:
a) N-(Benzyloxycarbonyl)-(L)-Val-(L)-(4-isobutyloxy-Phe)-morpholin-4-ylamide A solution of 1.93 g (4 mmol) of N-(benzyloxycarbonyl)-(L)-Val-(L)-Tyr-morpholin-4-ylamide (Example 41 A) c)) in 8 ml of 1/1 DMF/dioxane is treated with 2.6 g (8 mmol) of caesium carbonate and 2.31 ml (20 mmol) of isobutyl iodide and then heated to 50° C. After 1.25 h, 2.6 g (8 mmol) of caesium carbonate and 2.31 ml (20 mmol) of isobutyl iodide are again added, followed by a further 2.31 ml (20 mmol) of isobutyl iodide after 2.15 h and after 4 h. After having been stirred for a total of 5.75 h at 50° C., the reaction mixture is poured onto ice/water and extracted three times with methylene chloride. Drying over sodium sulfate is followed by concentration in a rotary evaporator. Column chromatography (SiO$_2$, ethyl acetate/hexane 4/1 ) yields the title compound: TLC R$_f$ (B)=0.43.

b) H-(L)-Val-(L)-(4-isobutyloxy-Phe)-morpholin-4-ylamide

Analogously to Example 10 e), 1.5 g (2.78 mmol) of N-(benzyloxycarbonyl)-(L)-Val-(L)-(4-isobutyloxy-Phe)-morpholin-4-ylamide in 40 ml of methanol are hydrogenated in the presence of 0.2 g of 10% Pd/C. The title compound is further used without being further purified: TLC R$_f$ (F)= 0.44.

c) 5(S)-(Boc-amino)-4(S)-(tert-butyldimethylsilyloxy)-6-phenyl-2(R)-benzylhexanoyl-(L)-Val-(L)-(4-isobutyloxy-Phe)-morpholin-4-ylamide Analogously to Example 10 f), 118 mg (0.22 mmol) of 5(S)-(Boc-amino)-4(S)-(tert-butyldimethylsilyloxy)-6-phenyl-2(R)-benzylhexanoic acid and 100 mg (0.25 mmol) of H-(L)-Val-(L)-(4-isobutyloxy-Phe)-morpholin-4-ylamide in 2.19 ml of NMM/CH$_3$CN 0.25M are reacted with 94.8 mg (0.24 mmol) of HBTU to give the title compound. Column chromatography (SiO$_2$, ethyl acetate/hexane: 4/1) yields the title compound: TLC R$_f$ (B)=0.54.

EXAMPLE 71

5(S)-(Boc-amino)-4(S)-hydroxy-6-phenyl-2(R)-benzylhexanoyl-(L)-Leu-(L)-(p-CH$_3$O-Phe)-morpholin-4-ylamide Analogously to Example 1, 189 mg (0.22 mmol) of 5(S)-(Boc-amino)-4(S)-(tert-butyldimethylsilyloxy)-6-phenyl-2(R)-benzylhexanoyl-(L)-Leu-(L)-(p-CH$_3$O-Phe)-morpholin-4-ylamide are deprotected with 139 mg (0.44 mmol) of TBAF in 5 ml of DMF over a period of 18 h. Column chromatography (SiO$_2$, ethyl acetate/hexane: 4/1) yields the title compound: TLC R$_f$(B)=0.37; t$_{Ret}$(I)=16.6 min; FAB-MS (M+H$^+$)=773.

The starting compounds are prepared as follows:

a) N-(Benzyloxycarbonyl)-(L)-Leu-(L)-(p-CH$_3$O-Phe)-morpholinylamide 0.45 g (1.68 mmol) of (L)-N-benzyloxycarbonyl-leucine (Fluka, Buchs, Switzerland) and 0.444 g (1.68 mmol) of H-(L)-(p-CH$_3$O-Phe)-morpholinylamide in 70 ml of methylene chloride are reacted with 0.347 g (1.68 mmol) of DCC and 0.25 g of HOBT to give the title compound. Column chromatography (SiO$_2$, ethyl acetate/hexane: 4/1) yields the title compound: TLC R$_f$ (B)=0.28.

b) H-(L)-Leu-(L)-(p-CH$_3$O-Phe)-morpholin-4-ylamide

Analogously to Example 10 e), 0.73 g (1.43 mmol) of N-(benzyloxycarbonyl)-(L)-Leu-(L)-(p-CH$_3$O-Phe)-morpholin-4-ylamide in 20 ml of methanol is hydrogenated in the presence of 0.1 g of 10% Pd/C. The title compound is further used without being further purified: TLC R$_f$ (F)= 0.47.

c) 5(S)-(Boc-amino)-4(S)-(tert-butyldimethylsilyloxy)-6-phenyl-2(R)-benzylhexanoyl-(L)-Leu-(L)-(p-CH$_3$O-Phe)-morpholin-4-ylamide Analogously to Example 10 f), 118 mg (0.22 mmol) of 5(S)-(Boc-amino)-4(S)-(tert-butyldimethylsilyloxy)-6-phenyl-2(R)-benzylhexanoic acid and 91 mg (0.25 mmol) of H-(L)-Leu-(L)-(p-CH$_3$O-Phe)-morpholin-4-ylamide in 2.19 ml of NMM/CH$_3$CN 0.25M are reacted with 94.8 mg (0.24 mmol) of HBTU to give the title compound. Column chromatography (SiO$_2$, ethyl acetate/hexane: 4/1) yields the title compound: TLC R$_f$ (B)=0.57.

d) Z-(L)-(p-CH$_3$O-Phe)-morpholin-4-ylamide

Analogously to Example 70 a), a solution of 2 g (5.2 mmol) of Z-(L)-Tyr-morpholin-4-ylamide (Example 70 e)) in 100 ml of 1:1 DMF/dioxane is reacted with 3.38 g (10.4 mmol) of caesium carbonate and 0.324 ml (5.2 mmol) of methyl iodide. Column chromatography (SiO$_2$, ethyl acetate/hexane: 4/1 ) yields the title compound: TLC R$_f$ (ethyl acetate/hexane: 4/1)=0.34.

e) H-(L)-(p-CH$_3$O-Phe)-morpholin-4-ylamide

Analogously to Example 70 b), a solution of 3.9 g (9.8 mmol) of Z-(L)-(p-CH$_3$O-Phe)-morpholin-4-ylamide in 150 ml of methanol is hydrogenated in the presence of 1.2 g of 10% Pd/C. After working up, the title compound is further used without additional purification. TLC R$_f$ (F)=0.32.

EXAMPLE 72

5(S)-(Boc-amino)-4(S)-hydroxy-6-phenyl-2(R)-benzylhexanoyl-(L)-Val-(L)-(4-n-butyloxy-Phe)-morpholin-4-ylamide Analogously to Example 1, 201 mg (0.22 mmol) of 5(S)-(Boc-amino)-4(S)-(tert-butyldimethylsilyloxy)-6-phenyl-2(R)-benzylhexanoyl-(L)-Val-(L)-(4-n-butyloxy-Phe)-morpholin-4-ylamide are deprotected with 139 mg (0.44 mmol) of TBAF in 5 ml of DMF over a period of 16.5 h. Column chromatography (SiO$_2$, ethyl acetate/hexane: 4/1) yields the title compound: TLC R$_f$(B)=0.39; t$_{Ret}$(I)=18.2 min; FAB-MS (M+H$^+$)=801.

The starting compounds are prepared as follows:

a) N-(Benzyloxycarbonyl)-(L)-Val-(L)-(4-n-butyloxy-Phe)-morpholin-4-ylamide

Analogously to Example 70 a), a solution of 0.48 g (0.1 mmol) of N-(benzyloxy-carbonyl)-(L)-Val-(L)-Tyr-morpholin-4-ylamide in 0.2 ml of 1/1 DMF/dioxane is treated with 65 mg (0.2 mmol) of caesium carbonate and 11.9 µl (0.1 mmol) of n-butyl iodide. Column chromatography (SiO$_2$, ethyl acetate/hexane 4/1) yields the title compound: TLC R$_f$ (B)=0.47.

b) H-(L)-Val-(L)-(4-n-butyloxy-Phe)-morpholin-4-ylamide

Analogously to Example 10 e), 1.38 g (2.6 mmol) of N-(benzyloxycarbonyl)-(L)-Val-(L)-(4-n-butyloxy-Phe)-morpholin-4-ylamide in 40 ml of methanol are hydrogenated in the presence of 0.2 g of 10% Pd/C. The title compound is further used without being further purified: TLC R$_f$ (F)= 0.45.

c) 5(S)-(Boc-amino)-4(S)-(tert-butyldimethylsilyloxy)-6-phenyl-2(R)-benzylhexanoyl-(L)-Val-(L)-(4-n-butyloxy-Phe)-morpholin-4-ylamide Analogously to Example 10 f), 118 mg (0.22 mmol) of 5(S)-(Boc-amino)-4(S)-(tert-butyldimethylsilyloxy-6-phenyl-2(R)-benzylhexanoic acid and 98 mg (0.25 mmol) of H-(L)-Val-(L)-(4-n-butyloxy-Phe)-morpholin-4-ylamide in 2.19 ml of NMM/CH$_3$CN 0.25M are reacted with 94.8 mg (0.24 mmol) of HBTU to yield the title compound. The title compound, TLC R$_f$ (B)=0.57, is further used without additional purification.

EXAMPLE 73

5(S)-(Boc-amino)-4(S)-hydroxy-6-phenyl-2(R)-benzylhexanoyl-(L)-phenylglycyl-(L)-(p-CH$_3$O-Phe)-morpholin-4-ylamide Analogously to Example 1, 380 mg (0.41 mmol) of 5(S)-(Boc-amino)-4(S)-(tert-butyldimethylsilyloxy)-6-phenyl-2(R)-benzylhexanoyl-(L)-phenylglycyl-(L)-(p-CH$_3$O-Phe)-morpholin-4-ylamide are deprotected with 265 mg (0.82 mmol) of TBAF in 10 ml of DMF over a period of 17 h. Column chromatography (SiO$_2$, ethyl acetate/hexane: 2/1 to 4/1) yields the title compound: TLC R$_f$(B)=0.47; t$_{Ret}$(I)=16.4 min; FAB-MS (M+H$^+$)=793.

The starting compounds are prepared as follows:

a) N-(t-Butyloxycarbonyl)-(L)-phenylglycyl-(L)-(p-CH$_3$O-Phe)-morpholin-4-ylamide 0.44 g (2 mmol) of N-tert-butyloxycarbonyl-(L)-phenylglycine and 0.53 g (2 mmol) of H-(L)-(p-CH$_3$O-Phe)-morpholinylamide in 80 ml of methylene chloride are reacted with 0.413 g (2 mmol) of DCC and 0.297 g of HOBT to give the title compound. Column chromatography (SiO$_2$, ethyl acetate/hexane: 4/1) yields the title compound: TLC R$_f$ (ethyl acetate/hexane: 4/1)=0.31.

b) H-(L)-Phenylglycyl-(L)-(p-CH$_3$O-Phe)-morpholin-4-ylamide

A solution of 900 mg (1.81 mmol) of N-(t-butyloxycarbonyl)-(L)-phenylglycyl-(L)-(p-CH$_3$O-Phe)-morpholin-4-ylamide in 19 ml of formic acid is stirred for 2 h and then concentrated in a rotary evaporator and dissolved in ethyl acetate. The solution is washed in succession 4 times with sodium bicarbonate, once with water and once with brine, dried over Na$_2$SO$_4$, and then concentrated. The title compound is further used without being further purified. TLC R$_f$ (B)=0.12.

c) 5(S)-(Boc-amino)-4(S)-(tert-butyldimethylsilyloxy)-6-phenyl-2(R)-benzylhexanoyl-(L)-phenylglycyl-(L)-(p-CH$_3$O-Phe)-morpholin-4-ylamide Analogously to Example 10 f), 118 mg (0.22 mmol) of 5(S)-(Boc-amino)-4(S)-(tert-butyldimethylsilyloxy)-6-phenyl-2(R)-benzylhexanoic acid and 96 mg (0.25 mmol) of H-(L)-phenylglycyl-(L)-(p-CH$_3$O-Phe)-morpholin-4-ylamide in 2.19 ml of NMM/CH$_3$CN 0.25M are reacted with 94.8 mg (0.24 mmol) of HBTU to give the title compound. Column chromatography (SiO$_2$, ethyl acetate/hexane: 4/1) yields the title compound: TLC R$_f$ (B)=0.57.

EXAMPLE 74

Boc-Phe[C](3,4-dimethoxy)Phe-(L)-Val-(L)-Phe-morpholin-4-ylamide

Analogously to Example 56 O), 141 mg of 5(S)-(Boc-amino)-4(S)-(tert-butyldimethylsilyloxy)-6-phenyl-2(R)-(3,4-dimethoxyphenylmethyl)-hexanoyl-(L)-Val-(L)-Phe-morpholin-4-ylamide in 3 ml of DMF are desilylated with 100.4 mg of TBAF to yield the title compound. Purification is carried out by chromatography twice on silica gel (eluants ethyl acetate/hexane 4:1 and B). TLC R$_f$(B)=0.21. FAB-MS (M+H)$^+$=789.

The starting material is prepared as follows:

74 a) 3,4-Dimethoxybenzyl Chloride

Analogously to Example 56 O) a), the title compound is obtained from 10 g of 3,4-dimethoxybenzyl alcohol (Fluka, Buchs, Switzerland), 46.2 g of diisopropylaminomethylpolystyrene (poly-Hünig base) and 4.62 ml of thionyl chloride in 200 ml of abs. ether. TLC R$_f$(C)=0.31. $^1$H-NMR (200 MHz, CDCl$_3$): 7.0–6.87 (m, 2H); 6.82 (d, 1H); 4.56 (s, 2H); 3.9 (s, 3H); 3.87 (s, 3H).

74 b) 3,4-Dimethoxybenzyl Iodide

Analogously to Example 56 O) b), the title compound is obtained from 6.185 g of 3,4-dimethoxybenzyl chloride and 24.19 g of sodium iodide in 62 ml of abs. acetone. TLC R$_f$(C)=0.40. $^1$H-NMR (200 MHz, CDCl$_3$): 6.95 (dxd, 1H); 6.88 (d, 1H); 6.75 (d, 1H); 4.47 (s, 2H); 3.87 (s, 3H); 3.86 (s, 3H).

74 c) 5(S)-[1(S)-(Boc-amino)-2-phenylethyl]-3(R)-(3,4-dimethoxyphenylmethyl)-dihydro-furan-2-(3H)-one Analogously to Example 56 O) c), 1 g of 5(S)-[1(S)-(Boc-amino)-2-phenylethyl]-dihydrofuran-2-(3H)-one [prepared according to Example 2i)] in 4 ml of abs. THF is deprotonated (−75° C.) with 6.42 ml of lithium bis(trimethylsilyl)amide (1M in THF) and with the addition of 0.66 ml of DMPU, and alkylated with 911 mg of 3,4-dimethoxybenzyl iodide. Chromatography on silica gel (eluants D, A and hexane/ethyl acetate 1:2) yields the pure title compound. TLC R$_f$(A)=0.42. MS M$^+$=455.

74 d) 5(S)-(Boc-amino)-4(S)-hydroxy-6-phenyl-2(R)-(3,4-dimethoxyphenylmethyl)-hexanoic acid Analogously to Example 56 O) d), 778 mg of 5(S)-[1(S)(Boc-amino)-2-phenylethyl]-3(R)-(3,4-dimethoxyphenylmethyl)-dihydrofuran-2-(3H)-one in 27.67 ml of dimethoxyethane and 13.91 ml of water are hydrolysed with 6.83 ml of lithium hydroxide solution 1M to yield the title compound which is directly further processed. TLC R$_f$(A)=0.07.

74 e) 5(S)-(Boc-amino)-4(S)-(tert-butyldimethylsilyloxy)-6-phenyl-2(R)-(3,4-dimethoxyphenylmethyl)-hexanoic acid Analogously to Example 56 O) e), 804 mg of 5(S)-(Boc-amino)-4(S)-hydroxy-6-phenyl-2(R)-(3,4-dimethoxyphenylmethyl)-hexanoic acid in 5.94 ml of DMF are silylated with 1.162 g of tert-butyldimethylchlorosilane and 946.6 mg of imidazole. Purification of the title compound is carried out by chromatography twice on silica gel (eluants D, A, ethyl acetate/hexane 2:1 and B). TLC R$_f$(A) =0.27. MS M$^+$=557.

74 f) 5(S)-(Boc-amino)-4(S)-(tert-butyldimethylsilyloxy)-6-phenyl-2(R)-(3,4-dimethoxyphenylmethyl)-hexanoyl-(L)-Val-(L)-Phe-morpholin-4-ylamide Analogously to Example 56 O) f), 100 mg of 5(S)-(Boc-amino)-4(S)-(tert-butyldimethylsilyloxy)-6-phenyl-2(R)-(3,4-dimethoxyphenylmethyl)-hexanoic acid and 62.3 mg of H-(L)-Val-(L)-Phe-morpholin-4-ylamide [prepared according to Example 1o)] in 1.59 ml of NMM/CH$_3$CN 0.25M are reacted with 70.9 mg of HBTU to yield the title compound. TLC R$_f$ (ethyl acetate/hexane 2:1)=0.19. FAB-MS (M+H)$^+$ =903.

EXAMPLE 75

Boc-Phe[C](3,4,5-trimethoxy)Phe-(L)-Val-(L)-Phe-morpholin-4-ylamide

Analogously to Example 56 O), 511 mg of 5(S)-(Boc-amino)-4(S)-(tert-butyldimethylsilyloxy)-6-phenyl-2(R)-(3,4,5-trimethoxyphenylmethyl)-hexanoyl-(L)-Val-(L)-Phe-morpholin-4-ylamide in 9.36 ml of DMF are desilylated with 323.5 mg of TBAF to yield the title compound. Purification is carried out by chromatography on silica gel (eluants B and H). TLC R$_f$(B)=0.13. FAB-MS (M+H)$^+$=819.

The starting material is prepared as follows:

75 a) 3,4,5-Trimethoxybenzyl Iodide

Analogously to Example 56 O) b), the title compound is obtained from 5 g of 3,4,5-trimethoxybenzyl chloride (Fluka, Buchs, Switzerland) and 16.89 g of sodium iodide in 40 ml of abs. acetone. TLC R$_f$(C)=0.27. $^1$H-NMR (360 MHz, CDCl$_3$): 6.60 (s, 2H); 4.44 (s, 2H); 3.86 (s, 6H); 3.83 (s, 3H).

75 b) 5(S)-[1(S)-(Boc-amino)-2-phenylethyl]-3(R)-(3,4,5-trimethoxyphenylmethyl)-dihydrofuran-2-(3H)-one Analogously to Example 56 O) c), 1 g of 5(S)-[1(S)-(Boc-amino)-2-phenylethyl]-dihydrofuran-2-(3H)-one [prepared according to Example 2i)] in 4 ml of abs. THF is deprotonated (−75° C.) with 6.42 ml of lithium bis(trimethylsilyl)amide (1M in THF) and with the addition of 0.66 ml of DMPU, and alkylated with 1.008 g of 3,4,5-trimethoxybenzyl iodide. Chromatography on silica gel (eluants hexane/acetone 3:1) yields the title compound. TLC R$_f$(hexane/acetone 3:1)=0.22. FAB-MS M$^+$=485.

75 c) 5(S)-(Boc-amino)-4(S)-hydroxy-6-phenyl-2(R)-(3,4,5-trimethoxyphenylmethyl)-hexanoic acid Analogously to Example 56 O) d), 1.097 g of 5(S)-[1(S)-(Boc-amino)-2-phenylethyl]-3(R)-(3,4,5-trimethoxyphenylmethyl)-dihydrofuran-2-(3H)-one in 36.48 ml of dimethoxyethane and 18.39 ml of water are hydrolysed with 9.03 ml of lithium hydroxide solution 1M to yield the title compound, which is further processed without being purified.

75 d) 5(S)-(Boc-amino)-4(S)-(tert-butyldimethylsilyloxy)-6-phenyl-2(R)-(3,4,5-trimethoxyphenylmethyl)-hexanoic acid Analogously to Example 56 O) e), 1.526 g of 5(S)-(Boc-amino)-4(S)-hydroxy-6-phenyl-2(R)-(3,4,5-trimethoxyphenylmethyl)-hexanoic acid in 15.16 ml of DMF are silylated with 2.11 g of tert-butyldimethylchlorosilane and 1.683 g of imidazole. Purification of the title compound is carried out by chromatography twice on silica gel (solvents: hexane, A, ethyl acetate/hexane 2:1). TLC $R_f(B)$=0.39. FAB-MS $(M+H)^+$=618.

75 e) 5(S)-(Boc-amino)-4(S)-(tert-butyldimethylsilyloxy)-6-phenyl-2(R)-(3,4,5-trimethoxyphenylmethyl)-hexanoyl-(L)-Val-(L)-Phe-morpholin-4-ylamide Analogously to Example 56 O) f), 316.5 mg of 5(S)-(Boc-amino)-4(S)-(tert-butyldimethylsilyloxy)-6-phenyl-2(R)-(3,4,5-trimethoxyphenylmethyl)-hexanoic acid and 171 mg of H-(L)-Val-(L)-Phe-morpholin-4-ylamide [prepared according to Example 1o)] in 4.82 ml of NMM/CH$_3$CN 0.25M are reacted with 213.39 mg of HBTU to yield the title compound. TLC $R_f(B)$=0.45. FAB-MS $(M+H)^+$=933.

EXAMPLE 76

Boc-Phe[C](2.3.4-trimethoxy)Phe-(L)-Val-(L)-Phe-morpholin-4-ylamide

Analogously to Example 56 O), 407 mg of 5(S)-(Boc-amino)-4(S)-(tert-butyldimethylsilyloxy)-6-phenyl-2(R)-(2,3,4-trimethoxyphenylmethyl)-hexanoyl-(L)-Val-(L)-Phe-morpholin-4-ylamide in 7.41 ml of DMF are desilylated with 256 mg of TBAF to yield the title compound. Purification is carried out by chromatography on silica gel (eluant: B). TLC $R_f(B)$=0.12. FAB-MS $(M+H)^+$=819.

The starting material is prepared as follows:

76 a) 2,3,4-Trimethoxybenzyl Chloride

Analogously to Example 56 O) a), the title compound is obtained from 10.22 g of 2,3,4-trimethoxybenzyl alcohol (Aldrich, Steinheim, Federal Republic of Germany), 33.75 g of diisopropylaminomethylpolystyrene (poly-Hünig base) and 10.6 ml of thionyl chloride in 200 ml of abs. ether. Purification is carried out by chromatography on silica gel (eluant: E). TLC $R_f(E)$=0.47. $^1$H-NMR (360 MHz, CDCl$_3$): 7.05 (d, 1H); 6.65 (d, 1H); 4.61 (s, 2H); 3.98 (s, 3H); 3.86 (s, 3H); 3.85 (s, 3H).

76 b) 2,3,4-Trimethoxybenzyl Iodide

The title compound is obtained from 2.34 g of 2,3,4-trimethoxybenzyl chloride and 7.87 g of sodium iodide in 18.6 ml of abs. acetone analogously to Example 56 O) b), and is further processed without being purified. TLC $R_f$(hexane/ethyl acetate 2.5:1)=0.44. $^1$H-NMR (200 MHz, CDCl$_3$): 7.03 (d, 1H); 6.60 (d, 1H); 4.50 (s, 2H); 4.05 (s, 3H); 3.85 (2×s, 6H).

76 c) 5(S)-[1(S)-(Boc-amino)-2-phenylethyl]-3(R)-(2,3,4-trimethoxyphenylmethyl)-dihydrofuran-2-(3H)-one Analogously to Example 56 O) c), 1.5 g of 5(S)-[1(S)-(Boc-amino)-2-phenylethyl]-dihydrofuran-2-(3H)-one [prepared according to Example 2i)] in 6 ml of abs. THF are deprotonated (−75° C.) with 9.62 ml of lithium bis (trimethylsilyl)amide (1M in THF) and with the addition of 0.998 ml of DMPU, and alkylated with 1.51 g of 2,3,4-trimethoxybenzyl iodide. Chromatography on silica gel (eluants: hexane/ethyl acetate 1:2) yields the pure title compound. TLC $R_f(A)$=0.53. FAB-MS $M^+$=485.

76 d) 5(S)-(Boc-amino)-4(S)-hydroxy-6-phenyl-2(R)-(2,3,4-trimethoxyphenylmethyl)-hexanoic acid Analogously to Example 56 O) d), 1.354 g of 5(S)-[1(S)-(Boc-amino)-2-phenylethyl]-3(R)-(2,3,4-trimethoxyphenylmethyl)-dihydrofuran-2-(3H)-one in 43.36 ml of dimethoxyethane and 21.86 ml of water are hydrolysed with 10.74 ml of lithium hydroxide solution 1M to yield the title compound, which is further processed without being purified. TLC $R_f(A)$=0.03. MS $M^+$-H$_2$O=485.

76 e) 5(S)-(Boc-amino)-4(S)-(tert-butyldimethylsilyloxy)6-phenyl-2(R)-(2,3,4-trimethoxyphenylmethyl)-hexanoic acid Analogously to Example 56 O) e), 1.308 g of 5(S)-(Boc-amino)-4(S)-hydroxy-6-phenyl-2(R)-(2,3,4-trimethoxyphenylmethyl)-hexanoic acid in 13 ml of DMF are silylated with 1.816 g of tert-butyldimethylchlorosilane and 1.443 g of imidazole. Purification of the title compound is carried out by chromatography twice on silica gel (solvents: A and ethyl acetate/hexane 1.5:1). TLC $R_f$(ethyl acetate/hexane 2:1)=0.02. FAB-MS $(M+H)^+$=618.

76 f) 5(S)-(Boc-amino)-4(S)-(tert-butyldimethylsilyloxy)-6-phenyl-2(R)-(2,3,4-trimethoxyphenylmethyl)-hexanoyl-(L)-Val-(L)-Phe-morpholin-4-ylamide Analogously to Example 56 O) f), 250 mg of 5(S)-(Boc-amino)-4(S)-(tert-butyldimethylsilyloxy)-6-phenyl-2(R)-(2,3,4-trimethoxyphenylmethyl)-hexanoic acid and 148.4 mg of H-(L)-Val-(L)-Phe-morpholin-4-ylamide [prepared according to Example 1o)] in 3.807 ml of NMM/CH$_3$CN 0.25M are reacted with 168.8 mg of HBTU to yield the title compound. TLC $R_f(B)$=0.64.

EXAMPLES OF COMPOUNDS OF FORMULA I'

EXAMPLE 77

5(S)-(Boc-amino)-4(S)-(2-furanylcarboxy)-6-phenyl-2(R)-phenylmethylhexanoyl-(L)-Val-(L)-Phe-morpholin-4-ylamide Under a nitrogen atmosphere, 74 μl (0.75 mmol) of 2-furancarboxylic acid chloride (Fluka; Buchs/Switzerland) are added to a solution of 365 mg (0.50 mmol) of Boc-Phe[C]Phe-(L)-Val-(L)-Phe-morpholin-4-ylamide (Example 2) and 10 mg of DMAP in 3 ml of dioxane and 0.6 ml of pyridine and the mixture is stirred for 44 h at RT. Since, according to HPLC, there is still some starting material present, a further 0.1 ml of 2-furanecarboxylic acid chloride and 1 ml of pyridine are added. After a further 2 days, the reaction mixture is diluted with ethyl acetate and washed with sat. NaHCO$_3$ solution, water and brine. The aqueous phases are extracted with 2 portions of ethyl acetate and the combined organic phases are dried with Na$_2$SO$_4$ and concentrated by evaporation. Precipitation with DIPE/hexane 1:2 from a concentrated solution in methylene chloride yields the pure title compound: TLC $R_f(I)$=0.23; $t_{Ref}(I)$=17.5 min; FAB-MS $(M+H)^+$=823.

EXAMPLE 78

5(S)-(Boc-amino)-4(S)-(N,N-dimethylaminoacetyloxy)-6-phenyl-2(R)-phenylmethylhexanoyl-(L)-Val-(L)-Phe-morpholin-4-ylamide Under a nitrogen atmosphere, 130 mg (0.82 mmol) of N,N-dimethylacetyl chloride (in the form of the hydrochloride salt) [preparation: N. H. Krämer and H. F. G. Linde, Arch. Pharm. (Weinheim) 324, 433 (1991)] are added to a solution of 300 mg (0.41 mmol) of Boc-Phe[C]Phe-(L)-Val-(L)-Phe-morpholin-4-ylamide (Example 2) and a small amount of DMAP in 1 ml of pyridine, and the mixture is stirred for 9 h at 60° C. Since, according to HPLC, there is still some starting material present, a further 130 mg of N,N-dimethylacetyl chloride hydrochloride is added. After a further 2 h at 60° C., the reaction mixture is diluted with ethyl acetate and washed with sat. NaHCO$_3$ solution, 2×water and brine. The aqueous phases are extracted with 2 portions of ethyl acetate, and the combined organic phases are dried with Na$_2$SO$_4$ and concentrated by evaporation. Column chromatography (SiO$_2$, ethyl acetate/ethanol 97:3→95:5) and digestion in DIPE in an ultrasound bath yields the crystalline title compound: TLC R$_f$(T)=0.11; t$_{Ret}$(II)=19.5 min; FAB-MS (M+H)$^+$=814.

EXAMPLE 79

5(S)-(Boc-amino)-4(S)-[4-(dimethylamino)-butyryloxy]-6-phenyl-2(R)-phenylmethylhexanoyl-(L)-Val-(L)-Phe-morpholin-4-ylamide Analogously to Example 77), 200 mg (0.27 mmol) of Boc-Phe[C]Phe-(L)-Val-(L)-Phe-morpholin-4-ylamide (Example 2) and a small amount of DMAP in 5 ml of dioxane/acetonitrile 4:1 and 372 µl (2.2 mmol) of N-ethyldiisopropylamine are reacted with 161 mg (0.87 mmol) of 3-(dimethylamino)butyryl chloride (in the form of the hydrochloride salt). Digestion of the crude product from DIPE yields the title compound: t$_{Ret}$(I)=13.8 min; FAB-MS (M+H)$^+$=842.

The starting material is prepared as follows:
a: 4-(Dimethylamino)butyryl Chloride Hydrochloride 10 g (60 mmol) of 4-dimethylaminobutyric acid hydrochloride (Janssen; Brüggen/Germany) are heated for approximately 3 h at 65° C. in 30 ml of SOCl$_2$. SOCl$_2$ is evaporated off and the residue is stirred to yield the title compound: TLC of a sample dissolved in methanol, R$_f$(U) =0.67; TLC of 4-dimethylaminobutyric acid hydrochloride, R$_f$(U)=0.50.

EXAMPLE 80

5(S)-(Boc-amino)-4(S)-(N-Z-N-methylaminoacetyloxy)-6-phenyl-2(R)-phenylmethylhexanoyl-(L)-Val-(L)-Phe-morpholin-4-ylamide Under a nitrogen atmosphere, 339 µl (2.4 mmol) of 1-chloro-N,N,2-trimethyl-1-propenamine [B. Haveaux, A. Dekoker, M. Rens, A. R. Sidani, J. Toye, L. Ghosez, M. Murakami, M. Yoshioka, and W. Nagata, Organic Syntheses 59, 26 (1980)] are added at 0° C. to 446 mg (2.00 mmol) of Z-sarcosine (Bachem; Bubendorf/Switzerland) in 10 ml of methylene chloride. After 2 h at 0° C., the mixture is concentrated by evaporation under HV. The residue is taken up in 2 ml of dioxane and, with ice-cooling, a solution of 1.093 g (1.5 mmol) of Boc-Phe[C]Phe-(L)-Val-(L)-Phe-morpholin-4-ylamide (Example 2) in 1.3 ml of pyridine and 10 ml of dioxane is added. Since, according to HPLC, there is still some starting material present after 60 h at RT, 17 mg of DMAP and an additional 2.0 mmol of Z-sarcosyl chloride (preparation analogous to above) in 2 ml of dioxane are added. After 18 h at RT, the mixture is concentrated by evaporation and chromatographed (SiO$_2$, ethyl acetate/hexane 3:1). Digestion in hexane yields the pure title compound: TLC R$_f$(B)=0.74; t$_{Ret}$(I)=18.6 min; FAB-MS (M+H)$^+$=934; Anal: calc. C 68.15%, H 7.23%, N 7.50%; found C 68.15%, H 7.54%, N 7.50%.

EXAMPLE 81

5(S)-(Boc-amino)-4(S)-(methylaminoacetyloxy)-6-phenyl-2(R)-phenylmethylhexanoyl-(L)-Val-(L)-Phe-morpholin-4-ylamide 200 mg (0.21 mmol) of 5(S)-(Boc-amino)-4(S)-(N-Z-N-methylaminoacetyloxy)-6-phenyl-2(R)-phenylmethylhexanoyl-(L)-Val-(L)-Phe-morpholin-4-ylamide (Example 80) dissolved in 10 ml of ethyl acetate are hydrogenated at RT in the presence of 0.20 g of 10% Pd/C (approximately 3 d), the mixture is filtered through ®Celite, the filtrate is concentrated by evaporation and the oil obtained is crystallised from hexane (ultrasound bath) to yield the title compound: TLC R$_f$(B)=0.45; t$_{Ret}$(I)=13.3 min; FAB-MS (M+H)$^+$=800.

EXAMPLE 82

5(S)-(Boc-amino)-4(S)-[N-(imidazol-4-methyl)-N-methylaminoacetyloxy]-6-phenyl-2(R)-phenylmethylhexanoyl-(L)-Val-(L)-Phe-morpholin-4-ylamide A solution of 160 mg (0.20 mmol) of 5(S)-(Boc-amino)-4(S)-(methylaminoacetyloxy)-6-phenyl-2(R)-phenylmethylhexanoyl-(L)-Val-(L)-Phe-morpholin-4-ylamide (Example 81) and 23 mg (0.24 mmol) of imidazole-4-carbaldehyde (Ph.D. Stein and St.E. Hall, U.S. Pat. No. 4,977,174, 11th Dec. 1990) in 2 ml of methanol and 26 mg (0.44 mmol) of acetic acid is hydrogenated in the presence of 20 mg of 5% Pd/C at RT for approximately 3 h. The mixture is filtered through ®Celite, and the filtrate is concentrated by evaporation and partitioned between 3 portions of ethyl acetate, sat. NaHCO$_3$ solution, water and brine, subjected to column chromatography (SiO$_2$, ethyl acetate/THF 3:1→1:3) and crystallised from acetonitrile/DIPE/hexane to yield the title compound: TLC R$_f$(U)=0.13; t$_{Ret}$(I)=12.2 min; FAB-MS (M+H)$^+$=880.

EXAMPLE 83

5(S)-(Boc-amino)-4(S)-[N-(pyridine-2-methyl)-N-methylaminoacetyloxy]-6-phenyl-2(R)-phenylmethylhexanoyl-(L)-Val-(L)-Phe-morpholin-4-ylamide A solution of 80 mg (0.10 mmol) of 5(S)-(Boc-amino)-4(S)-(methylaminoacetyloxy)-6-phenyl-2(R)-phenylmethylhexanoyl-(L)-Val-(L)-Phe-morpholin-4-ylamide (Example 81) and 12.9 mg (0.12 mmol) of freshly distilled pyridine-2-carbaldehyde (Fluka; Buchs/Switzerland) in 1.5 ml of methanol and 13 mg (0.22 mmol) of acetic acid is hydrogenated at RT in the presence of 15 mg of 5% Pd/C. Filtration through ®Celite and column chromatography (SiO$_2$, ethyl acetate→ethyl acetate/ethanol/triethylamine 90:10:1) yields the title compound: TLC R$_f$(V) =0.3; t$_{Ret}$(I)=14.3 min; FAB-MS (M+H)$^+$=891.

EXAMPLE 84

5(S)-(Boc-amino)-4(S)-[3-(1-triphenylmethylimidazol-4-yl)-propionyloxy]-6-phenyl-2(R)-phenylmethylhexanoyl-(L)-Val-(L)-Phe-morpholin-4-ylamide Analogously to Example 80), 2.0 g (5.2 mmol) of 3-(1-triphenylmethylimidazol-4-yl)-propionic acid dissolved in 20 ml of methylene chloride are converted into the acid chloride with 1.1 ml (7.8 mmol) of 1-chloro-N,N,2-trimethyl-1-propenamine. The evaporation residue is dissolved in 12 ml of dioxane and added to a solution of 1.23 g (1.7 mmol) of Boc-Phe[C]Phe-(L)-Val-(L)-Phe-morpholin-4-ylamide (Example 2) in 4 ml of pyridine. According to HPLC, there is still a large amount of starting material present after 18 h at RT, and therefore 50 mg of DMAP and a further 3 mmol of 3-(1-triphenylmethylimidazol-4-yl)-propionic acid chloride (preparation as described above) are added. After a further 24 h at RT, the reaction mixture is concentrated by evaporation, and the residue is dissolved in ethyl acetate and washed with 3× water and brine. The aqueous phases are extracted with 2 portions of ethyl acetate. Column chromatography (SiO$_2$, methylene chloride/THF 9:1→methylene chloride/THF/triethylamine 90:10:1) yields the title compound: $t_{Ref}$(I)=17.7 min; FAB-MS (M+H)$^+$=1093.

The starting material is prepared as follows:

a: Imidazol-4-ylpropionic Acid (Sodium Salt)

1.38 g (10 mmol) of urocanic acid (Aldrich) are dissolved in 10 ml of 1N aqueous NaOH solution. The solution is diluted with 10 ml of methanol, 80 mg of 5% Pd/C catalyst are added and the mixture is hydrogenated for approximately 1 h at RT. Filtration through ®Celite and concentration by evaporation yields the title compound: $^1$H-NMR (200 MHz, C$_2$O): 2.40 and 2.73 (2t, J=7 Hz, each 2 H), 6.77 and 7.56 (2s, each 1 H).

b: 3-(1-Triphenylmethylimidazol-4-yl)-propionic Acid

With stirring, 3.4 g (12.2 mmol) of triphenylchloromethane are added in portions over a period of 4 h to a 2-phase mixture of 10 mmol of imidazol-4-ylpropionic acid (in the form of the sodium salt), 4 ml of water, 4.6 ml (33 mmol) of triethylamine and 8 ml of $^i$propanol. After the reaction mixture has been stirred for a further 4 h, 10 g of silica gel are added and the mixture is concentrated to dryness and applied in the form of a powder to a silica gel column (methylene chloride). Elution with methylene chloride/$^i$propanol/methanol/triethylamine 8:3:3:1 yields the title compound: TLC R$_f$(W)=0.77; $t_{Ref}$(I)=11.8 min; FAB-MS (M+H)$^+$=383.

EXAMPLE 85

5(S)-(Boc-amino)-4(S)-[3-(4-imidazolyl)-propionyloxy]-6-phenyl-2(R)-phenylmethylhexanoyl-(L)-Val-(L)-Phe-morpholin-4-ylamide 0.50 mmol of 5(S)-(Boc-amino)-4(S)-[3-(1-triphenylmethylimidazol-4-yl)-propionyloxy]-6-phenyl-2(R)-phenylmethylhexanoyl-(L)-Val-(L)-Phe-morpholin-4-ylamide (Example 84) dissolved in 20 ml of ethyl acetate are hydrogenated for 8 days at 60° C. and at a hydrogen pressure of approximately 4 atm (approximately 4.052 bar or 0.4052 MPa) in the presence of 0.3 g of 20% palladium hydroxide on carbon. Removal of the catalyst by filtration, concentration of the filtrate by evaporation, and column chromatography (SiO$_2$, acetonitrile/ethyl acetate/triethylamine 50:50:1) yields the title compound: TLC R$_f$(X)=0.09; $t_{Ref}$(I)=13.3 min; FAB-MS (M+H)$^+$=851.

EXAMPLE 86

5(S)-(Boc-amino)-4(S)-(methoxyacetyloxy)-6-(p-fluorophenyl)-2(R)-(p-fluorophenylmethyl)-hexanoyl-(L)-Val-(L)-Phe-morpholin-4-ylamide Analogously to Example 77), 100 mg (0.13 mmol) of Boc-(p-F)Phe[C](p-F)Phe-(L)-Val-(L)-Phe-morpholin-4-ylamide [Example 21 B) 1)] and a small amount of DMAP in 1 ml of dioxane and 0.16 ml of pyridine are reacted with 36 µl (0.39 mmol) of methoxyacetic acid chloride (Fluka; Buchs/Switzerland). Digestion in DIPE yields the title compound: TLC R$_f$(B)=0.38; $t_{Ref}$(I)=16.9 min; FAB-MS (M+H)$^+$=837.

EXAMPLE 87

5(S)-(Boc-amino)-4(S)-(2-picolinoyl)-6-(p-fluorophenyl)-2(R)-(p-fluorophenylmethyl)-hexanoyl-(L)-Val-(L)-Phe-morpholin-4-ylamide Under a nitrogen atmosphere, 32.2 mg (0.26 mmol) of 2-picolinic acid (Fluka; Buchs/Switzerland) in 0.5 ml of methylene chloride are converted into the acid chloride at 0° C. with 22 µl (0.157 mmol) of 1-chloro-N,N,2-trimethyl-1-propenamine [B. Haveaux, A. Dekoker, M. Rens, A. R. Sidani, J. Toye, L. Ghosez, M. Murakami, M. Yoshioka, and W. Nagata, Organic Syntheses 59, 26 (1980)]. After 45 min, 1 ml of dioxane, 0.26 ml of pyridine, 100 mg (0.13 mmol) of Boc-(p-F)Phe[C](p-F)Phe-(L)-Val-(L)-Phe-morpholin-4-ylamide [Example 21 B) 1)] and 0.3 mg of DMAP are added. Since, according to HPLC, the reaction is not complete after 18 h at RT, further acid chloride is added until complete conversion has taken place. The dark reaction mixture is diluted with methylene chloride and washed twice with sat. NaHCO$_3$ solution, water and brine. The aqueous phases are extracted with 2 portions of methylene chloride, and the organic phases are dried with Na$_2$SO$_4$, concentrated by evaporation and chromatographed (SiO$_2$, ethyl acetate). Decolouration of the red-coloured solution of the product in ethyl acetate using activated carbon yields the title compound: TLC R$_f$(B)=0.16; $t_{Ref}$(I)=16.9 min; FAB-MS (M+H)$^+$=870.

EXAMPLE 88

5(S)-(Boc-amino)-4(S)-(pyridine-2-carboxyl)-6-phenyl-2(R)-(p-fluorophenylmethyl)-hexanoyl-(L)-Val-(L)-Phe-morpholin-4-ylamide Analogously to Example 87), 49 mg (0.40 mmol) of 2-picolinic acid in 3 ml of methylene chloride are converted into the acid chloride at RT with 62 µl (0.44 mmol) of 1-chloro-N,N,2-trimethyl-1-propenamine (17 h). A solution of 150 mg (0.20 mmol) of Boc-Phe[C](p-F)Phe-(L)-Val-(L)-Phe-morpholin-4-ylamide [Example 21 D) 1)] and 1.5 mg of DMAP in 2.3 ml of pyridine is added thereto. Since, according to HPLC, there is still some starting material present after 17 h at RT, a further 0.6 mmol of 2-picolinic acid chloride is added. After a further 17 h, the reaction mixture is poured onto sat. NaHCO$_3$ solution and extracted with 3 portions of methylene chloride. The organic phases are washed with water and brine, dried with Na$_2$SO$_4$ and concentrated by evaporation. The dark-red product is dissolved in ethyl acetate, treated with activated carbon, filtered, and concentrated by evaporation again. Digestion in an ultrasound bath in DIPE yields the title compound: TLC R$_f$(B)=0.52; $t_{Ref}$(I)=18.8 min; FAB-MS (M+H)$^+$=852.

EXAMPLE 89

5(S)-(Boc-amino)-4(S)-(methoxyacetyloxy)-6-phenyl-2(R)-(p-fluorophenylmethyl)-hexanoyl-(L)-Val-(L)-Phe-morpholin-4-ylamide Analogously to Example 77), 150 mg (0.20 mmol) of Boc-Phe[C](p-F)Phe-(L)-Val-(L)-Phe-morpholin-4-ylamide

[Example 21 D) 1)] and 1.2 mg of DMAP in 1.5 ml of dioxane and 0.24 ml of pyridine are reacted with 27 µl (0.30 mmol) of methoxyacetic acid chloride (Fluka; Buchs/ Switzerland). Extraction with ethyl acetate yields the title compound: TLC $R_f(B)$=0.7; $t_{Ret}(I)$=16.9 min; FAB-MS $(M+H)^+$=819.

EXAMPLE 90

5(S)-(Boc-amino)-4(S)-(benzyloxyacetyloxy)-6-phenyl-2(R)-(p-fluorophenylmethyl)-hexanoyl-(L)-Val-(L)-Phe-morpholin-4-ylamide Analogously to Example 77), 150 mg (0.20 mmol) of Boc-Phe[C](p-F)Phe-(L)-Val-(L)-Phe-morpholin-4-ylamide [Example 21 D) 1)] and 1.2 mg of DMAP in 1.5 ml of dioxane and 0.24 ml of pyridine are reacted with 2 portions each of 47.5 µl (0.30 mmol) of benzyloxyacetyl chloride (Fluka; Buchs/Switzerland). Digestion in hexane/DIPE 1:4 yields the title compound in the form of a foam: TLC $R_f(A)$=0.24; $t_{Ret}(I)$=18.7 min; FAB-MS $(M+H)^+$=895.

EXAMPLE 91

5(S)-(Boc-amino)-4(S)-[(S)-α-methoxy-α-phenylacetyloxy]-6-phenyl-2(R)-(p-fluorophenylmethyl)-hexanoyl-(L)-Val-(L)-Phe-morpholin-4-ylamide Under a nitrogen atmosphere, 66.5 mg (0.40 mmol) of (S)-α-methoxy-α-phenylacetic acid (Fluka; Buchs/ Switzerland) in 3 ml of methylene chloride are converted at RT into the acid chloride with 62 µl (0.44 mmol) of 1-chloro-N,N,2-trimethyl-1-propenamine [B. Haveaux, A. Dekoker, M. Rens, A. R. Sidani, J. Toye, L. Ghosez, M. Murakami, M. Yoshioka, and W. Nagata, Organic Syntheses 59, 26 (1980)]. After 30 min, a solution of 150 mg (0.20 mmol) of Boc-Phe[C](p-F)Phe-(L)-Val-(L)-Phe-morpholin-4-ylamide [Example 21 D) 1)] and 1.5 mg of DMAP in 2.3 ml of pyridine is added and the mixture is then stirred for 3 h. The reaction mixture is then poured onto NaHCO₃ solution and extracted with 3 portions of methylene chloride. The organic phases are washed with water and brine, dried with Na₂SO₄ and concentrated by evaporation. Digestion in DIPE yields the title compound in the form of a foam: TLC $R_f(B)$=0.73; $t_{Ret}(I)$=18.6 min; FAB-MS $(M+H)^+$=895.

EXAMPLE 92

5(S)-(Boc-amino)-4(S)-[(R)-α-methoxy-α-phenylacetyloxy]-6-phenyl-2(R)-(p-fluorophenylmethyl)-hexanoyl-(L)-Val-(L)-Phe-morpholin-4-ylamide Analogously to Example 91), 66.5 mg (0.40 mmol) of (R)-α-methoxy-α-phenylacetic acid (Fluka; Buchs/ Switzerland) in 3 ml of methylene chloride are converted into the acid chloride with 62 µl (0.44 mmol) of 1-chloro-N,N,2-trimethyl-1-propenamine, and reacted with a solution of 150 mg (0.20 mmol) of Boc-Phe[C](p-F)Phe-(L)-Val-(L) -Phe-morpholin-4-ylamide [Example 21 D) 1)] and 1.5 mg of DMAP in 2.3 ml of pyridine to yield the title compound: TLC $R_f(A)$=0.30; $t_{Ret}(I)$=18.4 min; FAB-MS $(M+H)^+$=895.

EXAMPLE 93

5(S)-(Boc-amino)-4(S)-(1-pyrazolylacetyloxy)-6-phenyl-2(R)-phenylmethylhexanoyl-(L)-Val-(L)-Phe-morpholin-4-ylamide Analogously to Example 80, 340 µl (2.4 mmol) of 1-chloro-N,N,2-trimethyl-1-propenamine [B. Haveaux, A. Dekoker, M. Rens, A. R. Sidani, J. Toye, L. Ghosez, M. Murakami, M. Yoshioka and W. Nagata, Organic Syntheses 59, 26, (1980)] are added at 0° C., under a nitrogen atmosphere, to 252 mg (2 mmol) of 1-pyrazolylacetic acid (Jones et al., J. Org. Chem. 19, 1428–32 (1954)) in 15 ml of methylene chloride. After the mixture has been stirred for 30 minutes at room temperature, a solution of 729 mg (1 mmol) of Boc-Phe[C]Phe-(L)-Val-(L)-Phe-morpholin-4-ylamide (Example 2) and 5 mg of 4-dimethylaminopyridine in 5 ml of pyridine is added. After 155 minutes at room temperature, the mixture is stirred for a further 2 hours at 40° C. Since, according to TLC, there is still some starting material present, an additional 2 mmol of 1-pyrazolylacetic acid chloride (for preparation see above) is added. After a further 1.5 hours, the reaction mixture is poured onto 150 ml of a 2:1 mixture (v/v) of water/saturated aqueous sodium bicarbonate solution and extracted three times with methylene chloride. The combined organic phases are washed in succession with water and brine, dried over sodium sulfate, and then concentrated. Drying under HV is followed by chromatography (SiO₂, methylene chloride/methanol from 100:0 to 97:3). Digestion in diisopropyl ether and a brief treatment in an ultrasound bath yields the pure title compound: TLC $R_f$(ethyl acetate)=0.34. $t_{Ret}(I)$=16.8 min.

EXAMPLE 94

5(S)-(Boc-amino)-4(S)-(isoquinoline-3-carbonyloxy)-6-phenyl-2(R)-phenylmethylhexanoyl-(L)-Val-(L)-Phe-morpholin-4-ylamide Analogously to Example 80, the corresponding acid chloride is prepared from 173 mg (1 mmol) of isoquinoline-3-carboxylic acid (Aldrich, Federal Republic of Germany) with 250 µl of 1-chloro-N,N,2-trimethyl-1-propenamine. In the subsequent step, a solution of 365 mg (0.5 mmol) of Boc-Phe[C]Phe-(L)-Val-(L)-Phe-morpholin-4-ylamide (Example 2) and 5 mg of 4-dimethylaminopyridine in 3 ml of pyridine is added to the acid chloride. After working up analogously to Example 93, the product is chromatographed (SiO₂, ethyl acetate/hexane from 4:1 to 100:0). Digestion in diisopropyl ether yields the pure title compound: TLC $R_f$(ethyl acetate)=0.28; $t_{Ret}(I)$=17.2 min.

EXAMPLE 95

5(S)-(Boc-amino)-4(S)-(pyrazinecarbonyloxy)-6-phenyl-2(R)-phenylmethylhexanoyl-(L)-Val-(L)-Phe-morpholin-4-ylamide Analogously to Example 80, the corresponding acid chloride is prepared from 248 mg (2 mmol) of pyrazinecarboxylic acid (Fluka, Switzerland) with 340 µl of 1-chloro-N,N, 2-trimethyl-1-propenamine. In the subsequent step, a solution of 729 mg of Boc-Phe[C]Phe-(L)-Val-(L)-Phe-morpholin-4-ylamide (Example 2) and 5 mg 4-dimethylaminopyridine in 5 ml of pyridine is added to the acid chloride. After working up analogously to Example 93, the product is chromatographed (SiO₂, ethyl acetate/hexane from 4:1 to 100:0). Digestion in diisopropyl ether yields the pure title compound: TLC $R_f$(ethyl acetate)=0.31; $t_{Ret}(I)$= 16.4 min.

EXAMPLE 96

5(S)-(Boc-amino)-4(S)-(4-α-chloromethylbenzoyloxy)-6-phenyl-2(R)-phenylmethylhexanoyl-(L)-Val-(L)-Phe-morpholin-4-ylamide Analogously to Example 80, the corresponding acid chloride is prepared from 680 mg (4 mmol) of α-choro-p-toluic acid (Fluka, Switzerland) with 800 μl of 1-chloro-N,N,2-trimethyl-1-propenamine. In the subsequent step, a solution of 729 mg (1 mmol) of Boc-Phe[C]Phe-(L)-Val-(L)-Phe-morpholin-4-ylamide (Example 2) in 5 ml of pyridine is added to the acid chloride. After working up analogously to Example 93, the product is chromatographed (SiO$_2$, ethyl acetate). Digestion in diisopropyl ether yields the pure title compound: TLC R$_f$(ethyl acetate) 0.5; t$_{Ret}$(II)=28.2 min.

EXAMPLE 97

5(S)-(Boc-amino)-4(S)-[4-(4-morpholino)methylbenzoyloxy]-6-phenyl-2(R)-phenylmethylhexanoyl-(L)-Val-(L)-Phe-morpholin-4-ylamide Analogously to Example 80, the corresponding acid chloride is prepared from 258 mg (1 mmol) of α-(4-morpholino)-p-toluic acid (p-(morpholin-4-ylmethyl)benzoic acid; preparation according to U.S. Pat. No. 4,623,486 dated 18 Nov. 1986 (Lombardino et al.)) with 350 μl of 1-chloro-N,N,2-trimethyl-1-propenamine. In the subsequent step, a solution of 365 mg (0.5 mmol) of Boc-Phe[C]Phe-(L)-Val-(L)-Phe-morpholin-4-ylamide (Example 2) in 2.5 ml of pyridine is added to the acid chloride. After working up analogously to Example 93, column chromatography (SiO$_2$, ethyl acetate then methylene chloride/methanol 100:0 to 96:4) yields the pure title compound: TLC R$_f$(ethyl acetate) =0.28; t$_{Ret}$(II)=20.1 min;

EXAMPLE 98

5(S)-(Boc-amino)-4(S)-(isonicotinoyloxy)-6-phenyl-2(R)-phenylmethyl-hexanoyl-(L)-Val-(L)-Phe-morpholin-4-ylamide Analogously to Example 80, the corresponding acid chloride is prepared from 260 mg (2 mmol) of isonicotinic acid (Fluka, Switzerland) with 340 μl of 1-chloro-N,N,2-trimethyl-1-propenamine. A solution of 729 mg (1 mmol) of Boc-Phe[C]Phe-(L)-Val-(L)-Phe-morpholin-4-ylamide (Example 2) and 5 mg of 4-N,N-dimethylaminopyridine in 5 ml of pyridine is then added. After working up analogously to Example 93, column chromatography (SiO$_2$, ethyl acetate) yields the pure title compound: TLC R$_f$ (ethyl acetate)=0.27; t$_{Ret}$(I)=15.3 min; FAB-MS (M+H$^+$)=834.

EXAMPLE 99

5(S)-(Boc-amino)-4(S)-(nicotinoyloxy)-6-phenyl-2(R)-phenylmethylhexanoyl-(L)-Val-(L)-Phe-morpholin-4-ylamide Analogously to Example 80, the corresponding acid chloride is prepared from 740 mg (6 mmol) of nicotinic acid (Fluka, Switzerland) with 1200 μl of 1-chloro-N,N,2-trimethyl-1-propenamine. In the subsequent step, a solution of 1100 mg (1.5 mmol) of Boc-Phe[C]Phe-(L)-Val-(L)-Phe-morpholin-4-ylamide (Example 2) and 10 mg of 4-N,N-dimethylaminopyridine in 5.5 ml of pyridine is added to the acid chloride. After working up analogously to Example 93, column chromatography (SiO$_2$, ethyl acetate) yields the pure title compound: TLC R$_f$(ethyl acetate)=0.33; t$_{Ret}$(II)=22.4 min.

EXAMPLE 100

5(S)-(Boc-amino)-4(S)-(2-picolinoyloxy)-6-phenyl-2(R)-phenylmethylhexanoyl-(L)-Val-(L)-Phe-morpholin-4-ylamide Analogously to Example 80, the corresponding acid chloride is prepared from 985 mg (8 mmol) of 2-picolinic acid (Fluka, Switzerland) with 1600 μl of 1-chloro-N,N,2-trimethyl-1-propenamine. In the subsequent step, a solution of 1450 mg (2 mmol) of Boc-Phe[C]Phe-(L)-Val-(L)-Phe-morpholin-4-ylamide (Example 2) and 10 mg of 4-N,N-dimethylaminopyridine in 7.5 ml of pyridine is added to the acid chloride. After working up analogously to Example 93, column chromatography (SiO$_2$, hexane/ethyl acetate 1/1 to ethyl acetate) yields the pure title compound: TLC R$_f$(ethyl acetate)=0.23; t$_{Ret}$(II)=28.4 min.

EXAMPLE 101

5(S)-(Boc-amino)-4(S)-(3-methoxypropanoyloxy)-6-phenyl-2(R)-phenylmethylhexanoyl-(L)-Val-(L)-Phe-morpholin-4-ylamide Analogously to Example 80, the corresponding acid chloride is prepared from 387 μl (4 mmol) of 3-methoxypropionic acid (Fluka, Switzerland) with 680 μl of 1-chloro-N,N,2-trimethyl-1-propenamine. In the subsequent step, a solution of 1450 mg (2 mmol) of Boc-Phe[C]Phe-(L)-Val-(L)-Phe-morpholin-4-ylamide (Example 2) and 10 mg of 4-N,N-dimethylaminopyridine in 10 ml of pyridine is added to the acid chloride. After working up analogously to Example 93, column chromatography (SiO$_2$, ethyl acetate) yields the pure title compound: TLC R$_f$(ethyl acetate)=0.37; t$_{Ret}$(I)=17.3 min; FAB-MS (M+H$^+$)=815.

EXAMPLE 102

5(S)-(Boc-amino)-4(S)-[(4-chlorophenoxy)methoxyacetyloxy)]-6-phenyl-2(R)-phenylmethylhexanoyl-(L)-Val-(L)-Phe-morpholin-4-ylamide Analogously to Example 80, the corresponding acid chloride is prepared from 217 mg (1 mmol) of (4-chlorophenoxy)methoxyacetic acid (Cretin et al., Phytochemistry 22(12), 2661–64 (1983)) with 170 μl of 1-chloro-N,N,2-trimethyl-1-propenamine. In the subsequent step, a solution of 365 mg (0.5 mmol) of Boc-Phe[C]Phe-(L)-Val-(L)-Phe-morpholin-4-ylamide (Example 2) and 5 mg of 4-N,N-dimethylaminopyridine in 2.5 ml of pyridine is added to the acid chloride. After working up analogously to Example 93, column chromatography (SiO$_2$, ethyl acetate) yields the pure title compound: TLC R$_f$(ethyl acetate)=0.5; t$_{Ret}$(I)=19.1 min; FAB-MS (M+H$^+$)=927.

EXAMPLE 103

5(S)-(Boc-amino)-4(S)-[2-(2-methoxyethoxy)-acetyloxy)]-6-phenyl-2(R)-phenylmethylhexanoyl-(L)-Val-(L)-Phe-morpholin-4-ylamide Analogously to Example 80, the corresponding acid chloride is prepared from 240 μl (2 mmol) of 2-(2-methoxyethoxy)acetic acid (Fluka, Switzerland) with 340 μl of 1-chloro-N,N,2-trimethyl-1-propenamine. In the subsequent step a solution of 729 mg (1 mmol) of Boc-Phe[C]Phe-(L)-Val-(L)-Phe-morpholin-4-ylamide (Example 2) and 5 mg of 4-N,N-dimethylaminopyridine in 5 ml of pyridine is added to the acid chloride. After working up analogously to Example 93, column chromatography (SiO$_2$, methylene chloride/methanol: 100/0 to 97/3) yields the pure title compound: TLC R$_f$(ethyl acetate)=0.33; t$_{Ret}$(I)=16.9 min; FAB-MS (M+H$^+$)=845.

EXAMPLE 104

5(S)-(Boc-amino)-4(S)-(butyloxyacetyloxy)-6-phenyl-2(R)-phenylmethylhexanoyl-(L)-Val-(L)-Phe-morpholin-4-ylamide Analogously to Example 80, the corresponding acid chloride is prepared from 265 mg (2 mmol) of 2-(n-butoxy)

acetic acid (Janssen, Netherlands) with 340 µl of 1-chloro-N,N,2-trimethyl-1-propenamine. In the subsequent step, a solution of 729 mg (1 mmol) of Boc-Phe[C]Phe-(L)-Val-(L)-Phe-morpholin-4-ylamide (Example 2) and 5 mg of 4-N,N-dimethylaminopyridine in 5 ml of pyridine is added to the acid chloride. After working up analogously to Example 93, column chromatography (SiO$_2$, ethyl acetate) yields the pure title compound: TLC R$_f$(ethyl acetate)=0.44; t$_{Ref}$(I)=18.7 min; FAB-MS (M+H$^+$)=843.

EXAMPLE 105

5(S)-(Boc-amino)-4(S)-[2-[2-(2-methoxyethoxy)-ethoxy]acetyloxy)]-6-phenyl-2(R)-phenylmethylhexanoyl-(L)-Val-(L)-Phe-morpholin-4-ylamide Analogously to Example 80, the corresponding acid chloride is prepared from 314 µl (2 mmol) of 2-[2-(2-methoxyethoxy)ethoxy]acetic acid (Fluka, Switzerland) with 340 µl of 1-chloro-N,N,2-trimethyl-1-propenamine. In the subsequent step, a solution of 729 mg (1 mmol) of Boc-Phe[C]Phe-(L)-Val-(L)-Phe-morpholin-4-ylamide (Example 2) and 5 mg of 4-N,N-dimethylaminopyridine in 5 ml of pyridine is added to the acid chloride. After working up analogously to Example 93, column chromatography (SiO$_2$, methylene chloride/methanol: 100/0 to 97/3) yields the pure title compound: TLC R$_f$(ethyl acetate)=0.27; t$_{Ref}$(I)=16.7 min; FAB-MS (M+H$^+$)=889.

EXAMPLE 106

5(S)-(Boc-amino)-4(S)-(methoxyacetyloxy)-6-phenyl-2(R)-phenylmethylhexanoyl-(L)-Val-(L)-Phe-morpholin-4-ylamide Analogously to Example 111, 729 mg (1 mmol) of Boc-Phe[C]Phe-(L)-Val-(L)-Phe-morpholin-4-ylamide (Example 2) are converted with 100 µl (1.1 mmol) of methoxyacetic acid chloride (Fluka, Switzerland) into the title compound, which is purified by column chromatography (SiO$_2$, ethyl acetate/hexane: 4/1). TLC R$_f$(ethyl acetate) =0.43; t$_{Ref}$(I)=16.8 min; FAB-MS (M+H$^+$)=801.

EXAMPLE 107

5(S)-(Boc-amino)-4(S)-(phenoxyacetyloxy)-6-phenyl-2(R)-phenylmethylhexanoyl-(L)-Val-(L)-Phe-morpholin-4-ylamide Analogously to Example 111, 1450 mg (2 mmol) of Boc-Phe[C]Phe-(L)-Val-(L)-Phe-morpholin-4-ylamide (Example 2) are converted with 360 µl (2.6 mmol) of phenoxyacetyl chloride (Fluka, Switzerland) into the title compound, which is purified by column chromatography (SiO$_2$, ethyl acetate/hexane: 4/1). TLC R$_f$(ethyl acetate/hexane: 4/1)=0.37; t$_{Ref}$(I)=18.5 min; FAB-MS (M+H$^+$)=863.

EXAMPLE 108

5(S)-(Boc-amino)-4(S)-[(S)-α-methoxy-α-phenylacetyloxy)-6-phenyl-2(R)-phenylmethylhexanoyl-(L)-Val-(L)-Phe-morpholin-4-ylamide Analogously to Example 80, the corresponding acid chloride is prepared from 332.4 mg (2 mmol) of (S)-α-methoxy-α-phenylacetic acid (Fluka, Switzerland) with 340 µl of 1-chloro-N,N,2-trimethyl-1-propenamine. In the subsequent step, a solution of 729 mg (1 mmol) of Boc-Phe[C]Phe-(L)-Val-(L)-Phe-morpholin-4-ylamide (Example 2) and 5 mg of 4-N,N-dimethylaminopyridine in 5 ml of pyridine is added to the acid chloride. After working up analogously to Example 93, column chromatography (SiO$_2$, ethyl acetate) yields the pure title compound: TLC R$_f$(ethyl acetate)=0.43; t$_{Ref}$(I)=18.5 min; FAB-MS (M+H$^+$)=877.

EXAMPLE 109

5(S)-(Boc-amino)-4(S)-[(R)-α-methoxy-α-phenylacetyloxy)]-6-phenyl-2(R)-phenylmethylhexanoyl-(L)-Val-(L)-Phe-morpholin-4-ylamide Analogously to Example 80, the corresponding acid chloride is prepared from 333 mg (2 mmol) of (S)-α-methoxy-α-phenylacetic acid (Fluka, Switzerland) with 340 µl of 1-chloro-N,N,2-trimethyl-1-propenamine. In the subsequent step, a solution of 729 mg (1 mmol) of Boc-Phe[C]Phe-(L)-Val-(L)-Phe-morpholin-4-ylamide (Example 2) and 5 mg of 4-N,N-dimethylaminopyridine in 5 ml of pyridine is added to the acid chloride. After working up analogously to Example 93, column chromatography (SiO$_2$, ethyl acetate) yields the pure title compound: TLC R$_f$(ethyl acetate)=0.5; t$_{Ref}$(I)=18.3 min; FAB-MS (M+H$^+$)=877.

EXAMPLE 110

5(S)-(Boc-amino)-4(S)-(valeroyloxy)-6-phenyl-2(R)-phenylmethylhexanoyl-(L)-Val-(L)-Phe-morpholin-4-ylamide Analogously to Example 111, 729 mg (1 mmol) of Boc-Phe[C]Phe-(L)-Val-(L)-Phe-morpholin-4-ylamide (Example 2) are converted with 181 µl (1.5 mmol) of valeroyl chloride (Fluka, Switzerland) into the title compound, which is purified by column chromatography (SiO$_2$, ethyl acetate/hexane: 4/1). TLC R$_f$(ethyl acetate/hexane: 4/1)=0.33; t$_{Ref}$(I)=18.9 min; FAB-MS (M+H$^+$)=813.

EXAMPLE 111

5(S)-(Boc-amino)-4(S)-(pivaloyloxy)-6-phenyl-2(R)-phenylmethylhexanoyl-(L)-Val-(L)-Phe-morpholin-4-ylamide Under an argon atmosphere, a solution of 130 µl (1.05 mmol) of pivaloyl chloride in 0.4 ml of pyridine is added over a period of 10 minutes to a solution of 510 mg (0.7 mmol) of Boc-Phe[C]Phe-(L)-Val-(L)-Phe-morpholin-4-ylamide (Example 2) in 4 ml of pyridine. After the further addition twice of 150 µl of pivaloyl chloride and 5 mg of 4-N,N-dimethylaminopyridine, no more starting material can be detected by TLC after a total reaction time of 3.75 hours at 50° C. The reaction mixture is poured onto approximately 40 ml of saturated aqueous sodium bicarbonate solution and extracted three times with methylene chloride. The combined extracts are washed with brine, dried over sodium sulfate and concentrated. The subsequent column chromatography (SiO$_2$, methylene chloride/methanol: 100/0 to 98.5/1.5) yields the pure title compound. TLC R$_f$(methylene chloride/methanol: 95/5)=0.6; t$_{Ref}$(II)=28.3 min; FAB-MS (M+H$^+$)=813.

EXAMPLE 112

5(S)-(Boc-amino)-4(S)-(palmitoyloxy)-6-phenyl-2(R)-phenylmethylhexanoyl-(L)-Val-(L)-Phe-morpholin-4-ylamide Analogously to Example 111, 729 mg (1 mmol) of Boc-Phe[C]Phe-(L)-Val-(L)-Phe-morpholin-4-ylamide (Example 2) are converted with 456 μl (1.5 mmol) of palmitic acid chloride (Fluka, Switzerland) into the title compound, which is purified by column chromatography (SiO₂, ethyl acetate/hexane: 1/1). TLC R_f(ethyl acetate/hexane: 4/1)=0.43; t_Ref(100% acetonitrile)=13.8 min; FAB-MS (M+H⁺)=967.

EXAMPLE 113

5(S)-(Boc-amino)-4(S)-(butyroyloxy)-6-phenyl-2(R)-phenylmethylhexanoyl-(L)-Val-(L)-Phe-morpholin-4-ylamide Analogously to Example 111, 729 mg (1 mmol) of Boc-Phe[C]Phe-(L)-Val-(L)-Phe-morpholin-4-ylamide (Example 2) are converted with 156 μl (1.5 mmol) of butyric acid chloride (Fluka, Switzerland) into the title compound, which is purified by column chromatography (SiO₂, ethyl acetate/hexane: 4/1). TLC R_f(ethyl acetate)=0.43; t_Ref(I)= 18.3 min; FAB-MS (M+H⁺)=799.

EXAMPLE 114

5(S)-(Boc-amino)-4(S)-(propanoyloxy)-6-phenyl-2(R)-phenylmethylhexanoyl-(L)-Val-(L)-Phe-morpholin-4-ylamide Analogously to Example 111, 729 mg (1 mmol) of Boc-Phe[C]Phe-(L)-Val-(L)-Phe-morpholin-4-ylamide (Example 2) are converted with 131 μl (1.5 mmol) of propionyl chloride (Fluka, Switzerland) into the title compound, which is purified by column chromatography (SiO₂, ethyl acetate/hexane: 4/1). TLC R_f(ethyl acetate)= 0.43; t_Ref(I)=17.6 min; FAB-MS (M+H⁺)=785.

EXAMPLE 115

5(S)-(Boc-amino)-4(S)-(benzoyloxy)-6-phenyl-2(R)-phenylmethylhexanoyl-(L)-Val-(L)-Phe-morpholin-4-ylamide Analogously to Example 111, 365 mg (1 mmol) of Boc-Phe[C]Phe-(L)-Val-(L)-Phe-morpholin-4-ylamide (Example 2) are converted with 64 μl (1.1 mmol) of benzoyl chloride (Aldrich, Federal Republic of Germany) into the title compound, which is purified by column chromatography (SiO₂, ethyl acetate). TLC R_f(ethyl acetate)=0.5; t_Ref(II) =27.6 min; FAB-MS (M+H⁺)=833.

EXAMPLE 116

5(S)-(Boc-amino)-4(S)-(methylpropionyloxy)-6-phenyl-2(R)-phenylmethylhexanoyl-(L)-Val-(L)-Phe-morpholin-4-ylamide Analogously to Example 78, Boc-Phe[C]Phe-(L)-Val-(L)-Phe-morpholin-4-ylamide (Example 2) is reacted with an excess of isobutyric acid chloride (Fluka; Buchs/Switzerland): t_Ref(I)=18.2 min; FAB-MS (M+H)⁺=799.

EXAMPLE 117

The following compounds are prepared analogously to one of the above processes:

A) 5(S)-(Boc-amino)-4(S)-[3-(dimethylamino)-propionyloxy]-6-phenyl-2(R)-phenylmethylhexanoyl-(L)-Val-(L)-Phe-morpholin-4-ylamide B) 5(S)-(Boc-amino)-4(S)-[3-(N-Z-N-methylamino)-propionyloxy]-6-phenyl-2(R)-phenylmethylhexanoyl-(L)-Val-(L)-Phe-morpholin-4-ylamide C) 5(S)-(Boc-amino)-4(S)-(3-methylaminopropionyloxy)-6-phenyl-2(R)-phenylmethylhexanoyl-(L)-Val-(L)-Phe-morpholin-4-ylamide D) 5(S)-(Boc-amino)-4(S)-[(dimethylaminoethoxy)-acetyloxy]-6-phenyl-2(R)-(p-fluorophenylmethyl)-hexanoyl-(L)-Val-(L)-Phe-morpholin-4-ylamide E) 5(S)-(Boc-amino)-4(S)-[(2-pyridylmethoxy)-acetyloxy]-6-phenyl-2(R)-(p-fluorophenylmethyl)-hexanoyl-(L)-Val-(L)-Phe-morpholin-4-ylamide F) 5(S)-(Boc-amino)-4(S)-(methoxyacetyloxy)-6-phenyl-2(R)-(p-methoxyphenylmethyl)-hexanoyl-(L)-Val-(L)-(p-CH₃O-Phe)-morpholin-4-ylamide G) 5(S)-(Boc-amino)-4(S)-(pyridine-2-carboxyl)-6-phenyl-2(R)-(p-methoxyphenylmethyl)-hexanoyl-(L)-Val-(L)-(p-CH₃O-Phe)-morpholin-4-ylamide H): 5(S)-(Boc-amino)-4(S)-(2-methylthio)acetyloxy-6-phenyl-2(R)-benzylhexanoyl-(L)-Val-(L)-Phe-morpholin-4-ylamide Analogously to Example 80, a solution of 546 mg (0.75 mmol) of 5(S)-(Boc-amino)-4(S)-hydroxy-6-phenyl-2(R)-benzylhexanoyl-(L)-Val-(L)-Phe-morpholin-4-ylamide and 5 mg of DMAP in 5 ml of pyridine is added to a mixture of 0.174 ml (2 mmol) of 2-methylthioacetic acid (Fluka, Buchs, Switzerland) and 0.34 ml (2.4 mmol) of 1-chloro-N,N,2-trimethyl-1-propenamine in 15 ml of methylene chloride. After working up and column chromatography (SiO₂, ethyl acetate/hexane: 4/1), the title compound is isolated: TLC R_f(B)=0.41; t_Ref(I)=17.9 min; FAB-MS (M+H⁺)=817.

I) 5(S)-(Boc-amino)-4(S)-(benzylthioacetyloxy)-6-phenyl-2(R)-phenylmethylhexanoyl-(L)-Val-(L)-Phe-morpholin-4-ylamide J): 5(S)-(Boc-amino)-4(S)-[(L)-(prolyl)oxy]-6-phenyl-2(R)-phenylmethylhexanoyl-(L)-Val-(L)-Phe-morpholin-4-ylamide 1.12 g (1.166 mmol) of 5(S)-(Boc-amino)-4(S)-[(L)-(N-Z-prolyl)oxy]-6-phenyl-2(R)-phenylmethylhexanoyl-(L)-Val-(L)-Phe-morpholin-4-ylamide (Example 117 L)) in 20 ml of ethyl acetate are hydrogenated in the presence of 120 mg of 10% Pd/C. Filtration, concentration of the filtrate by evaporation, and digestion from DIPE yields the title compound: t_Ref(I)=13.8 min; FAB-MS (M+H)⁺=826.

K) 5(S)-(Boc-amino)-4(S)-[(D)-(prolyl)oxy]-6-phenyl-2(R)-phenylmethylhexanoyl-(L)-Val-(L)-Phe-morpholin-4-ylamide 950 mg (0.989 mmol) of 5(S)-(Boc-amino)-4(S)-[(D)-(N-Z-prolyl)oxy]-6-phenyl-2(R)-phenylmethylhexanoyl-(L)-Val-(L)-Phe-morpholin-4-ylamide (Example 117 M) in 20 ml of ethyl acetate are hydrogenated in the presence of 0.20 g of 10% Pd/C. Filtration, concentration of the filtrate by evaporation, column chromatography (SiO₂, THF/ether 1:1) and digestion from DIPE yields the title compound: t_Ref(I) =13.5 min; FAB-MS (M+H)⁺=826.

L) 5(S)-(Boc-amino)-4(S)-[(L)-(N-Z-prolyl)oxy]-6-phenyl-2(R)-phenylmethylhexanoyl-(L)-Val-(L)-Phe-morpholin-4-ylamide Under a nitrogen atmosphere, 683 mg (2.74 mmol) of Z-(L)-proline in 5 ml of methylene chloride are reacted at RT with 232 μl (1.644 mmol) of 1-chloro-N,N,2-trimethyl-1-propenamine [B. Haveaux, A. Dekoker, M. Rens, A. R. Sidani, J. Toye, L. Ghosez, M. Murakami, M. Yoshioka, and W. Nagata, Organic Syntheses 59, 26 (1980)]. After 30 min, 2.7 ml of pyridine, 1.00 g (1.37 mmol) of Boc-Phe[C]Phe-(L)-Val-(L)-Phe-morpholin-4-ylamide (Example 2) and 3 mg of DMAP are added. Since, according to HPLC, there is still some starting material present after 17 h at RT, a further 1.3 mmol of Z-(L)-proline is activated with 0.8 mmol of 1-chloro-N,N,2-trimethyl-1-propenamine and added. After a further 17 h, the reaction mixture is poured onto sat. NaHCO$_3$ solution and extracted with 3 portions of methylene chloride. The organic phases are washed with water and brine, dried with Na$_2$SO$_4$ and concentrated by evaporation. Column chromatography (SiO$_2$, ethyl acetate) yields the title compound: TLC R$_f$(B)=0.50; t$_{Ref}$(I)=20.0 min; FAB-MS (M+H)$^+$=961.

M) 5(S)-(Boc-amino)-4(S)-[(D)-(N-Z-prolyl)oxy]-6-phenyl-2(R)-phenylmethylhexanoyl-(L)-Val-(L)-Phe-morpholin-4-ylamide Under a nitrogen atmosphere, 683 mg (2.74 mmol) of Z-(D)-proline in 5 ml of methylene chloride are reacted at RT with 232 µl (1.644 mmol) of 1-chloro-N,N,2-trimethyl-1-propenamine. After 30 min, 2.7 ml of pyridine, 1.00 g (1.37 mmol) of Boc-Phe[C]Phe-(L)-Val-(L)-Phe-morpholin-4-ylamide (Example 2) and 3 mg of DMAP are added. Since, according to HPLC, there is still some starting material present after 17 h at RT, a further 683 mg of Z-(D)-proline are activated with 232 µl of 1-chloro-N,N,2-trimethyl-1-propenamine and added. After a further 17 h, working up is carried out analogously to Example 117L): TLC R$_f$(B)=0.47; t$_{Ref}$(I)=19.3 min; FAB-MS (M+H)$^+$=960.

There is used as starting material for a number of compounds 5(S)-(Boc-amino)-4(S)-(chloroacetyloxy)-6-phenyl-2(R)-(p-fluorophenylmethyl)-hexanoyl-(L)-Val-(L)-Phe-morpholin-4-ylamide (which can be prepared by reacting chloroacetic acid with 5(S)-(Boc-amino)-4(S)-hydroxy-6-phenyl-2(R)-(p-fluorophenylmethyl)-hexanoyl-(L)-Val-(L)-Phe-morpholin-4-ylamide analogously to Example 80) in which the chlorine atom is converted into a substituted N, S or O atom by nucleophilic substitution, for example in the preparation of compounds D) with dimethylaminoethanol, and compounds E) with 2-pyridylmethanol.

EXAMPLE 118

Analogously to one of the processes described in Examples 77 to 117, unless specifically described in the afore-mentioned Examples the compounds of formula I of Examples 1 to 22 and 33 to 56 are converted, by replacing the 4(S)-hydroxy group in the central non-hydrolysable peptide building block, into the corresponding 4(S)-acyloxy compounds in which one of the following radicals stands in place of the 4(S)-hydroxy group in each case:

A) 4(S)-(2-furanylcarboxy)-;
B) 4(S)-[4-(dimethylamino)butyryloxy];
C) 4(S)-(N-Z-N-methylaminoacetyloxy);
D) 4(S)-(methylaminoacetyloxy);
E) 4(S)-[N(imidazol-4-methyl)-N-methylaminoacetyloxy];
F) 4(S)-[3-(1-triphenylmethylimidazol-4-yl)-propionyloxy];
G) 4(S)-[3-(4-imidazolyl)-propionyloxy];
H) 4(S)-(methoxyacetyloxy);
I) 4(S)-((2-picolinoyl);
J) 4(S)-(benzyloxyacetyloxy);
K) 4(S)-[(S)-α-methoxy-α-phenylacetyloxy];
L) 4(S)-[(R)-α-methoxy-α-phenylacetyloxy];
M) 4(S)-(1-pyrazolylacetyloxy);
N) 4(S)-(isoquinoline-3-carbonyloxy);
O) 4(S)-(pyrazinecarbonyloxy);
P) 4(S)-(4-α-chloromethylbenzoyloxy);
Q) 4(S)-[4-(4-morpholino)methylbenzoyloxy];
R) 4(S)-(isonicotinoyloxy);
S) 4(S)-(nicotinoyloxy);
T) 4(S)-(3-methoxypropanoyloxy)
U) 4(S)-[(4-chlorophenoxy)methoxyacetyloxy)];
V) 4(S)-[2-(2-methoxyethoxy)acetyloxy)];
W) 4(S)-(butyloxyacetyloxy);
X) 4(S)-[2-[2-(2-methoxyethoxy)ethoxy]acetyloxy)];
Y) 4(S)-(methoxyacetyloxy);
Z) 4(S)-(phenoxyacetyloxy);
AA) 4(S)-[(S)-α-methoxy-α-phenylacetyloxy];
AB) 4(S)-[(R)-α-methoxy-α-phenylacetyloxy)];
AC) (N,N-dimethylaminoacetyloxy);
AD) 4(S)-[N-(pyridine-2-methyl)-N-methylaminoacetyloxy].

EXAMPLE 119

Analogously to one of the processes described in Examples 77 to 117, unless specifically described in the afore-mentioned Examples the compounds of formula I of Examples 1 to 22 and 33 to 56 are converted, by replacing the 4(S)-hydroxy group in the central non-hydrolysable peptide building block, into the corresponding 4(S)-acyloxy compounds in which one of the following radicals stands in place of the 4(S)-hydroxy group in each case:

A) 4(S)-[3-(dimethylamino)-propionyloxy];
B) 4(S)-[3-(N-Z-N-methylamino)-propionyloxy];
C) 4(S)-(3-methylaminopropionyloxy);
D) 4(S)-[(dimethylaminoethoxy)-acetyloxy];
E) 4(S)-[(2-pyridylmethoxy)-acetyloxy];
F) 4(S)-(methoxyacetyloxy);
G) 4(S)-(pyridine-2-carboxyl);
H) 4(S)-(methylthioacetyloxy);
I) 4(S)-(benzylthioacetyloxy);
J) 4(S)-((L)-prolyloxy);
K) 4(S)-((D)-prolyloxy);
L) 4(S)-((L)-(N-Z-prolyl)oxy);
M) 4(S)-((D)-(N-Z-prolyl)oxy).

EXAMPLE 120

5(S)-(Boc-amino)-4(S)-[3-(N-Z-amino)-propionyloxy]-6-phenyl-2(R)-phenylmethylhexanoyl-(L)-Val-(L)-Phe-morpholin-4-ylamide Under a nitrogen atmosphere, 612 mg (2.74 mmol) of Z-β-alanine in 5 ml of methylene chloride are reacted at RT with 232 µl (1.644 mmol) of 1-chloro-N,N,2-trimethyl-1-propenamine. After 40 min, 2.7 ml of pyridine, 1.00 g (1.37 mmol) of Boc-Phe[C]Phe-(L)-Val-(L)-Phe-morpholin-4-ylamide (Example 2) and 3 mg of DMAP are added. Since, according to HPLC, there is still some starting material present after 17 h at RT, a further 612 mg of Z-β-alanine are activated with 232 µl 1-chloro-N,N,2-trimethyl-1-propenamine and added. After a further 17 h, working up is carried out analogously to Example 117 L): TLC R$_f$(B)= 0.38; t$_{Ref}$(I)=18.3 min; FAB-MS (M+H)$^+$=934.

EXAMPLE 121

5(S)-(Boc-amino)-4(S)-(3-aminopropionyloxy)-6-phenyl-2(R)-phenylmethylhexanoyl-(L)-Val-(L)-Phe-morpholin-4-ylamide Hydrogenation of 1.00 g (1.07 mmol) of 5(S)-(Boc-amino)-4(S)-[3-(N-Z-amino)-propionyloxy]-6-phenyl-2(R)-phenylmethylhexanoyl-(L)-Val-(L)-Phe-morpholin-4-ylamide in 20 ml of ethyl acetate in the presence of 0.2 g of 10% Pd/C, followed by filtration, concentration of the filtrate by evaporation and digestion from DIPE, yields the title compound: t$_{Ref}$(I)=13.1 min; FAB-MS (M+H)$^+$=800.

EXAMPLE 122

5(S)-(Boc-amino)-4(S)-[(3-dimethylaminopropoxy)-acetyloxy]-6-phenyl-2(R)-phenylmethylhexanoyl-(L)-Val-(L)-Phe-morpholin-4-ylamide A solution of 0.124 mmol of 5(S)-(Boc-amino)-4(S)-(iodoacetyloxy)-6phenyl-2(R)-phenylmethylhexanoyl-(L)-

Val-(L)-Phe-morpholin-4-ylamide in 0.3 ml acetone is added to 13 mg (0.124 mmol) of 3-dimethylaminopropanol (Fluka; Buchs, Switzerland), the mixture is then washed twice with 0.3 ml of acetone each time and, after the addition of 15.6 mg (0.187 mmol) of NaHCO$_3$, is stirred for 17 h at RT (HPLC: fully reacted). The solvent is carried off in a stream of nitrogen, and the residue is suspended in a small amount of methylene chloride and poured onto a mixture of ice-water and methylene chloride. The organic phase is removed and washed with water and brine, and the aqueous phases are extracted twice with methylene chloride. The organic phases are dried with Na$_2$SO$_4$, concentrated by evaporation, and precipitated with DIPE from a concentrated solution in acetone to yield the title compound: t$_{Ref}$(I)=13.5 min; FAB-MS (M+H)$^+$=872.

The starting material is prepared as follows:

a) 5(S)-(Boc-amino)-4(S)-(iodoacetyloxy)-6-phenyl-2(R)-phenylmethylhexanoyl-(L)-Val-(L)-Phe-morpholin-4-ylamide 90.5 mg (0.604 mmol) of sodium iodide are added to a solution of 100 mg (0.124 mmol) of 5(S)-(Boc-amino)-4(S)-(chloroacetyloxy)-6-phenyl-2(R)-phenylmethylhexanoyl-(L)-Val-(L)-Phe-morpholin-4-ylamide in 0.3 ml of acetone, and the mixture is stirred for 1.5 h at RT, during the course of which a precipitate separates out. Since HPLC after 1 h already indicates complete reaction to the title compound, the supernatant solution is pipetted off and immediately used in the above step: t$_{Ref}$(I)=18.2 min.

b) 5(S)-(Boc-amino )-4(S)-(chloroacetyloxy)-6-phenyl-2(R)-phenylmethylhexanoyl-(L)-Val-(L)-Phe-morpholin-4-ylamide Under a nitrogen atmosphere 2.00 g (2.74 mmol) of Boc-Phe[C]Phe-(L)-Val(L)-Phe-morpholin-4-ylamide (Example 2) are introduced into 20 ml of acetonitrile and 12 ml of dioxane, and 1.3 ml of pyridine, a small amount of DMAP and finally 1.17 g (6.85 mmol) of chloroacetic acid anhydride are added. After having been stirred for 24 h at RT, the mixture is poured onto ice-water and extracted three times with ethyl acetate. The organic phases are washed with 2 portions of sat. NaHCO$_3$ solution, water and brine, dried with Na$_2$SO$_4$ and concentrated by evaporation. Column chromatography (SiO$_2$, methylene chloride/ether 1:1) yields the title compound: TLC R$_f$(A')=0.16; t$_{Ref}$(I)=17.7 min; FAB-MS (M+H)$^+$=805.

EXAMPLE 123

5(S)-(Boc-amino)-4(S)-[2-(2-dimethylaminoethoxy)-ethoxyacetyloxy]-6-phenyl-2(R)-phenylmethylhexanoyl-(L)-Val-(L)-Phe-morpholin-4-ylamide A solution of 0.285 mmol of 5(S)-(Boc-amino)-4(S)-(iodoacetyloxy)-6-phenyl-2(R)-phenylmethylhexanoyl-(L)-Val-(L)-Phe-morpholin-4-ylamide in acetone (Example 122 a) is added to 37.9 mg (0.285 mmol) of 2-(2-dimethylaminoethoxy)-ethanol (BASF; Ludwigshafen, Germany), the mixture is then washed twice with 0.7 ml of acetone each time, 36 mg (0.43 mmol) of NaHCO$_3$ are added, and the mixture is stirred for 20 h at RT to complete the reaction. The mixture is worked up analogously to Example 122 and the crude product is stirred with DIPE to yield the title compound: t$_{Ref}$(I)=13.5 min; FAB-MS (M+H)$^+$=902.

EXAMPLE 124

5(S)-(Boc-amino)-4(S)-[(4-dimethylaminobutoxy)-acetyloxy]-6-phenyl-2(R)-phenylmethylhexanoyl-(L)-Val-(L)-Phe-morpholin-4-ylamide A solution of 0.124 mmol of 5(S)-(Boc-amino)-4(S)-(iodoacetyloxy)-6-phenyl-2(R)-phenylmethylhexanoyl-(L)-Val-(L)-Phe-morpholin-4-ylamide in acetone (Example 122 a) is added to 14.5 mg (0.124 mmol) of 4-dimethylamino-1-butanol (BASF; Ludwigshafen, Germany), and the mixture is then washed twice with 0.3 ml of acetone each time and, after the addition of 26 mg (0.187 mmol) of K$_2$CO$_3$, stirred for 18 h at RT to complete the reaction. Since, according to HPLC, there is still some iodoacetate present, a further 0.25 equivalents of 4-dimethylamino-1-butanol is added. Working up after 17 h analogously to Example 122 yields the title compound: t$_{Ref}$(I)=13.5 min; FAB-MS (M+H)$^+$=886.

EXAMPLE 125

5(S)-(Boc-amino)-4(S)-[2-(2-methoxyethoxy)-acetyloxy]-6-phenyl-2(R)-(p-methoxyphenyl)methylhexanoyl-(L)-Val-(L)-Phe-morpholin-4-ylamide Under a nitrogen atmosphere, 0.25 ml of pyridine, 150 mg (0.198 mmol) of Boc-Phe[C](p-CH$_3$O)Phe-(L)-Val-(L)-Phe-morpholin-4-ylamide (Example 21 F) 1)) and a small amount of DMAP are added to 75 mg (≈60% strength; 0.296 mmol) of 2-(2-methoxyethoxy)-acetic acid chloride in 1.5 ml of dioxane. After 17 h at RT, the reaction mixture is poured onto sat. NaHCO$_3$ solution and extracted three times with methylene chloride, and the organic phases are washed with sat. NaHCO$_3$ solution, water and brine, dried with Na$_2$SO$_4$ and concentrated by evaporation. Column chromatography (SiO$_2$, methylene chloride/THF 4:1) and stirring with hexane yields the title compound: TLC R$_f$(B')=0.37; t$_{Ref}$(I)=16.7 min; FAB-MS (M+H)$^+$=875.

The starting material is prepared as follows:

a) 2-(2-Methoxyethoxy)-acetic Acid Chloride

Under a nitrogen atmosphere, 2.56 ml (29.8 mmol) of oxalyl chloride and 2 drops of DMF are added to 1.69 ml (14.9 mmol) of 2-(2-methoxyethoxy)-acetic acid (Fluka; Buchs/Switzerland) in 75 ml of methylene chloride. After 17 h at RT, the reaction mixture is carefully concentrated by evaporation in a RE with the exclusion of moisture. A $^1$H-NMR spectrum of the residue exhibits the signals of the title compound in addition to signals of ≈40% solvent (especially methylene chloride): $^1$H-NMR (200 MHz, CDCl$_3$): 3.37 (s, MeO), 3.58 and 3.77 (2d, J=5 Hz, CH$_2$—CH$_2$), 4.48 (s, CH$_2$). That mixture is used above.

EXAMPLE 126

5(S)-(Boc-amino)-4(S)-(2-picolinoyloxy)-6-phenyl-2(R)-(p-methoxyphenyl)methylhexanoyl-(L)-Val-(L)-Phe-morpholin-4-ylamide Under a nitrogen atmosphere, 48.6 mg (0.395 mmol) of 2-picolinic acid in 0.78 ml of methylene chloride are reacted at 0° C. with 33.5 µl (0.237 mmol) of 1-chloro-N,N,2-trimethyl-1-propenamine. After 30 min, 0.39 ml of pyridine, 150 mg (0.198 mmol) of Boc-Phe[C](p-CH$_3$O)Phe-(L)-Val-(L)-Phe-morpholin-4-ylamide (Example 21 F) 1)) and 0.4 mg of DMAP are added thereto. Since, according to HPLC, there is still some Boc-Phe[C](p-CH$_3$O)Phe-(L)-Val-(L)-Phe-morpholin-4-ylamide present after 17 h at RT, portions each of 48.6 mg of 2-picolinic acid are each activated with 33.5 µl of 1-chloro-N,N,2-trimethyl-1-propenamine and added until, after a reaction time of 16 h in each case, all starting material has reacted. Working up analogously to Example 117 L) and column chromatography (SiO$_2$, methylene chloride/THF 4:1) yields the title compound: TLC R$_f$(B')=0.30; t$_{Ref}$(I)=16.5 min; FAB-MS (M+H)$^+$=865.

EXAMPLE 127

5(S)-(Boc-amino)-4(S)-{2-[2-(2-methoxyethoxy)
ethoxy]-acetyloxy}-6-phenyl-2(R)-(p-
methoxyphenyl)methylhexanoyl-(L)-Val-(L)-(p-
CH$_3$O-Phe)-morpholin-4-ylamide Under a nitrogen atmosphere, 58 µl (0.38 mmol) of 2-[2-(2-methoxyethoxy)ethoxy]-acetic acid (Fluka; Buchs/ Switzerland) in 0.7 ml of methylene chloride are reacted at 0° C. with 32 µl (0.228 mmol) of 1-chloro-N,N,2-trimethyl-1-propenamine. After 30 min, 0.37 ml of pyridine, 150 mg (0.190 mmol) of Boc-Phe[C](p-CH$_3$O)Phe-(L)-Val-(L)-(p-CH$_3$O-Phe)-morpholin-4-ylamide (Example 21 F) 3)) and a small amount of DMAP are added thereto. Since, according to HPLC, there is still some Boc-Phe[C](p-CH$_3$O)Phe-(L)-Val-(L)-(p-CH$_3$O-Phe)-morpholin-4-ylamide present after 19 h at RT, a further 58 µl of 2-[2-(2-methoxyethoxy)ethoxy] -acetic acid is activated with 32 µl of 1-chloro-N,N,2-trimethyl-1-propenamine and added. Working up after 17 h analogously to Example 117 L), column chromatography (SiO$_2$, methylene chloride/THF 4:1) and stirring in DIPE yields the title compound: TLC R$_f$(B')=0.23; t$_{Ref}$(I)=16.5 min; FAB-MS (M+H)$^+$=949.

EXAMPLE 128

5(S)-(Boc-amino)-4(S)-(2-picolinoyloxy)-6-phenyl-2
(R)-(p-methoxyphenyl)methylhexanoyl-(L)-Val-(L)-
(p-CH$_3$O-Phe)-morpholin-4-ylamide Under a nitrogen atmosphere, 46.8 mg (0.380 mmol) of 2-picolinic acid in 0.75 ml of methylene chloride are reacted at 0° C. with 32 µl (0.228 mmol) of 1-chloro-N,N,2-trimethyl-1-propenamine. After 30 min, 150 mg (0.190 mmol) of Boc-Phe[C](p-CH$_3$O)Phe-(L)-Val-(L)-(p-CH$_3$O-Phe)-morpholin-4-ylamide (Example 21 F) 3)) in 0.38 ml of pyridine and 0.4 mg of DMAP are added thereto. Since, according to HPLC, there is still some Boc-Phe[C](p-CH$_3$O)Phe-(L)-Val-(L)-(p-CH$_3$O-Phe)-morpholin-4-ylamide present after 17 h at RT, a further 46.8 mg of 2-picolinic acid is activated with 32 µl of 1-chloro-N,N,2-trimethyl-1-propenamine and added. Working up after 18 h analogously to Example 117 L), column chromatography (SiO$_2$, methylene chloride/THF 4:1) and stirring with hexane yields the title compound: TLC R$_f$(B')=0.37; t$_{Ref}$(I)=16.4 min; FAB-MS (M+H)$^+$=894.

EXAMPLE 129

5(S)-(Boc-amino)-4(S)-(2-benzyloxy)acetyloxy-6-
phenyl-2(R)-benzylhexanoyl-(L)-Val-(L)-Phe-
morpholin-4-ylamide Analogously to Example 77, 730 mg (1 mmol) of 5(S)-(Boc-amino)-4(S)-hydroxy-6-phenyl-2(R)-benzylhexanoyl-(L)-Val-(L)-Phe-morpholin-4-ylamide are reacted with 0.237 ml (1.5 mmol) of benzyloxyacetyl chloride (Fluka, Buchs, Switzerland) and 5 mg of DMAP in 5 ml of pyridine to yield the title compound. Column chromatography (SiO$_2$, ethyl acetate) yields the title compound: TLC R$_f$(B)=0.5; t$_{Ref}$(I)=19 min; FAB-MS (M+H$^+$)=877.

EXAMPLE 130

5(S)-(Boc-amino)-4(S)-(2-acetyloxy)acetyloxy-6-
phenyl-2(R)-benzylhexanoyl-(L)-Val-(L)-Phe-
morpholin-4-ylamide Analogously to Example 77, 730 mg (1 mmol) of 5(S)-(Boc-amino)-4(S)-hydroxy-6-phenyl-2(R)-benzylhexanoyl-(L)-Val-(L)-Phe-morpholin-4-ylamide are reacted with 0.166 ml (1.5 mmol) of acetyloxyacetyl chloride (Aldrich, Steinheim, Federal Republic of Germany) and 5 mg of DMAP in 5 ml of pyridine to give the title compound. Column chromatography (SiO$_2$, ethyl acetate) yields the title compound: TLC R$_f$(B)=0.41; t$_{Ref}$(I)=17.3 min; FAB-MS (M+H$^+$)=829.

EXAMPLE 131

5(S)-(Boc-amino)-4(S)-[2-(4-tetrahydropyranyloxy)
acetyloxy-6-phenyl-2(R)-benzylhexanoyl-(L)-Val-
(L)-Phe-morpholin-4-ylamide Analogously to Example 80, a solution of 365 mg (0.5 mmol) of 5(S)-(Boc-amino)-4(S)-hydroxy-6-phenyl-2(R)-benzylhexanoyl-(L)-Val-(L)-Phe-morpholin-4-ylamide and 5 mg of DMAP in 4 ml of pyridine is added to a mixture of 160 mg (1 mmol) of 4-tetrahydropyranylacetic acid (Chemical Abstracts-Registry No. 85064-61-5) and 0.17 ml (1.2 mmol) of 1-chloro-N,N,2-trimethyl-1-propenamine in 10 ml of methylene chloride. After working up and column chromatography (SiO$_2$, ethyl acetate/hexane: 4/1) the title compound is isolated: TLC R$_f$ (methylene chloride/ methanol: 4/1)=0.57; t$_{Ref}$(I)=16.9 min; FAB-MS (M+H$^+$)= 871.

EXAMPLE 132

5(S)-(Boc-amino)-4(S)-[2(R)-(4-
tetrahydropyranyloxy)]-propionyloxy-6-phenyl-2(R)
-benzylhexanoyl-(L)-Val-(L)-Phe-morpholin-4-
ylamide Analogously to Example 80, a solution of 219 mg (0.3 mmol) of 5(S)-(Boc-amino)-4(S)-hydroxy-6-phenyl-2(R)-benzylhexanoyl-(L)-Val-(L)-Phe-morpholin-4-ylamide and 5 mg of DMAP in 1.5 ml of pyridine is added to a mixture of 105 mg (0.6 mmol) of 2(R)-(4-tetrahydropyranyl-propionic acid (Beilstein E III/IV, Vol. 18, p 3851) and 0.11 ml (0.72 mmol) of 1-chloro-N,N,2-trimethyl-1-propenamine in 5 ml of methylene chloride. After working up and column chromatography (SiO$_2$, ethyl acetate/hexane: 4/1) the title compound is isolated: TLC R$_f$(B)=0.37; t$_{Ref}$(I)=17.3 min; FAB-MS (M+H$^+$)=885.

EXAMPLE 133

5(S)-(Boc-amino)-4(S)-[2-(2-aminoethoxy)
ethoxyacetyloxy)]-6-phenyl-2(R)-benzylhexanoyl-
(L)-Val-(L)-Phe-morpholin-4-ylamide Analogously to Example 121, 0.83 g (0.82 mmol) of 5(S)-(Boc-amino)-4(S)-[2-(2-benzyloxycarbonylaminoethoxy)ethoxyacetyloxy)]-6-phenyl-2(R)-benzylhexanoyl-(L)-Val-(L)-Phe-morpholin-4-ylamide (Example 134) in 20 ml of methanol is hydrogenated in the presence of 0.1 g of 10% Pd/C. Column chromatography (SiO$_2$, methylene chloride/methanol: 95/5 to 80/20) yields the title compound: TLC R$_f$ (methylene chloride/methanol: 9/1)=0.15; t$_{Ref}$(I)=13.1 min; FAB-MS (M+H$^+$)=874.

EXAMPLE 134

5(S)-(Boc-amino)-4(S)-[2-(2-
benzyloxycarbonylaminoethoxy)ethoxyacetyloxy)]-
6-phenyl-2(R)-benzylhexanoyl-(L)-Val-(L)-Phe-
morpholin-4-ylamide Analogously to Example 80, a solution of 1.09 g (1.5 mmol) of 5(S)-(Boc-amino)-4(S)-hydroxy-6-phenyl-2(R)- benzylhexanoyl-(L)-Val-(L)-Phe-morpholin-4-ylamide and 10 mg of DMAP in 7.5 ml of pyridine is added to a mixture of 0.9 g (3 mmol) of 2-(2-benzyloxycarbonylamino)-ethoxy)-ethoxyacetic acid and 0.51 ml (3.6 mmol) of 1-chloro-N,N,2-trimethyl-1-propenamine in 20 ml of methylene chloride. After working up and column chromatography (SiO$_2$, methylene chloride to methylene chloride/methanol: 98/2) the title compound is isolated: TLC R$_f$(B)=0.41; t$_{Ref}$(I)= 17.95 min; FAB-MS (M+H$^+$)=1008.

The starting compounds are prepared as follows:
a) 2-[2-(Phthalimidoethoxy)-ethoxy]-acetic Acid Ethyl Ester A solution of 10.5 g (50 mmol) of 2-[2-(chloroethoxy)-ethoxy]-acetic acid ethyl ester (Chemical Abstracts-Registry No. 82227-25-6) in 100 ml of DMF is reacted with 9.25 g (50 mmol) of potassium phthalimide (Fluka, Buchs, Switzerland) and 50 mg of 18-crown-6 ether (1,4,7,10,13,16-hexaoxacyclooctadecane, Fluka, Buchs, Switzerland) and the mixture is stirred for 2.5 h at 100° C. The reaction mixture is cooled and then concentrated under reduced pressure. The residue is taken up in ether and washed twice in each case with water and brine. After drying and concentrating, the title compound is obtained by column chromatography (SiO$_2$, ethyl acetate/hexane: 1/1); TLC R$_f$ (ethyl acetate/hexane: 4/1)=0.45;

b) 2-[2-(Aminoethoxy)-ethoxy]-acetic Acid (see also E.P. 0 410 280 A1)

A solution of 9.6 g (29.9 mmol) of 2-[2-(phthalimidoethoxy)-ethoxy]-acetic acid ethyl ester in 195 ml of 20% aqueous HCl is stirred at reflux for 1.5 h. The mixture is cooled and then concentrated in a rotary evaporator, and the residue obtained is taken up in 45 ml of water. Insoluble material is removed by filtration and the filtrate is extracted three times with ethyl acetate. The combined organic phases are washed with water and brine, dried and concentrated. The white crystalline material obtained is stirred in 110 ml of 6N HCl for 17.5 h, cooled and concentrated, and the residue is taken up in 20 ml of water. The aqueous phase is washed three times with ethyl acetate and lyophilised under a high vacuum. TLC R$_f$ (methyl ethyl ketone/acetic acid/water: 3/1/1)=0.45.

c) 2-[2-(Benzyloxycarbonylaminoethoxy)-ethoxy]-acetic Acid

A suspension of 6.7 g (12.5 mmol) of 2-[2-(aminoethoxy) ethoxy]-acetic acid in 30 ml of THF and 10 ml of water is adjusted to pH 10 with 2N NaOH, and reacted dropwise with 1.95 ml of chloroformic acid benzyl ester (Fluka, Buchs, Switzerland). While the mixture is being stirred for 2.5 h, the pH is maintained between 9 and 9.5 by 2N NaOH. After concentration of the reaction mixture under reduced pressure, the resulting aqueous phase is washed twice with ethyl acetate, adjusted to pH 1.8 with 2N sulfuric acid and extracted 3 times with ethyl acetate. The combined organic phases are then washed with water and brine, dried and concentrated under reduced pressure. The title compound so obtained is further used without being further purified. TLC R$_f$ (ethyl acetate/acetic acid: 9/1)=0.39.

EXAMPLE 135

5(S)-(Boc-amino)-4(S)-[(methoxycarbonylmethoxy)-acetyloxy]-6-phenyl-2(R)-benzylhexanoyl-(L)-Val-(L)-Phe-morpholin-4-ylamide Analogously to Example 80, a solution of 219 mg (0.3 mmol) of 5(S)-(Boc-amino)-4(S)-hydroxy-6-phenyl-2(R)-benzylhexanoyl-(L)-Val-(L)-Phe-morpholin-4-ylamide and 5 mg of DMAP in 1.5 ml of pyridine is added to a mixture of 89 mg (0.6 mmol) of diglycolic acid monomethyl ester (Chem. Ber. 55, 670 (1922) and 0.11 ml (0.72 mmol) of 1-chloro-N,N,2-trimethyl-1-propenamine in 5 ml of methylene chloride. After working up and column chromatography (SiO$_2$, ethyl acetate/hexane: 4/1) the title compound is isolated. TLC R$_f$(B)=0.35; t$_{Ref}$(IV)=16.84 min; FAB-MS (M+H$^+$)=859.

EXAMPLE 136

5(S)-(Boc-amino)-4(S)-[(methoxycarbonylmethylthio)-acetyloxy]-6-phenyl-2 (R)-benzylhexanoyl-(L)-Val-(L)-Phe-morpholin-4-ylamide Analogously to Example 80, a solution of 219 mg (0.3 mmol) of 5(S)-(Boc-amino)-4(S)-hydroxy-6-phenyl-2(R)-benzylhexanoyl-(L)-Val-(L)-Phe-morpholin-4-ylamide and 5 mg of DMAP in 1.5 ml of pyridine is added to a mixture of 98 mg (0.6 mmol) of thiodiglycolic acid monomethyl acetate (Indian J. Chem. 25B, 880 (1986)) and 0.11 ml (0.72 mmol) of 1-chloro-N,N,2-trimethyl-1-propenamine in 5 ml of methylene chloride. Working up and column chromatography (SiO$_2$, ethyl acetate/hexane: 4/1) yield the title compound.

EXAMPLE 137

5(S)-(Boc-amino)-4(S)-[(methoxycarbonylmethylsulfo)-acetyloxy]-6-phenyl-2(R)-benzylhexanoyl-(L)-Val-(L)-Phe-morpholin-4-ylamide Analogously to Example 80, a solution of 219 mg (0.3 mmol) of 5(S)-(Boc-amino)-4(S)-hydroxy-6-phenyl-2(R)-benzylhexanoyl-(L)-Val-(L)-Phe-morpholin-4-ylamide and 5 mg of DMAP in 1.5 ml of pyridine is added to a mixture of 117 mg (0.6 mmol) of S,S-dioxothiodiglycolic acid monomethyl ester and 0.11 ml (0.72 mmol) of 1-chloro-N,N,2-trimethyl-1-propenamine in 5 ml of methylene chloride. After working up and column chromatography (SiO$_2$, ethyl acetate/hexane: 4/1) the title compound is isolated.

The starting compound is prepared as follows:
a) S,S-Dioxo-thiodiglycolic Acid Monomethyl Ester Thiodiglycolic acid monomethyl ether (Indian J. Chem. 25B, 880 (1986)) in a methanol/water mixture is oxidised with potassium peroxomonosulfate at approximately 25° C. to yield the title compound, which is further used.

EXAMPLE 138

5(S)-(Boc-amino)-4(S)-[(pivaloyloxymethoxycarbonylmethoxy)-acetyloxy]-6-phenyl-2(R)-benzylhexanoyl-(L)-Val-(L)-Phe-morpholin-4-ylamide Iodomethyl pivalate (Chem. Abstr. Registry No. 53064-79-2) is added to 5(S)-(Boc-amino)-4(S)-[(carboxymethoxy)-acetyloxy]-6-phenyl-2(R)-benzylhexanoyl-(L)-Val-(L)-Phe-morpholin-4-ylamide. The subsequent column chromatography yields the title compound.

EXAMPLE 139

5(S)-(Boc-amino)-4(S)-[(carboxymethoxy)-acetyloxy]-6-phenyl-2(R)-benzylhexanoyl-(L)-Val-(L)-Phe-morpholin-4-ylamide Diglycolic acid anhydride (Fluka, Buchs, Switzerland) is added to a solution of 219 mg (0.3 mmol) of 5(S)-(Boc-amino)-4(S)-hydroxy-6-phenyl-2(R)-benzylhexanoyl-(L)-Val-(L)-Phe-morpholin-4-ylamide in pyridine. After working up and column chromatography (SiO$_2$, ethyl acetate) the title compound is isolated.

EXAMPLE 140

(S)-(Boc-amino)-4(S)-[(acetoxymethoxycarbonylmethoxy)-acetyloxy]-6-phenyl-2(R)-benzylhexanoyl-(L)-Val-(L)-Phe-morpholin-4-ylamide Analogously to Example 138, 5(S)-(Boc-amino)-4(S)-[(carboxymethoxy)-acetyloxy]-6-phenyl-2(R)-benzylhexanoyl-(L)-Val-(L)-Phe-morpholin-4-ylamide is reacted with bromomethyl acetate (Aldrich, Steinheim, Federal Republic of Germany). The subsequent column chromatography yields the title compound.

EXAMPLE 141

Analogously to one of the processes described in Examples 77 to 140, unless explicitly described in the afore-mentioned Examples the compounds of formula I of Examples 57 to 64 are converted, by replacing the 4(S)-hydroxy group in the central non-hydrolysable peptide building block, into the corresponding 4(S)-acyloxy compounds in which one of the following radicals stands in place of the 4(S)-hydroxy group:
A) 4(S)-(2-furanylcarboxy)-;
B) 4(S)-[4-(dimethylamino)-butyryloxy];
C) 4(S)-(N-Z-N-methylaminoacetyloxy);
D) 4(S)-(methylaminoacetyloxy);
E) 4(S)-[N-(imidazole-4-methyl)-N-methylaminoacetyloxy];
F) 4(S)-[3-(1-triphenylmethylimidazol-4-yl)-propionyloxy];
G) 4(S)-[3-(4-imidazolyl)-propionyloxy];
H) 4(S)-(methoxyacetyloxy);
I) 4(S)-((2-picolinoyl);
J) 4(S)-(benzyloxyacetyloxy);
K) 4(S)-[(S)-α-methoxy-α-phenylacetyloxy];
L) 4(S)-[(R)-α-methoxy-α-phenylacetyloxy];
M) 4(S)-(1-pyrazolylacetyloxy);
N) 4(S)-(isoquinoline-3-carbonyloxy);
O) 4(S)-(pyrazinecarbonyloxy);
P) 4(S)-(4-α-chloromethylbenzoyloxy);
Q) 4(S)-[4-(4-morpholino)-methylbenzoyloxy];
R) 4(S)-(isonicotinoyloxy);
S) 4(S)-(nicotinoyloxy);
T) 4(S)-(3-methoxypropanoyloxy)
U) 4(S)-[(4-chlorophenoxy)-methoxyacetyloxy)];
V) 4(S)-[2-(2-methoxyethoxy)-acetyloxy)];
W) 4(S)-(butyloxyacetyloxy);
X) 4(S)-[2-[2-(2-methoxyethoxy)-ethoxy]-acetyloxy];
Y) 4(S)-(methoxyacetyloxy);
Z) 4(S)-(phenoxyacetyloxy);
AA) 4(S)-[(S)-α-methoxy-α-phenylacetyloxy);
AB) 4(S)-[(R)-α-methoxy-α-phenylacetyloxy)];
AC) (N,N-dimethylaminoacetyloxy);
AD) 4(S)-[N-(pyridine-2-methyl)-N-methylaminoacetyloxy];
AE) 4(S)-[3-(dimethylamino)-propionyloxy];
AF) 4(S)-[3-(N-Z-N-methylamino)-propionyloxy];
AG) 4(S)-(3-methylaminopropionyloxy);
AH) 4(S)-[(dimethylaminoethoxy)-acetyloxy];
AI) 4(S)-[(2-pyridylmethoxy)-acetyloxy];
AJ) 4(S)-(methoxyacetyloxy);
AK) 4(S)-(pyridine-2-carboxyl);
AL) 4(S)-(methylthioacetyloxy);
AM) 4(S)-(benzylthioacetyloxy);
AN) 4(S)-((L)-prolyloxy);
AO) 4(S)-((D)-prolyloxy);
AP) 4(S)-((L)-(N-Z-prolyl)oxy);
AQ) 4(S)-((D)-(N-Z-prolyl)oxy).

EXAMPLE 142

Analogously to one of the processes described in Examples 77 to 140, unless explicitly described in the afore-mentioned Examples the compounds of formula I of Examples 1 to 22 and 33 to 64 are converted, by replacing the 4(S)-hydroxy group in the central non-hydrolysable peptide building block, into the corresponding 4(S)-acyloxy compounds in which one of the following radicals stands in place of the 4(S)-hydroxy group:
3-(N-Z-amino)-propionyloxy;
3-aminopropionyloxy;
(3-dimethylaminopropoxy)acetyloxy;
2-(2-dimethylaminoethoxy)-ethoxyacetyloxy;
(4-dimethylaminobutoxy)acetyloxy;
(2-benzyloxy)acetyloxy;
2-acetyloxy)acetyloxy;
2-(4-tetrahydropyranyloxy)-acetyloxy;
2(R)-(4-tetrahydropyranyloxy)propionyloxy;
2-(2-aminoethoxy)-ethoxyacetyloxy);
2-(2-benzyloxycarbonylaminoethoxy)-ethoxyacetyloxy);
(methoxycarbonylmethoxy)-acetyloxy;
(methoxycarbonylmethylthio)-acetyloxy;
(methoxycarbonylmethylsulfo)-acetyloxy;
(pivaloyloxymethoxycarbonylmethoxy;
(carboxymethoxy)acetyloxy;
(acetoxymethoxycarbonylmethoxy)acetyloxy.

EXAMPLE 143

Gelatin Solution

A sterile-filtered aqueous solution of one of the compounds of formula I' mentioned in the preceding Examples 77 to 142 or of formula I from the Examples 42 to 76 that in addition comprises 20% cyclodextrin, and a sterile gelatin solution preserved with phenol, are so mixed under aseptic conditions, with heating, that 1.0 ml of a solution of the following composition is obtained:
active ingredient 3 mg
gelatin 150.0 mg
phenol 4.7 mg
dist. water with 20% cyclodextrins 1.0 ml

EXAMPLE 144

Sterile Dry Substance for Injection 5 mg of one of the compounds of formula I' mentioned in the preceding Examples 77 to 142, or of formula I from the Examples 42 to 76, are dissolved as active ingredient in 1 ml of an aqueous solution with 20 mg of mannitol and 20% cyclodextrins as solubilisers. The solution is sterile-filtered and introduced under aseptic conditions into a 2 ml ampoule, deep-frozen and lyophilised. Before use, the lyophilisate is dissolved in 1 ml of distilled water or 1 ml of physiological saline. The solution is administered intramuscularly or intravenously. The formulation can also be introduced into double-chamber disposable syringes.

EXAMPLE 145

Nasal Spray 500 mg of finely ground (<5.0 μm) powder of one of the compounds of formula I' mentioned in the preceding

183

Examples 77 to 142, or of formula I from the Examples 42 to 76, are suspended as active ingredient in a mixture of 3.5 ml of Myglyol 812® and 0.08 g of benzyl alcohol. The suspension is introduced into a container fitted with a metering valve. 5.0 g of Freon 12® are introduced under pressure into the container through the valve. The "Freon" is dissolved in the Myglyol/benzyl alcohol mixture by shaking. The spray container contains approximately 100 single doses which can be administered individually.

EXAMPLE 146

Film-coated Tablets

The following ingredients are processed to produce 10 000 tablets each comprising 100 mg of active ingredient:
active ingredient 1000 g
corn starch 680 g
colloidal silicic acid 200 g
magnesium stearate 20 g
stearic acid 50 g
sodium carboxymethyl starch 250 g
water quantum satis A mixture of one of the compounds of formula I' mentioned in the preceding Examples 77 to 142, or of formula I from the Examples 42 to 76, as active ingredient, 50 g of corn starch and colloidal silicic acid is processed with starch paste prepared from 250 g of corn starch and 2.2 kg of demineralised water to form a moist mass which is forced through a sieve of 3 mm mesh size and dried in a fluidised bed drier at 45° for 30 min. The dry granules are pressed through a sieve of 1 mm mesh size, mixed with a pre-sieved mixture (1 mm sieve) of 330 g of corn starch, the magnesium stearate, the stearic acid and the sodium carboxymethyl starch, and compressed into slightly biconvex tablets.

EXAMPLE 147

Orally Administrable Dispersion 1

625 mg of one of the compounds of formula I' mentioned in the preceding Examples 77 to 142, or of formula I from the Examples 42 to 76, as active ingredient, and 625 mg of POPC (1-palmitoyl-2-oleoylphosphatidylcholine=1-hexadecanoyl-2-(9-cis-octadecenoyl)-3-sn-phosphatidylcholine) are dissolved in 25 ml of ethanol. The solution is diluted with ten times the amount of water. The ethanolic solution is for that purpose added dropwise at room temperature, at a rate of 10 ml/min, to the prescribed mount of water. The ethanol is removed from the mixture by tangential dialysis ("Cross Flow Filtration") against 1750 ml of water (System: Minitan®, 700 cm² polyethersulphone membrane with an exclusion limit of 100 kD, supplied by Millipore (USA)). The mixture is concentrated to 15 mg of active ingredient by ultrafiltration using the same system. After the addition of 1.24 mg/ml of citric acid and 1.24 mg/ml of disodium hydrogen phosphate.2 H₂O to adjust the pH to 4.2 and the addition of 1 mg/ml of sorbic acid as antimicrobial preservative, the dispersion is concentrated to 15 mg/ml again and introduced into vials, for example having a capacity of 20 ml. The dispersion particles have a diameter of from 0.1–2 μm. They are stable for at least six months at from +2° to 8° C. and are suitable for oral administration.

EXAMPLE 148

Orally Administrable Dispersion 2

The preparation is carried out analogously to Example 147, except that 25 mg of active ingredient and 50 mg of POPC are used to prepare the ethanolic solution.

184

EXAMPLE 149

Orally Administrable Dispersion 3

The preparation is carried out analogously to Example 147, except that 25 mg of active ingredient and 125 mg of POPC are used to prepare the ethanolic solution.

EXAMPLE 150

Orally Administrable Dispersion 4

The preparation is carried out analogously to Example 147, except that 50 mg of active ingredient and 50 mg of POPC are used to prepare the ethanolic solution.

EXAMPLE 151

Orally Administrable Dispersion 5

The preparation is carried out analogously to any one of Examples 147 to 150, except that active ingredient and phosphatidyl choline from soybeans or phosphatidylcholine from egg yolk (70–100% pure) are used instead of POPC to prepare the ethanolic solution. If desired, an antioxidant, such as ascorbic acid, is added in a concentration of 5 mg/ml.

What is claimed is:

1. A compound of the formula

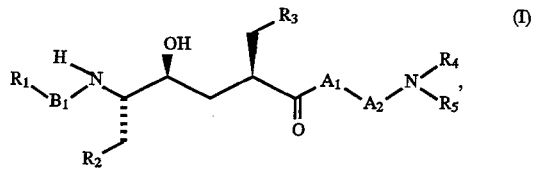

wherein $R_1$ is hydrogen; lower alkoxycarbonyl benzyloxycarbonyl that is unsubstituted or substituted by up to three radicals which may be the same or different and are selected from fluorine, halo-lower alkyl, lower alkanoyl, sulfo, lower alkylsulfonyl and cyano; or lower alkylsulfonyl; $B_1$ is a bond or a bivalent radical of an a-amino acid selected from glycine, valine, norvaline, alanine, leucine, norleucine and isoleucine, which radical is bonded N-terminally to $R_1$ and C-terminally to the amino group at the $R_2$—$CH_2$-carrying carbon atom, each of $R_2$ and $R_3$, independently of the other, is phenyl or cyclohexyl, those radicals being unsubstituted or substituted by from one to three radicals which may be the same or different and are selected from hydroxy, lower alkoxy, halogen, halo-lower alkyl, sulfo, lower alkylsulfonyl, cyano and nitro, $A_1$ is a bond between —C═O and $A_2$ or is a bivalent radical of an a-amino acid selected from glycine, valine, norvaline, alanine, leucine, norleucine and isoleucine, which radical is bonded N-terminally to the group —C═O and C-terminally to $A_2$, $A_2$ is a bivalent radical of an a-amino acid selected from phenylalanine, p-fluorophenylalanine, p-methoxyphenylalanine, tyrosine, phenylglycine, a-naphthylalanine, cyclohexylalanine, cyclohexylglycine, glycine, valine, norvaline, alanine, leucine, norleucine and isoleucine, which radical is bonded N-terminally to $A_1$ and C-terminally to the group $NR_4R_5$, and $R_5$, together with the bonding nitrogen atom, are morpholino which is unsubstituted or substituted at one or more of the carbon atoms by lower alkyl, or a pharmaceutically acceptable salt of that compound if salt-forming groups are present.

2. A compound of formula I according to claim 1, wherein $R_1$ is hydrogen, lower alkoxycarbonyl, or benzyloxycarbonyl that is unsubstituted or substituted by up to three radicals which may be the same or different and are selected from fluorine, halo-lower alkyl, lower alkanoyl, sulfo, lower alkylsulfonyl and cyano, $B_1$ is a bond or a bivalent radical of an a-amino acid selected from glycine, valine, norvaline, alanine, leucine, norleucine and isoleucine, which radical is bonded N-terminally to $R_1$ and C-terminally to the amino group at the $R_2$—$CH_2$-carrying carbon atom, each of $R_2$ and $R_3$, independently of the other, is phenyl or cyclohexyl, those radicals being unsubstituted or substituted by from one to three radicals which may be the same or different and are selected from halogen, halo-lower alkyl, sulfo, lower alkylsulfonyl, cyano and nitro, $A_1$ is a bond between —C=O and $A_2$ or is a bivalent radical of an a-amino acid selected from glycine, valine, norvaline, alanine, leucine, norleucine and isoleucine, which radical is bonded N-terminally to the group —C=O and C-terminally to $A_2$, $A_2$ is a bivalent radical of an a-amino acid selected from glycine, valine, phenylalanine, p-fluorophenylalanine, tyrosine, p-methoxyphenylalanine, phenylglycine, a-naphthylalanine, cyclohexylalanine and cyclohexylglycine, which radical is bonded N-terminally to $A_1$ and C-terminally to the group $NR_4R_5$, and $R_4$ and $R_5$, together with the bonding nitrogen atom, are unsubstituted morpholino, or a pharmaceutically acceptable salt of that compound, if salt-forming groups are present.

3. A compound of formula I according to claim 1, wherein $R_1$ is hydrogen, lower alkoxycarbonyl, benzyloxycarbonyl that is unsubstituted or substituted by up to three radicals which may be the same or different and are selected from fluorine, halo-lower alkyl, lower alkanoyl, sulfo, lower alkylsulfonyl and cyano, or lower alkylsulfonyl, $B_1$ is a bond or a bivalent radical of an a-amino acid selected from glycine, valine, norvaline, alanine, leucine, norleucine and isoleucine, which radical is bonded N-terminally to $R_1$ and C-terminally to the amino group at the $R_2$—$CH_2$-carrying carbon atom, each of $R_2$ and $R_3$, independently of the other, is phenyl or cyclohexyl, those radicals being unsubstituted or substituted by from one to three radicals which may be the same or different and are selected from hydroxy, methoxy, halogen, halo-lower alkyl, sulfo, lower alkylsulfonyl, cyano and nitro, $A_1$ forms a bond between —C=O and $A_2$ or is a bivalent radical of an a-amino acid selected from glycine, valine, norvaline, alanine, leucine, norleucine and isoleucine, which radical is bonded N-terminally to the group —C=O and C-terminally to $A_2$, $A_2$ is a bivalent radical of an a-amino acid selected from glycine, valine, phenylalanine, p-fluorophenylalanine, tyrosine, p-methoxyphenylalanine, phenylglycine, a-naphthylalanine, cyclohexylalanine and cyclohexylglycine, which radical is bonded N-terminally to $A_1$ and C-terminally to the group $NR_4R_5$, and $R_4$ and $R_5$, together with the bonding nitrogen atom, are unsubstituted morpholino; or a pharmaceutically acceptable salt of that compound, if salt-forming groups are present.

4. A compound of formula I according to claim 3, wherein $R_1$ is lower alkylsulfonyl and the other radicals are as defined, or a pharmaceutically acceptable salt thereof, if salt-forming groups are present.

5. A compound of formula I according to claim 1, wherein at least one of the radicals $R_2$ and $R_3$ is substituted by from one to three radicals selected from halogen, halo-lower alkyl, sulfo, lower alkylsulfonyl, cyano and nitro, and the other radicals $R_1$, $B_1$, $A_1$, $A_2$ and $NR_4R_5$ are as defined, or a salt thereof, if salt-forming groups are present.

6. A compound of formula I according to claim 1, wherein $R_1$ is hydrogen, tert-butoxycarbonyl, isobutoxycarbonyl, or benzyloxycarbonyl substituted by up to three radicals which may be the same or different and are selected from fluorine, halo-lower alkyl, lower alkanoyl, sulfo, lower alkylsulfonyl and cyano, $B_1$ is a bond or a bivalent radical of an a-amino acid selected from glycine, valine, norvaline, alanine, leucine, norleucine and isoleucine, which radical is bonded N-terminally to $R_1$ and C-terminally to the amino group at the $R_2$—$CH_2$-carrying carbon atom, each of $R_2$ and $R_3$, independently of the other, is phenyl or cyclohexyl, those radicals being unsubstituted or substituted by one or two radicals which may be the same or different and are selected from hydroxy, methoxy, fluorine, sulfo, lower alkylsulfonyl, trifluoromethyl and cyano, $A_1$ is a bivalent radical of a hydrophobic a-amino acid selected from glycine, valine, norvaline, alanine, leucine, norleucine and isoleucine, which radical is bonded N-terminally to the group —C=O and C-terminally to $A_2$, $A_2$ is a bivalent radical of a hydrophobic a-amino acid selected from glycine, valine, phenylalanine, p-fluorophenylalanine, p-methoxyphenylalanine and cyclohexylalanine, which radical is bonded N-terminally to $A_1$ and C-terminally to the radical $NR_4R_5$, and $R_4$ and $R_5$, together with the bonding nitrogen atom, are morpholino, or a pharmaceutically acceptable salt of that compound, if salt-forming groups are present.

7. A compound of formula I according to claim 2, wherein $R_1$ is hydrogen, tert-butoxycarbonyl, isobutoxycarbonyl, or benzyloxycarbonyl that is substituted by up to three radicals which may be the same or different and are selected from fluorine, halo-lower alkyl, lower alkanoyl, sulfo, lower alkylsulfonyl and cyano, $B_1$ is a bond or a bivalent radical of an a-amino acid selected from glycine, valine, norvaline, alanine, leucine, norleucine and isoleucine, which radical is bonded N-terminally to $R_1$ and C-terminally to the amino group at the $R_2$—$CH_2$-carrying carbon atom, each of $R_2$ and $R_3$, independently of the other, is phenyl or cyclohexyl, those radicals being unsubstituted or substituted by one or two radicals which may be the same or different and are selected from fluorine, sulfo, lower alkylsulfonyl and cyano, $A_1$ is a bivalent radical of a hydrophobic a-amino acid selected from glycine, valine, norvaline, alanine, leucine, norleucine and isoleucine, which radical is bonded N-terminally to the group —C=O and C-terminally to $A_2$, $A_2$ is a bivalent radical of a hydrophobic a-amino acid selected from glycine, valine, phenylalanine, p-fluorophenylalanine, p-methoxyphenylalanine and cyclohexylalanine, which radical is bonded N-terminally to $A_1$ and C-terminally to the radical $NR_4R_5$, and $R_4$ and $R_5$, together with the bonding nitrogen atom, are morpholino, or a pharmaceutically acceptable salt of that compound, if salt-forming groups are present.

8. A compound of formula I according to claim 1, wherein $R_1$ is hydrogen, tert-butoxycarbonyl, or isobutoxycarbonyl, $B_1$ is a bond or a bivalent radical of the a-amino acid valine, which radical is bonded N-terminally to $R_1$ and C-terminally to the amino group at the $R_2$—$CH_2$-carrying carbon atom, each of $R_2$ and $R_3$, independently of the other, is phenyl or cyclohexyl, those radicals being unsubstituted or substituted by one or two radicals which may be the same or different and are selected from hydroxy, methoxy, fluorine, sulfo, lower alkylsulfonyl, trifluoromethyl and cyano, $A_1$ is a bivalent radical of one of the a-amino acids glycine, valine and isoleucine, which radical is bonded N-terminally to the group —C=O and C-terminally to $A_2$, $A_2$ is a bivalent radical of one of the a-amino acids glycine, valine, phenylalanine, tyrosine, cyclohexylalanine, p-methoxyphenylalanine and p-fluorophenylalanine, which radical is bonded N-terminally to $A_1$ and C-terminally to the group $NR_4R_5$, and $R_4$ and $R_5$, together with the bonding nitrogen atom, are morpholino, or a pharmaceutically acceptable salt of that compound, if salt-forming groups are present.

9. A compound of formula I according to claim 1, wherein $R_1$ is hydrogen, tert-butoxycarbonyl, or isobutoxycarbonyl, $B_1$ is a bond or a bivalent radical of the a-amino acid valine, which radical is bonded N-terminally to $R_1$ and C-terminally to the amino group at the $R_2$—$CH_2$-carrying carbon atom, each of $R_2$ and $R_3$, independently of the other, is phenyl or cyclohexyl, those radicals being unsubstituted or substituted by one or two radicals which may be the same or different and are selected from hydroxy, methoxy, fluorine, trifluoromethyl and cyano, $A_1$ and $A_2$ together form a bivalent radical of a dipeptide of the formula Val-Phe, Ile-Phe, Val-Cha, Ile-Cha, Ile-Gly, Val-Val, Val-Gly, Val-(p-F-Phe), Val-(p-CH$_3$O-Phe), Gly-(p-F-Phe) or Val-Tyr, which is bonded N-terminally to the group —C=O and C-terminally to the group $NR_4R_5$, and $R_4$ and $R_5$, together with the bonding nitrogen atom, are morpholino, or a pharmaceutically acceptable salt of that compound, if salt-forming groups are present.

10. The compound of formula I according to claim 1, wherein $R_1$ is tert-butoxycarbonyl, $B_1$ is a bond, $R_2$ and $R_3$ are each phenyl, $A_1$ is the bivalent radical of valine which radical is bonded N-terminally to the group —C=O and C-terminally to $A_2$, $A_2$ is the bivalent radical of phenylalanine which radical is bonded N-terminally to $A_1$ and C-terminally to the group $NR_4R_5$, and $R_4$ and $R_5$ together with the bonding nitrogen atom are morpholino.

11. Any one compound of formula I according to claim 1 being selected from the compounds of formula I with the name Boc-Cha[C](p-F)Phe-(L)-Ile-(L)-Phe-morpholin-4-ylamide Boc-(p-F)Phe[C](p-F)Phe-(L)-Val-(L)-Phe-morpholin-4-ylamide, Boc-(p-F)Phe[C](p-F)Phe-(L)-Val-(L)-(p-F-Phe)-morpholin-4-ylamide, Boc-(p-F)Phe[C](p-F)Phe-(L)-Val-(L)-(p-CH$_3$O-Phe)-morpholin-4- ylamide, Boc-(p-F)Phe[C](p-F)Phe-(L)-Val-(L)-Cha-morpholin-4-ylamide, Boc-(p-F)Phe[C](p-F)Phe-(L)-Ile-(L)-Phe-morpholin-4-ylamide, Boc-(p-F)Phe[C](p-CN)Phe-(L)-Val-(L)-Phe-morpholin-4-ylamide, Boc-(p-F)Phe[C](p-CN)Phe-(L)-Val-(L)-(p-F-Phe)-morpholin-4-yl amide, Boc-(p-F)Phe[C](p-CN)Phe-(L)-Val-(L)-(p-CH$_3$O-Phe)-morpholin-4-ylamide, Boc-(p-F)Phe[C](p-CN)Phe-(L)-Val-(L)-Cha-morpholin-4-ylamide, Boc-(p-F)Phe[C](p-CN)Phe-(L)-Ile-(L)-Phe-morpholin-4-ylamide, Boc-Phe[C](p-F)Phe-(L)-Val-(L)-Phe-morpholin-4-ylamide, Boc-Phe[C](p-F)Phe-(L)-Val-(L)-(p-F-Phe)-morpholin-4-ylamide, Boc-Phe[C](p-F)Phe-(L)-Val-(L)-(p-CH$_3$O-Phe)-morpholin-4-ylami de, Boc-Phe[C](p-F)Phe-(L)-Val-(L)-Cha-morpholin-4-ylamide, Boc-Phe[C](p-F)Phe-(L)-Ile-(L)-Phe-morpholin-4-ylamide, Boc-Phe[C](p-CN)Phe-(L)-Val-(L)-Phe-morpholin-4-ylamide, Boc-Phe[C](p-CN)Phe-(L)-Val-(L)-(p-F-Phe)-morpholin-4-ylamide, Boc-Phe[C](p-CN)Phe-(L)-Val-(L)-(p-CH$_3$O-Phe)-morpholino-4-ylam ide, Boc-Phe[C](p-CN)Phe-(L)-Val-(L)-Cha-morpholin-4-ylamide, Boc-Phe[C](p-CN)Phe-(L)-Ile-(L)-Phe-morpholin-4-ylamide, Boc-Phe[C](p-CH$_3$O)Phe-(L)-Val-(L)-(p-F-Phe)-morpholin-4-ylami de, Boc-Phe[C](p-CH$_3$O)Phe-(L)-Val-(L)-(p-CH$_3$O-Phe)-morpholin-4-yl amide, Boc-Phe[C](p-CH$_3$O)Phe-(L)-Val-(L)-Cha-morpholin-4-ylamide, Boc-Phe[C](p-CH$_3$O)Phe-(L)-Ile-(L)-Phe-morpholin-4-ylamide, Boc-Phe[C](p-CF$_3$)Phe-(L)-Val-(L)-Phe-morpholin-4-ylamide, Boc-Phe[C](p-CF$_3$)Phe-(L)-Val-(L)-(p-F-Phe)-morpholin-4-ylamid e, Boc-Phe[C](p-CF$_3$)Phe-(L)-Val-(L)-(p-CH$_3$O-Phe)-morpholin-4-yl amide, Boc-Phe[C](p-CF$_3$)Phe-(L)-Val-(L)-Cha-morpholin-4-ylamide, Boc-Phe[C](p-CF$_3$)Phe-(L)-Ile-(L)-Phe-morpholin-4-ylamide, Boc-Cha[C](p-CN)Phe-(L)-Val-(L)-(p-F-Phe)-morpholin-4-ylamide, Boc-Cha[C](p-CN)Phe-(L)-Val-(L)-(p-CH$_3$O-Phe)-morpholin-4-ylam ide, Boc-Cha[C](p-CN)Phe-(L)-Val-(L)-Cha-morpholin-4-ylamide, Boc-Cha[C](p-CN)Phe-(L)-Ile-(L)-Phe-morpholin-4-ylamide, Boc-Cha[C](p-CH$_3$O)Phe-(L)-Val-(L)-Phe-morpholin-4-ylamide, Boc-Cha[C](p-CH$_3$O)Phe-(L)-Val-(L)-(p-F-Phe)-morpholin-4-ylamide, Boc-Cha[C](p-CH$_3$O)Phe-(L)-Val-(L)-(p-CH$_3$O-Phe)-morpholin-4-yl amide, Boc-Cha[C](p-CH$_3$O)Phe-(L)-Val-(L)-Cha-morpholin-4-ylamide, Boc-Cha[C](p-CH$_3$O)Phe-(L)-Ile-(L)-Phe-morpholin-4-ylamide, Boc-Cha[C](p-CF$_3$)Phe-(L)-Val-(L)-Phe-morpholin-4-ylamide, Boc-Cha[C](p-CF$_3$)Phe-(L)-Val-(L)-(p-F-Phe)-morpholin-4-ylamid e, Boc-Cha[C](p-CF$_3$)Phe-(L)-Val-(L)-(p-CH$_3$O-Phe)-morpholin-4-ylamide, Boc-Cha[C](p-CF$_3$)Phe-(L)-Val-(L)-Cha-morpholin-4-ylamide, Boc-Cha[C](p-CF$_3$)Phe-(L)-Ile-(L)-Phe-morpholin-4-ylamide and Boc-Cha[C](p-F)Phe-(L)-Val-(L)-(p-F-Phe)-morpholin-4-ylamide, Boc-Cha[C](p-F)Phe-(L)-Val-(L)-(p-CH$_3$O-Phe)-morpholin-4-ylamide, Boc-Cha[C](p-F)Phe-(L)-Val-(L)-Cha-morpholin-4-ylamide, Boc-Phe[C]Phe-(L)-Val-(L)-(p-F-Phe)-morpholin-4-ylamide, Boc-Phe[C]Phe-(L)-Val-(L)-(p-CH₃O-Phe)-morpholin-4-ylamide, Boc-Phe[C]Phe-(L)-Val-(L)-Cha-morpholin-4-ylamide, Boc-Phe[C]Phe-(L)-Ile-(L)-Phe-morpholin-4-ylamide, Boc-Phe[C]Phe-(L)-Val-Gly-morpholin-4-ylamide, Boc-Phe[C]Phe-(L)-Ile-Gly-morpholin-4-ylamide and Boc-Phe[C]Phe-(L)-Val-(L)-Val-morpholin-4-ylamide, or a salt thereof provided that at least one salt-forming group is present.

12. A method for the treatment of warm-blooded animals suffering from AIDS, comprising administering a dose, effective in the treatment of AIDS, of a compound of formula I according to claim 1, or of a pharmaceutically acceptable salt thereof, to a warm-blooded animal in need of such treatment.

13. A pharmaceutical composition suitable for administration to a warm-blooded animal for the treatment of AIDS or the preliminary stages thereof comprising an amount that is therapeutically effective against AIDS and the preliminary stages thereof of a compound of formula I according to claim 1, or of a pharmaceutically acceptable salt thereof, if salt-forming groups are present, and a pharmaceutically acceptable carrier.

14. A compound of formula I

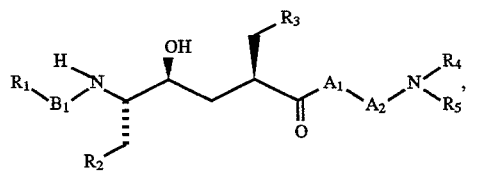

wherein

R₁ is hydrogen, lower alkoxycarbonyl, benzyloxycarbonyl that is unsubstituted or substituted by up to three radicals selected independently of one another from fluorine, halo-lower alkyl, lower alkanoyl, sulfo, lower alkylsulfonyl and cyano, or lower alkylsulfonyl R₂ is phenyl, cyclohexyl, lower alkoxyphenyl, benzyloxyphenyl, p-fluorophenyl, p-trifluoromethylphenyl or p-hydroxyphenyl;

R₃ is phenyl, lower alkoxyphenyl, m- or p-methoxyphenyl, p-trifluoromethylphenyl, o-, m- or p-cyanophenyl, benzyloxyphenyl, p-benzyloxyphenyl, o-, m or p-fluorophenyl or hydroxyphenyl, A₁ is the bivalent residue of the amino acid (L)-valine, (L)-isoleucine or glycine bonded N-terminally to the group —C=O and C-terminally to A₂;

A₂ is the bivalent residue of the amino acid glycine, alanine, valine, leucine, isoleucine, phenylalanine, tyrosine, cyclohexylalanine, p-lower alkoxyphenylalanine, p-benzyloxyphenylalanine or p-fluorophenylalanine bonded N-terminally to A₁ and C-terminally to the group NR₄R₅, and R₄ and R₅ together with the bonding nitrogen atom form unsubstituted morpholino, with the proviso that at least either one of the radicals R₂ and R₃ is benzyloxyphenyl or A₂ is the bivalent residue of p-benzyloxyphenylalanine, while the remaining radicals are as defined, when either R₃ is other than o- or m-fluorophenyl, o- or m-cyanophenyl or o- or m-methoxyphenyl, or when A₂ is other than alanine or leucine;

or a pharmaceutically acceptable salt of such a compound where salt-forming groups are present.

15. A compound of formula I according to claim 14, wherein R₁ is tert-butoxycarbonyl, R₂ is phenyl, p-benzyloxyphenyl or o-, m- or p-methoxyphenyl, R₃ is phenyl, p-benzyloxyphenyl, o-, m- or p-methoxyphenyl, o-, m- or p-fluorophenyl or hydroxyphenyl, A₁ is the bivalent residue of the amino acid (L)-valine, (L)-isoleucine or glycine bonded N-terminally to the group —C=O and C-terminally to A₂, A₂ is the bivalent residue of the amino acid glycine, alanine, valine, leucine, isoleucine, phenylalanine, tyrosine, cyclohexylalanine, p-lower alkoxyphenylalanine, p-benzyloxyphenylalanine or p-fluorophenylalanine bonded N-terminally to A₁ and C-terminally to the group NR₄R₅, and R₄ and R₅ together with the bonding nitrogen atom form morpholino, with the proviso that at least either one of the radicals R₂ and R₃ is benzyloxyphenyl or A₂ is the bivalent residue of p-benzyloxyphenylalanine, while the remaining radicals are as defined.

16. A compound of formula I according to claim 14, wherein R₁ is tert-butoxycarbonyl, R₂ is phenyl, R₃ is o- or m-fluorophenyl, o- or m-cyanophenyl or o- or m-lower alkoxyphenyl, A₁ is the bivalent residue of the amino acid (L)-valine, (L)-isoleucine or glycine bonded N-terminally to the group —C=O and C-terminally to A₂, A₂ is the bivalent residue of the amino acid glycine, alanine, valine, leucine, isoleucine, phenylalanine, tyrosine, cyclohexylalanine, p-lower alkoxyphenylalanine, p-benzyloxyphenylalanine or p-fluorophenylalanine bonded N-terminally to A₁ and C-terminally to the group NR₄R₅, and R₄ and R₅ together with the bonding nitrogen atom form morpholino.

17. A method of treating warm-blooded animals suffering from AIDS, wherein a compound of formula I according to claim 14, or a pharmaceutically acceptable salt thereof where salt-forming groups are present, is administered in a dose effective in the treatment of AIDS to a warm-blooded animal requiring such treatment.

18. A pharmaceutical composition suitable for administration to a warm-blooded animal for the treatment of AIDS or the preliminary stages thereof comprising an amount that is therapeutically effective against AIDS and the preliminary stages thereof of a compound of formula I according to claim 14, and a pharmaceutically acceptable carrier.

19. A method of treating warm-blooded animals suffering from AIDS, wherein a compound of formula I according to claim 2, or a pharmaceutically acceptable salt thereof where salt-forming groups are present, is administered in a dose effective in the treatment of AIDS to a warm-blooded animal requiring such treatment.

20. A pharmaceutical composition suitable for administration to a warm-blooded animal for the treatment of AIDS or the preliminary stages thereof, comprising an antiretrovirally effective amount that is therapeutically effective against AIDS and the preliminary stages thereof of a compound of formula I according to claim 2, and a pharmaceutically acceptable carrier.

21. A compound of formula I according to claim 14 selected from the group consisting of Boc-Phe[C](o-CN)Phe-(L)-Val-(L)-Phe-morpholin-4-ylamide;

Boc-Phe[C](m-CN)Phe-(L)-Val-(L)-Phe-morpholin-4-ylamide;

Boc-Phe[C](p-BzlO)Phe-(L)-Val-(L)-Phe-morpholin-4-ylamide;

Boc-Phe[C](p-BzlO)Phe-(L)-Val-(L)-(p-BzlOPhe)-morpholin-4-ylamide;

Boc-(p-BzlO)Phe[C]Phe-(L)-Val-(L)-Phe-morpholin-4-ylamide;

Boc-(p-BzlO)Phe[C]Phe-(L)-Val-(L)-(p-BzlOPhe)-morpholin-4-ylamide;

Boc-(p-BzlO)Phe[C](p-BzlO)Phe-(L)-Val-(L)-Phe-morpholin-4-ylamide;

Boc-(p-BzlO)Phe[C](p-BzlO)Phe-(L)-Val-(L)-(p-BzlOPhe)-morpholin-4-ylamide;

Boc-Phe[C](o-F)Phe-(L)-Val-(L)-Phe-morpholin-4-ylamide;

Boc-Phe[C](o-F)Phe-(L)-Val-(L)-(p-CH$_3$O-Phe)-morpholin-4-ylamide;

Boc-Phe[C](m-F)Phe-(L)-Val-(L)-Phe-morpholin-4-ylamide;

Boc-Phe[C](m-F)Phe-(L)-Val-(L)-(p-CH$_3$O-Phe)-morpholin-4-ylamide;

Boc-Phe[C]Phe-(L)-Val-(L)-Leu-morpholin-4-ylamide;

Boc-Phe[C]Phe-(L)-Val-(L)-Ala-morpholin-4-ylamide;

Boc-(p-CH$_3$O)Phe[C](p-BzlO)Phe-(L)-Val-(L)-Phe-morpholin-4-ylamide;

Boc-(p-CH$_3$O)Phe[C](p-BzlO)Phe-(L)-Val-(L)-(p-CH$_3$O-Phe)-morpholin-4-ylamide;

Boc-(p-CH$_3$O)Phe[C](p-BzlO)Phe-(L)-Val-(L)-Tyr-morpholin-4-ylamide;

Boc-(p-CH$_3$O)Phe[C](3-CH$_3$O)Phe-(L)-Val-(L)-Phe-morpholin-4-ylamide;

Boc-(p-CH$_3$O)Phe[C](2-CH$_3$O)Phe-(L)-Val-(L)-Phe-morpholin-4-ylamide;

Boc-Phe[C](3-CH$_3$O)Phe-(L)-Val-(L)-Phe-morpholin-4-ylamide;

Boc-Phe[C](2-CH$_3$O)Phe-(L)-Val-(L)-Phe-morpholin-4-ylamide;

Boc-Phe[C](3-CH$_3$O)Phe-(L)-Val-(L)-(p-CH$_3$O-Phe)-morpholin-4-ylamide;

Boc-Phe[C](2-CH$_3$O)Phe-(L)-Val-(L)-(p-CH$_3$O-Phe)-morpholin-4-ylamide;

Boc-Phe[C](p-BzlO)Phe-(L)-Val-(L)-(p-CH$_3$O-Phe)-morpholin-4-ylamide;

Boc-(p-CH$_3$O)-Phe[C]Phe-(L)-Val-(L)-Phe-morpholin-4-ylamide;

Boc-(p-CH$_3$O)Phe[C](p-CH$_3$O)Phe-(L)-Val-(L)-Phe-morpholin-4-ylamide;

Boc-(p-CH$_3$O)Phe[C]Tyr-(L)-Val-(L)-Phe-morpholin-4-ylamide;

Boc-(p-CH$_3$O)Phe[C]Phe-(L)-Val-(L)-(p-CH$_3$O-Phe)-morpholin-4-ylamide;

Boc-(p-CH$_3$O)Phe[C]Phe-(L)-Val-(L)-Tyr-morpholin-4-ylamide;

Boc-(p-CH$_3$O)Phe[C](p-CH$_3$O)Phe-(L)-Val-(L)-(p-CH$_3$O-Phe)-morpholin-4-ylamide;

Boc-(p-CH$_3$O)Phe[C](p-CH$_3$O)Phe-(L)-Val-(L)-Tyr-morpholin-4-ylamide;

Boc-(p-CH$_3$O)Phe[C]Tyr-(L)-Val-(L)-(p-CH$_3$O-Phe)-morpholin-4-ylamide; and

Boc-(p-CH$_3$O)Phe[C]Tyr-(L)-Val-(L)-Tyr-morpholin-4-ylamide.

22. Any one compound of formula I according to claim 1 being selected from the compounds of formula I with the name Boc-Cha[C](p-CN)Phe-(L)-Val-(L)-Phe-morpholin-4-ylamide, Boc-(L)-Val-Phe[C]Phe-(L)-Val-(L)-Phe-morpholin-4-ylamide, H-(L)-Val-Phe[C]Phe-(L)-Val-(L)-Phe-morpholin-4-ylamide, Boc-Phe[C]Phe-(L)-Val-(D)-Phe-morpholin-4-ylamide, Isobutyloxycarbonyl-Phe[C]Phe-(L)-Val-(L)-Phe-morpholin-4-ylamide, H-Phe[C]Phe-(L)-Val-(L)-Phe-morpholin-4-ylamide, and Boc-Cha[C]Cha-(L)-Val-(L)-Cha-morpholin-4-ylamide, or a pharmaceutically acceptable salt thereof where a salt-forming group is present.

23. Any one compound of formula I according to claim 1 being selected from the compounds of formula I with the name Boc-(p-CF$_3$)Phe[C]Phe-(L)-Val-(L)-Phe-morpholin-4-ylamide, Boc-(p-CF$_3$)Phe[C]Phe-(L)-Val-(L)-(p-F)Phe-morpholin-4-ylamide, Boc-(p-CF$_3$)Phe[C]Phe-(L)-Val-(L)-(p-CH$_3$O)Phe-morpholin-4-ylamide, Boc-(p-CF$_3$)Phe[C]Phe-(L)-Val-(L)-Cha-morpholin-4-ylamide, Boc-(p-CF$_3$)Phe[C]Phe-(L)-Ile-(L)-Phe-morpholin-4-ylamide, Boc-(p-CF$_3$)Phe[C](p-F)Phe-(L)-Val-(L)-Phe-morpholin-4-ylamide, Boc-(p-CF$_3$)Phe[C](p-F)Phe-(L)-Val-(L)-(p-F)Phe-morpholin-4-ylamide, Boc-(p-CF$_3$)Phe[C](p-F)Phe-(L)-Val-(L)-Cha-morpholin-4-ylamide, Boc-(p-CF$_3$)Phe[C](p-F)Phe-(L)-Val-(L)-(p-CH$_3$O)Phe-morpholin-4-ylamide, Boc-(p-CF$_3$)Phe[C](p-F)Phe-(L)-Ile-(L)-Phe-morpholin-4-ylamide, Boc-(p-CF$_3$)Phe[C](p-CF$_3$)Phe-(L)-Val-(L)-Phe-morpholin-4-ylamide, Boc-(p-CF$_3$)Phe[C](p-CF$_3$)Phe-(L)-Val-(L)-(p-F)Phe-morpholin-4-ylamide, Boc-(p-CF$_3$)Phe[C](p-CF$_3$)Phe-(L)-Ile-(L)-Phe-morpholin-4-ylamide, Boc-(p-CF$_3$)Phe[C](p-CF$_3$)Phe-(L)-Val-(L)-(p-CH$_3$O)Phe-morpholin-4-ylamide and Boc-(p-CF$_3$)Phe[C](p-CF$_3$)Phe-(L)-Val-(L)-Cha-morpholin-4-ylamide, or a pharmaceutically acceptable salt thereof where a salt-forming group is present.

24. A compound of formula I according to claim 1, said compound having the name Boc-Phe[C](p-CH$_3$O)Phe-(L)-Val-(L)-Phe-morpholin-4-ylamide.

25. A compound of formula I according to claim 1, said compound having the name 5(S)-(Boc-amino)-4(S)-hydroxy-6-cyclohexyl-2(R)-(4-methoxyphenylmethyl)hexanoyl-(L)-Val-(L)-Phe-morpholin-4-ylamide.

* * * * *